(12) United States Patent
Magalhaes et al.

(10) Patent No.: US 12,378,580 B2
(45) Date of Patent: Aug. 5, 2025

(54) CO-PRODUCTION PATHWAY FOR 3-HPA AND ACETYL-COA DERIVATIVES FROM MALONATE SEMIALDEHYDE

(71) Applicant: Braskem S.A., Sao Paulo (BR)

(72) Inventors: Beatriz Leite Magalhaes, Campinas (BR); Paulo Moises Raduan Alexandrino, Campinas (BR); Felipe Galzerani, Paulínia (BR)

(73) Assignee: Braskem S.A., Sao Paulo (BR)

( * ) Notice: Subject to any disclaimer, the term of this patent is extended or adjusted under 35 U.S.C. 154(b) by 265 days.

(21) Appl. No.: 17/856,863

(22) Filed: Jul. 1, 2022

(65) Prior Publication Data

US 2023/0037707 A1    Feb. 9, 2023

Related U.S. Application Data

(63) Continuation of application No. 16/719,833, filed on Dec. 18, 2019, now Pat. No. 11,377,671.

(60) Provisional application No. 62/781,511, filed on Dec. 18, 2018.

(51) Int. Cl.
| | |
|---|---|
| *C12P 7/42* | (2006.01) |
| *C12N 1/16* | (2006.01) |
| *C12N 1/18* | (2006.01) |
| *C12R 1/865* | (2006.01) |

(52) U.S. Cl.
CPC ............... *C12P 7/42* (2013.01); *C12N 1/16* (2013.01); *C12N 1/185* (2021.05); *C12R 2001/865* (2021.05); *C12Y 101/01* (2013.01); *C12Y 203/01009* (2013.01)

(58) Field of Classification Search
None
See application file for complete search history.

(56) References Cited

U.S. PATENT DOCUMENTS

| | | | |
|---|---|---|---|
| 2,469,701 | A | 5/1949 | Redmon |
| 8,048,624 | B1 | 11/2011 | Lynch |
| 8,198,481 | B2 | 6/2012 | Kuppinger et al. |
| 8,809,027 | B1 | 8/2014 | Lynch et al. |
| 8,846,353 | B2 | 9/2014 | Tsobanakis et al. |
| 10,358,664 | B2 | 7/2019 | Frias et al. |
| 11,377,671 | B2 * | 7/2022 | Magalhaes ............ C12Y 102/01 |
| 2010/0021978 | A1 | 1/2010 | Burk et al. |
| 2011/0252501 | A1 | 10/2011 | Abad et al. |
| 2014/0135526 | A1 | 5/2014 | Lynch |
| 2018/0044684 | A1 | 2/2018 | Jessen et al. |
| 2018/0312886 | A1 | 11/2018 | Lynch et al. |

FOREIGN PATENT DOCUMENTS

| | | |
|---|---|---|
| WO | 2011031897 A1 | 3/2011 |
| WO | 2011038364 B1 | 3/2011 |
| WO | 2013043758 A2 | 3/2013 |
| WO | 2016100910 A1 | 6/2016 |
| WO | 2017040378 A1 | 3/2017 |
| WO | 2018213349 A1 | 11/2018 |
| WO | 2019011945 A1 | 1/2019 |
| WO | 2019011948 A1 | 1/2019 |

OTHER PUBLICATIONS

Birgit Alber et al., "Malonyl-Coenzyme A Reductase in the Modified 3-Hydroxypropionate Cycle for Autotrophic Carbon Fixation in Archaeal Metallosphaera and Sulfolobus spp.," Journal of Bacteriology, Dec. 2006, vol. 188, No. 24, pp. 8551-8559.

Gorm Andersen et al., "A gene duplication led to specialized γ-aminobutyrate and β-alanine aminotransferase in yeast," The FEBS Journal, 2007, vol. 274, pp. 1804-1817.

Priya Batra et al., "Anti-cancer potential of flavonoids: recent trends and future perspectives," 3 Biotech, Dec. 2013, vol. 3, No. 6, pp. 439-459.

Ângela Carvalho et al., "Designing microorganisms for heterologous biosynthesis of cannabinoids," FEMS Yeast Research, Jun. 2017, vol. 17, No. 4, fox037.

Hun Su Chu et al., "Direct fermentation route for the production of acrylic acid," Metabolic Engineering, 2015, vol. 32, pp. 23-29.

Onur Erbilgin et al., "The Structural Basis of Coenzyme A Recycling in a Bacterial Organelle," PLoS Biology, Mar. 2016, vol. 14, No. 3: e1002399.

David S. Gogerty et al., "Formation of isobutene from 3-hydroxy-3-methylbutyrate by diphosphomevalonate decarboxylase," Applied and Enviromental Microbiology, Dec. 2010, vol. 76, No. 24, pp. 8004-8010.

L. Hiser et al., "ERG10 from Saccharomyces cerevisiae encodes acetoacetyl-CoA thiolase," Journal of Biological Chemistry, Dec. 16, 1994, vol. 269, No. 50, pp. 31383-31389.

Abayomi Oluwanbe Johnson et al., "Design and application of genetically-encoded malonyl-CoA biosensors for metabolic engineering of microbial cell factories," Metabolic Engineering, Nov. 2017, vol. 44, pp. 253-264.

Irene Martínez et al., "Replacing Escherichia coli NAD-dependent glyceraldehyde 3-phosphate dehydrogenase (GAPDH) with a NADP-dependent enzyme from Clostridium acetobutylicum facilitates NADPH dependent pathways," Metabolic Engineering, Nov. 2008, vol. 10, No. 6, pp. 352-359.

(Continued)

*Primary Examiner* — Anand U Desai
(74) *Attorney, Agent, or Firm* — Morgan, Lewis & Bockius LLP

(57) ABSTRACT

The present disclosure provides methods for utilizing genetically modified microbes to co-produce 3-hydroxypropionic acid (3-HP) and acetyl-CoA, and derivatives thereof from malonate semialdehyde as a common single intermediate. The disclosure further provides modified microbe that co-produce the 3-HP and acetyl-CoA derivatives from malonate semialdehyde.

22 Claims, 25 Drawing Sheets

Specification includes a Sequence Listing.

(56) References Cited

OTHER PUBLICATIONS

Wangshu Mou et al., "Transcriptomic Analysis Reveals Possible Influences of ABA on Secondary Metabolism of Pigments, Flavonoids and Antioxidants in Tomato Fruit during Ripening," PLOS ONE, Jun. 8, 2015, vol. 10, No. 6, e0129598.
Chelladurai Rathnasingh et al., "Production of 3-hydroxypropionic acid via malonyl-CoA pathway using recombinant Escherichia coli strains," Journal of Biotechnology, Feb. 20, 2012, vol. 157, Issue 4, pp. 633-640.
Dieter J. Reinscheid et al., "Cloning, sequence analysis, expression and inactivation of the Corynebacterium glutamicum pta-ack operon encoding phosphotransacetylase and acetate kinase," Microbiology, Feb. 1999, vol. 145 (Pt 2), pp. 503-513.
Akiko Suyama et al., "Production of 3-hydroxypropionic acid via the malonyl-CoA pathway using recombinant fission yeast strains," Journal of Bioscience and Bioengineering, Oct. 2017, vol. 124, Issue 4, pp. 392-399.
Hideyuki Tamakawa et al., "Metabolic engineering of Candida utilis for isopropanol production," Applied Microbiology and Biotechnology, Jul. 2013, vol. 97, No. 14, pp. 6231-6239.
Jianrong Wang et al., "Cloning and Characterization of Farnesyl Diphosphate Synthase Gene Involved in Triterpenoids Biosynthesis from Poria cocos," International Journal of Molecular Sciences, Dec. 2014, vol. 15, No. 12, pp. 22188-22202.
Matthew Wilding et al., "A B-Alanine Catabolismpathway Containing a Highly Promiscuous w-Transaminase in the 12-Aminododecanate-Degrading Pseudomonas sp. Strain AAC," Applied and Environmental Microbiology, Jul. 1, 2016, vol. 82, No. 13, pp. 3846-3856.
Fang Yang et al., "Biosynthesis of phloroglucinol compounds in microorganisms—review," Applied Microbiology and Biotechnology, Jan. 2012, vol. 93, No. 2, pp. 487-495.
International Search Report and Written Opinion for Application No. PCT/IB2019/001345, dated Jul. 7, 2020.
Toshiaki Fukui et al., "Microbial synthesis of poly((R)-3-hydroxybutyrate-co-3-hydroxypropionate) from unrelated carbon sources by engineered Cupriavidus necator," Biomacromolecules 2009, 10, 700-706.
Jonathan D. Todd et al., "Molecular dissection of bacterial acrylate catabolismunexpected links with dimethylsulfoniopropionate catabolismand dimethyl sulfide production," Environmental Microbiology, 2010, vol. 12, No. 2, pp. 327-343 (17 pages). DOI: 10.1111/j.1462-2920.2009.02071.x.
UNIPROT_A0A2C1ZL92 (2 pages).
UNIPROT_A5YBJ3 (2 pages).
UNIPROT_A7BJC4 (2 pages).
UNIPROT: F8GV48 (2 pages).

\* cited by examiner

Case 1-propanol + acetone, aerobic:

3 Glc + 1 O2 → 2 acetone + 2 1-propanol + 4 H2O + 6 CO2

1 Glc + 0.33 O2 → 0.67 acetone + 0.67 1-propanol + 1.33 H2O + 2 CO2

0.437 g/g Glc

Case 1-propanol + acetone, anaerobic:

5 Glc → 3 acetone + 4 1-propanol + 4 H2O + 9 CO2

1 Glc → 0.6 acetone + 0.8 1-propanol + 0.8 H2O + 1.8 CO2

0.46 g/g Glc

Case 1-propanol + 2-propanol, aerobic:

6 Glc + 4.5 O2 → 5 2-propanol+ 2 1-propanol + 11 H2O + 15 CO2

1 Glc + 0.75 O2 → 0.83 2-propanol + 0.4 1-propanol + 2.2 H2O + 2.5 CO2

0.39 g/g Glc

Case 1-propanol + 2-propanol, anaerobic:

3 Glc → 2 2-Propanol + 2 1-propanol + 2 H2O + 6 CO2

1 Glc → 0.67 2-Propanol + 0.67 1-propanol + 0.67 H2O + 2 CO2

0.44 g/g Glc

Case 2-propanol, aerobic:

1 Glc + 1.5 O2 → 1 2-propanol + 3 H2O + 3 CO2

0.33 g/g Glc

Enzyme N°6
Km = 13 mM
Vm = 2,5 nM.min$^{-1}$.mg$^{-1}$

Enzyme N°9
Km = 27 mM
Vm = 2,42 nM.min$^{-1}$.mg$^{-1}$

SEQUENCE LISTING

```
Sequence total quantity: 285
SEQ ID NO: 1         moltype = AA  length = 528
FEATURE              Location/Qualifiers
REGION               1..528
                     note = Modified amino acid sequence of the enzymes able to
                     catalyze thedecarboxylation of oxaloacetate into malonic
                     semi-aldehyde
SITE                 109
                     note = Variant - Xaa in position 109 is selected from the
                     group consisting ofleucine, lysine, arginine and valine
SITE                 110
                     note = Variant - Xaa in position 110 is selected from the
                     group consisting ofleucine and lysine
SITE                 377
                     note = Variant - Xaa in position 377 is selected from the
```

| | | |
|---|---|---|
| SITE | | group consisting ofthreonine and serine |
| | 397 | |
| | | note = Variant - Xaa in position 397 is selected from the group consisting ofphenylalanine, asparagine, alanine, isoleucine and valine |
| SITE | 398 | |
| | | note = Variant - Xaa in position 398 is selected from the group consisting ofcysteine and arginine |
| SITE | 403 | |
| | | note = Variant - Xaa in position 403 is selected from the group consisting ofleucine, asparagine and alanine |
| SITE | 460 | |
| | | note = Variant - Xaa in position 460 is selected from the group consisting ofalanine and leucine |
| source | 1..528 | |
| | mol_type = protein | |
| | organism = synthetic construct | |

SEQUENCE: 1

```
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEAXX TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HQYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESXSTT AQMWQRLNMR NPGSYYXXAA GGXGFALPAA IGVQLAEPER  420
QVIAVIGDGS ANYSISALWT AAQYNIPTIF VIMNNGTYGX LRWFAGVLEA ENVPGLDVPG  480
IDFRALAKGY GVQALKADNL EQLKGSLQEA LSAKGPVLIE VSTVSPVK              528
```

| SEQ ID NO: 2 | moltype = AA length = 528 |
|---|---|
| FEATURE | Location/Qualifiers |
| REGION | 1..528 |
| | note = Modified Enzyme No. 2 |
| source | 1..528 |
| | mol_type = protein |
| | organism = synthetic construct |

SEQUENCE: 2

```
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HQYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLNMR NPGSYYFCAA GGLGFALPAA IGVQLAEPER  420
QVIAVIGDGS ANYSISALWT AAQYNIPTIF VIMNNGTYGA LRWFAGVLEA ENVPGLDVPG  480
IDFRALAKGY GVQALKADNL EQLKGSLQEA LSAKGPVLIE VSTVSPVK              528
```

| SEQ ID NO: 3 | moltype = AA length = 528 |
|---|---|
| FEATURE | Location/Qualifiers |
| REGION | 1..528 |
| | note = Modified Enzyme No. 2 |
| source | 1..528 |
| | mol_type = protein |
| | organism = synthetic construct |

SEQUENCE: 3

```
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HQYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLNMR NPGSYYNCAA GGLGFALPAA IGVQLAEPER  420
QVIAVIGDGS ANYSISALWT AAQYNIPTIF VIMNNGTYGA LRWFAGVLEA ENVPGLDVPG  480
IDFRALAKGY GVQALKADNL EQLKGSLQEA LSAKGPVLIE VSTVSPVK              528
```

| SEQ ID NO: 4 | moltype = AA length = 528 |
|---|---|
| FEATURE | Location/Qualifiers |
| REGION | 1..528 |
| | note = Modified Enzyme No. 3 |
| source | 1..528 |
| | mol_type = protein |
| | organism = synthetic construct |

SEQUENCE: 4

```
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEAKL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HQYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLNMR NPGSYYNCAA GGLGFALPAA IGVQLAEPER  420
```

```
QVIAVIGDGS ANYSISALWT AAQYNIPTIF VIMNNGTYGA LRWFAGVLEA ENVPGLDVPG   480
IDFRALAKGY GVQALKADNL EQLKGSLQEA LSAKGPVLIE VSTVSPVK               528

SEQ ID NO: 5            moltype = AA  length = 528
FEATURE                 Location/Qualifiers
REGION                  1..528
                        note = Modified Enzyme No. 4
source                  1..528
                        mol_type = protein
                        organism = synthetic construct
SEQUENCE: 5
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWWVAPSAPRC   240
PFPTRHPCFR GLMPAGIAAI SQLLEGHDVV LVIGAPVFRY HQYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYNCAA GGLGFALPAA IGVQLAEPER   420
QVIAVIGDGS ANYSISALWT AAQYNIPTIF VIMNNGTYGL LRWFAGVLEA ENVPGLDVPG   480
IDFRALAKGY GVQALKADNL EQLKGSLQEA LSAKGPVLIE VSTVSPVK               528

SEQ ID NO: 6            moltype = AA  length = 528
FEATURE                 Location/Qualifiers
REGION                  1..528
                        note = Modified Enzyme No. 5
source                  1..528
                        mol_type = protein
                        organism = synthetic construct
SEQUENCE: 6
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEAVK TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWWVAPSAPRC   240
PFPTRHPCFR GLMPAGIAAI SQLLEGHDVV LVIGAPVFRY HQYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYNCAA GGNGFALPAA IGVQLAEPER   420
QVIAVIGDGS ANYSISALWT AAQYNIPTIF VIMNNGTYGA LRWFAGVLEA ENVPGLDVPG   480
IDFRALAKGY GVQALKADNL EQLKGSLQEA LSAKGPVLIE VSTVSPVK               528

SEQ ID NO: 7            moltype = AA  length = 248
FEATURE                 Location/Qualifiers
source                  1..248
                        mol_type = protein
                        organism = Escherichia coli
SEQUENCE: 7
MIVLVTGATA GFGECITRRF IQQGHKVIAT GRRQERLQEL KDELGDNLYI AQLDVRNRAA    60
IEEMLASLPA EWCNIDILVN NAGLALGMEP AHKASVEDWE TMIDTNNKGL VYMTRAVLPG   120
MVERNHGHII NIGSTAGSWP YAGGNVYGAT KAFVRQFSLN LRTDLHGTAV RVTDIEPGLV   180
GGTEFSNVRF KGDDGKAEKT YQNTVALTPE DVSEAVWWVS TLPAHVNINT LEMMPVTQSY   240
AGLNVHRQ                                                           248

SEQ ID NO: 8            moltype = AA  length = 1824
FEATURE                 Location/Qualifiers
source                  1..1824
                        mol_type = protein
                        organism = Chloroflexus aggregans
SEQUENCE: 8
MAIDTAPPAP SRAPRSNPIR DRVDWETQRA AALANPGAFH GAIARTVIHW YDPKHNCWIR    60
FDESSQRWEG LDAATGAPVT VDYPADYQPW QQAFDDSEAP FYRWFYGGLT NACFNEVDRH   120
VMMGYGDEVA YYFEGDRWDN SLNNGRGGPV VQETITRRRL LVEVVKAAQV LRDLGLKKGD   180
RIALNMPNIM PQIYYTEAAK RLGIIYTPVF GGFSDKTLSD RIHNAGARVV ITSDGAYRNA   240
QVVPYKEAYT DQALDKYVPV ETVRRIVAET LTTLPLRDDQ RQKIIDEVES VLSGEITIER   300
SDVMRGVGAA LAQIRDLDAA TQANVRTVLA QALVASPPRV EAVIVVRHTG QDILWNADRD   360
RWSHELLEAA LAKILANARA IGIDVHSEAD LLKLPDDQLI RALYASVPCE PVDAEYPMFI   420
IYTSGSTGKP KGVIHVHGGY VSGVVHTLRV SFDAEPGDTI YVIADPGWIT GQSYMLTATM   480
AGRLTGIIAE GSPLFPSSGR YASIIERYGV QIFKAGVTFL KTVMSNPQNI EDVRLYNMSS   540
LRVATFCAEP VSPAVQQFGM QIMTPQYINS YWATEHGGIV WTHFYGNNDF PLRPDAHTYP   600
LPWVAGDVWV AETDESGNVR YRVADYEEKG EIVITAPYYP LTRTIWGDVP GFEAYLRGEI   660
PLKAWKGDAE RFIKTYWRRG PHGEWGYIQG DFAMKYPDGS FTLHGRSDDV INVSGHRMGT   720
EEIEGAILRD RQITPDSPVG NCIVVGAPHR EKGLTPVAFI QPAPGRRLTA ADRRRLDELV   780
RTEKGAVSVP EDYIEVSAFP ETRSGKYMRR FLRNMMLDEP LGDTTTLRNP EVLEEIAAKI   840
AEWKRKQRLA EEQQIIERYR YFRIEYHPPA ASAGKLAVVT VTNPPVNALN ERALDELNTI   900
VDHLSRRNDV AAIVFTGQGA KSFVAGADIR QLLEEIHTVE EAMALPNNAH LAFRKIERMN   960
KPCIAAINGV ALGGGLEFAM ACHYRVADVY AEFGQPEINL RLLPGYGGTQ RLPRLLHRRS  1020
NGTGLLRALE MILGGRSVPA DEALELGLID AIATGDADAL MLACSLAREA IASDGTLRED  1080
AAVTKAFRQR HAQLEEWRKP DPHFTDDQLR SIIAHPRIER IIKQAHTVGR DVAVHRALDA  1140
IRYGFIHGFE AGLEHEAKLF AEAVVDPNGG KRGIREFLDR HSAPLPTRRP LISREQEQLL  1200
LEQKELLPIG SPFFPGVDRI PKWQYAQAFI RDPETGAAMH GDPIVAEKQI IIPVERPRAN  1260
QALIYVLASE VNFNDIWAIT GIPVSRFDEH DRDWHVTGSG GIGLVVALGE EARREGRLKI  1320
```

```
GDLVAIYSGQ TDLLSPLMGL DPMAADFVIQ GNDTPDGSHQ QFMVAQAPQC MPVLPDMTLE 1380
AAGSYILNLG TIYRALFTTL RVQPGRTIFI EGAATGTGLD AVRTAARNGL NVIGMVSSPS 1440
RAATVLSAGG KGAINRKDPA IANCFTRVPE DPSEWAAWEA AGHPLLEMFR AQNGGRLADY 1500
VVSHAGETAF PRSFQLLGEP HDGHIPTLTF YGASSGYHFT FIGKPGAASP TEMLRRAGLR 1560
AGEGVLIYYG VGSPELIDGA GLEAIEAARL MGARIVVVTA SDAQREFVLS LGFGAALRGV 1620
ISITELKRRF GDEFDWPKTM PPLPDSRKDP QGLKEAVRRF NDLTFKPIGS AVGGFLRTPD 1680
NPRGYPDLII ERAGHDALAV SAMLIKPFTG RIVYFEDIGG RRYSFFAPQI WVRQRRIYMP 1740
TAQIFGTHLS NAYEIVRMNE EISAGLITIT EPAVVPWDQL PEAHQAMWEN RHTAATYVVN 1800
HALPRLGIKT KDELYEAWTA ADRE                                      1824

SEQ ID NO: 9          moltype = AA  length = 1912
FEATURE               Location/Qualifiers
source                1..1912
                      mol_type = protein
                      organism = Roseiflexus castenholzii
SEQUENCE: 9
MTTIESALRP PRINPVRTRA DWEAQRKAAL TDPGAFHGAI ARSAIHWYDR HLDAWITWDE 60
EEGCWKGLRY SDGAPIDVPY GPDHEPWERA FNGDDPPFYR WFEGGLTNAC FNEVDRHVLT 120
GYGDEVAFYF EGDRWDSSLN NGRGGPVVSF AVTRKQLMLE VVKAAQVLRD LGLNMGDRIA 180
LNMPNIMEQL YYTEAAKRLG IIYTPVFGGF SDKTLSDRIH NAGARLVITS DGAYRNAQVV 240
PYKEQYTDQA LDKFVPVETA LDIIEAALSG SEGSPVPGAP LLAPDQIKHI LAQVRDALKE 300
DITIERSDAM RAVGRAIEGL TGVDALAQSR ARTAVAQALV NTPPRVDAVI VVRHTGQDIL 360
WRPERDRWSH ELTARALETI LANARAVGVE VYSEDELLNL PTDQFVKALY ATSRAEPLDA 420
EYPMFIIYTS GSTGKPKGVV HVHGGYVAGV AYTMRVSFDA EPGDTIYVVA DPGWITGQSY 480
MICATLTTRC TGIITEGSPV FPSAGRFASI IERYKVRIFK AGVTFLKTVM SDPQNTADAR 540
QYDMSSLRVC TFCAEPVSPA VQQFGMELMS PQYINSYWAT EHGGIVWTHF YGNEDFPLRP 600
DAHTYPLPWI AGEVWVLEGG DRDATGAEAP RYRIADYEEK GEIVITAPYP YLTRTIWGDV 660
KGFEAWVAAM QHGNGATAPR WRGDAERFIK TYWRRGPNDE WGYIQGDFAM KYPDGSFTLH 720
GRSDDVINVS GHRMGTEEIE GAILRDKIIT PDSPVGNCIV VGAPHREKGL TPVAFILTAP 780
GRKLTGEDRR RLNELVRNEK GAVSVPEDYI EVSAFPETRS GKYMRRFLRN LMLGEPLGDT 840
TTLRNPESLK EIAEKIEAWK RKQRMAEEQR IFERYRYFRI EYHAVRERWT PSGNGSAAAE 900
QKALTQRIAI VTVTNPPVNA LNERALDELN TIVDHLARRE DVAAVFTGS GTKSFVAGAD 960
IKQMLEEMHT VEDAMALPNN AHLAFRKIET MNKPCIAAIN GVALGGGMEF ALACHYRIAD 1020
LHAEFGQPEI NLRLLPGYGG TQRLPRLLYS RRGEAGLIKA LMIIMGGRTL NAERAYEIGL 1080
IDKVAHGHEE ALTLATQMAR EMILAERNGK PTELRVIPNT SDDPTTFFSP FHDPATAGEG 1140
LWPPLPEAYA LRRQLTAQWE TPDPAMVDLL EKALRDPLIT RIINQAQWAG RARAIERIID 1200
ALRTGFTKGM LAGLEREARL FAEAVVAPDE GKIGIQDFLD KRSAPLPTRR RIHLTPDEEK 1260
RMIDAGMLLP IGAPFFPGVT PIPVAQYAMA VVRDEVTGAP AHGDPIEAEK QIIIPVEKPG 1320
PNDVLLYILA SEVNFNDIWA ITGVPVSQFD EHDRDWHVTG SGGIGLIVSV GEETKREGRL 1380
KVGDLVAIYS GQNDLLSPMV GLDPMAADFV IQGYNTPDAS HQQFMVAQAP QCFPVLPDLT 1440
LEAAGSYMLN LGTVYRALFT TLKIQPGRRI FVEGAATGTG LDAARSAARN GLYVTGMVSS 1500
QERAAVVRAA GAVGVINRRD PRYAGIFTRV PEDPAKWAEW EAAGRPLLED YRAQNGGHLA 1560
DYAVSHAGET AFPRSFQLLG EPHDGHIPTL TFYGASSGYH FTFLGKPGAA DPVEMLRRAG 1620
LRAGEAVMIY YGVDDRSYLG DEGYESGAVP ETLERRTTLV DQVGLEAIES ARAMGARIVV 1680
VTYTDAQREF VLSLGFGASL KGVVSLEELH RRYGDEFDWP ETMPPLPDAK SDIHGFKAAV 1740
RRFNDLTFKP LGTAVGQFLR SNDNPRGYPD LIIERSGHDT LAVSVMLIKP FTGRVVYFEN 1800
MDGQRYSFFA PQVWMRQRRI YMPTANIWGT HLSNAYEIVR LNDEISAGLL SITEPTLVEW 1860
NDLPQAHQAM WENRHQGATY VVNHALPRPG LKDKDELYEA WSEMLQNREY GV         1912

SEQ ID NO: 10         moltype = AA  length = 1823
FEATURE               Location/Qualifiers
source                1..1823
                      mol_type = protein
                      organism = Chloroflexus aurantiacus
SEQUENCE: 10
MAIDTAPLAP PRAPRSNPIR DRVDWEAQRA AALADPGAFH GAIARTVIHW YDPQHHCWIR 60
FNESSQRWEG LDAATGAPVT VDYPADYQPW QQAFDDSEAP FYRWFSGGLT NACFNEVDRH 120
VTMGYGDEVA YYFEGDRWDN SLNNGRGGPV VQETITRRRL LVEVVKAAQV LRDLGLKKGD 180
RIALNMPNIM PQIYYTEAAK RLGILYTPVF GGFSDKTLSN HNAGARVV ITSDGAYRNA 240
QVVPYKEAYT DQALDKYIPV ETAQAIVAQT LATLPLTESQ RQTIITEVEA ALAGEITVER 300
SDVMRGVGSA LAKLRDLDAS VQAKVRTVLA QALVESPPRV EAVVVRHTG QEILWNEGRD 360
RWSHDLLDAA LAKILANARA AGFDVHSEND LLNLPDDQLI RALYASIPCE PVDAEYPMFI 420
IYTSGSTGKP KGVIHVHGGY VAGVVHTLRV SFDAEPGDTI YVIADPGWIT GQSYMLTATM 480
AGRLTGVIAE GSPLFPSAGR YASIIERYGV QIFKAGVTFL KTVMSNPQNV EDVRLYDMHS 540
LRVATFCAEP VSPAVQQFGM QIMTPQYINS YWATEHGGIV WTHFYGNQDF PLRPDAHTYP 600
LPWVMGDVWV AETDESGTTR YRVADFDEKG EIVITAPYPY LTRTLWGDVP GFEAYLRGEI 660
PLRAWKGDAE RFVKTYWRRG PNGEWGYIQG DFAIKYPDGS FTLHGRSDDV INVSGHRMGT 720
EEIEGAILRD RQITPDSPVG NCIVVGAPHR EKGLTPVAFI QPAPGRHLTG ADRRRLDELV 780
RTEKGAVSVP EDYIEVSAFP ETRSGKYMRR FLRNMMLDEP LGDTTTLRNP EVLEEIAAKI 840
AEWKRRQRMA EEQQIIERYR YFRIEYHPPT ASAGKLAVVT VTNPPVNALN ERALDELNTI 900
VDHLARRQDV AAIVFTGQGA RSFVAGADIR QLLEEIHTVE EAMALPNNAH LAFRKIERMN 960
KPCIAAINGA ALGGGLEFAM ACHYRVADVY AEFGQPEINL RLLPGYGGTQ RLPRLLYKRN 1020
NGTGLLRALE MILGGRSVPA DEALELGLID AIATGDQDSL SLACALARAA IGADGQLIES 1080
AAVTQAFRHR HEQLDEWRKP DPRFADDELR SIIAHPRIER IIRQAHTVGR DAAVHRALDA 1140
IRYGIIHGFE AGLEHEAKLF AEAVVDPNGG KRGIREFLDR QSAPLPTRRR LITPEQEQLL 1200
RDQKELLPVG SPFFPGVDRI PKWQYAQAVI RDPDTGAAAH GDPIVAEKQI IVPVERPRAN 1260
QALIYVLASE VNFNDIWAIT GIPVSRFDEH DRDWHVTGSG GIGLIVALGE EARREGRLKV 1320
GDLVAIYSGQ SDLLSPLMGL DPMAADFVIQ GNDTPDGSHQ QFMLAQAPQC LPIPTDMSIE 1380
AAGSYILNLG TIYRALFTTL QIKAGRTIFI EGAATGTGLD AARSAARNGL RVIGMVSSSS 1440
```

```
RASTLLAAGA HGAINRKDPE VADCFTRVPE DPSAWAAWEA AGQPLLAMFR AQNDGRLADY  1500
VVSHAGETAF PRSFQLLGEP RDGHIPTLTF YGATSGYHFT FLGKPGSASP TEMLRRANLR  1560
AGEAVLIYYG VGSDDLVDTG GLEAIEAARQ MGARIVVVTV SDAQREFVLS LGFGAALRGV  1620
VSLAELKRRF GDEFEWPRTM PPLPNARQDP QGLKEAVRRF NDLVFKPLGS AVGVFLRSAD  1680
NPRGYPDLII ERAAHDALAV SAMLIKPFTG RIVYFEDIGG RRYSFFAPQI WVRQRRIYMP  1740
TAQIFGTHLS NAYEILRLND EISAGLLTIT EPAVVPWDEL PEAHQAMWEN RHTAATYVVN  1800
HALPRLGLKN RDELYEAWTA GER                                        1823

SEQ ID NO: 11           moltype = AA   length = 865
FEATURE                 Location/Qualifiers
source                  1..865
                        mol_type = protein
                        organism = Clostridium beijerinckii
SEQUENCE: 11
MARVTNPEEL TKRIEQIREA QREFAKFSQE EVDEIFRQAA MAANNARITL AKMAVEESGM  60
GIVEDKVIKN HFAAEYIYNQ YKDTKTCGVI ERDEMFGITH IAEPIGVIAA IVPTTNPTST  120
AIFKTLIALK TRNGIIISPH PRAKNSTIAA AKIVLEAAER AGAPKGIIGW IDEPSIELSR  180
NVMAESDIIL ATGGPGMVRA AYSSGKPAIG VGAGNTPAII DDTAHIKMAV NSILLSKTFD  240
NGVVCASEQS IIAMESVYDE VLKELDERGA YILKGDEVDK VRSIILDSKG SLNSEIVGQS  300
AYKIAKMAGV EISEAVKVLI GEVESPELEE PFSHEKLSPI LGMYKAKTFD DALRLASRMI  360
ELGGFGHTSI LYTNQVESVD RIEKFGVAMK TARTLINMPA SQGAIGDIYN FKLAPSLTLG  420
CGSWGGNSIS ENVGPKHLIN VKRIAERREN MLWFRVPDKI YFKFGCLPVA LEELNAMKKK  480
RAFIVTDRVL FDLGYTHKIT NILSENHIEY KIFSDVEPDP TLKAAKLGAD AMRDFNPDVI  540
IAIGGGSPMD AAKIMWVMYE HPDVRFEDLA MRFMDIRKRV YEFPPMGEKA ILVAIPTSAG  600
TGSEVTPFAV ITDQQTGVKY PLADYALTPN MAIIDAELMM SMPKGLTAAS GIDALVHAIE  660
AYVSVLASEY TNGLALEAIR LTFKYLPDAY NGGTTNIKAR EKMAHASSVA GMAFANAFLG  720
ICHSMAHKLG AFHHVPHGIA NALLIDEVIR FNATDAPRKQ AAFPQYKYPN AGWRYARIAD  780
YLNLGGNTEE EKVELLIKAI DDLKGKVGIP KSIKEFGVSE EKFYASMDEM VEQAFDDQCT  840
GANPRYPLMS EIKEMYIKSY NVSNK                                      865

SEQ ID NO: 12           moltype = AA   length = 869
FEATURE                 Location/Qualifiers
source                  1..869
                        mol_type = protein
                        organism = Clostridium arbusti
SEQUENCE: 12
MAKVSNIDEL NVRLEEIREA QRKFGTYTQE QVDEIFRQAA MAALDARIPL AKMAAEETGM  60
GLVEDKVIKN HFAAEYITNQ YKDEKTCGVV ETDKSYGITK IAEPIGIVAA VIPTTNPTST  120
AIFKTLISLK TRNAIMLSPH PRAKKSTIAA AKIILDAAVK AGAPEGIIGW IDEPSIELTQ  180
ILMQEADITL ATGGPSMVKS AYSSGKPAIG VGPGNTPVII DESAHIKMAV SSVILSKTFD  240
NGVICASEQS VIVLDSIYDE VRKEFAERGA YIIKESEIDK VRKTIFINGS INSKIVGQSA  300
YKIAEMSGIK VPETARILIG EVTSFGVKEE FAHEKLSTVL AMYRAENFDD ALDKAVTLVN  360
LGGLGHTSAI YADIIKAKDK IDKFSNAMKT VRTFINIPAA QGASGDLYNF KIAPSFTLGC  420
GSWGGNSVSE NVGPKHLLNI KRVAERRENM LWFRVPEKVY FKFGCLQFAL RELKDLNKKR  480
AFIVTDKVLY DLGYADAITK VLEEIGVDFK VFTEVEPDPT LSTARKGTEE MMDFKPDTII  540
SLGGGSAMDA AKIMWVMYEH PEVKFEDLAM RFMDIRKRIY NFPKLGEKAM MIAVATSAGT  600
GSEVTPFAVI TDEKTGVKYP LADYELTPNM AIVDAELMMN MPKGLTAASG IDALIHGIEA  660
YTSVLASEYT NGLALEAIRL IFKYLPTAYA EGTTNEKARE KMAHASTMAG MAFANAFLGV  720
CHSMAHKLGA EHHIAHGTAN ALLIEEVIRF NSADNPVKQA AYPQYKYPNA KWRYGKIADY  780
LNLGGNTDDE KVELLIKAIH ELKEKINIPM SIKDAGVSEK NFYATLDKMC ELAFDDQCTG  840
ANPRYPLISE IKQMLITAFD KTEINTEIK                                  869

SEQ ID NO: 13           moltype = AA   length = 554
FEATURE                 Location/Qualifiers
source                  1..554
                        mol_type = protein
                        organism = Saccharomyces cerevisiae
SEQUENCE: 13
CCAAAATAGG GGGCGGGTTA CACAGAATAT ATAACATCGT AGGTGTCTGG GTGAACAGTT  60
TATTCCTGGC ATCCACTAAA TATAATGGAG CCCGCTTTTT AAGCTGGCAT CCAGAAAAAA  120
AAGAATCCCC AGCACCAAAA TATTGTTTTC TTCACCAACC ATCAGTTCAT AGGTCCATTC  180
TCTTAGCGCA ACTACAGAGA ACAGGGGCAC AAACAGGCAA AAACGGGCA CAACCTCAAT  240
GGAGTGATGC AACCTGCCTG GAGTAAATGA TGACACAAGG CAATTGACCC ACGCATGTAT  300
CTATCTCATT TTCTTACACC TTCTATTACC TTCTGCTCTC TCTGATTTGG AAAAAGCTGA  360
AAAAAAAGGT TGAAACCAGT TCCCTGAAAT TATTCCCCTA CTTGACTAAT AAGTATATAA  420
AGACGGTAGG TATTGATTGT AATTCTGTAA ATCTATTTCT TAAACTTCTT AAATTCTACT  480
TTTATAGTTA GTCTTTTTTT TAGTTTTAAA ACACCAAGAA CTTAGTTTCG AATAAACACA  540
CATAAACAAA CAAA                                                   554

SEQ ID NO: 14           moltype = DNA   length = 550
FEATURE                 Location/Qualifiers
source                  1..550
                        mol_type = genomic DNA
                        organism = Saccharomyces cerevisiae
SEQUENCE: 14
cgctcagcat ctgcttcttc ccaaagatga acgcggcgtt atgtcactaa cgacgtgcac  60
caacttgcgg aaagtggaat cccgttccaa aactggcatc cactaattga tacatctaca  120
caccgcacgc cttttttctg aagcccactt tcgtggactt tgccatatgc aaaattcatg  180
aagtgtgata ccaagtcagc atacacctca ctagggtagt ttctttggtt gtattgatca  240
```

```
tttggttcat cgtggttcat taattttttt tctccattgc tttctggctt tgatcttact   300
atcatttgga tttttgtcga aggttgtaga attgtatgtg acaagtggca ccaagcatat   360
ataaaaaaaa aaagcattat cttcctacca gagttgattg ttaaaaacgt atttatagca   420
aacgcaattg taattaattc ttattttgta tctttcttc ccttgtctca atcttttatt    480
tttattttat ttttcttttc ttagtttctt tcataacacc aagcaactaa tactataaca   540
tacaataata                                                          550

SEQ ID NO: 15           moltype = DNA   length = 419
FEATURE                 Location/Qualifiers
source                  1..419
                        mol_type = genomic DNA
                        organism = Saccharomyces cerevisiae
SEQUENCE: 15
ctctctcgca ataacaatga acactgggtc aatcatagcc tacacaggtg aacagagtag   60
cgtttataca gggtttatac ggtgattcct acggcaaaaa tttttcattt ctaaaaaaaa   120
aaagaaaaat tttctcttcc aacgctagaa ggaaaagaaa aatctaatta aattgatttg   180
gtgatttttct gagagttccc ttttttcatat atcgaattt gaatataaaa ggagatcgaa   240
aaaattttc tattcaatct gttttctggt ttatttgat agtttttttg tgtattatta    300
ttatggatta gtactggttt atatgggttt ttctgtataa cttctttta ttttagtttg    360
tttaatctta ttttgagtta cattatagtt ccctaactgc aagagaagta acattaaaa    419

SEQ ID NO: 16           moltype = DNA   length = 598
FEATURE                 Location/Qualifiers
source                  1..598
                        mol_type = genomic DNA
                        organism = Saccharomyces cerevisiae
SEQUENCE: 16
ggctgataat agcgtataaa caatgcatac tttgtacgtt caaaatacaa tgcagtagat   60
atatttatgc atattacata taatacatat cacataggaa gcaacaggcg cgttggactt   120
ttaattttcg aggaccgcga atccttacat cacacccaat cccccacaag tgatccccca   180
cacaccatag cttcaaaatg tttctactcc ttttttactc ttccagattt tctcggactc   240
cgcgcatcgc cgtaccactt caaaacaccc aagcacagca tactaaattt ccctctttc    300
ttcctctagg gtgtcgttaa ttacccgtac taaaggtttg gaaagaaaa aagagaccgc    360
ctcgttttctt tttcttcgtc gaaaaaggca ataaaaattt ttatcacgtt tcttttttctt 420
gaaaatttt ttttttgatt ttttttctct tcgatgacct cccattgata tttaagttaa   480
taaacggtct tcaatttctc aagtttcagt ttcattttttc ttgttctatt acaactttt   540
ttacttcttg ctcattagaa agaaagcata gcaatctaat ctaagttta attacaaa     598

SEQ ID NO: 17           moltype = DNA   length = 383
FEATURE                 Location/Qualifiers
source                  1..383
                        mol_type = genomic DNA
                        organism = Saccharomyces cerevisiae
SEQUENCE: 17
gtttagcttg cctcgtcccc gccgggtcac ccggccagcg acatggaggc ccagaatacc   60
ctccttgaca gtcttgacgt gcgcagctca ggggcatgat gtgactgtcg cccgtacatt   120
tagcccatac atcccatgt ataatcattt gcatcgctat attttgatgg cgcacggcg    180
cgaagcaaaa attacggctc ctcgctgcag acctgcgagc agggaaacgc tcccctcaca   240
gacgcgttga attgtcccca cgccgcgccc ctgtagagaa atataaaagg ttaggatttg   300
ccactgaggt tcttctttca tatacttcct tttaaaatct tgctacgata cagttctcac   360
atcacatccg aacataaaca acc                                          383

SEQ ID NO: 18           moltype = DNA   length = 700
FEATURE                 Location/Qualifiers
source                  1..700
                        mol_type = genomic DNA
                        organism = Saccharomyces cerevisiae
SEQUENCE: 18
gggtgtacaa tatggacttc ctctttttctg gcaaccaaac ccatacatcg ggattcctat  60
aataccttcg ttggtctccc taacatgtag gtggcggagg ggagatatac aatagaacag   120
ataccagaca agacataatg ggctaaacaa gactacacca attacactgc ctcattgatg   180
gtggtacata acgaactaat actgtagccc tagacttgat agccatcatc atatcgaagt   240
ttcactaccc ttttttccatt tgccatctat tgaagtaata ataggcgcat gcaacttctt  300
ttctttttt ttctttctc tctccccgt tgttgtctca ccatatccgc aatgacaaaa     360
aaatgatgga agacactaaa ggaaaaaatt aacgacaaag acagcaccaa cagatgtcgt   420
tgttccagag ctgatgaggg gtatctcgaa gcacacgaaa cttttttctt ccttcattca   480
cgcacactac tctctaatga gcaacggtat acggccttcc ttccagttac ttgaatttga   540
aataaaaaaa agtttgctgt cttgctatca agtataaata gacctgcaat tattaatctt   600
ttgtttcctc gtcattgttc tcgttccctt tcttccttgt ttctttttct gcacaatatt   660
tcaagctata ccaagcatac aatcaactat ctcatataca                        700

SEQ ID NO: 19           moltype = DNA   length = 549
FEATURE                 Location/Qualifiers
source                  1..549
                        mol_type = genomic DNA
                        organism = Saccharomyces cerevisiae
SEQUENCE: 19
gccaaacttt tcggttaaca catgcagtga tgcacgcgcg atggtgctaa gttacatata   60
tatatatata tatatatata tatatatata gccatagtga tgtctaagta acctttatgg   120
```

-continued

```
tatatttctt aatgtggaaa gatactagcg cgcgcaccca cacacaagct tcgtcttttc     180
ttgaagaaaa gaggaagctc gctaaatggg attccacttt ccgttccctg ccagctgatg    240
gaaaaaggtt agtggaacga tgaagaataa aagagagat ccactgaggt gaaatttcag     300
ctgacagcga gtttcatgat cgtgatgaac aatggtaacg agttgtggct gttgccaggg    360
agggtggttc tcaactttta atgtatggcc aaatcgtcac ttgggtttgt tatataacaa    420
agaagaaata atgaactgat tctcttcctc cttcttgtcc tttcttaatt ctgttgtaat    480
taccttcctt tgtaattttt tttgtaatta ttcttcttaa taatccaaac aaacacacat    540
attacaata                                                            549

SEQ ID NO: 20          moltype = DNA   length = 650
FEATURE                Location/Qualifiers
source                 1..650
                       mol_type = genomic DNA
                       organism = Saccharomyces cerevisiae
SEQUENCE: 20
acgcaagccc taagaaatga ataacaatac tgacagtact aaataattgc ctacttggct     60
tcacatacgt tgcatacgtc gatatagata ataatgataa tgacagcagg attatcgtaa   120
tacgtaatag ttgaaaatct caaaaatgtg tgggtcatta cgtaaataat gataggaatg   180
ggattcttct attttccctt tttccattct agcagccgtc gggaaaacgt ggcatcctct   240
ctttcgggct caattggagt cacgctgccg tgagcatcct ctctttccat atctaacaac   300
tgagcacgta accaatggaa aagcatgagc ttagcgttgc tccaaaaaag tattggatgg   360
ttaataccat ttgtctgttc tcttctgact ttgactcctc aaaaaaaaaa aatctacaat   420
caacagatcg cttcaattac gccctcacaa aaacttttt cctcttcttc gcccacgtt    480
aaatttttatc cctcatgttg tctaacggat ttctgcactt gatttattat aaaaagacaa   540
agacataata cttctctatc aattttcagtt attgttcttc cttgcgttat tcttctgttc   600
ttcttttttct tttgtcatat ataaccataa ccaagtaata catattcaaa              650

SEQ ID NO: 21          moltype = DNA   length = 700
FEATURE                Location/Qualifiers
source                 1..700
                       mol_type = genomic DNA
                       organism = Saccharomyces cerevisiae
SEQUENCE: 21
ttatttacct atctctaaac ttcaacacct tatatcataa ctaatatttc ttgagataag    60
cacactgcac ccataccttc cttaaaaacg tagcttccag tttttggtgg ttccggcttc   120
cttcccgatt ccgcccgcta aacgcatatt tttgttgcct ggtggcattt gcaaaatgca   180
taacctatgc atttaaaaga ttatgtatgc tcttctgact tttcgtgtga tgaggctcgt   240
ggaaaaaatg aataatttat gaatttgaga acaattttgt gttgttacgg tattttacta   300
tggaataatc aatcaattga ggattttatg caaatatcgt ttgaatatt ttccgaccct    360
ttgagtactt tcttcatcaa ttgcataata ttgtccgctg ccccttttc tgttagacgg    420
tgtcttgatc tacttgctat cgttcaacac caccttattt tctaactatt ttttttttag   480
ctcatttgaa tcagcttatg gtgatggcac atttttgcat aaacctagct gtcctcgttg   540
aacataggaa aaaaaatat ataaacaagg ctcttcact ctccttgcaa tcagatttgg     600
gtttgttccc tttatttca tatttcttgt catattcctt tctcaattat tattttctac    660
tcataacctc acgcaaaata acacagtcaa atcaatcaaa                         700

SEQ ID NO: 22          moltype = DNA   length = 998
FEATURE                Location/Qualifiers
source                 1..998
                       mol_type = genomic DNA
                       organism = Saccharomyces cerevisiae
SEQUENCE: 22
aaccagggca aagcaaaata aaagaaactt aatacgttat gccgtaatga agggctacca    60
aaaacgataa tctcaactgt aaacaggtac aatgcggacc cttttgccac aaaacataca   120
tcattcattg ccggaaaaag aaagaagtga agacagcagt gcagccagcc atgttgcgct   180
aatctaatta tagatgctgg tgccctgagg atgtatctgg agccagccat ggcatcatgc   240
gctaccgccg gatgtaaaat ccgacacgca aagaaaacc ttcgaggttg cgcacttcgc    300
ccacccatga accacacggt tagtccaaaa ggggcagttc agattccaga tgcgggaatt   360
agcttgctgc caccctcacc tcactaacgc tgcggtgtgc ggatacttca tgctatttat   420
agacgcgcgt gtcggaatca gcacgcgcaa gaaccaaatg ggaaaatcgg aatgggtcca   480
gaactgcttt gagtgctggc tattggcgtc tgatttccgt tttgggaatc ctttgccgcg   540
cgccctctc aaaactccgc acaagtccca gaaagcggga aagaaataaa acgccaccaa    600
aaaaaaaat aaaagccaat cctcgaagcg tgggtgtag gccctggatt atcccgtaca    660
agtattctc aggagtaaaa aaaccgtttg ttttggaatt ccccatttcg cggccaccta   720
cgccgctatc tttgcaacaa ctatctgcga taactcagca aatttgcat attcgtgttg    780
cagtattgcg ataatgggag tcttacttcc aacataacgg cagaaagaaa tgtgagaaaa   840
ttttgcatcc tttgcctccg ttcaagtata taagtcggc atgcttgata atctttcttt    900
ccatcctaca ttgttctaat tattcttatt ctccttatt ctttcctaac ataccaagaa    960
attaatcttc tgtcattcgc ttaaacacta tatcaata                           998

SEQ ID NO: 23          moltype = DNA   length = 700
FEATURE                Location/Qualifiers
source                 1..700
                       mol_type = genomic DNA
                       organism = Saccharomyces cerevisiae
SEQUENCE: 23
gtgagtaagg aaagagtgag gaactatcgc ataccctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
```

```
aattaccgtc gctcgtgatt tgtttgcaaa aagaacaaaa ctgaaaaaac ccagacacgc    240
tcgacttcct gtcttcctat tgattgcagc ttccaatttc gtcacacaac aaggtcctag    300
cgacggctca caggttttgt aacaagcaat cgaaggttct ggaatggcgg gaaagggttt    360
agtaccacat gctatgatgc ccactgtgat ctccagagca aagttcgttc gatcgtactg    420
ttactctctc tcttttcaaac agaattgtcc gaatcgtgtg acaacaacag cctgttctca    480
cacactcttt tcttctaacc aaggggggtgg tttagtttag tagaacctcg tgaaacttac    540
atttacatat atataaactt gcataaaattg tcaatgcaa gaaatacata tttggtcttt    600
tctaattcgt agtttttcaa gttcttagat gctttctttt tctcttttttt acagatcatc    660
aaggaagtaa ttatctactt tttacaacaa atataaaaca                          700

SEQ ID NO: 24           moltype = DNA   length = 400
FEATURE                 Location/Qualifiers
source                  1..400
                        mol_type = genomic DNA
                        organism = Saccharomyces cerevisiae
SEQUENCE: 24
agattttggt gttagatggt actcttgcat atgtaacctt taataaattt tgcaaatcga    60
attcctttgt aacgtgcaaa gcattttata gcctggcgct cgcattgtta agcaacaggc    120
ggtgcggcaa cgttgaaatg tttcacgcag ggttttttac gtactgcacg gcattctgga    180
gtgaaaaaaa atgaaaagta cagctcgaag ttttttgtcc atcggttgta ctttgcagag    240
tattagtcat ttttgatatc agagtactac tatcgaagca tttttacgct tgaataactt    300
gaatattatt gaaagcttag ttcaaccaag ctgaaaagaa ccattattca acataattgg    360
aaatcatttc gttactaaat cgtccgaaaa ttgcagaaaa                          400

SEQ ID NO: 25           moltype = DNA   length = 505
FEATURE                 Location/Qualifiers
source                  1..505
                        mol_type = genomic DNA
                        organism = Saccharomyces cerevisiae
SEQUENCE: 25
cggcaaactt caacgatttc tatgatgcat tttataatta gtaagccgat cccattaccg    60
acatttgggc gctatacgtg catatgttca tgtatgtatc tgtatttaaa acacttttgt    120
attatttttc ctcatatatg tgtataggtt tatacggatg atttaattat tacttcacca    180
ccctttattt caggctgata tcttagcctt gttactagtt agaaaaagac attttttgctg    240
tcagtcactg tcaagagatt cttttgctgg catttcttcc agaagcaaaa agagcgatgc    300
gtcttttccg ctgaaccgtt ccagcaaaaa agactaccaa cgcaatatgg attgtcagaa    360
tcatataaaa gagaagcaaa taactccttg tcttgtatca attgcattat aatatcttct    420
tgttagtgca atatcatata gaagtcatcg aaatagatat taagaaaaac aaactgtaca    480
atcaatcaat caatcatcac ataaa                                          505

SEQ ID NO: 26           moltype = DNA   length = 500
FEATURE                 Location/Qualifiers
source                  1..500
                        mol_type = genomic DNA
                        organism = Candida glabrata
SEQUENCE: 26
cacaccacac aaccgtcagc accccggctg tacgtctgtg aaggctgcgg tatagacacg    60
gactgcgata cagaactcat gacttatatc tgtagactcc tctgcttcaa tgcgaactcc    120
aggatcaccg aatagcatgc gatgagctgt tgattcttat atataattat ctattgcatt    180
ttttttttaa tgctgcatgg gggggcctag taaatcaccc gtacaagtca cgcgtgagag    240
aaagagaagg gcccttttcgt cgtggaagcg tggatcgtga gcgacctgtt ctaaatata    300
gcttttgggt aggatattat attaagtgaa atttttattag agggtaaatg tatgtgaaag    360
ttatgtataa tatgttgcta aattagcgat cgtgaatgca tagaatctaa tcgttataga    420
aaaccgcaac ttgtgctgtt ttgttgtgtt ttccttgtcgt tttttttatat tatttatcta    480
gtattttgct ttagttgtta                                                 500

SEQ ID NO: 27           moltype = DNA   length = 425
FEATURE                 Location/Qualifiers
source                  1..425
                        mol_type = genomic DNA
                        organism = Saccharomyces bayanus
SEQUENCE: 27
agaaggaggg gtcctattac caatacttgg acgctatacg tgcatatgta catgtacgta    60
tctgtattta aacacttttg tattattttc tttatatatg tttatataggtt tacatggttg    120
actttatca ttgtttgtgc acatttgcaa tggccatttt tttgtttttg agaaaggtat    180
tattgctgtc actattcgag atgctttgc tgacattcct cctagaagcc aaaaggccga    240
tgcgtttttt ccgctgagag gataccagca aaaaaagcta ccagtacaag atgggacggc    300
aaaagcgtat aaaagaagaa gcaaaatgac cagatatgct ttcaatttca tcaatgtttc    360
tttctccctg ttatgatcca gaagaataat caaaagcaaa acatctattc aatcaatctc    420
ataaa                                                                 425

SEQ ID NO: 28           moltype = DNA   length = 741
FEATURE                 Location/Qualifiers
misc_feature            1..741
                        note = Modified pACU1
source                  1..741
                        mol_type = other DNA
                        organism = synthetic construct
SEQUENCE: 28
```

```
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataaattc gccatttctt gaatgtattt    180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tcgaaaaaga cattttttgct gtcagtcact gtcaagagat tcttttgctg gcatttcttc   420
cagaagcaaa aagagcgatg cgtctttttcc gctgaaccgt tccagcaaaa aagactacca   480
acgaattcta attaagttag tcaaggcgcc atcctcatga aaactgtgta acataataac   540
cgaagtgtcg aaaaggtggc accttgtcca attgaacacg ctcgatgaaa aaaataagat   600
atatataagg ttaagtaaag cgtctgttag aaaggaagtt tttccttttt cttgctctct   660
tgtcttttca tctactattt ccttcgtgta atacagggtc gtcagataca tagatacaat   720
tctattaccc ccatccatac a                                             741

SEQ ID NO: 29         moltype = DNA  length = 757
FEATURE               Location/Qualifiers
misc_feature          1..757
                      note = Modified pACU2
source                1..757
                      mol_type = other DNA
                      organism = synthetic construct
SEQUENCE: 29
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataaattc gccatttctt gaatgtattt    180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccgaatt cgaaaaagac attttttgctg tcagtcactg   360
tcaagagatt cttttgctgg catttcttcc agaagcaaaa agagcgatgc gtctttttccg   420
ctgaaccgtt ccagcaaaaa agactaccaa cgaattccac gtgaagctgt cgatattggg   480
gaactgtggt ggttggcaaa tgactaatta agttagtcaa ggcgccatcc tcatgaaaac   540
tgtgtaacat aataaccgaa gtgtcgaaaa ggtggcacct tgtccaattg aacacgctcg   600
atgaaaaaaa taagatatat ataaggttaa gtaaagcgtc tgttagaaag gaagtttttc   660
cttttttcttg ctctctttgtc ttttcatcta ctatttcctt cgtgtaatac agggtcgtca   720
gatacataga tacaattcta ttccccccat ccataca                             757

SEQ ID NO: 30         moltype = DNA  length = 498
FEATURE               Location/Qualifiers
misc_feature          1..498
                      note = Modified pACU3p
source                1..498
                      mol_type = other DNA
                      organism = synthetic construct
SEQUENCE: 30
ttatattgaa ttttcaaaaa ttcttacttt ttttttggat ggacgcaaag aagtttaata    60
atcatattac atgcattac caccatatac atatccat ctaatcttac ttatatgttg     120
tggaaatgta aagagcccga attcgaaaaa gacattttttg ctgtcagtca ctgtcaagag   180
attcttttgc tggcatttct tccagaagca aaaagagcga tgcgtctttt ccgctgaacc   240
gttccagcaa aaaagactac caacgaattc ggatgataat gcgattagtt ttttagcctt   300
atttctgggg taattaatca gcgaagcgat gattttgat ctattaacag atatataaat    360
ggaaaagctg cataaccact ttaactaata cttcaacat tttcagtttg tattacttct    420
tattcaaatg tcataaaagt atcaacaaaa aattgttaat atacctctat actttaacgt   480
caaggagaaa aaactata                                                 498

SEQ ID NO: 31         moltype = DNA  length = 498
FEATURE               Location/Qualifiers
misc_feature          1..498
                      note = Modified pACU4p
source                1..498
                      mol_type = other DNA
                      organism = synthetic construct
SEQUENCE: 31
ttatattgaa ttttcaaaaa ttcttacttt ttttttggat ggacgcaaag aagtttaata    60
atcatattac atgcattac caccatatac atatccat ctaatcttac ttatatgttg     120
tggaaatgta aagagcccga attcgttggt agtctttttt gctggaacgg ttcagcggaa   180
aagacgcatc gctcttttttg cttctggaag aaatgccagc aaaagaatct cttgacagtg   240
actgacagca aaaatgtctt tttcgaattc ggatgataat gcgattagtt ttttagcctt   300
atttctgggg taattaatca gcgaagcgat gattttgat ctattaacag atatataaat    360
ggaaaagctg cataaccact ttaactaata cttcaacat tttcagtttg tattacttct    420
tattcaaatg tcataaaagt atcaacaaaa aattgttaat atacctctat actttaacgt   480
caaggagaaa aaactata                                                 498

SEQ ID NO: 32         moltype = DNA  length = 530
FEATURE               Location/Qualifiers
misc_feature          1..530
                      note = Modified pACU5
source                1..530
                      mol_type = other DNA
                      organism = synthetic construct
```

```
SEQUENCE: 32
ggaggacgaa acaaaaaagt gaaaaaaaat gaaaattttt ttggaaaacc aagaaatgaa    60
ttatatttcc gtgtgagacg acatcgtcga atatgattca gggtaacagt attgatgtaa   120
tcaatttcct acctgaatct aaaattcccg gaattcgaaa aagacatttt tgctgtcagt   180
cactgtcaag agattctttt gctggcattt cttccagaag caaaaagagc gatgcgtctt   240
ttccgctgaa ccgttccagc aaaaaagact accaacgaat tccgagcaga tccgccaggc   300
gtgtatatat agcgtggatg gccaggcaac tttagtgctg acacatacag gcatatatat   360
atgtgtgcga cgacacatga tcatatggca tgcatgtgct ctgtatgtat ataaaactct   420
tgttttcttc ttttctctaa atattctttc cttatacatt aggacctttg cagcataaat   480
tactatactt ctatagacac acaaacacaa atacacacac taaattaata              530

SEQ ID NO: 33           moltype = DNA   length = 867
FEATURE                 Location/Qualifiers
misc_feature            1..867
                        note = Modified pACU6
source                  1..867
                        mol_type = other DNA
                        organism = synthetic construct
SEQUENCE: 33
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttttattc caacactaag aaataatttc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tcgaaaaaga cattttttgct gtcagtcact gtcaagagat tcttttgctg gcatttcttc   420
cagaagcaaa aagagcgatg cgtctttttcc gctgaaccgt tccagcaaaa aagactacca   480
acgaattcga aaaagacatt tttgctgtca gtcactgtca agagattctt ttgctggcat   540
ttcttccaga agcaaaaaga gcgatgcgtc ttttccgctg aaccgttcca gcaaaaaaga   600
ctaccaacga attctaatta agttagtcaa ggcgccatcc tcatgaaaac tgtgtaacat   660
aataaccgaa gtgtcgaaaa ggtggcacct tgtccaattg aacacgctcg atgaaaaaaa   720
taagatatat ataaggttaa gtaaagcgtc tgttagaaag gaagttttttc cttttttcttg   780
ctctcttgtc ttttcatcta ctatttcctt cgtgtaatac agggtcgtca gatacataga   840
tacaattcta ttaccccccat ccataca                                       867

SEQ ID NO: 34           moltype = DNA   length = 867
FEATURE                 Location/Qualifiers
misc_feature            1..867
                        note = Modified pACU7
source                  1..867
                        mol_type = other DNA
                        organism = synthetic construct
SEQUENCE: 34
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttttattc caacactaag aaataatttc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tcgttggtag tctttttttgc tggaacggtt cagcggaaaa gacgcatcgc tcttttttgct   420
tctggaagaa atgccagcaa aagaatctct tgacagtgac tgacagcaaa aatgtctttt   480
tcgaattcgt tggtagtctt ttttgctgga acggttcagc ggaaaagacg catcgctctt   540
tttgcttctg gaagaaatgc cagcaaaaga atctcttgac agtgactgac agcaaaaatg   600
tcttttttcga attctaatta agttagtcaa ggcgccatcc tcatgaaaac tgtgtaacat   660
aataaccgaa gtgtcgaaaa ggtggcacct tgtccaattg aacacgctcg atgaaaaaaa   720
taagatatat ataaggttaa gtaaagcgtc tgttagaaag gaagttttttc cttttttcttg   780
ctctcttgtc ttttcatcta ctatttcctt cgtgtaatac agggtcgtca gatacataga   840
tacaattcta ttaccccccat ccataca                                       867

SEQ ID NO: 35           moltype = DNA   length = 1119
FEATURE                 Location/Qualifiers
misc_feature            1..1119
                        note = Modified pACU8
source                  1..1119
                        mol_type = other DNA
                        organism = synthetic construct
SEQUENCE: 35
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttttattc caacactaag aaataatttc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tcgaaaaaga cattttttgct gtcagtcact gtcaagagat tcttttgctg gcatttcttc   420
cagaagcaaa aagagcgatg cgtctttttcc gctgaaccgt tccagcaaaa aagactacca   480
acgaattcga aaaagacatt tttgctgtca gtcactgtca agagattctt ttgctggcat   540
ttcttccaga agcaaaaaga gcgatgcgtc ttttccgctg aaccgttcca gcaaaaaaga   600
ctaccaacga attcgaaaaa gacattttttg ctgtcagtca ctgtcaagag attcttttgc   660
tggcatttct tccagaagca aaaagagcga tgcgtctttt ccgctgaacc gttccagcaa   720
```

```
aaaagactac caacgaattc gaaaaagaca tttttgctgt cagtcactgt caagagattc   780
ttttgctggc atttcttcca gaagcaaaaa gagcgatgcg tcttttccgc tgaaccgttc   840
cagcaaaaaa gactaccaac gaattctaat taagttagtc aaggcgccat cctcatgaaa   900
actgtgtaac ataataaccg aagtgtcgaa aaggtggcac cttgtccaat tgaacacgct   960
cgatgaaaaa aataagatat atataaggtt aagtaaagtc tgttagaa aggaagtttt  1020
tcctttttct tgctctcttg tcttttcatc tactatttcc ttcgtgtaat acagggtcgt  1080
cagatacata gatacaattc tattacccc atccataca                          1119

SEQ ID NO: 36          moltype = DNA   length = 624
FEATURE                Location/Qualifiers
misc_feature           1..624
                       note = Modified pACU9
source                 1..624
                       mol_type = other DNA
                       organism = synthetic construct
SEQUENCE: 36
tatagttttt tctccttgac gttaaagtat agaggtatat taacaatttt ttgttgatac    60
ttttatgaca tttgaataag aagtaataca aactgaaaat gttgaaagta ttagttaaag   120
tggttatgca gcttttccat ttatatatct gttaatagat caaaaatcat cgcttcgctg   180
attaattacc ccagaaataa ggctaaaaaa ctaatcgcat tatcatccga attcgaaaaa   240
gacatttttg ctgtcagtca ctgtcaagag attcttttgc tggcatttct tccagaagca   300
aaaagagcga tgcgtctttt ccgctgaacc gttccagcaa aaaagactac caacgaattc   360
gaaaaagaca tttttgctgt cagtcactgt caagagattc ttttgctggc atttcttcca   420
gaagcaaaaa gagcgatgcg tcttttccgc tgaaccgttc cagcaaaaaa gactaccaac   480
gaattcgggc tctttacatt tccacaacat ataagtaaga ttagatatgg atatgtatat   540
ggtggtaatg ccatgtaata tgattattaa acttctttgc gtccatccaa aaaaaaagta   600
agaattttg aaaattcaat ataa                                          624

SEQ ID NO: 37          moltype = DNA   length = 876
FEATURE                Location/Qualifiers
misc_feature           1..876
                       note = Modified pACU10p
source                 1..876
                       mol_type = other DNA
                       organism = synthetic construct
SEQUENCE: 37
ttatattgaa tttcaaaaaa ttcttacttt ttttttggat ggacgcaaag aagtttaata    60
atcatattac atggcattac caccatatac atatccatat ctaatcttac ttatatgttg   120
tggaaatgta aagagcccga attggttggt agtcttttt gctggaacgg ttcagcggaa   180
aagacgcatc gctcttttg cttctggaag aaatgccagc aaaagaatct cttgacagtg   240
actgacagca aaaatgtctt tttcgaattc gttggtagtc tttttttgctg gaacggttca   300
gcggaaaaga cgcatcgctc tttttgcttc tggaagaaat gccagcaaaa gaatctcttg   360
acagtgactg acagcaaaaa tgtcttttc gaattcgttg gtagtctttt ttgctggaac   420
ggttcagcgg aaaagacgca tcgctctttt tgcttctgga agaaatgcca gcaaaagaat   480
ctcttgacag tgactgacag caaaaatgtc tttttcgaat tcgttggtag tctttttgc   540
tggaacggtt cagcggaaaa gacgcatcgc tcttttgct tctggaagaa atgccagcaa   600
aagaatctct tgacagtgac tgacagcaaa aatgtctttt tccaattcgg atgataatgc   660
gattagtttt ttagccttat ttctgggta attaatcagc gaagcgatga ttttttgatct   720
attaacagat atataaatgg aaaagctgca taaccactt aactaatact ttcaacattt   780
tcagtttgta ttacttctta ttcaaatgtc ataaagtat caacaaaaaa ttgttaatat   840
acctctatac tttaacgtca aggagaaaaa actata                            876

SEQ ID NO: 38          moltype = DNA   length = 633
FEATURE                Location/Qualifiers
misc_feature           1..633
                       note = Modified pACU11
source                 1..633
                       mol_type = other DNA
                       organism = synthetic construct
SEQUENCE: 38
gctcagcatc tgcttcttcc caaagatgaa cgcggcgtta tgtcactaac gacgtgcacc    60
aacttgcggg aattcgaaaa agacatttt gctgtcagtc actgtcaaga gattcttttg   120
ctggcatttc ttcagaagc aaaagagcg atgcgtcttt tccgctgaac cgttccagca   180
aaaagacta ccaacgaatt ccaccgcacg ccttttttct gaagcccact ttcgtggact   240
ttgccatata tgcaaaattc atgaagtgtg ataccaagtc agcatacacc tcactaggt   300
agtttctttg gttgtattga tcatttggtt catcgtggtt cattaatttt ttttctccat   360
tgctttctgg cttgatctt actatcattt ggatttttgt cgaaggttgt agaattgtat   420
gtgacaagtg gcaccaagca tatataaaaa aaaaagcat tatcttccta ccagagttga   480
ttgttaaaaa cgtatttata gcaaacgcaa ttgtaattaa ttcttattt gtatcttttg   540
ttcccttgtc tcaatctttt attttttttt tattttttcct ttctagtttt ctttcataac   600
accaagcaac taatactata acatacaata ata                                633

SEQ ID NO: 39          moltype = DNA   length = 1119
FEATURE                Location/Qualifiers
misc_feature           1..1119
                       note = Modified pACU12
source                 1..1119
                       mol_type = other DNA
                       organism = synthetic construct
```

```
SEQUENCE: 39
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataaattc gccatttctt gaatgtattt    180
aaagatattt aatgctataa tagacattta aatccaattc ttccaacata atgggagt     240
ttggccgagt ggtttaaggc gtcagattta ggtggattta acctctaaaa tctctgatat   300
cttcggatgc aagggttcga atcccttagc tctcattatt ttttgctttt tctcttgaat   360
tggttggtag tcttttttgc tggaacggtt cagcggaaaa gacgcatcgc tcttttttgct 420
tctggaagaa atgccagcaa aagaatctct tgacagtgac tgacagcaaa aatgtctttt   480
tcgaattcgt tggtagtctt ttttgctgga acggttcagc ggaaaagacg catcgctctt   540
tttgcttctg gaagaaatgc cagcaaaaga atctcttgac agtgactgac agcaaaaatg   600
tctttttcga attcgttggt agtctttttt gctggaacgg ttcagcggaa aagacgcatc   660
gctctttttg cttctggaag aaatgccagc aaaagaatct cttgacagtg actgacagca   720
aaaatgtctt tttcgaattc gttggtagtc ttttttgctg gaacggttca gcggaaaaga   780
cgcatcgctc tttttgcttc tggaagaaat gccagcaaaa gaatctcttg acagtgactg   840
acagcaaaaa tgtctttttc caattctaat taagttagtc aaggcgccat cctcatgaaa   900
actgtgtaac ataataaccg aagtgtcgaa aaggtggcac cttgtccaat gaacacgct    960
cgatgaaaaa aataagatat ataaggttaa gtaaagcg tctgttagaa aggaagtttt    1020
tcctttttct tgctctcttg tcttttcatc tactatttcc ttcgtgtaat acagggtcgt  1080
cagatacata gatacaattc tattacccc atccataca                           1119

SEQ ID NO: 40            moltype = DNA   length = 1497
FEATURE                  Location/Qualifiers
misc_feature             1..1497
                         note = Modified pACU13
source                   1..1497
                         mol_type = other DNA
                         organism = synthetic construct
SEQUENCE: 40
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataaattc gccatttctt gaatgtattt    180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tggttggtag tcttttttgc tggaacggtt cagcggaaaa gacgcatcgc tcttttttgct 420
tctggaagaa atgccagcaa aagaatctct tgacagtgac tgacagcaaa aatgtctttt   480
tcgaattcgt tggtagtctt ttttgctgga acggttcagc ggaaaagacg catcgctctt   540
tttgcttctg gaagaaatgc cagcaaaaga atctcttgac agtgactgac agcaaaaatg   600
tctttttcga attcgttggt agtctttttt gctggaacgg ttcagcggaa aagacgcatc   660
gctctttttg cttctggaag aaatgccagc aaaagaatct cttgacagtg actgacagca   720
aaaatgtctt tttcgaattc gttggtagtc ttttttgctg gaacggttca gcggaaaaga   780
cgcatcgctc tttttgcttc tggaagaaat gccagcaaaa gaatctcttg acagtgactg   840
acagcaaaaa tgtctttttc gaattcgttg gtagtctttt ttgctggaac ggttcagcgg   900
aaaagacgca tcgctctttt tgcttctgga agaaatgcca gcaaaagaat ctcttgacag   960
tgactgacag caaaaatgtc ttttttcgaat tcgttggtag tcttttttgc tggaacggtt  1020
cagcggaaaa gacgcatcgc tcttttttgct tctggaagaa atgccagcaa aagaatctct  1080
tgacagtgac tgacagcaaa aatgtctttt tcgaattcgt tggtagtctt ttttgctgga  1140
acggttcagc ggaaaagacg catcgctctt tttgcttctg gaagaaatgc cagcaaaaga  1200
atctcttgac agtgactgac agcaaaaatg tctttttcca attctaatta agttagtcaa  1260
ggcgccatcc tcatgaaaac tgtgtaacat aataaccgaa gtgtcgaaaa ggtggcatc   1320
tgtccaattg aacacgctcg atgaaaaaaa taagatatat aaggttaa gtaaagcgtc    1380
tgttagaaag gaagttttt ctttttcttg ctctcttgtc ttttcatcta ctatttcctt   1440
cgtgtaatac agggtcgtca gatacataga tacaattcta ttaccccat ccataca     1497

SEQ ID NO: 41            moltype = DNA   length = 1011
FEATURE                  Location/Qualifiers
misc_feature             1..1011
                         note = Modified pACU14
source                   1..1011
                         mol_type = other DNA
                         organism = synthetic construct
SEQUENCE: 41
gctcagcatc tgcttcttcc caaagatgaa cgcggcgtta tgtcactaac gacgtgcacc    60
aacttgcggg aattggaaaa agacattttt gctgtcagtc actgtcaaga gattcttttg   120
ctggcatttc ttcagaagc aaaaagagcg atgcgtcttt tccgctgaac cgttccagca   180
aaaaagacta ccaacgaatt cgaaaagac attttgctg tcagtcactg tcaagagatt    240
cttttgctgg catttcttcc agaagcaaaa agagcgatgc gtcttttccg ctgaaccgtt   300
ccagcaaaaa agactaccaa cgaattcgaa aagacatttt gctgtcagtc actgtcaa    360
gagattctt tgctggcatt tcttccagaa gcaaaaagag cgatgcgtct tttccgctga   420
accgttccag caaaaagac taccaacgaa ttcgaaaaag acattttgc tgtcagtcac    480
tgtcaagaga ttcttttgct ggcatttctt ccagaagcaa aaagagcgat gcgtctttc    540
cgctgaaccg ttccagcaaa aagactacc aaccaattcc accgcacgcc tttttcta    600
agcccactt cgtggacttt gccatatatg caaaattcat gaagttgat accagtcag    660
catcacccct actagggtag tttctttggt tgtattgatc atttggttca tcgtggtca   720
ttaattttttt ttctccattg ctttctggct ttgatcttac tatcatttgg attttttgtcg  780
aaggttgtag aattgtatgt gacaagtggc accaagcata tataaaaaaa aaagcatta   840
tcttcctacc agagttgatt gttaaaaacg tatttatagc aaacgcaatt gtaattaatt   900
cttattttgt atcttttctt cccttgtctc aatctttat ttttatttta ttttttcttt   960
```

```
cttagtttct ttcataacac caagcaacta atactataac atacaataat a            1011

SEQ ID NO: 42           moltype = DNA   length = 398
FEATURE                 Location/Qualifiers
misc_feature            1..398
                        note = Modified pACU15
source                  1..398
                        mol_type = other DNA
                        organism = synthetic construct
SEQUENCE: 42
tatagttttt tctccttgac gttaaagtat agaggtatat taacaatttt ttgttgatac   60
ttttatgaca tttgaataag aagtaataca aactgaaaat gttgaaagta ttagttaaag   120
tggttatgca gcttttccat ttatatatct gttaatagat caaaaatcat cgcttcgctg   180
attaattacc ccagaaataa ggctaaaaaa ctaatcgaat tatcatccga attcgttgtc   240
agtctttttt gctggaacgg ttcagcggaa aagacgcatc gctctttttg cttctggaag   300
aaatgccagc aaaagaatct cttgacagtg actgacagca aaaatgtctt tttcgaattc   360
gggctcttta catttccaca acatataagt aagattag                           398

SEQ ID NO: 43           moltype = DNA   length = 428
FEATURE                 Location/Qualifiers
misc_feature            1..428
                        note = Modified pGAL/CUP1p
source                  1..428
                        mol_type = other DNA
                        organism = synthetic construct
SEQUENCE: 43
ttatattgaa ttttcaaaaa ttcttacttt tttttggat ggacgcaaag aagtttaata    60
atcatattac atggcattac caccatatac atatccatat ctaatcttac ttatatgttg   120
tggaaatgta aagagcccga attcgaaaaa gacattttg ctgtcagtca ctgtcaagag    180
attcttttgc tggcatttct tccagaagca aaaagacga tgcgtctttt ccgctgaacc    240
gttccagcaa aaagactac caacgcaata tggattgtga gaatcatata aaagagaagc    300
aaataactcc ttgtcttgta tcaattgcat tataatatct tcttgttagt gcaatatcat   360
atagaagtca tcgaaataga tattaagaaa acaaactgt acaatcaatc aatcaatcat    420
cacataaa                                                            428

SEQ ID NO: 44           moltype = DNA   length = 518
FEATURE                 Location/Qualifiers
source                  1..518
                        mol_type = genomic DNA
                        organism = Saccharomyces cerevisiae
SEQUENCE: 44
gtggacgaaa agacataact gcagaagtac agctgccttt atttcttgtg gtcatttatt   60
gcttttattt tcaagtcaga tatacaagaa aatcaaatcc catcgtcaac gtcacgtata   120
aacgattaat ttacagtaat accatactct accaacatta ttttagtccg acgttcagtc   180
ctgtaggtgt tccaaatcct tctggcattg acttctgtgc agaaaccctt caaaatgagt   240
tccactttac gtcagatcgc ataacaaccg gtcatatatt ttttctttt gctaaacccc    300
ctactgcaag cactttaag aaaaagaaca ataatgcatc ttttattgct gtgtggaagt    360
gattttgtc tttcggacaa aaaaaggata gggatgcgag agggctgtga agtagtgatc    420
aagcggggcc tatataagaa gggcgcacat cgtccccct aagaatagcg aagcgatatt    480
acactgaaca ctacaatgtc aaatagtact caataaat                           518

SEQ ID NO: 45           moltype = DNA   length = 510
FEATURE                 Location/Qualifiers
source                  1..510
                        mol_type = genomic DNA
                        organism = Saccharomyces cerevisiae
SEQUENCE: 45
gatctctgct gacgttgtat ccacagatct aattgcaaga tagcctcttg cgaccttatt   60
aaaagcctct ccgtgatatc ctctagggct tgggttgcca ttaatcgatg tgtccttgtt   120
tccttatgcg agctgtttct tatctatcat atggtcccat tctttactgc actgtttaca   180
ttttgatcaa ttgcgaaatg ttcctactat tttctttttt ctctttttcgc gagtactaat  240
caccgcgaac ggaaactaat gagtcctctg cgcggagaca tgattccgca tgggcggctc   300
ctgttaagcc ccagcgggaaa tgtaattcca ctgagtgtca ttaaatagtg ccaaagcttt   360
atcaaattgt ttgcgatgag ataagataaa agggacaata tgaggaggaa cacaggtata   420
taaatatcgc caaataaaag gaaaatgttt atacagtttt ctcttttta agtgctggat    480
agacaagaga caggaaaatt aaccagcgag                                    510

SEQ ID NO: 46           moltype = DNA   length = 601
FEATURE                 Location/Qualifiers
source                  1..601
                        mol_type = genomic DNA
                        organism = Saccharomyces cerevisiae
SEQUENCE: 46
caagtccgat tgttcctctt caggagcttc ctgaaccaaa cttttttccgc aaggccgcat   60
tttgaaccgt attttgctcg ttccagcctt tccacgtttt tgttatctaa gcaacttggc   120
acatttccct actatactac aaaccgata gtaaatactt ccctaaatag catatgaatt    180
attcagtaat ttttaaggat cgaaactgca cctcaactat tcgttactgt ggttatgttc   240
tcatgtattg atgcaaatca tgggatattt gctcaagacg acggtaaaat gagcaaaat    300
ggcacgatcc tgaaaagagc acttttcaag attcgggcta caaaatgcaa cataaaaaat   360
```

```
gttgtattgt catctcgaca gggtcttgta tgttttattc ctcttatgat tagttcacat   420
tagtaaaaca gatacgcagt gtgctcttaa taaacaacta ctccatagct ttatttgcat   480
aacaaaactt ttaagcacaa acttaaacag gtggagtaat agttcggcgg cgactcaaat   540
tacatttgtt ggaagaatcg aatagaaaat aaaaaaaagt gtattatatt tgacattcaa   600
a                                                                  601

SEQ ID NO: 47           moltype = DNA  length = 522
FEATURE                 Location/Qualifiers
source                  1..522
                        mol_type = genomic DNA
                        organism = Saccharomyces cerevisiae
SEQUENCE: 47
gatgtgatga caaaacctct tccgataaaa acatttaaac tattaacaaa caaatggatt   60
cattagatct attacattat gggtggtatg ttggaataaa aatcaactat catctactaa   120
ctagtattta cgttactagt atattatcat atacggtgtt agaagatgac gcaaatgatg   180
agaaatagtc atctaaatta gtggaagctg aaacgcaagg attgataatg taataggatc   240
aatgaatatt aacatataaa acgatgataa taatattttat agaattgtgt agaattgcag   300
attcccttt atggattcct aaatcctcca ggagaacttc tagtatatct acatacctaa   360
tattattgcc ttattaaaaa tggaatccca acaattacat caaaatccac attctcttca   420
cttctccgat agacttgtaa tttatcttat ttcatttcct aacactttga tcgaagaaga   480
gggataacaa cagacgaaaa cacatttaag ggctatacaa ag                     522

SEQ ID NO: 48           moltype = DNA  length = 675
FEATURE                 Location/Qualifiers
source                  1..675
                        mol_type = genomic DNA
                        organism = Saccharomyces cerevisiae
SEQUENCE: 48
ttacattatc aatccttgcg tttcagcttc cactaattta gatgactatt tctcatcatt   60
tgcgtcatct tctaacaccg tatatgataa tatactagta acgtaaatac tagttagtag   120
atgatagttg atttttattc caacactaag aaataatttc gccatttctt gaatgtattt   180
aaagatattt aatgctataa tagacattta atccaattc ttcaacata caatgggagt    240
ttggccgagt ggtttaaggc gtcagattta ggtggattta acctctaaaa tctctgatat   300
cttcggatgc aagggttcga atcccttagc tctcattatt ttttgctttt tctcttgaat   360
tgtcatggga tatttgctca agacgacggt aaaatgagca aatatggcac gatcctcaat   420
tctaattaag ttagtcaagg cgccatcctc atgaaaactg tgtaacataa taaccgaagt   480
gtcgaaaagg tggcaccttg tccaattgaa cacgctcgat gaaaaaaata agatatatat   540
aaggttaagt aaagcgtctg ttagaaagga agttttttcct ttttcttgct ctcttgtctt   600
ttcatctact atttccttcg tgtaatacag ggtcgtcaga tacatagata caattctatt   660
acccccatcc ataca                                                   675

SEQ ID NO: 49           moltype = DNA  length = 674
FEATURE                 Location/Qualifiers
misc_feature            1..674
                        note = Modified pCUR2
source                  1..674
                        mol_type = other DNA
                        organism = synthetic construct
SEQUENCE: 49
ttacattatc aatccttgcg tttcagcttc cactaattta gatgactatt tctcatcatt   60
tgcgtcatct tctaacaccg tatatgataa tatactagta acgtaaatac tagttagtag   120
atgatagttg atttttattc caacactaag aaataatttc gccatttctt gaatgtattt   180
aaagatattt aatgctataa tagacattta atccaattc ttcaacata caatgggagt    240
ttggccgagt ggtttaaggc gtcagattta ggtggattta acctctaaaa tctctgatat   300
cttcggatgc aagggttcga atcccttagc tctcattatt ttttgctttt tctcttgatt   360
gaggatcgtg ccatatttgc tcatttttacc gtcgtcttga gcaaatatcc catgacaatt   420
ctaattaagt tagtcaaggc gccatcctca tgaaaactgt gtaacataat aaccgaagtg   480
tcgaaaaggt ggcaccttgt ccaattgaac acgctcgatg aaaaaaataa gatatatata   540
aggttaagta aagcgtctgt tagaaaggaa gttttttcctt ttcttgctc tcttgtcttt   600
tcatctacta tttccttcgt gtaatacagg gtcgtcagat acatagatac aattctatta   660
cccccatcca taca                                                    674

SEQ ID NO: 50           moltype = DNA  length = 794
FEATURE                 Location/Qualifiers
misc_feature            1..794
                        note = Modified pCUR3
source                  1..794
                        mol_type = other DNA
                        organism = synthetic construct
SEQUENCE: 50
ttacattatc aatccttgcg tttcagcttc cactaattta gatgactatt tctcatcatt   60
tgcgtcatct tctaacaccg tatatgataa tatactagta acgtaaatac tagttagtag   120
atgatagttg atttttattc caacactaag aaataatttc gccatttctt gaatgtattt   180
aaagatattt aatgctataa tagacattta atccaattc ttcaacata caatgggagt    240
ttggccgagt ggtttaaggc gtcagattta ggtggattta acctctaaaa tctctgatat   300
cttcggatgc aagggttcga atcccttagc tctcattatt ttttgctttt tctcttgaat   360
taggatcgtg ccatatttgc tcatttttacc gtcgtcttga gcaaatatcc catgacaatt   420
gaggatcgtg ccatatttgc tcatttttacc gtcgtcttga gcaaatatcc catgacaatt   480
gaggatcgtg ccatatttgc tcatttttacc gtcgtcttga gcaaatatcc catgacaatt   540
```

```
ctaattaagt tagtcaaggc gccatcctca tgaaaactgt gtaacataat aaccgaagtg    600
tcgaaaaggt ggcaccttgt ccaattgaac acgctcgatg aaaaaaataa gatatatata    660
aggttaagta aagcgtctgt tagaaaggaa gtttttcctt tttcttgctc tcttgtcttt    720
tcatctacta tttccttcgt gtaatacagg gtcgtcagat acatagatac aattctatta    780
cccccatcca taca                                                     794

SEQ ID NO: 51           moltype = DNA  length = 850
FEATURE                 Location/Qualifiers
misc_feature            1..850
                        note = Modified pCUR4
source                  1..850
                        mol_type = other DNA
                        organism = synthetic construct
SEQUENCE: 51
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataaattc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tgtcatggga tatttgctca agacgacggt aaaatgagca aatatggcac gatcctcaat    420
tgtcatggga tatttgctca agacgacggt aaaatgagca aatatggcac gatcctcaat    480
gtcatgggat atttgctcaa gacgacggta aaatgagcaa atatggcacg atcctcaatt    540
gtcatgggat atttgctcaa gacgacggta aaatgagcaa atatcccatg acaattctaa    600
ttaagttagt caaggcgcca tcctcatgaa aactgtgtaa cataataacc gaagtgtcga    660
aaaggtggca ccttgtccaa ttgaacacgc tcgatgaaaa aaataagata tatataaggt    720
taagtaaagc gtctgttaga aaggaagttt ttccttttc ttgctctctt gtcttttcat    780
ctactatttc cttcgtgtaa tacagggtcg tcagatacat agatacaatt ctattacccc    840
catccataca                                                           850

SEQ ID NO: 52           moltype = DNA  length = 491
FEATURE                 Location/Qualifiers
misc_feature            1..491
                        note = Modified pCUR5p
source                  1..491
                        mol_type = other DNA
                        organism = synthetic construct
SEQUENCE: 52
ttatattgaa ttttcaaaaa ttcttacttt tttttggat ggacgcaaag aagtttaata     60
atcatattac atggcattac caccatatac atatccatat ctaatcttac ttatatgttg    120
tggaaatgta aagagcccga attgtcatgg gatatttgct caagacgacg gtaaaatgag    180
caaatatggc acgatcctca attgtcatgg gatatttgct caagacgacg gtaaaatgag    240
caaatatggc acgatcccaa ttcggatgat aatgcgatta gttttttagc cttatttctg    300
gggtaattaa tcagcgaagc gatgattttt gatctattaa cagatatata aatggaaaag    360
ctgcataacc actttaacta atactttcaa catttttcagt ttgtattact tcttattcaa    420
atgtcataaa agtatcaaca aaaaattgtt aatatacctc tatactttaa cgtcaaggag    480
aaaaaactat a                                                         491

SEQ ID NO: 53           moltype = DNA  length = 833
FEATURE                 Location/Qualifiers
misc_feature            1..833
                        note = Modified pCUR6
source                  1..833
                        mol_type = other DNA
                        organism = synthetic construct
SEQUENCE: 53
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataaattc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccgaatt gaggatcgtg ccatatttgc tcattttacc    360
gtcgtcttga gcaaatatcc catgacaatt gaggatcgtg ccatatttgc tcattttacc    420
gtcgtcttga gcaaatatcc catgacaatt gaggatcgtg ccatatttgc tcattttacc    480
gtcgtcttga gcaaatatcc catgacaatt catgatcgca aaatggcaaa tggcacgtga    540
agctgtcgat attggggaac tgtggtggtt ggcaaatgac taattaagtt agtcaaggcg    600
ccatcctcat gaaaactgtg taacataata accgaagtgt cgaaaaggtg gcaccttgtc    660
caattgaaca cgctcgatga aaaaaataag atatatataa ggttaagtaa agcgtctgtt    720
agaaaggaag ttttcctttt tcttgctctc ttgtctttt catctactat ttccttcgtg    780
taatacaggg tcgtcagata catagataca attctattac ccccatccat aca           833

SEQ ID NO: 54           moltype = DNA  length = 803
FEATURE                 Location/Qualifiers
misc_feature            1..803
                        note = Modified pCUR7
source                  1..803
                        mol_type = other DNA
                        organism = synthetic construct
SEQUENCE: 54
```

```
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa aagaacaaaa ctgaattcag gatcgtgcca   240
tatttgctca ttttaccgtc gtcttgagca aatatcccat gacaattgag gatcgtgcca   300
tatttgctca ttttaccgtc gtcttgagca aatatcccat gagaattctt cctgtcttcc   360
tattgattgc agcttccaat ttcgtcacac aacaaggtcc tagcgacggc tcacaggttt   420
tgtaacaagc aatcgaaggt tctggaatgg cgggaaaggg tttagtacca catgctatga   480
tgcccactgt gatctccaga gcaaagttcg ttcgatcgta ctgttactct ctctctttca   540
aacagaattg tccgaatcgt gtgacaacaa cagcctgttc tcacacactc ttttcttcta   600
accaaggggg tggtttagtt tagtagaacc tcgtgaaact tacatttaca tatatataaa   660
cttgcataaa ttggtcaatg caagaaatac atatttggtc ttttctaatt cgtagttttt   720
caagttctta gatgctttct ttttctcttt tttacagatc atcaaggaag taattatcta   780
cttttttacaa caaatataaa aca                                            803

SEQ ID NO: 55          moltype = DNA   length = 863
FEATURE                Location/Qualifiers
misc_feature           1..863
                       note = Modified pCUR8
source                 1..863
                       mol_type = other DNA
                       organism = synthetic construct
SEQUENCE: 55
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa aagaacaaaa ctgaattcag gatcgtgcca   240
tatttgctca ttttaccgtc gtcttgagca aatatcccat gacaattgag gatcgtgcca   300
tatttgctca ttttaccgtc gtcttgagca aatatcccat gacaattgag gatcgtgcca   360
tatttgctca ttttaccgtc gtcttgagca aatatcccat gagaattctt cctgtcttcc   420
tattgattgc agcttccaat ttcgtcacac aacaaggtcc tagcgacggc tcacaggttt   480
tgtaacaagc aatcgaaggt tctggaatgg cgggaaaggg tttagtacca catgctatga   540
tgcccactgt gatctccaga gcaaagttcg ttcgatcgta ctgttactct ctctctttca   600
aacagaattg tccgaatcgt gtgacaacaa cagcctgttc tcacacactc ttttcttcta   660
accaaggggg tggtttagtt tagtagaacc tcgtgaaact tacatttaca tatatataaa   720
cttgcataaa ttggtcaatg caagaaatac atatttggtc ttttctaatt cgtagttttt   780
caagttctta gatgctttct ttttctcttt tttacagatc atcaaggaag taattatcta   840
cttttttacaa caaatataaa aca                                            863

SEQ ID NO: 56          moltype = DNA   length = 863
FEATURE                Location/Qualifiers
misc_feature           1..863
                       note = Modified pCUR9
source                 1..863
                       mol_type = other DNA
                       organism = synthetic construct
SEQUENCE: 56
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa aagaacaaaa ctgaattcag atgggatatt   240
tgctcaagac gacggtaaaa tgagcaaata tggcacgatc ctcaattgtc atgggatatt   300
tgctcaagac gacggtaaaa tgagcaaata tggcacgatc ctcaattgtc atgggatatt   360
tgctcaagac gacggtaaaa tgagcaaata tggcacgatc ctgaattctt cctgtcttcc   420
tattgattgc agcttccaat ttcgtcacac aacaaggtcc tagcgacggc tcacaggttt   480
tgtaacaagc aatcgaaggt tctggaatgg cgggaaaggg tttagtacca catgctatga   540
tgcccactgt gatctccaga gcaaagttcg ttcgatcgta ctgttactct ctctctttca   600
aacagaattg tccgaatcgt gtgacaacaa cagcctgttc tcacacactc ttttcttcta   660
accaaggggg tggtttagtt tagtagaacc tcgtgaaact tacatttaca tatatataaa   720
cttgcataaa ttggtcaatg caagaaatac atatttggtc ttttctaatt cgtagttttt   780
caagttctta gatgctttct ttttctcttt tttacagatc atcaaggaag taattatcta   840
cttttttacaa caaatataaa aca                                            863

SEQ ID NO: 57          moltype = DNA   length = 923
FEATURE                Location/Qualifiers
misc_feature           1..923
                       note = Modified pCUR10
source                 1..923
                       mol_type = other DNA
                       organism = synthetic construct
SEQUENCE: 57
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa aagaacaaaa ctgaattctc atgggatatt   240
tgctcaagac gacggtaaaa tgagcaaata tggcacgatc ctcaattgtc atgggatatt   300
tgctcaagac gacggtaaaa tgagcaaata tggcacgatc ctcaattgtc atgggatatt   360
tgctcaagac gacggtaaaa tgagcaaata tggcacgatc ctcaattgtc atgggatatt   420
tgctcaagac gacggtaaaa tgagcaaata tggcacgatc ctgaattctt cctgtcttcc   480
```

```
tattgattgc agcttccaat ttcgtcacac aacaaggtcc tagcgacggc tcacaggttt    540
tgtaacaagc aatcgaaggt tctggaatgg cgggaaaggg tttagtacca catgctatga    600
tgcccactgt gatctccaga gcaaagttcg ttcgatcgta ctgttactct ctctctttca    660
aacagaattg tccgaatcgt gtgacaacaa cagcctgttc tcacacactc tttcttcta    720
accaaggggg tggtttagtt tagtagaacc tcgtgaaact tacatttaca tatatataaa    780
cttgcataaa ttggtcaatg caagaaatac atatttggtc ttttctaatt cgtagttttt    840
caagttctta gatgctttct ttttctcttt tttacagatc atcaaggaag taattatcta    900
ctttttacaa caaatataaa aca                                            923

SEQ ID NO: 58          moltype = DNA   length = 983
FEATURE                Location/Qualifiers
misc_feature           1..983
                       note = Modified pCUR11
source                 1..983
                       mol_type = other DNA
                       organism = synthetic construct
SEQUENCE: 58
gtgagtaagg aaagagtgag gaactatcgc atacctgcat ttaaagatgc cgatttgggc     60
gcgaatcctt tatttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
tgctcaagac gacggtaaaa tgagcaaata tggcacgatc ctcaattgtc atgggatatt    300
tgctcaagac gacggtaaaa tgagcaaata tggcacgatc ctcaattgtc atgggatatt    360
tgctcaagac gacggtaaaa tgagcaaata tggcacgatc ctcaattgtc atgggatatt    420
tgctcaagac gacggtaaaa tgagcaaata tggcacgatc ctcaattgtc atgggatatt    480
tgctcaagac gacggtaaaa tgagcaaata tggcacgatc ctcaattgtc atgggatatt    540
tgctcaagac gacggtaaaa tgagcaaata tggcacgatc ctgaattctt cctgtcttcc    600
tattgattgc agcttccaat ttcgtcacac aacaaggtcc tagcgacggc tcacaggttt    660
tgtaacaagc aatcgaaggt tctggaatgg cgggaaaggg tttagtacca catgctatga    720
tgcccactgt gatctccaga gcaaagttcg ttcgatcgta ctgttactct ctctctttca    780
aacagaattg tccgaatcgt gtgacaacaa cagcctgttc tcacacactc tttcttcta    840
accaaggggg tggtttagtt tagtagaacc tcgtgaaact tacatttaca tatatataaa    900
cttgcataaa ttggtcaatg caagaaatac atatttggtc ttttctaatt cgtagttttt    960
caagttctta gatgctttct ttttctcttt tttacagatc atcaaggaag taattatcta   1020
ctttttacaa caaatataaa aca                                            983

SEQ ID NO: 59          moltype = DNA   length = 1043
FEATURE                Location/Qualifiers
misc_feature           1..1043
                       note = Modified pCUR12
source                 1..1043
                       mol_type = other DNA
                       organism = synthetic construct
SEQUENCE: 59
gtgagtaagg aaagagtgag gaactatcgc atacctgcat ttaaagatgc cgatttgggc     60
gcgaatcctt tatttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattcag gatcgtgcca    240
tatttgctca ttttaccgtc gtcttgagca aatatcccat gacaattgag gatcgtgcca    300
tatttgctca ttttaccgtc gtcttgagca aatatcccat gacaattgag gatcgtgcca    360
tatttgctca ttttaccgtc gtcttgagca aatatcccat gagaattcag gatcgtgcca    420
tatttgctca ttttaccgtc gtcttgagca aatatcccat gacaattgag gatcgtgcca    480
tatttgctca ttttaccgtc gtcttgagca aatatcccat gacaattgag gatcgtgcca    540
tatttgctca ttttaccgtc gtcttgagca aatatcccat gagaattctt cctgtcttcc    600
tattgattgc agcttccaat ttcgtcacac aacaaggtcc tagcgacggc tcacaggttt    660
tgtaacaagc aatcgaaggt tctggaatgg cgggaaaggg tttagtacca catgctatga    720
tgcccactgt gatctccaga gcaaagttcg ttcgatcgta ctgttactct ctctctttca    780
aacagaattg tccgaatcgt gtgacaacaa cagcctgttc tcacacactc tttcttcta    840
accaaggggg tggtttagtt tagtagaacc tcgtgaaact tacatttaca tatatataaa    900
cttgcataaa ttggtcaatg caagaaatac atatttggtc ttttctaatt cgtagttttt    960
caagttctta gatgctttct ttttctcttt tttacagatc atcaaggaag taattatcta   1020
ctttttacaa caaatataaa aca                                           1043

SEQ ID NO: 60          moltype = DNA   length = 1043
FEATURE                Location/Qualifiers
misc_feature           1..1043
                       note = Modified pCUR13
source                 1..1043
                       mol_type = other DNA
                       organism = synthetic construct
SEQUENCE: 60
gtgagtaagg aaagagtgag gaactatcgc atacctgcat ttaaagatgc cgatttgggc     60
gcgaatcctt tatttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
tgctcaagac gacggtaaaa tgagcaaata tggcacgatc ctcaattgtc atgggatatt    300
tgctcaagac gacggtaaaa tgagcaaata tggcacgatc ctcaattgtc atgggatatt    360
tgctcaagac gacggtaaaa tgagcaaata tggcacgatc ctgaattctc atgggatatt    420
tgctcaagac gacggtaaaa tgagcaaata tggcacgatc ctcaattgtc atgggatatt    480
tgctcaagac gacggtaaaa tgagcaaata tggcacgatc ctcaattgtc atgggatatt    540
```

```
tgctcaagac gacggtaaaa tgagcaaata tggcacgatc ctgaattctt cctgtcttcc    600
tattgattgc agcttccaat ttcgtcacac aacaaggtcc tagcgacggc tcacaggttt    660
tgtaacaagc aatcgaaggt tctggaatgg cgggaaggg tttagtacca catgctatga     720
tgcccactgt gatctccaga gcaaagttcg ttcgatcgta ctgttactct ctctctttca    780
aacagaattg tccgaatcgt gtgacaacaa cagcctgttc tcacacactc ttttcttcta    840
accaagggg tggtttagtt tagtagaacc tcgtgaaact tacatttaca tatatataaa     900
cttgcataaa ttggtcaatg caagaaatac atatttggtc ttttctaatt cgtagttttt    960
caagttctta gatgctttct ttttctcttt tttacagatc atcaaggaag taattatcta   1020
cttttttacaa caaatataaa aca                                          1043

SEQ ID NO: 61           moltype = DNA  length = 1223
FEATURE                 Location/Qualifiers
misc_feature            1..1223
                        note = Modified pCUR14
source                  1..1223
                        mol_type = other DNA
                        organism = synthetic construct
SEQUENCE: 61
gtgagtaagg aaagagtgag gaactatcgc atacctgcat ttaaagatgc cgatttgggc     60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa tgaattcag gatcgtgcca     240
tgctcaagac gacggtaaaa tgagcaaata tggcacgatc ctcaattgtc atgggatatt    300
tgctcaagac gacggtaaaa tgagcaaata tggcacgatc ctcaattgtc atgggatatt    360
tgctcaagac gacggtaaaa tgagcaaata tggcacgatc ctgaattctc atgggatatt    420
tgctcaagac gacggtaaaa tgagcaaata tggcacgatc ctcaattgtc atgggatatt    480
tgctcaagac gacggtaaaa tgagcaaata tggcacgatc ctcaattgtc atgggatatt    540
tgctcaagac gacggtaaaa tgagcaaata tggcacgatc ctgaattctc atgggatatt    600
tgctcaagac gacggtaaaa tgagcaaata tggcacgatc ctcaattgtc atgggatatt    660
tgctcaagac gacggtaaaa tgagcaaata tggcacgatc ctcaattgtc atgggatatt    720
tgctcaagac gacggtaaaa tgagcaaata tggcacgatc ctgaattctt cctgtcttcc    780
tattgattgc agcttccaat ttcgtcacac aacaaggtcc tagcgacggc tcacaggttt    840
tgtaacaagc aatcgaaggt tctggaatgg cgggaaggg tttagtacca catgctatga     900
tgcccactgt gatctccaga gcaaagttcg ttcgatcgta ctgttactct ctctctttca    960
aacagaattg tccgaatcgt gtgacaacaa cagcctgttc tcacacactc ttttcttcta   1020
accaagggg tggtttagtt tagtagaacc tcgtgaaact tacatttaca tatatataaa   1080
cttgcataaa ttggtcaatg caagaaatac atatttggtc ttttctaatt cgtagttttt  1140
caagttctta gatgctttct ttttctcttt tttacagatc atcaaggaag taattatcta  1200
cttttttacaa caaatataaa aca                                         1223

SEQ ID NO: 62           moltype = DNA  length = 1283
FEATURE                 Location/Qualifiers
misc_feature            1..1283
                        note = Modified pCUR15
source                  1..1283
                        mol_type = other DNA
                        organism = synthetic construct
SEQUENCE: 62
gtgagtaagg aaagagtgag gaactatcgc atacctgcat ttaaagatgc cgatttgggc     60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattcag gatcgtgcca    240
tatttgctca ttttaccgtc gtcttgagca aatatcccat gacaattgag gatcgtgcca    300
tatttgctca ttttaccgtc gtcttgagca aatatcccat gacaattgag gatcgtgcca    360
tatttgctca ttttaccgtc gtcttgagca aatatcccat gacaattgag gatcgtgcca    420
tatttgctca ttttaccgtc gtcttgagca aatatcccat gagaattcag gatcgtgcca    480
tatttgctca ttttaccgtc gtcttgagca aatatcccat gacaattgag gatcgtgcca    540
tatttgctca ttttaccgtc gtcttgagca aatatcccat gacaattgag gatcgtgcca    600
tatttgctca ttttaccgtc gtcttgagca aatatcccat gacaattgag gatcgtgcca    660
tatttgctca ttttaccgtc gtcttgagca aatatcccat gagaattcag gatcgtgcca    720
tatttgctca ttttaccgtc gtcttgagca aatatcccat gacaattgag gatcgtgcca    780
tatttgctca ttttaccgtc gtcttgagca aatatcccat gagaattctt cctgtcttcc    840
tattgattgc agcttccaat ttcgtcacac aacaaggtcc tagcgacggc tcacaggttt    900
tgtaacaagc aatcgaaggt tctggaatgg cgggaaggg tttagtacca catgctatga     960
tgcccactgt gatctccaga gcaaagttcg ttcgatcgta ctgttactct ctctctttca   1020
aacagaattg tccgaatcgt gtgacaacaa cagcctgttc tcacacactc ttttcttcta   1080
accaagggg tggtttagtt tagtagaacc tcgtgaaact tacatttaca tatatataaa   1140
cttgcataaa ttggtcaatg caagaaatac atatttggtc ttttctaatt cgtagttttt  1200
caagttctta gatgctttct ttttctcttt tttacagatc atcaaggaag taattatcta  1260
cttttttacaa caaatataaa aca                                         1283

SEQ ID NO: 63           moltype = DNA  length = 686
FEATURE                 Location/Qualifiers
misc_feature            1..686
                        note = Modified pCUR16
source                  1..686
                        mol_type = other DNA
                        organism = synthetic construct
SEQUENCE: 63
```

```
gctcagcatc tgcttcttcc caaagatgaa cgcggcgtta tgtcactaac gacgtgcacc   60
aacttgcggg aattctcatg ggatatttgc tcaagacgac ggtaaaatga gcaaatatgg  120
cacgatcctc aattgtcatg ggatatttgc tcaagacgac ggtaaaatga gcaaatatgg  180
cacgatcctc aatgtcatgg gatatttgct caagacgacg gtaaaatgag caaatatggc  240
acgatcctga attccaccgc acgccttttt tctgaagccc actttcgtgg actttgccat  300
atatgcaaaa ttcatgaagt gtgataccaa gtcagcatac acctcactag ggtagtttct  360
ttggttgtat tgatcatttg gttcatcgtg gttcattaat tttttttctc cattgctttc  420
tggctttgat cttactatca tttggatttt tgtcgaaggt tgtagaattg tatgtgacaa  480
gtggcaccaa gcatatataa aaaaaaaaag cattatcttc ctaccagagt tgattgttaa  540
aaacgtattt atagcaaacg caattgtaat taattcttat tttgtatctt ttcttcccct  600
gtctcaatct tttattttta ttttattttt cttttcttag tttctttcat aacaccaagc  660
aactaatact ataacataca ataata                                       686

SEQ ID NO: 64          moltype = DNA  length = 747
FEATURE                Location/Qualifiers
misc_feature           1..747
                       note = Modified pCUR17
source                 1..747
                       mol_type = other DNA
                       organism = synthetic construct
SEQUENCE: 64
gctcagcatc tgcttcttcc caaagatgaa cgcggcgtta tgtcactaac gacgtgcacc   60
aacttgcggg aattctcatg ggatatttgc tcaagacgac ggtaaaatga gcaaatatgg  120
cacgatcctc aattgtcatg ggatatttgc tcaagacgac ggtaaaatga gcaaatatgg  180
cacgatcctc aattctcatg ggatatttgc tcaagacgac ggtaaaatga gcaaatatgg  240
cacgatcctc aattctcatg ggatatttgc tcaagacgac ggtaaaatga gcaaatatgg  300
cacgatcctg aattccaccg cacgccttttt tctgaagcc cactttcgtg gactttgcca  360
tatatgcaaa attcatgaag tgtgatacca agtcagcata cacctcacta gggtagtttc  420
tttggttgta ttgatcattt ggttcatcgt ggttcattaa tttttttct ccattgcttt   480
ctggctttga tcttactatc atttggattt tgtcgaagt tgtagaatt gtatgtgaca   540
agtggcacca agcatatata aaaaaaaaa gcattatctt cctaccagag ttgattgtta   600
aaaacgtatt tatagcaaac gcaattgtaa ttaattctta tttgtatct tttcttccct   660
tgtctcaatc ttttatttt attttatttt tcttttctta gtttctttca taacaccaag   720
caactaatac tataacatac aataata                                      747

SEQ ID NO: 65          moltype = DNA  length = 500
FEATURE                Location/Qualifiers
source                 1..500
                       mol_type = genomic DNA
                       organism = Saccharomyces cerevisiae
SEQUENCE: 65
gcaagttaac attagggaga acgtggggcc ttcctccatg agtgcagagc aattgaagat   60
gtttagaggt ttaaggaga ataaccagtt gctggatagc ctacagttta                120
tgccaaattg gccccttcatg gtattcctga cggtgttaat ggacagtact tgagctaaa   180
tgaccctgcc ttggcggact ttatgccttg aggatagcag gtacatataa attgttacat  240
actaagtcga tgagtcaaaa aagactctta tacatttata cattttgcat tattatttt   300
tttttccagc ggaatttgga attccgtctc caaccgccaa aattcccctg cgatttcagc  360
gacaaagagt cataaagtca tcctcgagaa accacgatga aatatataaa agcccatct   420
tccctgacgg aaactggtat tttaggaggc ataccataag ataacaacga aaacgcttta  480
tttttcacac aaccgcaaaa                                              500

SEQ ID NO: 66          moltype = DNA  length = 650
FEATURE                Location/Qualifiers
source                 1..650
                       mol_type = genomic DNA
                       organism = Saccharomyces cerevisiae
SEQUENCE: 66
ttgaaaaatg cgaagttgaa gtgccataga agagaaacag cccacacagg ggagaagccc   60
actggaaagg gggcactgac caactttaaa taggaaacag aagataccac aagccagcga  120
tacaacagca ccaaacaccg aaaagaatag cccaaagctgt cctctggtgt tggaaaaact  180
ggaaaaaacg caactgcgtt ggctgctacg gtgaaaaatt ttcctatgac ttttttcact  240
gcttgttcgt gcgaaattac cgcaaacccg gtaaatgta cacgtatcaa gtgataaaca   300
atttcgtgtc aagtgagcag aatggagcga tttggaaaaa aaaattttt attgtttttt   360
ccccggat tttgctcgag atgactgaaa ttttgtaatc gtgagtcta taccagaga  420
agcaaatatc accaacatac acaggtatac acaatctcat gtccacacac acgtacagac  480
acgcacatat atatatatat atatatatcc ccataggtat ttatatatac aaaagaatcc  540
tcgtgtgttt gtgtgtgcaa tagctagttt tgcgctgcct cttatagtag acaatatcac  600
tttttcaata aaatagaact tgcaaggaaa caaaattgta tcgcttcaag               650

SEQ ID NO: 67          moltype = DNA  length = 500
FEATURE                Location/Qualifiers
source                 1..500
                       mol_type = genomic DNA
                       organism = Saccharomyces cerevisiae
SEQUENCE: 67
acatatgcaa gagtcttatg tatcgtatct aagtgccacg tagggggattc ccatcatttg   60
atgatttcca aatataatac ctgtagagag cggtggagca aaagtcaaat tttaatcgca  120
actgcagaca agtcaagctg aggaaattgt ggatgatctc ttgttttctt tgatattcac  180
cacaacagaa gtgaagagtg tgattgcggt tactactgac cacgaagcaa tgcgtttagt  240
```

```
agtgaaaaga attactcata ctctggaatc gaaattccgt tggaaaaatt cgctttgtag    300
tgaaaaataa agatgtcaat aaagggtatt gagaatttcc aatggaatta tcagcaatag    360
atgatagaaa gtagcacaga atttggctta atggtatata aaccgtaggg tcctggtaaa    420
attacatggg aaggatcctt aggcagtagg gaaaacttat caggacaatt gagttatatt    480
aacgtattat atattttaat                                                500

SEQ ID NO: 68           moltype = DNA   length = 494
FEATURE                 Location/Qualifiers
misc_feature            1..494
                        note = Modified pLYR1p
source                  1..494
                        mol_type = other DNA
                        organism = synthetic construct
SEQUENCE: 68
ttatattgaa tttcaaaaa ttcttacttt tttttggat ggacgcaaag aagtttaata    60
atcatattac atggcattac caccatatac atatccatat ctaatcttac ttatatgttg    120
tggaaatgta aagagcccga attcctcata ctctggaatc gaaattccgt tggaaaaatt    180
cgctttgtag tgaaaaataa agatgtcaat aaagggtatt gagaatttcc aatggaatta    240
tcagcaatag atgatagaaa gaattcggat gataatgcga ttagtttttt agccttattt    300
ctggggtaat taatcagcga agcgatgatt tttgatctat taacagatat ataaatggaa    360
aagctgcata accactttaa ctaatacttt caacattttc agtttgtatt acttcttatt    420
caaatgtcat aaaagtatca acaaaaaatt gttaatatac ctctatactt taacgtcaag    480
gagaaaaaac tata                                                      494

SEQ ID NO: 69           moltype = DNA   length = 494
FEATURE                 Location/Qualifiers
misc_feature            1..494
                        note = Modified pLYR2p
source                  1..494
                        mol_type = other DNA
                        organism = synthetic construct
SEQUENCE: 69
ttatattgaa tttcaaaaa ttcttacttt tttttggat ggacgcaaag aagtttaata    60
atcatattac atggcattac caccatatac atatccatat ctaatcttac ttatatgttg    120
tggaaatgta aagagcccga attctttcta tcatctattg ctgataattc cattggaaat    180
tctcaatacc cttattgac atctttattt ttcactacaa agcgaatttt tccaacggaa    240
tttcgattcc agagtatgag gaattcggat gataatgcga ttagtttttt agccttattt    300
ctggggtaat taatcagcga agcgatgatt tttgatctat taacagatat ataaatggaa    360
aagctgcata accactttaa ctaatacttt caacattttc agtttgtatt acttcttatt    420
caaatgtcat aaaagtatca acaaaaaatt gttaatatac ctctatactt taacgtcaag    480
gagaaaaaac tata                                                      494

SEQ ID NO: 70           moltype = DNA   length = 616
FEATURE                 Location/Qualifiers
misc_feature            1..616
                        note = Modified pLYR3p
source                  1..616
                        mol_type = other DNA
                        organism = synthetic construct
SEQUENCE: 70
ttatattgaa tttcaaaaa ttcttacttt tttttggat ggacgcaaag aagtttaata    60
atcatattac atggcattac caccatatac atatccatat ctaatcttac ttatatgttg    120
tggaaatgta aagagcccga attcctcata ctctggaatc gaaattccgt tggaaaaatt    180
cgctttgtag tgaaaaataa agatgtcaat aaagggtatt gagaatttcc aatggaatta    240
tcagcaatag atgatagaaa gaattcctca tactctggaa tcgaaattcc gttggaaaaa    300
ttcgctttgt agtgaaaaat aaagatgtca ataaagggta ttgagaattt ccaatggaat    360
tatcagcaat agatgataga aagaattcgg atgataatgc gattagtttt ttagccttat    420
ttctggggta attaatcagc gaagcgatga ttttgatct attaacagat ataaatgg    480
aaaagctgca taaccacttt aactaatact tcaacattt tcagtttgta ttacttctta    540
ttcaaatgtc ataaaagtat caacaaaaaa ttgttaatat acctctatac tttaacgtca    600
aggagaaaaa actata                                                    616

SEQ ID NO: 71           moltype = DNA   length = 616
FEATURE                 Location/Qualifiers
misc_feature            1..616
                        note = Modified pLYR4p
source                  1..616
                        mol_type = other DNA
                        organism = synthetic construct
SEQUENCE: 71
ttatattgaa tttcaaaaa ttcttacttt tttttggat ggacgcaaag aagtttaata    60
atcatattac atggcattac caccatatac atatccatat ctaatcttac ttatatgttg    120
tggaaatgta aagagcccga attctttcta tcatctattg ctgataattc cattggaaat    180
tctcaatacc cttattgac atctttattt ttcactacaa agcgaatttt tccaacggaa    240
tttcgattcc agagtatgag gaattctttc tatcatctat tgctgataat tccattggaa    300
attctcaata cccttattg acatctttat ttttcactac aaagcgaatt tttccaacgg    360
aatttcgatt ccagagtatg aggaattcgg atgataatgc gattagtttt ttagccttat    420
ttctggggta attaatcagc gaagcgatga ttttgatct attaacagat ataaatgg    480
aaaagctgca taaccacttt aactaatact tcaacattt tcagtttgta ttacttctta    540
```

```
ttcaaatgtc ataaaagtat caacaaaaaa ttgttaatat acctctatac tttaacgtca    600
aggagaaaaa actata                                                    616

SEQ ID NO: 72              moltype = DNA  length = 738
FEATURE                    Location/Qualifiers
misc_feature               1..738
                           note = Modified pLYR5p
source                     1..738
                           mol_type = other DNA
                           organism = synthetic construct
SEQUENCE: 72
ttatattgaa ttttcaaaaa ttcttacttt tttttggat ggacgcaaag aagtttaata    60
atcatattac atggcattac caccatatac atatccatat ctaatcttac ttatatgttg   120
tggaaatgta aagagcccga attctttcta tcatctattg ctgataattc cattggaaat   180
tctcaatacc ctttattgac atctttattt ttcactacaa agcgaatttt tccaacggaa   240
tttcgattcc agagtatgag gaattctttc tatcatctat tgctgataat tccattggaa   300
attctcaata ccctttattg acatctttat ttttcactac aaagcgaatt tttccaacgg   360
aatttcgatt ccagagtatg aggaattctt tctatcatct attgctgata attccattgg   420
aaattctcaa taccctttat tgacatcttt attttttcact acaaagcgaa tttttccaac   480
ggaatttcga ttccagagta tgaggaattc ggatgataat gcgattagtt ttttagcctt   540
atttctgggg taattaatca gcgaagcgat gattttgat ctattaacag atatataaat   600
ggaaaagctg cataaccact ttaactaata cttttcaacat tttcagtttg tattacttct   660
tattcaaatg tcataaaagt atcaacaaaa aattgttaat atacctctat actttaacgt   720
caaggagaaa aaactata                                                  738

SEQ ID NO: 73              moltype = DNA  length = 1104
FEATURE                    Location/Qualifiers
misc_feature               1..1104
                           note = Modified pLYR6p
source                     1..1104
                           mol_type = other DNA
                           organism = synthetic construct
SEQUENCE: 73
ttatattgaa ttttcaaaaa ttcttacttt tttttggat ggacgcaaag aagtttaata    60
atcatattac atggcattac caccatatac atatccatat ctaatcttac ttatatgttg   120
tggaaatgta aagagcccga attgctcata ctctggaatc gaaattccgt tggaaaaatt   180
cgctttgtag tgaaaaataa agatgtcaat aaagggtatt gagaatttcc aatggaatta   240
tcagcaatag atgatagaaa gaattcctca tactctggaa tcgaattcc gttggaaaaa   300
ttcgctttgt agtgaaaaat aaagatgtca ataaaggta ttgagaattt ccaatggaat   360
tatcagcaat agatgataga agaattcct catactctgg aatcgaaatt ccgttggaaa   420
aattcgcttt gtagtgaaaa ataaagatgt caataaaggg tattgagaat ttccaatgga   480
attatcagca atagatgata gaaacaattg ctcatactct ggaatcgaaa ttccgttgga   540
aaaattcgct ttgtagtgaa aaataaagat gtcaataaag ggtattgaga atttccaatg   600
gaattatcag caatagatga tagaaagaat tcctcatact ctggaatcga aattccgttg   660
gaaaaattcg ctttgtagtg aaaaataaag atgtcaataa agggtattga atttccaa    720
tggaattatc agcaatagat gatagaaaga attcctcata ctctggaatc gaaattccgt   780
tggaaaaatt cgctttgtag tgaaaaataa agatgtcaat aaagggtatt gagaatttcc   840
aatggaatta tcagcaatag atgatagaaa caattcggat gataatgcga ttagtttttt   900
agccttattt ctggggtaat taatcagcga agcgatgatt tttgatctat aacagatat   960
ataaatggaa aagctgcata accactttaa ctaatacttt caacattttc agtttgtatt  1020
acttcttatt caaatgtcat aaaagtatca acaaaaaatt gttaatatac ctctatactt  1080
taacgtcaag gagaaaaaac tata                                         1104

SEQ ID NO: 74              moltype = DNA  length = 1836
FEATURE                    Location/Qualifiers
misc_feature               1..1836
                           note = Modified pLYR7p
source                     1..1836
                           mol_type = other DNA
                           organism = synthetic construct
SEQUENCE: 74
ttatattgaa ttttcaaaaa ttcttacttt tttttggat ggacgcaaag aagtttaata    60
atcatattac atggcattac caccatatac atatccatat ctaatcttac ttatatgttg   120
tggaaatgta aagagcccga attgtttcta tcatctattg ctgataattc cattggaaat   180
tctcaatacc ctttattgac atctttattt ttcactacaa agcgaatttt tccaacggaa   240
tttcgattcc agagtatgag gaattctttc tatcatctat tgctgataat tccattggaa   300
attctcaata ccctttattg acatctttat ttttcactac aaagcgaatt tttccaacgg   360
aatttcgatt ccagagtatg aggaattctt tctatcatct attgctgata attccattgg   420
aaattctcaa taccctttat tgacatcttt attttttcact acaaagcgaa tttttccaac   480
ggaatttcga ttccagagta tgagcaattg tttctatcat ctattgctga taattccatt   540
ggaaattctc aatacccttt attgacatct ttattttttca ctacaaagcg aattttttcca   600
acggaatttc gattccagag tatgaggaat ctttctatc atctattgct gataattcca   660
ttggaaattc tcaataccct ttattgacat ctttattttt cactacaaag cgaatttttc   720
caacggaatt tcgattccag agtatgagga attctttcta tcatctattg ctgataattc   780
cattggaaat tctcaatacc ctttattgac atctttattt ttcactacaa agcgaatttt   840
tccaacggaa tttcgattcc agagtatgag caattgtttc tatcatctat tgctgataat   900
tccattggaa attctcaata ccctttattg acatctttat ttttcactac aaagcgaatt   960
tttccaacgg aatttcgatt ccagagtatg aggaattctt tctatcatct attgctgata  1020
attccattgg aaattctcaa taccctttat tgacatcttt attttttcact acaaagcgaa  1080
```

-continued

```
tttttccaac ggaatttcga ttccagagta tgaggaattc tttctatcat ctattgctga   1140
taattccatt ggaaattctc aatacccttt attgacatct ttattttca ctacaaagcg    1200
aattttccca acggaatttc gattccgag tatgagcaat tgtttctatc atctattgct    1260
gataattcca ttggaaattc tcaatacct ttattgacat ctttattttt cactacaaag    1320
cgaattttc caacggaatt tcgattccag agtatgagaa attctttcta tcatctattg    1380
ctgataattc cattggaaat tctcaatacc ctttattgac atctttattt ttcactacaa   1440
agcgaatttt ccaacggaa tttcgattcc agagtatgag gaattctttc tatcatctat    1500
tgctgataat tccattggaa attctcaata ccctttattg acatctttat ttttcactac   1560
aaagcgaatt tttccaacgg aatttcgatt ccagagtatg agcaattcgg atgataatgc   1620
gattagtttt ttagcttat ttctggggta attaatcagc gaagcgatga tttttgatct    1680
attaacagat atataaatgg aaaagctgca taaccacttt aactaatact ttcaacattt   1740
tcagtttgta ttacttctta ttcaaatgtc ataaaagtat caacaaaaaa ttgttaatat   1800
acctctatac tttaacgtca aggagaaaaa actata                             1836

SEQ ID NO: 75            moltype = DNA  length = 981
FEATURE                  Location/Qualifiers
misc_feature             1..981
                         note = Modified pLYR8
source                   1..981
                         mol_type = other DNA
                         organism = synthetic construct
SEQUENCE: 75
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataaattc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tgctcatact ctggaatcga aattccgttg aaaaattcg ctttgtagtg aaaaataaag    420
atgtcaataa agggtattga gaattcccaa tggaattcca gcaatagat gatagaaaga    480
attcctcata ctctggaatc gaaattccgt tggaaaaatt cgctttgtag tgaaaaataa    540
agatgtcaat aaaggggtatt gagaatttcc aatggaatta tcagcaatag atgatagaaa   600
gaattcctca tactctggaa tcgaaattcc gttggaaaaa ttcgctttgt agtgaaaaat   660
aaagatgtca ataaaggta ttgagaattt ccaatggaat tatcagcaat agatgataga    720
aacaattcta ttaagttag tcaaggcgcc atcctcatga aaactgtgta acataataac   780
cgaagtgtcg aaaaggtggc accttgtcca attgaacacg ctcgatgaaa aaataagat    840
atatataagg ttaagtaaag cgtctgttag aaaggaagtt tttcctttttt cttgctctct   900
tgtcttttca tctactattt ccttcgtgta atacagggtc gtcagataca tagatacaat    960
tctattaccc ccatccatac a                                              981

SEQ ID NO: 76            moltype = DNA  length = 981
FEATURE                  Location/Qualifiers
misc_feature             1..981
                         note = Modified 76
source                   1..981
                         mol_type = other DNA
                         organism = synthetic construct
SEQUENCE: 76
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataaattc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tgtttctatc atctattgct gataattcca ttggaaattc tcaatacct ttattgacat    420
ctttattttt cactacaaag cgaattttc caacggaatt tcgattccag agtatgagga    480
attctttcta tcatctattg ctgataattc cattggaaat tctcaatacc ctttattgac   540
atctttattt ttcactacaa agcgaatttt ccaacggaa tttcgattcc agagtatgag    600
gaattctttc tatcatctat tgctgataat tccattggaa attctcaata ccctttattg   660
acatctttat ttttcactac aaagcgaatt tttccaacgg aatttcgatt ccagagtatg    720
agcaattcta ttaagttag tcaaggcgcc atcctcatga aaactgtgta acataataac   780
cgaagtgtcg aaaaggtggc accttgtcca attgaacacg ctcgatgaaa aaataagat    840
atatataagg ttaagtaaag cgtctgttag aaaggaagtt tttcctttttt cttgctctct   900
tgtcttttca tctactattt ccttcgtgta atacagggtc gtcagataca tagatacaat    960
tctattaccc ccatccatac a                                              981

SEQ ID NO: 77            moltype = DNA  length = 1225
FEATURE                  Location/Qualifiers
misc_feature             1..1225
                         note = Modified pLYR10
source                   1..1225
                         mol_type = other DNA
                         organism = synthetic construct
SEQUENCE: 77
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataaattc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
```

```
cttcggatgc aagggttcga atcccttagc tctcattatt ttttgctttt tctcttgaat    360
tgtttctatc atctattgct gataattcca ttggaaattc tcaatacccct ttattgacat   420
ctttatttttt cactacaaag cgaattttc caacggaatt tcgattccag agtatgagga   480
attctttcta tcatctattg ctgataattc cattggaaat tctcaatacc ctttattgac   540
atctttatttt ttcactacaa agcgaatttt tccaacggaa tttcgattcc agagtatgag   600
gaattctttc tatcatctat tgctgataat tccattggaa attctcaata cccctttattg   660
acatctttat ttttcactac aaagcgaatt tttccaacgg aatttcgatt ccagagtatg   720
aggaattctt tctatcatct attgctgata attccattgg aaattctcaa tacccttta    780
tgacatcttt atttttcact acaaagcgaa tttttccaac ggaattttcga ttccagagta   840
tgaggaattc tttctatcat ctattgctga taattccatt ggaaattctc aatacccttt   900
attgacatct ttatttttca ctacaaagcg aatttttcca acggaatttc gattccagag   960
tatgagcaat ctaattaag ttagtcaagg cgccatcctc atgaaaactg tgtaacataa   1020
taaccgaagt gtcgaaaagg tggcaccttg tccaattgaa cacgctcgat gaaaaaaata   1080
agatatatat aaggttaagt aaagcgtctg ttagaaagga agttttcct ttttcttgct   1140
ctcttgtctt ttcatctact atttccttcg tgtaatacag ggtcgtcaga tacatagata   1200
caattctatt accccccatcc ataca                                        1225

SEQ ID NO: 78           moltype = DNA  length = 1347
FEATURE                 Location/Qualifiers
misc_feature            1..1347
                        note = Modified pLYR11
source                  1..1347
                        mol_type = other DNA
                        organism = synthetic construct
SEQUENCE: 78
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataaattc gccatttctt gaatgtattt   180
aaagatattt aatgctataa tagacattta atccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tgctcatact ctggaatcga aattccgttg aaaaattcg ctttgtagtg aaaaataaag   420
atgtcaataa agggtattga aatttccaa tggaattatc agcaatagat gatagaaaga   480
attcctcata ctctggaatc gaaattccgt tggaaaaatt cgctttgtag tgaaaaataa   540
agatgtcaat aaagggtatt gagaatttcc aatggaatta tcagcaatag atgatagaaa   600
gaattcctca tactctggaa tcgaaattcc gttggaaaaa ttcgctttgt agtgaaaaat   660
aaagatgtca ataaagggta ttgagaattt ccaatggaat tatcagcaat agatgataga   720
aagaattcct catactctgg aatcgaaatt ccgttggaaa aattcgcttt gtagtgaaaa   780
ataaagatgt caataaaggg tattgagaat tccaatggaa ttatcagca atagatgata   840
gaaagaattc ctcatactct ggaatcgaaa ttccgttgga aaaattcgct ttgtagtgaa   900
aaataaagat gtcaataaag ggtattgaga atttccaatg gaattatcag caatagatga   960
tagaaagaat tcctcatact ctggaatcga aattccgttg aaaaattcg ctttgtagtg  1020
aaaaataaag atgtcaataa agggtattga gaattccaa tggaattatc agcaatagat  1080
gatagaaaca attctaatta gttagtcaa ggcgccatcc tcatgaaaac tgtgtaacat  1140
aataaccgaa gtgtcgaaaa ggtggcacct tgtccaattg aacacgctcg atgaaaaaaa  1200
taagatatat aaggttaa gtaaagcgt ctgttagaaag gaagttttc cttttttcttg    1260
ctctcttgtc ttttcatcta ctatttcctt cgtgtaatac agggtcgtca gatacataga   1320
tacaattcta ttaccccccat ccataca                                    1347

SEQ ID NO: 79           moltype = DNA  length = 686
FEATURE                 Location/Qualifiers
misc_feature            1..686
                        note = Modified pMET17
source                  1..686
                        mol_type = other DNA
                        organism = synthetic construct
SEQUENCE: 79
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataaattc gccatttctt gaatgtattt   180
aaagatattt aatgctataa tagacattta atccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgagg   360
tcacatgatc gcaaaatggc aaatggcacg tgaagctgtc gatattgggg aactgtgatg   420
gttgcaaat gactaattaa gttagtcaag gcgccatcct catgaaaact gtgtaacata   480
ataaccgaag tgtcgaaaag gtggcacctt gtccaattga acacgctcga tgaaaaaaat   540
aagatatata taaggttaag taaagcgtct gttagaaagg aagttttcc ttttttcttgc   600
tctcttgtct tttcatctac tatttccttc gtgtaataca gggtcgtcag atacatagat   660
acaattctat taccccccatc cataca                                      686

SEQ ID NO: 80           moltype = DNA  length = 510
FEATURE                 Location/Qualifiers
source                  1..510
                        mol_type = genomic DNA
                        organism = Saccharomyces cerevisiae
SEQUENCE: 80
ccacaggaaa tatttcacgt gacttacaaa cagagtcgta cgtcaggacc ggagtcaggt    60
gaaaaatgt gggccggtaa agggaaaaa ccagaaacgg gactactatc gaactcgttt   120
agtcgcgaac gtgcaaaagg ccaatatttt tcgctagagt catcgcagtc atggcagctc   180
```

```
tttcgctcta tctcccggtc gcaaaactgt ggtagtcata gctcgttctg ctcaattgag    240
aactgtgaat gtgaatatgg aacaaatgcg atagatgcac taatttaagg gaagctagct    300
agttttccca actgcgaaag aaaaaaagga aagaaaaaaa aattctatat aagtgataga    360
tatttccatc tttactagca ttagtttctc ttttacgtat tcaatatttt tgttaaactc    420
ttcctttatc ataaaaaagc aagcatctaa gagcattgac aacactctaa gaaacaaaat    480
accaatataa tttcaaagta catatcaaaa                                     510

SEQ ID NO: 81          moltype = DNA   length = 508
FEATURE                Location/Qualifiers
source                 1..508
                       mol_type = genomic DNA
                       organism = Saccharomyces cerevisiae
SEQUENCE: 81
cctatgcatg tttagagcaa gcgcctttgt gagccctccc ggttacgacg ccttggcaat    60
gtagcagata actctgcact tctagaatca ttccactacg acatttggct catcaccagc    120
tcgcgagaaa tgtaaataag ccaacaacca agaatgcgta acattaaaga atacagttgc    180
tttcatttcg gcgtgatggt acggcaccca cggttcctta cattattctc gaaaaatagc    240
tgcacgcttt tccaggaata aaagaccgtg ccactaattc cacgtgatca atatatttac    300
aagccacctc aaaaaatgtg gcaatggaga agaggatgaa cgactcaata tgacttcaac    360
ttcatgaatt tgtcaaaata tctatataag atgcaaaatt tctatacaac atcagttgcg    420
tatccgttaa tgtcgttcat tttctctctt tgttcgaact tgacatcaag aaaagttgga    480
attatttctc caagcacact gtacacca                                       508

SEQ ID NO: 82          moltype = DNA   length = 552
FEATURE                Location/Qualifiers
source                 1..552
                       mol_type = genomic DNA
                       organism = Saccharomyces cerevisiae
SEQUENCE: 82
aacgatatgt acgtagtggt ataaggtgag ggggtccaca gatataacat cgtttaattt    60
agtactaaca gagactttg tcacaactac atataagtgt acaaatatag tacagatatg    120
acacacttgt agcgccaacg cgcatcctac ggattgctga cagaaaaaaa ggtcacgtga    180
ccagaaaagt cacgtgtaat tttgtaactc accgcattct agcggtccct gtcgtgcaca    240
ctgcactcaa caccataaac cttagcaacc tccaaaggaa atcaccgtat aacaaagcca    300
cagttttaca acttagtctc ttatgaagtt acttaccaat gagaaataga ggctctttct    360
cgacaaatat gaatatggat atatatatat atatatatat atatatatat atatatatgt    420
aaacttggtt cttttttagc ttgtgatctc tagcttgggt ctctctctgt cgtaacagtt    480
gtgatatcgt ttcttaacaa ttgaaaagga actaagaaag tataataata acaagaataa    540
agtataatta ac                                                        552

SEQ ID NO: 83          moltype = DNA   length = 363
FEATURE                Location/Qualifiers
source                 1..363
                       mol_type = genomic DNA
                       organism = Saccharomyces cerevisiae
SEQUENCE: 83
gaaacggacg taagacggaa atagaatttg aagataaagt tatatatcac tacacacgaa    60
tactttcttt tttttttttc acaggaaaac tgtggtggcg cccttgccta ctagtgcatt    120
tcttttttcg ggttcttgtc tcgacgaaat tttagcctca tcgtagtttt tcactctggt    180
atcgatgaaa aagggaagag taaaaagttt tccgtttagt acttaatggg attggtttgg    240
gacgtatata tcgactggtg ttgtctgtta ttcatcgttg ttttcggtt agcttcgaaa     300
aaaaaataga gtaaaaacca ggaatttacc ctaaaaacaa gaaaaaataa gataaacgaa    360
aat                                                                  363

SEQ ID NO: 84          moltype = DNA   length = 500
FEATURE                Location/Qualifiers
source                 1..500
                       mol_type = genomic DNA
                       organism = Saccharomyces cerevisiae
SEQUENCE: 84
gagctttgct ctattatata agataaaata tgcactaaaa gtttgcattt ctttacataa    60
ctaaaactaa gacattatgc atagcttacc tgatcaaaaa gtatgtaaac ttgttaacat    120
cttcacatgt gattcatctg gtcgtacttt cttgcggtgc agtgtaatat ttctacccac    180
gtgactataa ttgagcttga aaactgtggc gttttccac cgatgggtcc acgccagata    240
ttaaccgaag ccaaaatacc gatgaaattt ctgagatagc tcttgtaaac gacgtcaaat    300
cttcatatgc aaggagatct tgatttcttt ttggtagtca tctgtcgtct tgaggcgtat    360
aagaaggagg ttatatctgt cctttctaca agtattttc gagaatcttg cttctgcccc    420
tttttttcttt ttttaaaagg tttaaaaaac ataactgtct tcaatatatc cagtatttac    480
gacaatatac aaacataatc                                                500

SEQ ID NO: 85          moltype = DNA   length = 913
FEATURE                Location/Qualifiers
source                 1..913
                       mol_type = genomic DNA
                       organism = Saccharomyces cerevisiae
SEQUENCE: 85
ccttcgctaa ataataaacc tgaactgtac ttagcgaagc ttcatagca cctacgtaca     60
cgtatatata gacattttac gtaatggaga aactgaggtt tttgttttca cttttttttct   120
ttcttttttca ctattgctcg aaccgcctgc gatgagctaa gaaaaaaaag tgaaagaaat   180
```

```
catagaaagc aaaaatgaga ttatatagcc cagagccctc ttctggcgcc tgtcccaagg    240
cggaccaaca acaacacttg cccaaaccta agaaaatccc ctcatacttt tccgtttgta    300
tctcctactt tcttacttcc ttttttttctt ctttatttgc ttggtttacc attgaagtcc   360
attttttacta cagacaatag ctagtcattc gctatcttcc gtttgtcact ttttttcaaa   420
tttctcatct atatagcgaa gtacggaaaa gatgtcactt gccggcatct cggccttccc    480
cggccaaatg gactcatcat ctacgatacg gccccttaa tccgcaatta ctttgcccat     540
tcggccgtag ccgttctaaa gccgccgtgc cttgccccca atactcccct aatgatccgg    600
gaagttccgg tttttttcct ttgtttagtg catttttgtg ttgcccaagg ttgggaaggt    660
ccgatttgac tttaaggaac tacggaaggt atctaaggtt tctaaaaaca atatacacgt    720
gcgtgcgtag atatataaag ataaagattt atcgatatga gataaagatt gctgcatgat    780
tctcctt ctg attcttttc cctgtatata ttttctcccc ttctgtataa atcgtacagt    840
cagaagtagt ccagaatata gtgctgcaga ctattacaaa agttcaatac aatatcataa    900
aagttatagt aac                                                       913

SEQ ID NO: 86          moltype = DNA  length = 998
FEATURE                Location/Qualifiers
source                 1..998
                       mol_type = genomic DNA
                       organism = Saccharomyces cerevisiae
SEQUENCE: 86
aatgtgttta taaattattt ttttttgctgg tagcaaaatc aactcattgt cttccattca    60
gagtctaatc gaacgttatc gcaatgcttg cacacttttta aacaatacga tttagtttaa   120
gtggatggac ccccacgctt agtgttccac aggtttgtcc ccactgtttt tacattccac    180
tgtacatttt tgcaatagaa ggtcattgta tgctaccttg ggcggctaag aatacctgta    240
aaaatttgga gaaattagat tcgtaaagaa tgactcgcaa cgactccaat gatttcttct    300
tttcacccctt tgaacggccg atatccgcgc gggatccatc cccgcaatt tactccacta    360
gaccggcgtg tttctctttt tccttttcct ggggttagag cccaagagct aatagccgac    420
aaacggactc caaaaaaaaa aggaggcaca ggacaaacgc agcacctgcg tcattcacgc    480
tgaagcggca gcaagcattt tcgatcagct ccaattaaat gaagactatt cgccgtaccg    540
ttcccagatg ggtgcgaaag tcagtgatcg aggaagttat tgagcgccgg gcttgaaact    600
atttctccat ctcagagccg ccaagcctac cattattctc caccaggaag ttagtttgta    660
agcttctgca caccatccgg acgtccataa ttcttcactt aacggtcttt tgccccccct    720
tctactataa tgcattagaa cgttacctgg tcatttggat ggagatctaa gtaacactta    780
ctatctccta tggtactatc cttaccaaa aaaaaaaaa aaaaaaaaa aaaaatcag         840
caaagtgaag taccctcttg atgtataaat acattgcaca tcattgttga gaaatagttt    900
tggaagttgt ctagtccttc tcccttagat ctaaaaggaa gaagagtaac agtttcaaaa    960
gttttttcctc aaagagatta aatactgcta ctgaaaat                           998

SEQ ID NO: 87          moltype = DNA  length = 450
FEATURE                Location/Qualifiers
source                 1..450
                       mol_type = genomic DNA
                       organism = Saccharomyces cerevisiae
SEQUENCE: 87
ttttgctact cgtcatccga tgagaaaaac tgttcccttt tgccccaggt ttccattcat    60
ccgagcgatc acttatctga cttcgtcact ttttcatttc atccgaaaca atcaaaactg   120
aagccaatca ccacaaaatt aacactcaac gtcatctttc ataccctt acagaagaaa    180
atatccatag tccggactag catcccagta tgtgactcaa tattggtgca aaagagaaaa   240
gcataagtca gtccaaagtc cgcccttaac caggcacatc ggaattcaca aaacgtttct    300
ttattatata aaggagctgc ttcactggca aaattcttat tatttgtctt ggcttgctaa    360
tttcatctta tcctttttttt ctttttcacac ccaaatacct aacaattgag agaaaactct   420
tagcataaca taacaaaaag tcaacgaaaa                                     450

SEQ ID NO: 88          moltype = DNA  length = 598
FEATURE                Location/Qualifiers
source                 1..598
                       mol_type = genomic DNA
                       organism = Saccharomyces cerevisiae
SEQUENCE: 88
tatcttaact gatagtttga tcaaggggc aaaacgtagg ggcaaacaaa cggaaaaatc    60
gtttctcaaa ttttctgatg ccaagaactc taaccagtct tatctaaaaa ttgccttatg   120
atccgtctct ccggttacag cctgtgtaac tgattaatcc tgcctttcta atcaccattc    180
taatgtttta attaagggat tttgtcttca ttaacggctt tcgctcataa aaatgttatg    240
acgttttgcc cgcaggcggg aaaccatcca cttcacgaag ctgatctcct ctgccggtaa    300
accgggcatc tccaacttat aagttggaga aataagagaa tttcagattg agaatgaa     360
aaaaaaaaaa aaaaaaggca gaggagagca tagaaatggg gttcacttt tggtaaagct    420
atagcatgcc tatcacatat aaatagagtg ccagtagcga cttttttcac actcgaaata   480
ctcttactac tgctctcttg ttgttttta cacttcttgt ttcttcttgg taaatagaat    540
atcaagctac aaaaagcata caatcaacta tcaactatta actatatcgt aatacaca     598

SEQ ID NO: 89          moltype = DNA  length = 793
FEATURE                Location/Qualifiers
source                 1..793
                       mol_type = genomic DNA
                       organism = Saccharomyces cerevisiae
SEQUENCE: 89
tgtctaatgc gaaggtactt ttattttttt cagattcaaa gcaatattat ttagacaatt    60
gatactaagt gagcttaagg aggattaaac aactgtggaa tccttcacaa ggattcaata   120
tttgtttttc ctggttatttt tgccatcatt caactttcct cagacgtaaa attcgtgctt   180
```

-continued

```
agtgatgtct caatattccc gcagggtaat aaaattcaat aactatcact atatacgcaa    240
cagtattacc ctacattgct atcggctcaa tggaaatccc catatcatag cttccattgg    300
gccgatgaag ttagtcgacg gatagaagcg gttgtcccct ttcccggcga gccggcagtc    360
gggccgaggt tcgataaaat tttgtattgt gttttgattc tgtcatgagt attacttatg    420
ttctctttag gtaacccag gttaatcaat cacagtttca taccggctaa tattcaaatt     480
atgactttc ttctgcagtg tcagccttac gacgattatc tatgagcttt gaatatagtt     540
tgccgtgatt cgtatcttta attggataat aaaatgcgaa ggatcgatga cccttattat    600
tatttttcta cactggctac cgatttaact catcttcttg aaagtatata agtaacagta    660
aaatataccg tacttctgct aatgttattt gtccctatt tttcttttct tgtcttatgc     720
tatagtacct aagaataacg actattgttt tgaactaaac aaagtagtaa aagcacataa    780
aagaattaag aaa                                                       793
```

| SEQ ID NO: 90 | moltype = DNA  length = 300 |
|---|---|
| FEATURE | Location/Qualifiers |
| source | 1..300 |
| | mol_type = genomic DNA |
| | organism = Saccharomyces cerevisiae |

SEQUENCE: 90
```
atttaactcc ttaagttact ttaatgattt agttttatt attaataatt catgctcatg      60
acatctcata tacacgttta taaaacttaa atagattgaa aatgtattaa agattcctca    120
gggattcgat tttttggaa gttttgtgtt tttttccctt gagatgctgt agtatttggg     180
aacaattata caatcgaaag atatatgctt acattcgacc gttttagccg tgatcattat    240
cctatagtaa cataaccctga agcataactg acactactat catcaaatact tgtcacatga  300
```

| SEQ ID NO: 91 | moltype = DNA  length = 300 |
|---|---|
| FEATURE | Location/Qualifiers |
| source | 1..300 |
| | mol_type = genomic DNA |
| | organism = Saccharomyces cerevisiae |

SEQUENCE: 91
```
acaggcccct ttcctttgt cgatatcatg taattagtta tgtcacgctt acattcacgc      60
cctcctccca catcgctct aaccgaaaag gaaggagtta gacaacctga agtctaggtc     120
cctatttatt ttttttaata gttatgttag tattaagaac gttatttata tttcaaattt    180
ttctttttt tctgtacaaa cgcgtgtacg catgtaacat tatactgaaa accttgcttg     240
agaaggtttt gggacgctcg aaggcttaa tttgcaagct tcgcagttta cactctcatc     300
```

| SEQ ID NO: 92 | moltype = DNA  length = 300 |
|---|---|
| FEATURE | Location/Qualifiers |
| source | 1..300 |
| | mol_type = genomic DNA |
| | organism = Saccharomyces cerevisiae |

SEQUENCE: 92
```
gtgaatttac tttaaatctt gcatttaaat aaatttctt tttatagctt tatgacttag     60
tttcaattta tatactattt taatgacatt ttcgattcat tgattgaaag ctttgtgttt    120
tttcttgatg cgctattgca ttgttcttgt cttttttcgcc acatgtaata tctgtagtag   180
atacctgata cattgtggat gctgagtgaa attttagtta ataatggagg cgctcttaat   240
aattttgggg atattggctt tttttttaa agttacaaa tgaattttt ccgccaggat      300
```

| SEQ ID NO: 93 | moltype = DNA  length = 354 |
|---|---|
| FEATURE | Location/Qualifiers |
| source | 1..354 |
| | mol_type = genomic DNA |
| | organism = Saccharomyces cerevisiae |

SEQUENCE: 93
```
actagttcta gagcggccgc caccgcggtg ggcgaatttc ttatgattta tgattttat     60
tattaaataa gttataaaaa aaataagtgt atacaaattt taaagtgact cttaggttt    120
aaaacgaaaa ttcttattct tgagtaactc tttcctgtag gtcaggttgc tttctcaggt   180
atagcatgag gtcgctctta ttgaccacac ctctaccggc atgccagca aatgcctgca    240
aatcgctccc catttcaccc aattgtagat atgctaactc cagcaatgag ttgatgaatc    300
tcggtgtgta ttttatgtcc tcagaggaca acacctgttg taatcgttct tcca          354
```

| SEQ ID NO: 94 | moltype = DNA  length = 301 |
|---|---|
| FEATURE | Location/Qualifiers |
| source | 1..301 |
| | mol_type = genomic DNA |
| | organism = Saccharomyces cerevisiae |

SEQUENCE: 94
```
gcggatctct tatgtcttta cgatttatag ttttcattat caagtatgcc tatattagta    60
tatagcatct ttagatgaca gtgttcgaag tttcacgaat aaaagataat attctacttt   120
ttgctcccac cgcgttttgct agcacgagtg aacaccatcc ctcgcctgtg agttgtaccc  180
attcctctaa actgtagaca tggtagcttc agcagtgttc gttatgtacg gcatcctcca   240
acaaacagtc ggttatagtt tgtcctgctc ctctgaatcg tctccctcga tatttctcat   300
t                                                                    301
```

| SEQ ID NO: 95 | moltype = DNA  length = 299 |
|---|---|
| FEATURE | Location/Qualifiers |
| source | 1..299 |
| | mol_type = genomic DNA |
| | organism = Saccharomyces cerevisiae |

```
SEQUENCE: 95
gattaatata attatataaa aatattatct tcttttcttt atatctagtg ttatgtaaaa      60
taaattgatg actacggaaa gctttttat attgtttctt tttcattctg agccacttaa     120
atttcgtgaa tgttcttgta agggacggta gatttacaag tgatacaaca aaaagcaagg    180
cgcttttct aataaaaaga agaaaagcat ttaacaattg aacacctcta tatcaacgaa     240
gaatattact ttgtctctaa atccttgtaa aatgtgtacg atctctatat gggttactc     299

SEQ ID NO: 96           moltype = DNA   length = 299
FEATURE                 Location/Qualifiers
source                  1..299
                        mol_type = genomic DNA
                        organism = Saccharomyces cerevisiae
SEQUENCE: 96
gtgtgcgtaa tgagttgtaa aattatgtat aaacctactt tctctcacaa gtactatact      60
tttataaaac gaactttatt gaatgaata tccttttttt cccttgttac atgtcgtgac     120
tcgtactttg aacctaaatt gttctaacat caaagaacag tgttaattcg cagtcgagaa    180
gaaaaatatg gtgaacaaga ctcatctact tcatgagact actttacgcc tcctataaag    240
ctgtcacact ggataaattt attgtaggac caagttacaa aagaggatga tggaggttt     299

SEQ ID NO: 97           moltype = DNA   length = 305
FEATURE                 Location/Qualifiers
source                  1..305
                        mol_type = genomic DNA
                        organism = Saccharomyces cerevisiae
SEQUENCE: 97
ggatcctaaa gtgcttttaa ctaagaatta ttagtctttt ctgcttattt tttcatcata      60
gtttagaaca ctttatatta acgaatagtt tatgaatcta tttaggttta aaaattgata    120
cagtttata agttacttt tcaaagactc gtgctgtcta ttgcataatg cactggaagg      180
ggaaaaaaaa ggtgcacacg cgtggcttt tcttgaattt gcagtttgaa aaataactac     240
atggatgata agaaaacatg gagtacagtc actttgaaga ccttcaatca gctggtaacg    300
tcttc                                                                305

SEQ ID NO: 98           moltype = DNA   length = 300
FEATURE                 Location/Qualifiers
source                  1..300
                        mol_type = genomic DNA
                        organism = Saccharomyces cerevisiae
SEQUENCE: 98
tcgtcataaa atgctcccat ctcaaaagta gggcaaaatt catgatcgac cgcgcaaaat      60
aaatagattt gcaaataagt tttgtatgta catttattaa tatatataat atatcaaaag    120
aaaaaaatca aaaaaaaaaa aaaaaaaaaa ttgcactctt attcagtcat caattacaaa    180
acctagagat agcgatggtg catattcaat aaaaaactcc ttatactgtc gagaaagctt    240
attattggta cttctcgaag atactaaaaa aggttaattt ttggagacgg aggcaatagc    300

SEQ ID NO: 99           moltype = DNA   length = 301
FEATURE                 Location/Qualifiers
source                  1..301
                        mol_type = genomic DNA
                        organism = Saccharomyces cerevisiae
SEQUENCE: 99
attgaattga attgaaatcg atagatcaat ttttttcttt tctctttccc catcctttac      60
gctaaaataa tagtttattt tatttttga atatttttta tttatatacg tatatataga     120
ctattattta tcttttaatg attattaaga ttttttattaa aaaaaaattc gctcctcttt    180
taatgccttt atgcagtttt tttttcccat tcgatatttc tatgttcggg ttcagcgtat    240
tttaagttta ataactcgaa aattctgcgt tcgttaaagc tttcgagaag gatattattt    300
a                                                                    301

SEQ ID NO: 100          moltype = DNA   length = 300
FEATURE                 Location/Qualifiers
source                  1..300
                        mol_type = genomic DNA
                        organism = Saccharomyces cerevisiae
SEQUENCE: 100
taaagtaaga gcgctacatt ggtctacctt tttgttcttt tacttaaaca ttagttagtt      60
cgttttcttt ttctcatttt tttatgtttc ccccccaaag ttctgatttt ataatatttt    120
atttcacaca attccattta acagaggggg aatagattct ttagcttaga aaattagtga    180
tcaatatata tttgcctttc ttttcatctt ttcagtgata ttaatggttt cgagacactg    240
caatggcccct agttgtctaa gaggatagat gttactgtca aagatgatat tttgaatttc    300

SEQ ID NO: 101          moltype = DNA   length = 300
FEATURE                 Location/Qualifiers
source                  1..300
                        mol_type = genomic DNA
                        organism = Saccharomyces cerevisiae
SEQUENCE: 101
gaagttttgt tagaaaataa atcatttttt aattgagcat tcttattcct attttattta      60
aatagtttta tgtattgtta gctacataca acagtttaaa tcaaatttc ttttttcccaa    120
gtccaaaatg gaggttatt tgatgacccc gcatgcgatt atgttttgaa agtataagac     180
tacatacatg tacatatatt taaacatgta aacccgtcca ttatattgct tacttttcttc    240
```

```
ttttttgccg ttttgacttg gacctctggt ttgctatttc cttacaatct ttgctacaat    300

SEQ ID NO: 102              moltype = DNA   length = 300
FEATURE                     Location/Qualifiers
source                      1..300
                            mol_type = genomic DNA
                            organism = Saccharomyces cerevisiae
SEQUENCE: 102
gcggattgag agcaaatcgt taagttcagg tcaagtaaaa attgatttcg aaaactaatt     60
tctcttatac aatcctttga ttggaccgtc atcctttcga atataagatt ttgttaagaa    120
tattttagac agagatctac tttatattta atatctagat attacataat ttcctctcta    180
ataaaatatc attaataaaa taaaaatgaa gcgatttgat tttgtgttgt caacttagtt    240
tgccgctatg cctcttgggt aatgctatta ttgaatcgaa gggctttatt atattaccct    300

SEQ ID NO: 103              moltype = DNA   length = 300
FEATURE                     Location/Qualifiers
source                      1..300
                            mol_type = genomic DNA
                            organism = Saccharomyces cerevisiae
SEQUENCE: 103
gctggttgat ggaaaatata atttttattgg gcaaactttt gttatctgaa tgtgttttat     60
actattatct ttttaattaa tgattctata tacaaacctg tatatttttt ctttaaccaa    120
ttttttttt tatagaccta gagctgtact tttattctgc tatcaagcaa accctaccc     180
cctcttctca atcctcccct caggcagaac ttatctacct gtatcaagga gcggacgagg    240
gagtcctaat tgttctacgt ataccaatgc tagcagctta cataggtggt ggcactacca    300

SEQ ID NO: 104              moltype = DNA   length = 300
FEATURE                     Location/Qualifiers
source                      1..300
                            mol_type = genomic DNA
                            organism = Saccharomyces cerevisiae
SEQUENCE: 104
tcgaatttac gtagcccaat ctaccacttt ttttttttcat tttttaaagt gttatactta     60
gttatgctct aggataatga actacttttt tttttttttt tttactgtta tcataaatat    120
atataccttta ttgttgtttg caaccgtcgg ttaattcctt atcaaggttc cccaagttcg    180
gatcattacc atcaatttcc aacatttcat tgagttcttc ttcttcatta ccgtgtttta    240
gggggctgtt cgcacttcta ataggggctat caccaagctg ttctaattcg tccaaaagtt    300

SEQ ID NO: 105              moltype = AA    length = 1219
FEATURE                     Location/Qualifiers
source                      1..1219
                            mol_type = protein
                            note = strain ATCC 29366 / DSM 635 / J-10-fl
                            organism = Chloroflexus aurantiacus
SEQUENCE: 105
MSGTGRLAGK IALITGGAGN IGSELTRRFL AEGATVIISG RNRAKLTALA ERMQAEAGVP     60
AKRIDLEVMD GSDPVAVRAG IEAIVARHGQ IDILVNNAGS AGAQRRLAEI PLTEAELGPG    120
AEETLHASIA NLLGMGWHLM RIAAPHMPVG SAVINVSTIF SRAEYYGRIP YVTPKAALNA    180
LSQLAARELG ARGIRVNTIF PGPIESDRIR TVFQRMDQLK GRPEGDTAHH FLNTMRLCRA    240
NDQGALERRF PSVGDVADAA VFLASAESAA LSGETIEVTH GMELPACSET SLLARTDLRT    300
IDASGRTTLI CAGDQIEEVM ALTGMLRTCG SEVIIGFRSA AALAQFEQAV NESRRLAGAD    360
FTPPIALPLD PRDPATIDAV FDWAGENTGG IHAAVILPAT SHEPAPCVIE VDDERVLNFL    420
ADEITGTIVI ASRLARYWQS QRLTPGARAR GPRVIFLSNG ADQNGNVYGR IQSAAIGQLI    480
RVWRHEAELD YQRASAAGDH VLPPVWANQI VRFANRSLEG LEFACAWTAQ LLHSQRHINE    540
ITLNIPANIS ATTGARSASV GWAESLIGLH LGKVALITGG SAGIGGQIGR LLALSGARVM    600
LAARDRHKLE QMQAMIQSEL AEVGYTDVED RVHIAPGCDV SSEAQLADLV ERTLSAFGTV    660
DYLINNAGIA GVEEMVIDMP VEGWRHTLFA NLISNYSLMR KLAPLMKKQG SGYILNVSSY    720
FGGEKDAAIP YPNRADYAVS KAGQRAMAEV FARFLGPEIQ INAIAPGVPE GDRLRGTGER    780
PGLFARRARL ILENKRLNEL HAALIAAART DERSMHELVE LLLPNDVAAL EQNPAAPTAL    840
RELARRFRSE GDPAASSSSA LLNRSIAAKL LARLHNGGYV LPADIFANLP NPPDPFFTRA    900
QIDREARKVR DGIMGMLYLQ RMPTEFDVAM ATVYYLADRN VSGETFHPSG GLRYERTPTG    960
GELFGLPSPE RLAELVGSTV YLIGEHLTEH LNLLARAYLE RYGARQVVMI VETETGAETM   1020
RRLHDHVEA GRLMTIVAGD QIEAAIDQAI TRYGRPGPVV CTPFRPLPTV PLVGRKDSDW   1080
STVLSEAEFA ELCEHQLTHH FRVARKIALS DGASLALVTP ETTATSTTEQ FALANFIKTT   1140
LHAFTATIGV ESERTAQRIL INQVDLTRRA RAEEPRDPHE RQQELERFIE AVLLVTAPLP   1200
PEADTRYAGR IHRGRAITV                                                1219

SEQ ID NO: 106              moltype = AA    length = 297
FEATURE                     Location/Qualifiers
source                      1..297
                            mol_type = protein
                            organism = Arthrobacter enclensis
SEQUENCE: 106
MTDQYTFRNP VTAYEHISPP EQHQPEPGLD AALTPKADLG EDTYRGTGRL DGRRAVVTGA     60
DSGIGAATAI AFAREGADVV LSYLPEEEED AARIAGIIEA AGRKAVKVPG DLKDPASCRE    120
VVDTAVAVLG GIDILVNNAG KQVAQKDIAD ITDEQFDHTL KTNVYAMFWL TKAALPHMPA    180
GSAIINTTSI QAYNPSPTLV DYATTKASIN NFTKGLAQQL APRGIRVNAV APGPIWTPLQ    240
VSSGQPKEEL PEFGQSTPLG RAGQPAELAP AYVFLASAES SYVVGETLNV NGGSPTP       297
```

```
SEQ ID NO: 107           moltype = AA  length = 292
FEATURE                  Location/Qualifiers
source                   1..292
                         mol_type = protein
                         note = strain ATCC 14579 / DSM 31 / JCM 2152 / NBRC 15305 /
                           NCIMB 9373 / NRRL B-3711
                         organism = Bacillus cereus
SEQUENCE: 107
MEHKTLSIGF IGIGVMGKSM VYHLMQDGHK VYVYNRTKAK TDSLVQDGAN WCNTPKELVK   60
QVDIVMTMVG YPHDVEEVYF GIEGIIEHAK EGTIAIDFTT STPTLAKRIN EVAKRKNIYT  120
LDAPVSGGDV GAKEAKLAIM VGGEKEIYDR CLPLLEKLGT NIQLQGPAGS GQHTKMCNQI  180
AIASNMIGVC EAVAYAKKAG LNPDKVLESI STGAAGSWSL SNLAPRMLKG DFEPGFYVKH  240
FMKDMKIALE EAERLQLPVP GLSLAKELYE ELIKDGEENS GTQVLYKKYI RG          292

SEQ ID NO: 108           moltype = AA  length = 248
FEATURE                  Location/Qualifiers
source                   1..248
                         mol_type = protein
                         note = strain K12
                         organism = Escherichia coli
SEQUENCE: 108
MIVLVTGATA GFGECITRRF IQQGHKVIAT GRRQERLQEL KDELGDNLYI AQLDVRNRAA   60
IEEMLASLPA EWCNIDILVN NAGLALGMEP AHKASVEDWE TMIDTNNKGL VYMTRAVLPG  120
MVERNHGHII NIGSTAGSWP YAGGNVYGAT KAFVRQFSLN LRTDLHGTAV RVTDIEPGLV  180
GGTEFSNVRF KGDDGKAEKT YQNTVALTPE DVSEAVWWVS TLPAHVNINT LEMMPVTQSY  240
AGLNVHRQ                                                          248

SEQ ID NO: 109           moltype = AA  length = 267
FEATURE                  Location/Qualifiers
source                   1..267
                         mol_type = protein
                         note = strain ATCC 204508 / S288c
                         organism = Saccharomyces cerevisiae
SEQUENCE: 109
MSQGRKAAER LAKKTVLITG ASAGIGKATA LEYLEASNGD MKLILAARRL EKLEELKKTI   60
DQEFPNAKVH VAQLDITQAE KIKPFIENLP QEFKDIDILV NNAGKALGSD RVGQIATEDI  120
QDVFDTNVTA LINITQAVLP IFQAKNSGDI VNLGSIAGRD AYPTGSIYCA SKFAVGAFTD  180
SLRKELINTK IRVILIAPGL VETEFSLVRY RGNEEQAKNV YKDTTPLMAD DVADLIVYAT  240
SRKQNTVIAD TLIFPTNQAS PHHIFRG                                     267

SEQ ID NO: 110           moltype = AA  length = 354
FEATURE                  Location/Qualifiers
source                   1..354
                         mol_type = protein
                         note = strain SC5314 / ATCC MYA-2876
                         organism = Candida albicans
SEQUENCE: 110
MLRTSIRAFS TQPRLSTNYG FIGLGLMGQH MARHVYNQLE PSDKLYVYDV DPKHTTQFLT   60
EVTSQTPQNA PLLTPLNSLK DFTTEVDSQL DFIVTMVPEG KHVKSVVSEL VGHYKSTGNY  120
DPSIKTTFLD SSTIDIPTSR DVHQLVKSSI PEFDFIDTPV SGGVAGARKG TLSFMLSRET  180
HDDIDPSLTA LLSKMGINIF PCGATHGTGL AAKLANNYLL AITNIAAADS FQLAESFGLN  240
LQNYAKLVAV STGKSWASVD NCPIPGVYPD NNLPSDVNYE GGFITKLTRK DVVLATESAK  300
FNNRFLMLGD IGRHWYDKAC EREDIANRDL SVLFEWLGDL KQNEKGDVID VKRK        354

SEQ ID NO: 111           moltype = AA  length = 497
FEATURE                  Location/Qualifiers
source                   1..497
                         mol_type = protein
                         note = strain ATCC 15692 / DSM 22644 / CIP 104116 / JCM
                           14847 / LMG 12228 / 1C / PRS 101 / PAO1
                         organism = Pseudomonas aeruginosa
SEQUENCE: 111
MGTLHHLING EMVADNGRSA DVFNPSTGEA IHKVPLADGK TLQKAIDAAR AAFPAWRNTP   60
PAKRAQVLYR FKQLLEQNEA RISKLISEEH GKTLEDAAGE LKRGIENVEY ACAAPEILKG  120
EYSRNVGPNI DAWSDFQPIG VVAGITPFNF PAMVPLWMYP LAIACGNTFI LKPSERDPSS  180
TLLIAELFHE AGLPKGVLNV VHGDKEAVDG LLQAPEVKAI SFVGSTPIAE YIYAEGTKRG  240
KRVQALGGAK NHAVLMPDAD LDNAVSALMG AAYGSCGERC MAISVAVCVG DQVADALIAK  300
LVPIKALKI GAGTSCGLDM GPLVTAAAQH KVTGYIDSGV AQGAELVVDG RGYQVAGHEN  360
GFFLGGSLFD RVTPEMTIYK EEIFGPVLCV VRVNSLEEAM QLINDHEYGN GTCIFTRDGE  420
AARLFCDEIE VGMVGVNVPL PVPVAYHSFG GWKRSLFGDL HAYGPDGVRF YTRRKAITQR  480
WPQRASHEAS QFAFPSL                                                497

SEQ ID NO: 112           moltype = AA  length = 541
FEATURE                  Location/Qualifiers
source                   1..541
                         mol_type = protein
                         note = strain SC5314 / ATCC MYA-2876
                         organism = Candida albicans
SEQUENCE: 112
```

```
MTNIAASKLA TRNKSIISLS STTTEYPKGH TTANDEPYLT PSFVNNEFIK SESDTWFDIH   60
DPATNNVVSK VPQSTPEELE DAIASAHKAF PKWRDTSIIK RQGIAFKFVQ LLRENMDRIA  120
SVIVLEQGKT FADAQGDVLR GLQVAEAACN VTNDLKGESL EVATDMETKM IREPLGVIGS  180
ICPFNFPAMV PLWSLPLVLV TGNTAVVKPS ERVPGAAMII CELAAKAGVP AGVLNIVHGK  240
HDTVNKLIDD PRIKALTFVG GDKAGKYIYE RGSQLGKRVQ ANLGAKNHLV VLPDANKQSF  300
VNAVNGAAFG AAGQRCMAIS VLVTVGKTTK EWVKDVVADA KLLKTGSGFD PKSDLGPVIN  360
PESLTRAEEI IEDSVQNGAV LELDGRGYKP TNDPEQKFTK GNFLAPTILT NVKPGMRAYD  420
EEIFAPVLAV VNVDTIDEAI ELINSNKYGN GVSLFTNSGG SAQYFTKRID VGQVGINVPI  480
PVPLPMFSFT GSRGSFLGDL NFYGKAGITF LTKPKTITSA WKLNSVDEEI LKPSTSMPIQ  540
Q                                                                541

SEQ ID NO: 113          moltype = AA  length = 488
FEATURE                 Location/Qualifiers
source                  1..488
                        mol_type = protein
                        note = serovar 1/2a (strain ATCC BAA-679 / EGD-e)
                        organism = Listeria monocytogenes
SEQUENCE: 113
MADVRKLKNY IDGEWVESKT DKYEDVINPA TGEVLCQVPI STRAELDQAA VIAEQAFEKW   60
SQVAVPRRAR VLFGFQQLLI QHKEELARLI TLENGKNLSE ARGEVQRGIE NVEFAAGAPT  120
LMMGDSLASI ATDVEAANYR YPVGVVGGIA PFNFPMMVPC WMFPMAIALG NSFILKPSER  180
TPLLMEKLVE LFSEAGLPKG VFNVVYGAHD VVNGILENEI IKAVSFVGSK PVGEYVYKTG  240
SANLKRVQAL TGAKNHTIVL NDADLEDTVT NVISAAFGSA GERCMACAVV TVEEGIADEF  300
LEALRTAAQN VKIGNGLDDG VFLGPVIREE NQKRTIAYIE KGIEEGAKLT VDGRETGLSE  360
GHFVGPTILE DVTTDMTIWK DEIFAPVLSV IRVKNLQEAV RVANQSEFAN GACIFTNNAK  420
AIRYFREKID AGMLGVNLGV PAPMAFFPFS GWKSSFYGTL HANGKDSVDF YTHKKVVTAR  480
YSLKGYEE                                                         488

SEQ ID NO: 114          moltype = AA  length = 487
FEATURE                 Location/Qualifiers
source                  1..487
                        mol_type = protein
                        note = subsp. natto
                        organism = Bacillus subtilis
SEQUENCE: 114
MAEIRKLKNY INGEWVESKT DQYEDVVNPA TKEVLCQVPI STKEDIDYAA QTAAEAFETW   60
SKVAVPRRAR ILFNFQQLLS QHKEELAHLI TIENGKNTKE ALGEVGRGIE NVEFAAGAPS  120
LMMGDSLASI ATDVEAANYR YPIGVVGGIA PFNFPMMVPC WMFPMAIALG NTFILKPSER  180
TPLLTEKLVE LFEKAGLPKG VFNVVYGAHD VVNGILEHPE IKAISFVGSK PVGEYVYKKG  240
SEHLKRVQSL TGAKNHTIVL NDANLEDTVT NIVGAAFGSA GERCMACAVV TVEEGIADEF  300
MAKLQEKVAD IKIGNGLDDG VFLGPVIRED NKKRTLSYIE KGLEEGARLV CDGRENVSDD  360
GYFVGPTIFD NVTTEMTIWK DEIFAPVLSV IRVKNLKEAI EIANKSEFAN GACLFTSNSN  420
AIRYFRENID AGMLGINLGV PAPMAFFPFS GWKSSFFGTL HANGKDSVDF YTRKKVVTAR  480
FPAPDFN                                                          487

SEQ ID NO: 115          moltype = AA  length = 504
FEATURE                 Location/Qualifiers
source                  1..504
                        mol_type = protein
                        note = strain ATCC 43291 / DSM 13513 / N-1
                        organism = Cupriavidus necator
SEQUENCE: 115
MTAPYTSPSE VIHYVSGEPY EGNGKRAQAV FNPATGAVAR QVRLGTVEDV DAAVASAVAA   60
FPKWADTPPI RRARVMLKFL ELMNQHKDEL AAIITAEHGK VLSDAAGEVS RGIDIIEFAC  120
GVPQLLKGDF TDQVSTGMDN WTLRQPLGVV AGITPFNFPM MVPCWMFPVA IATGNCFILK  180
PSERDPSASL FMARLLKEAG LPDGVFNVIQ GDKTVVDALL HHRDVKAVSF VGSTPIANYI  240
YETGARLGKR VQALGGAKNH MVVMPDADID QALDGLIGAA YGSAGERCMA ISVAVLVGDV  300
ADKIMPKLEA RARELVIKNG MEADAEMGPV VTGQALERIE NYIALGVEEG AKLVVDGRNY  360
KVPGHEQGFF TGGTLFDNVT PEMRIYKEEI FGPVLSCVRV DDFAQAVKLI NEHEFGNGVA  420
CYTRDGQVAR EFCRRIEVGM VGINVPIPVP MAWHGFGGWK RSLFGDMHAY GEEGVRFYTR  480
QKSIMQRWPN DTARGAEFAM PTAK                                        504

SEQ ID NO: 116          moltype = AA  length = 486
FEATURE                 Location/Qualifiers
source                  1..486
                        mol_type = protein
                        organism = Bacillus cereus
SEQUENCE: 116
MITTEIKRVK NHINGEWVES TGTEVEVVPN PATGKIIAYV PLSPKEDVEK AVEAAKAAYE   60
KWSKVPVPNR SRQLYKYLQL LQENKEELAK IITLENGKTL TDATGEVQRG IEAVELATSA  120
PNLMMGQALP NIASGIDGSI WRYPIGVVAG ITPFNFPMMI PLWMFPLAIA CGNTFVLKTS  180
ERTPLLAERL VELFYEAGFP KGVLNLVQGG KDVVNSILEN KDIQAVSFVG SEPVARYVYE  240
TGTKHGKRVQ ALAGKNHAI VMPDCNLEKT VQGVIGSAFA SSGERCMACS VVAVVEIADK  300
EFIDVLVAET KKLKVGDGFN EDNYVGPLIR ESHKERVLGY INSGVADGAT LLVDGRKINE  360
EVGEGYFVGA TIFDGVNQEM KIWQDEIFAP VLSIVRVKDL EEGIKLTNQS KFANGAVIYT  420
SNGKHAQTFR DNIDAGMIGV NVNVPAPMAF FAFAGNKASF FGDLGTNGTD GVQFYTRKKV  480
VTERWF                                                           486

SEQ ID NO: 117          moltype = AA  length = 503
```

```
FEATURE              Location/Qualifiers
source               1..503
                     mol_type = protein
                     note = HTNK1
                     organism = Halomonas sp.
SEQUENCE: 117
MTIKRIEHYI NGHKTNGVAD SHQEVTNPAT GQVTGQVALA SQADVDSAVA AAQAAFPAWS    60
DTPPIRRARV MFKFLELLNA HKDELAEAIT REHGKVFTDA QGEVARGIDI VEFACGIPQL   120
LKGDYTEQVS TGIDNWTTRQ PLGVVAGITP FNFPVMVPMW MPPLAIAAGN SFVLKPSPLD   180
PSASLMMADL LKQAGLPDGV FNVVQGDKDS VEALIDHPDV KALSFVGSTP IANLIYERGA   240
RSGKRIQALG GAKNHMVVMP DANLDKAVDA LIGAAYGSAG ERCMAISVAV LVGDVADKIV   300
PRLAERARDL KIKNGLELDA EMGPIVTSQA HQRITGYIEK GVAEGAEMVV DGRDFDSSVT   360
GEGCADGFWM GGTLFDHVTP EMTIYREEIF GPVLACVRVP DVATAIQLIN DHEFGNGVSC   420
FTESGSVARE FGRRIQVGMV GINVPIPVPM AWHGFGGWKR SMFGDTHAYG EEGVRFYTKQ   480
KSIMQRWSDS IDAGAEFAMP TAK                                          503

SEQ ID NO: 118       moltype = AA  length = 492
FEATURE              Location/Qualifiers
source               1..492
                     mol_type = protein
                     organism = Lactobacillus casei
SEQUENCE: 118
MDTTKQNVKT LKNFINGKWV DAKTETFENV YNPATGDVLA RVPHSTSEDV ADAVTAAKEA    60
FKIWQKVSIP KRAKILFKYQ QLLVEHQEEL GRIVTEENGK SLDEAVAEVG RGIENVEFAA   120
GVPTLMMGDS LSSVATDVEA TNYRYPIGVV GGITPFNFPM MVPCWMFPMA VATGNTFILK   180
PSEKTPLTSQ RLVELFQEAG LPDGVLNIVN GAVDVVNGIL DHPDIKAISF VGSERVGEYV   240
YKRGSDHLKR VQALTGAKNH TIVLADADLD AAVKGIISSS FGSAGERCMA TSVLVLQDEI   300
ADKFMAKFTQ AAKDIKIGNG LDKGVFLGPV IRKENQERTL NYIQTGVKEG AKLVLDGSAE   360
AKKHDGYFVG PTIFEDVKTD MTIWHDEMFA PVLSVIRAKD LPQAVAIANT SELANGACLF   420
TDSAASIRYF RENIDAGMLG INLGVPAPIA VFPFSGWKHS FFGTLHANGK DSVDFYTHKK   480
VVTARYDQRR FK                                                      492

SEQ ID NO: 119       moltype = AA  length = 1822
FEATURE              Location/Qualifiers
source               1..1822
                     mol_type = protein
                     organism = Chloroflexus aurantiacus
SEQUENCE: 119
MIDTAPLAPP RAPRSNPIRD RVDWEAQRAA ALADPGAFHG AIARTVIHWY DPQHHCWIRF    60
NESSQRWEGL DAATGAPVTV DYPADYQPWQ QAFDDSEAPF YRWFSGGLTN ACFNEVDRHV   120
TMGYGDEVAY YFEGDRWDNS LNNGRGGPVV QETITRRRLL VEVVKAAQVL RDLGKKGDR   180
IALNMPNIMP QIYYTEAAKR LGILYTPVFG GFSDKTLSDR IHNAGARVVI TSDGAYRNAQ   240
VVPYKEAYTD QALDKYIPVE TAQAIVAQTL ATLPLTESQR QTIITEVEAA LAGEITVERS   300
DVMRGVGSAL AKLRDLDASV QAKVRTVLAQ ALVESPPRVE AVVVVRHTGQ EILWNEGRDR   360
WSHDLLDAAL AKILANARAA GFDVHSENDL LNLPDDQLIR ALYASIPCEP VDAEYPMFII   420
YTSGSTGKPK GVIHVGGYV AGVVHTLRVS FDAEPGDTIY VIADPGWITG QSYMLTATMA   480
GRLTGVIAEG SPLFPSAGRY ASIIERYGVQ IFKAGVTFLK TVMSNPQNVE DVRLYDMHSL   540
RVATFCAEPV SPAVQQFGMQ IMTPQYINSY WATEHGGIVW THFYGNQDFP LRPDAHTYPL   600
PWVMGDVWVA ETDESGTTRY RVADFDEKGE IVITAPYPYL TRTLWGDVPG FEAYLRGEIP   660
LRAWKGDAER FVKTYWRRGP NGEWGYIQGD FAIKYPDGSF TLHGRSDDVI NVSGHRMGTE   720
EIEGAILRDR QITPDSPVGN CIVVGAPHRE KGLTPVAFIQ PAPGRHLTGA DRRRLDELVR   780
TEKGAVSVPE DYIEVSAFPE TRSGKYMRRF LRNMMLDEPL GDTTTLRNPE VLEEIAAKIA   840
EWKRRQRMAE EQQIIERYRY FRIEYHPPTA SAGKLAVVTV TNPPVNALNE RALDELNTIV   900
DHLARRQDVA AIVFTGQGAR SFVAGADIRQ LLEEIHTVEE AMALPNNAHL AFRKIERMNK   960
PCIAAINGVA LGGGLEFAMA CHYRVADVYA EFGQPEINLR LLPGYGGTQR LPRLLYKRNN  1020
GTGLLRALEM ILGGRSVPAD EALELGLIDA IATGDQDSLS LACALARAAI GADGQLIESA  1080
AVTQAFRHRH EQLDEWRKPD PRFADDELRS IIAHPRIERI IRQAHTVGRD AAVHRALDAI  1140
RYGIIHGFEA GLEHEAKLFA EAVVDPNGGK RGIREFLDRQ SAPLPTRRPL ITPEQEQLLR  1200
DQKELLPVGS PFFPGVDRIP KWQYAQAVIR DPDTGAAAHG DPIVAEKQII VPVERPRANQ  1260
ALIYVLASEV NFNDIWAITG IPVSRFDEHD RDWHVTGSGG IGLIVALGEE ARREGRLKVG  1320
DLVAIYSGQS DLLSPLMGLD PMAADFVIQG NDTPDGSHQQ FMLAQAPQCL PIPTDMSIEA  1380
AGSYILNLGT IYRALFTTLQ IKAGRTIFIE GAATGTGLDA ARSAARNGLR VIGMVSSSSR  1440
ASTLLAAGAH GAINRKDPEV ADCFTRVPED PSAWAAWEEA GQPLLAMFRA QNDGRLADYV  1500
VSHAGETAFP RSFQLLGEPR DGHIPTLTFY GATSGYHFTF LGKPGSASPT EMLRRANLRA  1560
GEAVLIYYGV GSDDLVDTGG LEAIEEARQM GARIVVVTVS DAQREFVLSL GFGAALRGVV  1620
SLAELKRRFG DEFEWPRTMP PLPNARQDPQ GLKEAVRRFN DLVFKPLGSA VGVFLRSADN  1680
PRGYPDLIIE RAAHDALAVS AMLIKPFTGR IVYFEDIGGR RYSFFAPQIW VRQRRIYMPT  1740
AQIFGTHLSN AYEILRLNDE ISAGLLTITE PAVVPWDELP EAHQAMWENR HTAATYVVNH  1800
ALPRLGLKNR DELYEAWTAG ER                                         1822

SEQ ID NO: 120       moltype = AA  length = 535
FEATURE              Location/Qualifiers
source               1..535
                     mol_type = protein
                     note = strain MD-66 / DSM 9485
                     organism = Chloroflexus aggregans
SEQUENCE: 120
MSIIHSHIQT NSADFQANFA YHQALAADLR ERLAKIRQGG GPEQRRRHEE RGKLFVRDRI    60
DTLIDPDSAF LEIGALAAYN VYDEEVPAAG IVCGIGRVTG RPVMIIANDA TVKGGTYFPL   120
```

```
TVKKHLRAQE IARENRLPCI YLVDSGGAYL PLQSEVFPDR DHFGRIFYNQ AQMSAEGIPQ      180
IACVMGSCTA GGAYVPAMSD EVVIVKGNGT IFLGGPPLVK AATGEEVTAE ELGGADVHTR      240
ISGVADYFAN DDREALAIVR DIVAHLGPRQ RAQWELRDPE PPRYDPHEIY GILPRDFRQS      300
YDVREVIARI VDGSRLHEFK ARYGTTLVCG FAHIEGFPVG ILANNGILFS ESALKGAHFI      360
ELCCARNIPL VFLQNITGFM VGKQYENGGI AKDGAKLVTA VSCANVPKFT VIIGGSFGAG      420
NYGMCGRAFQ PRQLWMWPNA RISVMGGMQA ANVLLTVRRD NLRARGQDMT PEEQERFMAP      480
ILAKYEQEGH PYYASARLWD DGVIDPVETR RVLALGLAAA AEAPIQPTRF GVFRM           535

SEQ ID NO: 121         moltype = AA  length = 1912
FEATURE                Location/Qualifiers
source                 1..1912
                       mol_type = protein
                       note = strain DSM 13941 / HL08
                       organism = Roseiflexus castenholzii
SEQUENCE: 121
MTTIESALRP PRINPVRTRA DWEAQRKAAL TDPGAFHGAI ARSAIHWYDR HLDAWITWDE       60
EEGCWKGLRY SDGAPIDVPY GPDHEPWERA FNGDDPPFYR WFEGGLTNAC FNEVDRHVLT      120
GYGDEVAFYF EGDRWDSSLN NGRGGPVVSF AVTRKQLMLE VVKAAQVLRD LGLNMGDRIA      180
LNMPNIMEQL YYTEAAKRLG IIYTPVFGGF SDKTLSDRIH NAGARLVITS DGAYRNAQVV      240
PYKEQYTDQA LDKFVPVETA LDIIEAALSG SEGSPVPGAP LLAPDQIKHI LAQVRDALKE      300
DITIERSDAM RAVGRAIEGL TGVDALAQSR ARTAVAQALV NTPPRVDAVI VVRHTGQDIL      360
WRPERDRWSH ELTARALETI LANARAVGVE VYSEDELLNL PTDQFVKALY ATSRAEPLDA      420
EYPMFIIYTS GSTGKPKGVV HVHGGYVAGV AYTMRVSFDA EPGDTIYVVA DPGWITGQSY      480
MICATLTTRC TGIITEGSPV FPSAGRFASI IERYKVRIFK AGVTFLKTVM SDPQNTADAR      540
QYDMSSLRVC TFCAEPVSPA VQQFGMELMS PQYINSYWAT EHGGIVWTHF YGNEDFPLRP      600
DAHTYPLPWI AGEVWVLEGG DRDATGAEAP RYRIADYEEK GEIVITAPYP YLTRTIWGDV      660
KGFEAWVAAM QHGNGATAPR WRGDAERFIK TYWRRGPNDE WGYIQGDFAM KYPDGSFTLH      720
GRSDDVINVS GHRMGTEEIE GAILRDKIIT PDSPVGNCIV VGAPHREKGL TPVAFILTAP      780
GRKLTGEDRR RLNELVRNEK GAVSVPEDYI EVSAFPETRS GKYMRRFLRN LMLGEPLGDT      840
TTLRNPESLK EIAEKIEAWK RKQRMAEEQR IFERYRYFRI EYHAVRERWT PSGNGSAAAE      900
QKALTQRIAI VTVTNPPVNA LNERALDELN TIVDHLARRE DVAAVVFTGS GTKSFVAGAD      960
IKQMLEEMHT VEDAMALPNN AHLAFRKIET MNKPCIAAIN GVALGGGMEF ALACHYRIAD     1020
LHAEFGQPEI NLRLLPGYGG TQRLPRLLYS RRGEAGLIKA LMIIMGGRTL NAERAYEIGL     1080
IDKVAHGHEE ALTLATQMAR EMILAERNGK PTELRVIPNT SDDPTTFFSP PHDPATAGEG     1140
LWPPLPEAYA LRRQLTAQWE TPDPAMVDLL EKALRDPLIT RIINQAQWAG RARAIERIID     1200
ALRTGFTKGM LAGLEREARL FAEAVVAPDE GKIGIQDFLD KRSAPLPTRR RIHLTPDEEK     1260
RMIDAGMLLP IGAPFFPGVT PIPVAQYAMA VVRDEVGTAP AHGDPIEAEK QIIIPVEKPG     1320
PNDVLLYILA SEVNFNDIWA ITGVPVSQFD EHDRDWHVTG SGGIGLIVSV GEETKREGRL     1380
KVGDLVAIYS GQNDLLSPMV GLDPMAADFV IQGYNTPDAS HQQFMVAQAP QCFPVLPDLT     1440
LEAAGSYMLN LGTVYRALFT TLKIQPGRRI FVEGAATGTG LDAARSAARN GLYVTGMVSS     1500
QERAAVVRAA GAVGVINRRD PRYAGIFTRV PEDPAKWAEW EAAGRPLLED YRAQNGGHLA     1560
DYAVSHAGET AFPRSFQLLG EPHDGHIPTL TFYGASSGYH FTFLGKPGAA DPVEMLRRAG     1620
LRAGEAVMIY YGVDDRSYLG DEGYESGAVP ETLERRTTLV DQVGLEAIES ARAMGARIVV     1680
VTYTDAQREF VLSLGFGASL KGVVSLEELH RRYGDEFDWP ETMPPLPDAK SDIHGFKAAV     1740
RRFNDLTFKP LGTAVGQFLR SNDNPRGYPD LIIERSGHDT LAVSVMLIKP FTGRVVYFEN     1800
MDGQRYSFFA PQVWMRQRRI YMPTANIWGT HLSNAYEIVR LNDEISAGLL SITEPTLVEW     1860
NDLPQAHQAM WENRHQGATY VVNHALPRPG LKDKDELYEA WSEMLQNREY GV             1912

SEQ ID NO: 122         moltype = AA  length = 1804
FEATURE                Location/Qualifiers
source                 1..1804
                       mol_type = protein
                       organism = Natronococcus occultus
SEQUENCE: 122
MSERADEGAS STDDVRSNPI RTRDDWEQYR ERAREDPGSF HGSIAKREIH WYHDDEDAWL       60
SYDGEWTGFD AETGARTSRD YPEGHEPWDV AFDDSEAPLY EWFAGGLTNA CFNEVDRHVL      120
AGHGDETAFH FEGDRWDQSK NDGRGGPVVS EDVSRRELLV RVAEAAQVLQ NLGLERGDRI      180
ALNMPNIMEQ LYYTEAAKRL GIVYTPVFGG FSDKTLSDRI ARLGADVLIT SDGGYRNAEI      240
VPYKERYADP ALEDYLPVET VLEIVDETLA ELELDERHAE TIRERVERAI EGEATVDRGQ      300
AMRGVGNALE TFADRSGEEL AEIRTEIARA LVDSEDRLER VVVVEHTGQE IQTHDRDDWS      360
ADLIADARED ILAQARDAGF ALESYDDLLA LEDRELVRAI WASSRPVPVD AEYPLFVIFT      420
SGSTGKPKGV VHVHGGYTAG IANTMKVSFD VVPGEDTIFV IADPGWITGQ SYLISASLTT      480
RTTSLLEGA PVYPDAGRFS SVIERYGATV FKAGVTFLKG IMEDDESVAD MREWETDSLR      540
VATFCAEPVS PAVQEFGMEE ICERYINSYW ATEHGGIVWT HFFGNEDFEL RADAHTYPLP      600
WVFGNVWVEE EEHPDGTSEW READPEERGE IIVEEPYPYL MRYVWGDLEG WDGADWAGEW      660
TGNAERFEDV YWIEKDGEYA YLQGDVAKQY DDDSFSLHGR SDEVINVSGH RMGTEEIEGA      720
ILQDKRINPD SPVANAVVVG ADHHEKGLTP VAFVQTKPDD RLTNEVEARL SGLVRDEKGV      780
TAVPETFIEV EAFPETRSGK YMRRMLTAML DREPIGDTST LKNPGVVESI RPKCERWRRR      840
QELAAEEQELL EQYRNVTQQY NDVRGADERI ATVTIDSPPV NALTERALDE LNTVLEHLDR      900
REDVGAVVLT GAGPSNFVAG ADVEQFLEEV HEYEDAVAFP NTAHEAFRRI EELSVPVVAA      960
VNGTALGGGN ELQLAAHYSV AEQAAEFGQP ELNLNLIPGY GGTQRLPRVL GERRGTDGVR     1020
DAVTLITNGR TVDAEDALEM GLVDELETER TARIRAAALA REHVTDAGDT LADARERRLE     1080
NRSAWADPGE FPADVLEDPI VERNRRQCDH AGTGRAKAFE RAVEAIRVGF EEGIDAGLER     1140
EATHFAEAVV DPEGGKAGIE AFLDRASEPL PTRERFSPSP EEEQALLEDG RLLPPGEPFY     1200
PGVDEIPDYQ YAQLVRKDDE TGEAAHGDPE EAELEEVVPV EEPGPNEVLV YVLASEVNFN     1260
DIWAITGPVV SQFENHDQDY HVTGSGGVAL VVDAGEAVVR EGRVSVGDLV TIYSGQSDLL     1320
SPRMGLDPMY ADFSIQGYEG PNGSHQQFML AQGPQVLPIP EEATIEQAGA YVLATGTVWR     1380
ALFTTLDIEP ETSMFVEGAS TGTGWETTKL ATRNDVDVTG LCSSEERAER IERLGADALD     1440
RTADPYDDIW GRIPREENAW DDWKEAGREF VEAYEANHDG ERADYAVSHA GELSFPRSFQ     1500
```

```
LLEEGGKLTF YGASTGYYLT FLGKPGASTP DAMFERADVR AGDGVLIYYG TDTGPDGVVD    1560
ETGLRAIEDA REAGTRIAVV ASTDEQAEFV ESLGFGDAVE GTVSIEGLQR REDDFRWPET    1620
LPDLPDAQAD PEAFRGVVQS ITDEVFKPLG KAVGELLGTP KNPRGYPDVV FERADHDALY    1680
VSTMLAKPHT GRVVYSEDLE DRRYSMYAPQ VWMRQREVLM PTAEILGTHL SNAYEVEQLN    1740
EAVDAGEIDL TDPEVVGWDE LPEAHQAMWD NEHEASSYVA AHALPEDGLD SKEELFLAWA    1800
DRER                                                                1804

SEQ ID NO: 123          moltype = AA   length = 1850
FEATURE                 Location/Qualifiers
source                  1..1850
                        mol_type = protein
                        note = NAP1
                        organism = Erythrobacter sp.
SEQUENCE: 123
MIGEGDDIGS SNNLEKQSHG LRISDRDHFQ RLREECRSDP GEFHGRLAKR EICWLIEGPG    60
GNPAWAFYDD AAETWTGWDA SSAAPITLDL PESFEPWERA FNDDDPPNWR WFEGGLTSTA    120
FNEVDRHVLS GHGDEAAMIF EGDRWNMASE GGRGGPVDSE VISRRKLLLE SAKCALALKA    180
LGLEAGDRIA LNMPSIPEQI YWTEGAKRMG IVYTPVFGGF SDKTLSDRIA DAGARVVVTA    240
DGSYRNAQMV PFKPSYTDPA LDNFIAVPVA MELLGQALED GELVVAPEHA GLIRSEVAGL    300
LDGEVTVERS DVMRGVGKAL TAIASGEAAG GAMTPRQAAQ LRIAIASALV DSPPRVDAVV    360
VVKHTAQPDL PWNEARDHWS HDLTAAAGEE LLKAARDAGF DVADEEALLA LSDTEFVRAI    420
WAGAPVLAVD AEYPNFIIYT SGSTGKPKGV VHVHGGYASG VAATMPAAFG AEPGDVMYVV    480
ADPGWITGQS YQIAASLLSR VTTVITEGSP VFPHAGRFAS IIERYGVNVF KAGVTFLKSV    540
MQNPENLKDI QRYDLSSLKV ATFCAEPVSP AVQQAFAMEHI THRYINSYWA TEHGGMVWTH    600
FADADGFPLE ADAHTYPLPW IMGDVWVEDA DGSSNGPVEY ERDTGTGGAP WRVAEDGEKG    660
EIVIALPYPY LTRTIWGDVE NFTVEHVGNL ARVAGGWRGD EVRYADTYRR RWKGAWAYTQ    720
GDFAMRHPDG SFSLHGRSDD VINVSGHRIG TEEIEGAILR DKALDPNSPV GNVIVIGAPH    780
SQKGVTPIAF VTPVEGRRLT QDDKRRLTDL VRTEKGAVAV PQDFIELSEF PETRSGKYMR    840
RMVRAVVEGG EVGDASTLRN PESLDELARA VDGWKRRQSL SDTQALFERY RFFTIQYNLV    900
APGKRVATVT VKNPPVNALN ERALDELVII AEHLARKDNV AAVVFTGSGT ASFVAGADIR    960
QMLEEVNSVE EAKALPDNAQ LAFRTIEEMD KPCIAAIQGV ALGGGMEFAL ACHYRVAEPK    1020
ARFGQPEINL RLLPGYGGTQ RLPRLLADGG GETGLRDALD LILGGRAIDA DAALAVGAVD    1080
ALADGSDNAL SHAHAMVREF VRSGDDSALG KAFAARKTQT QSWHEPASID LDAVLEDEFL    1140
QRILNQLEWA GRDKAGERAL DAVRTGWTQG MTAGLECEAQ RPFAEAIIDPE GGKTGIQQFM    1200
DKQSPPLPVR RDGVWEDDQH EATKTALIEA GDLLPLGAPF YPGVTAIPPK QLAFGIARDP    1260
DTGAPRFGPP ETHERELVVN TPKPGANEAL IYLLSSEVNF NDIWALTGIP VSPFDAHDED    1320
VQITGSGGLA LVAALGSELK EEGRLQVGDL SVSYSGTSEL LSPLAGDDPM YAGFAIQGYE    1380
TKTGSHAQFL TVQGPQLHRP PADLTLEQAG AYTLNLGTVA RCLFTTLEIQ AGKTAFVEGS    1440
ATGTGLDALK SSVRTGLAVT GLVSSEDRAE FVKSHGSVGA INRKDPEIAD CFTPVPDDPD    1500
EARQWEADGE KLLLDAYRETN GGKLADYVVS HAGERAFPRS FQLLAEGGRL AFYGASSGYH    1560
FSFMGKGGEA RPDEMLARAN LRGGESVLLY YGPGSHELAD EKGLEMVEAA RLMKARMVIV    1620
TTSDGQREFL QSLGLEDAVE GIVSIEGLKR RLSDFHWPDT LPRLPDARTD IENFKIGVRA    1680
YQQNTMKPFG TAVGKLLRSP GNPRGVPDLV IERAGQDTLG VSTSLVKPFG GRVIYAEEMA    1740
GRRYTFYAPQ VWTRQRRIYM PSAEIFGTHL CNAYEVTMMN EMVAAGLLDV TEPTMVPWEG    1800
LPEAHQAMWD NRHSGATYVV NHALPAMGLT TKDELLEYWV AAQSDTGETS                1850

SEQ ID NO: 124          moltype = AA   length = 542
FEATURE                 Location/Qualifiers
source                  1..542
                        mol_type = protein
                        note = strain ATCC 17699 / H16 / DSM 428 / Stanier 337
                        organism = Cupriavidus necator
SEQUENCE: 124
MKVITAREAA ALVQDGWTVA SAGFVGAGHA EAVTEALEQR FLQSGLPRDL TLVYSAGQGD    60
RGARGVNHFG NAGMTASIVG GHWRSATRLA TLAMAEQCEG YNLPQGVLTH LYRAIAGGKP    120
GVMTKIGLHT FVDPRTAQDA RYHGGAVNER ARQAIAEGKA CWVDAVDFRG DEYLFYPSFP    180
IHCALIRCTA ADARGNLSTH REAPHHELLA MAQAAHNSGG IVIAQVESLV DHHEILQAIH    240
VPGILVDYVV VCDNPANHQM TFAESYNPAY VTPWQGEAAV AEAEAAPVAA GPLDARTIVQ    300
RRAVMELARR APRVVNLGVG MPAAVGMLAH QAGLDGFTLT VEAGPIGGTP ADGLSFGASA    360
YPEAVVDQPA QFDFYEGGGI DLAILGLAEL DGHGNVNVSK FGEGEGASIA GVGGFINITQ    420
SARAVVFMGT LTAGGLEVRA GDGGLQIVRE GRVKKIVPEV SHLSFNGPYV ASLGIPVLYI    480
TERAVFEMRA GADGEARLTL VEIAPGVDLQ RDVLDQCSTP IAVAQDLREM DARLFQAGPL    540
HL                                                                  542

SEQ ID NO: 125          moltype = AA   length = 524
FEATURE                 Location/Qualifiers
source                  1..524
                        mol_type = protein
                        organism = Anaerotignum propionicum
SEQUENCE: 125
MRKVPIITAD EAAKLIKDGD TVTTSGFVGN AIPEALDRAV EKRFLETGEP KNITYVYCGS    60
QGNRDGRGAE HFAHEGLLKR YIAGHWATVP ALGKMAMENK MEAYNVSQGA LCHLFRDIAS    120
HKPGVFTKVG IGTFIDPRNG GKVNDITKE DIVELVEIKG QEYLFYPAFP IHVALIRGTY    180
ADESGNITFE KEVAPLEGTS VCQAVKNSGG IVVVQVERVV KAGTLDPRHV KVPGIYVDYV    240
VVADPEDHQQ SLDCEYDPAL SGEHRRPEVV GEPLPLSAKK VIGRRGAIEL EKDVAVNLGV    300
GAPEYVASVA DEEGIVDFMT LTAESGAIGG VPAGGVRFGA SYNADALIDQ GYQFDYYDGG    360
GLDLCYLGLA ECDKEGNINV SRFGPRIAGC GGFINITQNT PKVFFCGTFT AGGLKVKIED    420
GKVIIVQEGK QKKFLKAVEQ ITFNGDVALA NKQQVTYITE RCVFLLKEDG LHLSEIAPGI    480
DLQTQILDVM DFAPIIDRDA NGQIKLMDAA LFAEGLMGLK EMKS                     524
```

```
SEQ ID NO: 126           moltype = AA   length = 517
FEATURE                  Location/Qualifiers
source                   1..517
                         mol_type = protein
                         note = DSM 20460
                         organism = Megasphaera elsdenii
SEQUENCE: 126
MRKVEIITAE QAAQLVKDND TITSIGFVSS AHPEALTKAL EKRFLDTNTP QNLTYIYAGS    60
QGKRDGRAAE HLAHTGLLKR AIIGHWQTVP AIGKLAVENK IEAYNFSQGT LVHWFRALAG   120
HKLGVFTDIG LETFLDPRQL GGKLNDVTKE DLVKLIEVDG HEQLFYPTFP VNVAFLRGTY   180
ADESGNITMD EEIGPFESTS VAQAVHNCGG KVVVQVKDVV AHGSLDPRMV KIPGIYVDYV   240
VVAAPEDHQQ TYDCEYDPSL SGEHRAPEGA TDAALPMSAK KIIGRRGALE LTENAVVNLG   300
VGAPEYVASV AGEEGIADTI TLTVEGGAIG GVPQGGARFG SSRNADAIID HTYQFDFYDG   360
GGLDIAYLGL AQCDGSGNIN VSKFGTNVAG CGGFPNISQQ TPNVYFCGTF TAGGLKIAVE   420
DGKVKILQEG KAKKFIKAVD QITFNGSYAA RNGKHVLYIT ERCVFELTKE GLKLIEVAPG   480
IDIEKDILAH MDFKPIIDNP KLMDARLFQD GPMGLKK                            517

SEQ ID NO: 127           moltype = AA   length = 628
FEATURE                  Location/Qualifiers
source                   1..628
                         mol_type = protein
                         note = strain LT2 / SGSC1412 / ATCC 700720
                         organism = Salmonella typhimurium
SEQUENCE: 127
MSFSEFYQRS INEPEAFWAE QARRIDWRQP FTQTLDHSRP PFARWFCGGT TNLCHNAVDR    60
WRDKQPEALA LIAVSSETDE ERTFTFSQLH DEVNIVAAML LSLGVQRGDR VLVYMPMIAE   120
AQITLLACAR IGAIHSVVFG GFASHSVAAR IDDARPALIV SADAGARGGK ILPYKKLLDD   180
AIAQAQAHQPK HVLLVDRGLA KMAWVDGRDL DFATLRQQHL GASVPAWLE SNETSCILYT   240
SGTTGKPKGV QRDVGGYAVA LATSMDTIFG GKAGGVFFCA SDIGWVVGHS YIVYAPLLAG   300
MATIVYEGLP TYPDCGVWWK IVEKYQVNRM FSAPTAIRVL KKFPTAQIRN HDLSSLEALY   360
LAGEPLDEPT ASWVTETLGV PVIDNYWQTE SGWPIMALAR ALDDRPSRLG SPGVPMYGYN   420
VQLLNEVTGE PCGINEKGML VIEGPLPPGC IQTIWGDDAR FVKTYWSLFN RQVYATFDWG   480
IRDAEGYYFI LGRTDDVINI AGHRLGTREI EESISSYPNV AEVAVVGIKD ALKGQVVAVF   540
VIPKQSDTLA DREAARDEEN AIMALVDNQI GHFGRPAHVW FVSQLPKTRS GKMLRRTIQA   600
ICEGRDPGDL TTIDDPASLQ QIRQAIEE                                     628

SEQ ID NO: 128           moltype = AA   length = 705
FEATURE                  Location/Qualifiers
source                   1..705
                         mol_type = protein
                         note = strain SCM1
                         organism = Nitrosopumilus maritimus
SEQUENCE: 128
MAAVKKIFDE IIETDHKVIT EESSKSILKN YGVKVPPYAL VTSAEEAAKE AKKIGFPLVM    60
KVVSPQILHK TDVGGVKVGL DNVADVKKTF TDMYGRLSKK KGVNVKGILL EKMVPKGVEL   120
IVGIQNDSQF GPIIMVGMGG IMTEVMKDVA FRMLPITTSG AKSMLNELKG SKLLKGPRGS   180
EPIDTNLVAK MLVNIGKLGV ENADYINSID FNPVIVYPKS HYVVDAKIIL NKEKKKNSIS   240
KAKPSITDME TFFTPKSVAL VGASASPGKI GNSILDSLVN YDFKGKVYPI NPKADKIFGQ   300
KCYPSVADIP GKVDLVVVSV DLSMTPPVLE DCAKKGVHSV VIVSGGGKEL GGERAAYEAE   360
VARLSKKHKI RIIGPNCIGM FNAANRLDCA FQGQERMVRS KLGPVAFFSQ SGTMGISMLE   420
SADTFGLSKM ISFGNRSDVD EADMIWYAAN DPQTKVIGLY VEGFGDGRKF INVAKRVMKE   480
KKKPIVIWKS GRTAAGAKQA ASHTGSLGGS NAIIMGAFKQ AGIISVDSYQ ELAGVLKALA   540
WQPAAKGNKV AMTSNGAGPM IGGIDQLEKF GLAIGKLSPK LLKKMKSRFP PAVPIHNGNP   600
ADVGGGATAD DYQFVIQQFM DEKNIDIAMP WFVQDDPLE ETIVDHLAGF QKKAKKPLLC   660
GGNGGPYTEK MIKLIEKHNV PVYQDLRTWV AAASALHQWG KISKK                  705

SEQ ID NO: 129           moltype = AA   length = 661
FEATURE                  Location/Qualifiers
source                   1..661
                         mol_type = protein
                         note = strain ATCC 51363 / DSM 5348 / JCM 9185 / NBRC 15509
                         / TH2
                         organism = Metallosphaera sedula
SEQUENCE: 129
MFMRYIMVEE QTLKTGSQEL EEKADYNMRY YAHLMKLSKE KPAEFWGSLA QDLLDWYEPW    60
KETMRQEDPM TRWFIGGKIN ASYNAVDRHL NGPRKFKAAV IWESELGERK IVTYQDMFYE   120
VNRWANALRS LGVGKGDRVT IYMPLTPEGI AAMLASARIG IVSVIFAGF GSQAIADRVE   180
DAKAKVVITA DAYPRRGKVV ELKKTVDEAL NSLGERSPVQ HVLVYRRMKT DVNMKEGRDV   240
FFDEVGKYRY VEPERMDSND PLFILYTSGT TGKPKGIMHS TGGYLTGTAV MLLWSYGLSQ   300
ENDVLFNTSD IGWIVGHSYI TYSPLIMGRT VVIYESAPDY PYPDKWAEII ERYRATTFGT   360
SATALRYFMK YGDEYVKNHD LSSIRIIVTN GEVLNYSPWK WGLEVGGGK VFMSHQWWQT   420
ETGAPNLGYL PGIIYMPMKS GPASGFPLPG NFVEVLDENG NPSAPRVRGY LVMRPPFPPN   480
MMMGMWNDNG ERLKKTYFSK FGSLYYPGDF AMVDEDGYIW VLGRADETLK IAAHRIGAGE   540
VESAITSHPS VAEAAVIGVP DSVKGEEVHA FVVLKQGYAP SSELAKDIQS HVRKVMGPIV   600
SPQIHFVDKL PKTRSGKVMR RVIKAVMMGS SAGDLTTIED EASMDEIKKA VEELKKELKT   660
S                                                                  661

SEQ ID NO: 130           moltype = AA   length = 628
```

```
FEATURE                 Location/Qualifiers
source                  1..628
                        mol_type = protein
                        note = strain K12
                        organism = Escherichia coli
SEQUENCE: 130
MSFSEFYQRS INEPEQFWAE QARRIDWQTP FTQTLDHSNP PFARWFCEGR TNLCHNAIDR     60
WLEKQPEALA LIAVSSETEE ERTFTFRQLH DEVNAVASML RSLGVQRGDR VLVYMPMIAE    120
AHITLLACAR IGAIHSVVFG GFASHSVAAR IDDAKPVLIV SADAGARGGK IIPYKKLLDD    180
AISQAQHQPR HVLLVDRGLA KMARVSGRDV DFASLRHQHI GARVPVAWLE SNETSCILYT    240
SGTTGKPKGV QRDVGGYAVA LATSMDTIFG GKAGSVFFCA SDIGWVVGHS YIVYAPLLAG    300
MATIVYEGLP TWPDCGVWWT IVEKYQVSRM FSAPTAIRVL KKFPTAEIRK HDLSSLEVLY    360
LAGEPLDEPT ASWVSNTLDV PVIDNYWQTE SGWPIMAIAR GLDDRPTRLG SPGVPMYGYN    420
VQLLNEVTGE PCGVNEKGML VVEGPLPPGC IQTIWGDDGR FVKTYWSLFS RPVYATFDWG    480
IRDADGYHFI LGRTDDVINV AGHRLGTREI EESISSHPGV AEVAVVGVKD ALKGQVAVAF    540
VIPKESDSLE DRDVAHSQEK AIMALVDSQI GNFGRPAHVW FVSQLPKTRS GKMLRRTIQA    600
ICEGRDPGDL TTIDDPASLD QIRQAMEE                                      628

SEQ ID NO: 131          moltype = AA  length = 542
FEATURE                 Location/Qualifiers
source                  1..542
                        mol_type = protein
                        note = strain ATCC 17699 / H16 / DSM 428 / Stanier 337
                        organism = Cupriavidus necator
SEQUENCE: 131
MKVITAREAA ALVQDGWTVA SAGFVGAGHA EAVTEALEQR FLQSGLPRDL TLVYSAGQGD     60
RGARGVNHFG NAGMTASIVG GHWRSATRLA TLAMAEQCEG YNLPQGVLTH LYRAIAGGKP    120
GVMTKIGLHT FVDPRTAQDA RYHGGAVNER ARQAIAEGKA CWVDAVDFRG DEYLFYPSFP    180
IHCALIRCTA ADARGNLSTH REAFHHELLA MAQAAHNSGG IVIAQVESLV DHHEILQAIH    240
VPGILVDYVV VCDNPANHQM TFAESYNPAY VTPWQGEAAV AEAEAAPVAA GPLDARTIVQ    300
RRAVMELARR APRVNLGVG  MPAAVGMLAH QAGLDGFTLT VEAGPIGGTP ADGLSFGASA    360
YPEAVVDQPA QFDFYEGGGI DLAILGLAEL DGHGNVNVSK FGEGEGASIA GVGGFINITQ    420
SARAVVFMGT LTAGGLEVRA GDGGLQIVRE GRVKKIVPEV SHLSFNGPYV ASLGIPVLYI    480
TERAVFEMRA GADGEARLTL VEIAPGVDLQ RDVLDQCSTP IAVAQDLREM DARLFQAGPL    540
HL                                                                  542

SEQ ID NO: 132          moltype = AA  length = 659
FEATURE                 Location/Qualifiers
source                  1..659
                        mol_type = protein
                        note = strain DSM 16993 / JCM 10545 / NBRC 100140 / 7
                        organism = Sulfurisphaera tokodaii
SEQUENCE: 132
MTEKLSEQLQ QLGEQNLEEK ADYNMRYYKY LYKKSIEEPD KFWGELAEEL ITWYEPWKQA     60
FVQEEGLLTK WFVGGKLNAS YNAVDRHLNS HRKYKAAIFW ESEKGEKKVV TYQDLFYEVN    120
KWANALRELG VKKGDRVTIY MPLTPEGVIA KLAVARLGAI HSVVFAGFGA QALADRIADA    180
GAKVVITADA YYRRGKLVEL KKTVDEALNI LGDKSPVQKV LVYKRTGTEI PFKEGRDVYF    240
DEVGKYKYIE PVPVEATEPL FILYTSGTTG KPKGIVHSTG GYLVGTAVML LWSYGLSQEN    300
DVLFNTSDIG WIVGHSYITY SPLVMGRSIV IYESAPDYPY PDKWAEMIEK YRATTFGTSA    360
TAIRTLMKYG EDYVKQHDLS SLRIIVTNGE PLNYAPWKWG LEVVGGGKVF MSHQWWQTET    420
GGPNIGYIPG VVYLPMKSGP AVGFALPGNK VTVVNEEGKE TKPRERGYLV MLPPFPPMMM    480
IGMWNDPDNE RLKKTYFSKF PGIYYPDYA  MIDEDGYIWV MGRADETIKV AAHRIGAGEV    540
ESIVTSHPAV AEAAAVGIPD PVKGEAVHLF VVLKVGYKPS PQLAREIQEH VRKYMGAIVT    600
PEVHFVDKLP KTRSGKIMRR VIKAVMMGQS AGDITTLEDE ASMDEIKKAV EEFKKSLSQ    659

SEQ ID NO: 133          moltype = AA  length = 259
FEATURE                 Location/Qualifiers
source                  1..259
                        mol_type = protein
                        note = strain ATCC 51363 / DSM 5348 / JCM 9185 / NBRC 15509
                        / TH2
                        organism = Metallosphaera sedula
SEQUENCE: 133
MEFETIETKK EGNLFWITLN RPDKLNALNA KLLEELDRAV SQAESDPEIR VIIITGKGKA     60
FCAGADITQF NQLTPAEAWK FSKKGREIMD KIEALSKPTI AMINGYALGG GLELALACDI    120
RIAAEEAQLG LPEINLGIYP GYGGTQRLTR VIGKGRALEM MMTGDRIPGK DAEKYGLVNR    180
VVPLANLEQE TRKLAEKIAK KSPISLALIK EVVNRGLDSP LLSGLALESV GWGVVFSTED    240
KKEGVSAFLE KREPTFKGK                                                259

SEQ ID NO: 134          moltype = AA  length = 258
FEATURE                 Location/Qualifiers
source                  1..258
                        mol_type = protein
                        note = FJAT-27225
                        organism = Bacillus sp.
SEQUENCE: 134
MEFTNILTRT EEHIGWIIIN RPEQRNALNL DTLLEIERAL NLWRTNDDIR VVIITGAGEK     60
SFAAGADISQ LNKRTMIEAL QPNMTATYRK IEDYEKPTIA AINGFALGGG LELALACDIR    120
VASLNAKLGL PEVGLGIIPG AGGTQRLTRI IGKGKAMELI LTGDIITAEE AEKLGIVSKA    180
```

```
VPKEELLETA TLYANKLTKK APLALRLAKA AVNRGADIEM ETALYIEKLS QTILMGSDDK    240
REGTEAFLEK RQPNFKGK                                                 258

SEQ ID NO: 135          moltype = AA  length = 259
FEATURE                 Location/Qualifiers
source                  1..259
                        mol_type = protein
                        note = DSM 13106
                        organism = Sporanaerobacter acetigenes
SEQUENCE: 135
MDFENLIFKR EGNIGILSIN RPKALNALNT QVLCELDKAI DMIENDEDIH ILIITGEGRA    60
FVAGADIAEM KEMNSKEARQ FAKNGLGVFR KIELMEKPVI AAVNGFALGG GCELSMCCDI    120
RIASEKAKFG QPEVGLGIIP GFAGTQRLAR LVGMGRAKEL IFTSDMIDAN EAYRIGLVNK    180
VVPQDELMNE AIALANKILS KGQIAVRFAK TSINRGMETD IETGMAIERD LFGLCFATED    240
QKEGMGAFLE KRSPNYKLR                                                259

SEQ ID NO: 136          moltype = AA  length = 309
FEATURE                 Location/Qualifiers
source                  1..309
                        mol_type = protein
                        note = strain ATCC 700808 / DSM 15171 / DSS-3
                        organism = Ruegeria pomeroyi
SEQUENCE: 136
MTWRCILSTL PCMLCWGAVR EEDMSVVAYE KDGRIARITL NRPEVMNAIN DELPGALAAA    60
VAQADADPGV HVMVLSGAGR AFCAGYDLTY YAEGNGAGEV TQPMPWDPIK DYRFMWANTQ    120
HFMSLWRAAK PVVCKVHGFA VAGGSDIALC ADMTIMAEDA QIGYMPSRVW GCPTTAMWVY    180
RLGAERAKRM LFTGDKITGR QAADMGLVLE AVPAEHLDDR VEELAARMAT VPINQLAMQK    240
LVINQAIEQT GLMQTQRLAT IFDGITRHSP EGIHFKERAE AVGWKQAVDE RDQGTWDWTA    300
NAEIPKGNR                                                           309

SEQ ID NO: 137          moltype = AA  length = 257
FEATURE                 Location/Qualifiers
source                  1..257
                        mol_type = protein
                        note = strain DSM 16993 / JCM 10545 / NBRC 100140 / 7
                        organism = Sulfurisphaera tokodaii
SEQUENCE: 137
METIVIKKET PIGWIYLNRP DRLNAINQQM IKELRQGIDE MVYDSDIKVI IITGNGKAFS    60
AGADISRFKE LNGYTAWQFA KSGRELMDYI ENISKPTIAM VNGYALGGGL ELAMACDIRI    120
AAEEAQLGLP EINLGIYPGF GGTQRLVRLI GKGKALELML TGDRISAKEA EKIGLVNKVV    180
PLSNLEQETR NFALKLAEKP PISIALIKLL VNQGIDLPIL AGLNMESLGW GVVFSTEDEK    240
EGVSAFLEKR KAQFKGK                                                  257

SEQ ID NO: 138          moltype = AA  length = 253
FEATURE                 Location/Qualifiers
source                  1..253
                        mol_type = protein
                        note = strain SCM1
                        organism = Nitrosopumilus maritimus
SEQUENCE: 138
MSLVTTSTSD GICTVKINRP DKLNAMNTDV AKELIKTFEE LNHNDDVKVI ILTGEGEKAF    60
SAGADIEYMS KISADESVEY AKTGQLVTAT VELVKQPTIA AVNGFALGGG CELAMSCDIR    120
IAADTAKLGQ PEVTIGVPPG WGGTQRLMRI VGIAKAKELV YTGKMIKAEE AKEIGLVNHV    180
VPLASLQEEA LKMAQQIAGN STMGVQMSKV AINKGRNADL DTGLGLEILA WRNCFTHPDR    240
QERMTAFVNK SKK                                                      253

SEQ ID NO: 139          moltype = AA  length = 201
FEATURE                 Location/Qualifiers
source                  1..201
                        mol_type = protein
                        note = strain ATCC 824 / DSM 792 / JCM 1419 / LMG 5710 /
                         VKM B-1787
                        organism = Clostridium acetobutylicum
SEQUENCE: 139
SFVAGADISE MKEMNTIEGR KFGILGNKVF RRLELLEKPV IAAVNGFALG GGCEIAMSCD    60
IRIASSNARF GQPEVGLGIT PGFGGTQRLS RLVGMGMAKQ LIFTAQNIKA DEALRIGLVN    120
KVVEPSELMN TAKEIANKIV SNAPVAVKLS KQAINRGMQC DIDTALAFES EAFGECFSTE    180
DQKDAMTAFI EKRKIEGFKN R                                             201

SEQ ID NO: 140          moltype = AA  length = 275
FEATURE                 Location/Qualifiers
source                  1..275
                        mol_type = protein
                        organism = Clostridium pasteurianum
SEQUENCE: 140
MENNNSKSNI IVHIILIIGA FAMLLPFLWM IITSLKTLTE STQVPPTFIP KIFNIGNYSD    60
VWNQLPFASF YVNTFLMMLF RIIFSVFFSA MAAYAFARIE FPGKNAFFMI ILIQMMIPGQ    120
IFIIPQYLIV SKLGLLNSVG ALVVPGIVSA FGTFLLRQFF IGIPVELEEA AVLDGCNRWQ    180
IFYKIMLPLT KSGLVAIGIF TALFAWKDLM WPLIVNTSIE KMPLASGLAS LQGQYATNFP    240
```

```
QLMAGSMIAI WPMLILFIIF QKQFIQGIAS TGSKN                              275

SEQ ID NO: 141          moltype = AA  length = 22
FEATURE                 Location/Qualifiers
SITE                    13
                        note = misc_feature - Xaa can be any naturally occurring
                         amino acid
SITE                    21
                        note = misc_feature - Xaa can be any naturally occurring
                         amino acid
source                  1..22
                        mol_type = protein
                        organism = Clostridium pasteurianum
SEQUENCE: 141
MGFNGGILEG EEXKAVVTIN XP                                            22

SEQ ID NO: 142          moltype = AA  length = 260
FEATURE                 Location/Qualifiers
source                  1..260
                        mol_type = protein
                        note = DSM 20460
                        organism = Megasphaera elsdenii
SEQUENCE: 142
MDYQNIIFAV EDGIATITIN RPKALNALNQ ATVSELKDVV EKIAADKAIK VVIITGAGAK   60
SFVGADIKE MASKNAAEGR EWGQFGQNVF TEIENLPQPV IAAINGFALG GGCELSCACD    120
IRYAAENAKF GQPEVGLGIT PGFGGTQRLT RVVGRGHAKE LIYTGGMIDA EKAKAIGLVN   180
EVFPQEELMP AAVKLAKKIA KNAPIAVQLS KAAINRGINC DVVTGIAYEA EVFGLCFSTA   240
DQKEGMAAFC EKRKATFEGK                                               260

SEQ ID NO: 143          moltype = AA  length = 255
FEATURE                 Location/Qualifiers
source                  1..255
                        mol_type = protein
                        note = strain DSM 21510 / WK1
                        organism = Anoxybacillus flavithermus
SEQUENCE: 143
MFSIQQEGYV AILALHRPPA NALASSVLKE LSERLDALKE DEQVRVIVLH GEGRFFSAGA   60
DIKEFTAIEA SEQAAELARA GQQVMEKIEQ FPKPIIAAIH GAALGGGLEL AMSCHLRIVA   120
ENAKLGLPEL QLGIIPGFAG TQRLLRHVGM AKALEMMWTS EPITGAEAVQ WGLANKAVPE   180
EQLLDTAKQL AQKIAQKSPI SVQAVLKLVN EARTKTFHEC VEKEAQLFGQ VFVTEDAKEG   240
ISAFIEKRTP QFQGK                                                    255

SEQ ID NO: 144          moltype = AA  length = 330
FEATURE                 Location/Qualifiers
source                  1..330
                        mol_type = protein
                        note = strain ATCC 700808 / DSM 15171 / DSS-3
                        organism = Ruegeria pomeroyi
SEQUENCE: 144
MFNALVVDKD EESGKTQAAV KQLSLTDLPV GEVTVAVEYS TVNYKDGLCI GPGGGLVRKY   60
PHVPGIDFAG TVENSSDERY KPGDKVVLTG WRVGEAHWGG YSQKANVRAD WLVPLPEGLD   120
TRQAMAVGTA GFTAMLAVMA LEDHGLTPGH GPVLVTGAAG GVGSVATAIL AHLGYEVAAV   180
TGRPETADYL TSLGATQIVA RDEINETVKR PLESEIWAGC VDAVGGAMLA RVLGQMKYGA   240
SVAAVGLAGG AGLPATVIPF LLRGVNLLGI DSVMQPYANR LRAWERIARD LPMDKLEAMI   300
RPATLSDLPG LGADILKGQV QGRVVVDVNA                                    330

SEQ ID NO: 145          moltype = AA  length = 324
FEATURE                 Location/Qualifiers
source                  1..324
                        mol_type = protein
                        note = strain K12
                        organism = Escherichia coli
SEQUENCE: 145
MQALLLEQQD GKTLASVQTL DESRLPEGDV TVDVHWSSLN YKDALAITGK GKIIRNFPMI   60
PGIDFAGTVR TSEDPRFHAG QEVLLTGWGV GENHWGGLAE QARVKGDWLV AMPQGLDARK   120
AMIIGTAGFT AMLCVMALED AGVRPQDGEI VVTGASGGVG STAVALLHKL GYQVVAVSGR   180
ESTHEYLKSL GASRVLPRDE FAESRPLEKQ VWAGAIDTVG DKVLAKVLAQ MNYGGCVAAC   240
GLAGGFTLPT TVMPFILRNV RLQGVDSVMT PPERRAQAWQ RLVADLPESF YTQAAKEISL   300
SEAPNFAEAI INNQIQGRTL VKVN                                          324

SEQ ID NO: 146          moltype = AA  length = 326
FEATURE                 Location/Qualifiers
source                  1..326
                        mol_type = protein
                        note = strain ATCC 17023 / 2.4.1 / NCIB 8253 / DSM 158
                        organism = Rhodobacter sphaeroides
SEQUENCE: 146
MRAVLIEKSD DTQSVSVTEL AEDQLPEGDV LVDVAYSTLN YKDALAITGK APVVRRFPMV   60
PGIDFTGTVA QSSHADFKPG DRVILNGWGV GEKHWGGLAE RARVRGDWLV PLPAPLDLRQ   120
```

```
AAMIGTAGYT AMLCVLALER HGVVPGNGEI VVSGAAGGVG SVATTLLAAK GYEVAAVTGR  180
ASEAEYLRGL GAASVIDRNE LTGKVRPLGQ ERWAGGIDVA GSTVLANMLS MMKYRGVVAA  240
CGLAAGMDLP ASVAPFILRG MTLAGVDSVM CPKTDRLAAW ARLASDLDPA KLEEMTTELP  300
FSEVIETAPK FLDGTVRGRI VIPVTP                                     326

SEQ ID NO: 147         moltype = AA   length = 330
FEATURE                Location/Qualifiers
source                 1..330
                       mol_type = protein
                       note = strain ATCC 700808 / DSM 15171 / DSS-3
                       organism = Ruegeria pomeroyi
SEQUENCE: 147
MFNALVVDKD EESGKTQAAV KQLSLTDLPV GEVTVAVEYS TVNYKDGLCI GPGGGLVRKY   60
PHVPGIDFAG TVENSSDERY KPGDKVVLTG WRVGEAHWGG YSQKANVRAD WLVPLPEGLD  120
TRQAMAVGTA GFTAMLAVMA LEDHGLTPGH GPVLVTGAAG GVGSVATAIL AHLGYEVAAV  180
TGRPETADYL TSLGATQIVA RDEINETVKR PLESEIWAGC VDAVGGAMLA RVLGQMKYGA  240
SVAAVGLAGG AGLPATVIPF LLRGVNLLGI DSVMQPYANR LRAWERIARD LPMDKLEAMI  300
RPATLSDLPG LGADILKGQV QGRVVVDVNA                                  330

SEQ ID NO: 148         moltype = AA   length = 326
FEATURE                Location/Qualifiers
source                 1..326
                       mol_type = protein
                       note = strain ATCC 17023 / 2.4.1 / NCIB 8253 / DSM 158
                       organism = Rhodobacter sphaeroides
SEQUENCE: 148
MRAVLIEKSD DTQSVSVTEL AEDQLPEGDV LVDVAYSTLN YKDALAITGK APVVRRFPMV   60
PGIDFTGTVA QSSHADFKPG DRVILNGWGV GEKHWGGLAE RARVRGDWLV PLPAPLDLRQ  120
AAMIGTAGYT AMLCVLALER HGVVPGNGEI VVSGAAGGVG SVATTLLAAK GYEVAAVTGR  180
ASEAEYLRGL GAASVIDRNE LTGKVRPLGQ ERWAGGIDVA GSTVLANMLS MMKYRGVVAA  240
CGLAAGMDLP ASVAPFILRG MTLAGVDSVM CPKTDRLAAW ARLASDLDPA KLEEMTTELP  300
FSEVIETAPK FLDGTVRGRI VIPVTP                                     326

SEQ ID NO: 149         moltype = AA   length = 394
FEATURE                Location/Qualifiers
source                 1..394
                       mol_type = protein
                       organism = Anaerotignum propionicum
SEQUENCE: 149
MFLLKIKKER MKRMDFSLTR EQEMLKKLAR QFAEIELEPV AEEIDREHVF PAENFKKMAE   60
IGLTGIGIPK EFGGSGGGTL EKVIAVSEFG KKCMASASIL SIHLIAPQAI YKYGTKEQKE  120
TYLPRLTKGG ELGAFALTEP NAGSDAGAVK TTAILDSQTN EYVLNGTKCF ISGGGRAGVL  180
VIFALTEPKK GLKGMSAIIV EKGTPGFSIG KVESKMGIAG SETAELIFED CRVPAANLLG  240
KEGKGFKIAM EALDGARIGV GAQAIGIAEG AIDLSVKYVH ERIQFGKPIA NLQGIQWYIA  300
DMATKTAAAR ALVEFAAYLE DAGKPFTKES AMCKLNASEN ARFVTNLALQ IHGGYGYMKD  360
YPLERMYRDA KITEIYEGTS EIHKVVIARE VMKR                             394

SEQ ID NO: 150         moltype = AA   length = 333
FEATURE                Location/Qualifiers
source                 1..333
                       mol_type = protein
                       organism = Alcaligenes faecalis
SEQUENCE: 150
MHGKDFQALV TRQNGETVSN ALEWRSPVSL SPGEVRIRTA YAGVNYKDCL AIQGLARIIR   60
DPPRVGGIEA VGQIIESANS SFAVGDPVMA HGFDMGIGYG GGFAQQLHVS GDHVQKIPSG  120
LSLREAAVLG VPGFTVGLAL DRFEAQGLTP QSGPVAVSGA NGAVGMLTIA LLAQAGYEVV  180
ALTRRRTELAP ALQQLGASEV LDTAITQSNR PLETARFAAA IDNVGGAVLS WLLRSMSDSG  240
QIASVGNAAG NTFEGSVLPF FVRRVQIFGV LANAPWEQRY RVWNRLATEW RPDFALLEPY  300
VHVVELADVP DLVQRQLEGA AHGRSLVAYG DVL                              333

SEQ ID NO: 151         moltype = AA   length = 334
FEATURE                Location/Qualifiers
source                 1..334
                       mol_type = protein
                       note = strain DSM 16993 / JCM 10545 / NBRC 100140 / 7
                       organism = Sulfurisphaera tokodaii
SEQUENCE: 151
MKAIVVPGPK QGYKLEEVPD PKPGKDEVII RVDRAALCYR DLLQLQGYYP RMKYPVILGH   60
EVVGTIEEVG ENIKGFEVGD KVISLLYAPD GTCEYCQIGE EAYCHHRLGY SEELDGFFAE  120
KAKIKVTSLV KVPKGTPDEG AVLVPCVTGM IYRGIRRAGG IRKGELVLVT GASGGVGIHA  180
IQVAKALGAK VIGVTTSEEK AKIIKQYADY VIVGTKFSEE AKKIGDVTLV IDTVGTPTFD  240
ESLKSLWMGG RIVQIGNVDP SQIYNLRLGY IILKDLKIVG HASATKKDAE DTLKLTQEGK  300
IKPVIAGTVS LENIDEGYKM IKDKNKVGKV LVKP                             334

SEQ ID NO: 152         moltype = AA   length = 324
FEATURE                Location/Qualifiers
source                 1..324
                       mol_type = protein
                       note = strain K12
```

```
                              organism = Escherichia coli
SEQUENCE: 152
MQALLLEQQD GKTLASVQTL DESRLPEGDV TVDVHWSSLN YKDALAITGK GKIIRNFPMI    60
PGIDFAGTVR TSEDPRFHAG QEVLLTGWGV GENHWGGLAE QARVKGDWLV AMPQGLDARK   120
AMIIGTAGFT AMLCVMALED AGVRPQDGEI VVTGASGGVG STAVALLHKL GYQVVAVSGR   180
ESTHEYLKSL GASRVLPRDE FAESRPLEKQ VWAGAIDTVG DKVLAKVLAQ MNYGGCVAAC   240
GLAGGGFTLPT TVMPFILRNV RLQGVDSVMT PPERRAQAWQ RLVADLPESF YTQAAKEISL   300
SEAPNFAEAI INNQIQGRTL VKVN                                          324

SEQ ID NO: 153          moltype = AA  length = 332
FEATURE                 Location/Qualifiers
source                  1..332
                        mol_type = protein
                        note = strain ATCC 51363 / DSM 5348 / JCM 9185 / NBRC 15509
                        / TH2
                        organism = Metallosphaera sedula
SEQUENCE: 153
MKAVVVKGHK QGYEVREVQD PKPASGEVII KVRRAALCYR DLLQLQGFYP RMKYPVVLGH    60
EVVGEILEVG EGVTGFSPGD RVISLLYAPD GTCHYCRQGE EAYCHSRLGY SEELDGFFSE   120
MAKVKVTSLV KVPTRASDEG AVMVPCVTGM VYRGLRRANL REGETVLVTG ASGGVGIHAL   180
QVAKAMGARV VGVTTSEEKA SIVGKYADRV IVGSKFSEEA KKEDINVVID TVGTPTFDES   240
LKSLWMGGRI VQIGNVDPTQ SYQLRLGYTI LKDAIIGHA SATRRDAEGA LKLTAEGKIR   300
PVVAGTVHLE EIDKGYEMLK DKHKVGKVLL TT                                 332

SEQ ID NO: 154          moltype = AA  length = 361
FEATURE                 Location/Qualifiers
source                  1..361
                        mol_type = protein
                        note = strain SCM1
                        organism = Nitrosopumilus maritimus
SEQUENCE: 154
MKKIMKALVY EEYTTDDDFS KILKIKDLPI PEPKSNEVVF KVKAAALNYD DIWGMRGKPL    60
AIPLPHISGT DAAGEVTAVG EDVKNFKVGD RVVSHGNMSC RVCKRCTSGR EYDCKKRTIW   120
GFETGPLWGG YCEYTHLPEV NVVKIPEGIS YEEAAAASMT MLTSWHMLVG RAKIQPGQLV   180
LIMGGGSGVG NYGIQIAKLF GCTVIATASP DKLDQLLELG ADYAIDHRKE DWHKEVRAIA   240
KKLPKPFGEV PGVDVIFEHI GGSHWNKELT LLNYGGTVIT TGATTGYMAK TDLRHIFFKG   300
LNILGSTQGT RAELEEGFYW MSKGKIKSII DSEYTLEQAA EAHTKMLGKG GLFGKIIMKP   360
N                                                                   361

SEQ ID NO: 155          moltype = AA  length = 858
FEATURE                 Location/Qualifiers
source                  1..858
                        mol_type = protein
                        organism = Clostridium acetobutylicum
SEQUENCE: 155
MKVTNQKELK QKLNELREAQ KKFATYTQEQ VDKIFKQCAI AAAKERINLA KLAVEETGIG    60
LVEDKIIKNH FAAEYIYNKY KNEKTCGIID HDDSLGEVIA AEPIGIVAAI VPTTNPTSTA   120
IFKSLISLKT RNAIFFSPHP RAKKSTIAAA KLILDAAVKA GAPKNIIGWI DEPSIELSQD   180
LMSEADIILA TGGPSMVKAA YSSGKPAIGV GAGNTPAIID ESADIDMAVS SIILSKTYDN   240
GVICASEQSI LVMNSIYEKV KEEFVKRGSY ILNQNEIAKI KETMFKNGAI NADIVGKSAY   300
IIAKMAGIEV PQTTKILIGE VQSVEKSELF SHEKLSPVLA MYKVKDFDEA LKKAQRLIEL   360
GGSGHTSSLY IDSQNNKDKV KEFGLAMKTS RTFINMPSSQ GASGDLYNFA IAPSFTLGCG   420
TWGGNSVSQN VEPKHLLNIK SVAERRENML WFKVPQKIYF KYGCLRFALK ELKDMNKKRA   480
FIVTDKDLFK LGYVNKITKV LDEIDIKYSI FTDIKSDPTI DSVKKGAKEM LNFEPDTIIS   540
IGGGSPMDAA KVMHLLYEYP EAEIENLAIN FMDIRKRICN FPKLGTKAIS VAIPTTAGTG   600
SEATPFAVIT NDETGMKYPL TSYELTPNMA IIDTELMLNM PRKLTAATGI DALVHAIEAY   660
VSVMATDYTD EALRAIKMI FKYLPRAYKN GTNDIEAREK MAHASNIAGM AFANAFLGVC   720
HSMAHKLGAM HHVPHGIACA VLIEEVIKYN ATDCPTKQTA FPQYKSPNAK RKYAEIAEYL   780
NLKGTSDTEK VTALIEAISK LKIDLSIPQN ISAAGINKKD FYNTLDKMSE LAFDDQCTTA   840
NPRYPLISEL KDIYIKSF                                                 858

SEQ ID NO: 156          moltype = AA  length = 864
FEATURE                 Location/Qualifiers
source                  1..864
                        mol_type = protein
                        organism = Clostridium beijerinckii
SEQUENCE: 156
MRVTNPEELT KRIEQIREAQ REFAKFSQEE VDEIFRQAAM AANNARITLA KMAVEESGMG    60
IVEDKVIKNH FAAEYIYNQY KDTKTCGVIE RDEMFGITHI AEPIGVIAAI VPTTNPTSTA   120
IFKTLIALKT RNGIIISPHP RAKNSTIAAA KIVLEAAERA GAPKGIIGWI DEPSIELSRN   180
VMAESDIILA TGGPGMVRAA YSSGKPAIGV GAGNTPAIID DTAHIKMAVN SILLSKTFDN   240
GVVCASEQSI IAMESVYDEV LKELDERGAY ILKGDEVDKV RSIILDSKGS LNSEIVGQSA   300
YKIAKMAGVE ISEAKVLIG EVESPELEEP FSHEKLSPIL GMYKAKTFDD ALRLASRMIE   360
LGGFGHTSIL YTNQVESVDR IEKFGVAMKT ARTLINMPAS QGAIGDIYNF KLAPSLTLGC   420
GSWGGNSISE NVGPKHLINV KRIAERRENM LWFRVPDKIY FKFGCLPVAL EELNAMKKKR   480
APIVTDRVLF DLGYTHKITN ILSENHIEYK IFSDVEPDPT LKAAKLGADA MRDFNPDVII   540
AIGGGSPMDA AKIMWVMYEH PDVRFEDLAM RFMDIRKRVY EFPPMGEKAI LVAIPTSAGT   600
GSEVTPFAVI TDQQTGVKYP LADYALTPNM AIIDAELMMS MPKGLTAASG IDALVHAIEA   660
YVSVLASEYT NGLALEAIRL TFKYLPDAYN GGTTNIKARE KMAHASSVAG MAFANAFLGI   720
```

```
CHSMAHKLGA FHHVPHGIAN ALLIDEVIRF NATDAPRKQA AFPQYKYPNA GWRYARIADY   780
LNLGGNTEEE KVELLIKAID DLKGKVGIPK SIKEFGVSEE KFYASMDEMV EQAFDDQCTG   840
ANPRYPLMSE IKEMYIKSYN VSNK                                         864

SEQ ID NO: 157           moltype = AA   length = 878
FEATURE                  Location/Qualifiers
source                   1..878
                         mol_type = protein
                         organism = Salmonella typhimurium
SEQUENCE: 157
MAVTNVAELN ALVERVKKAQ REYASFTQEQ VDKIFRAAAL AAADARIPLA KMAVAESGMG    60
IVEDKVIKNH FASEYIYNAY KDEKTCGVLS EDDTFRTITI AEPIGIICGI VPTTNPTSTA   120
IFKSLISLKT RNAIIFSPHP RAKEATNKAA DIVSKALSLP ARRKIRLARS INLPVELSNV   180
DAPPGYIPDP ATGSRHGYSC IQLGSTLSAI GQATLRLVLM KPLIDSNAAC GLCLDAYNLC   240
YRGNLCFCTS LFVVDSAYLH MRPDFRQHGG YMRRPELKAV QRYPEKWRSE RAIVGQPAYK   300
IAELAGFSVP ETTKILIGEV TVVDESEPFA HEKLSPTLAM YRAKDFEEAV EKAEKLVAMG   360
GIGHTSCLYT DQDNQPERVA YFGQMKNARI LINTPASQGG IGDLYNFKLP PSLTLGCGSW   420
GGNSISENVG PKHLIYKKTV AKRAENMWHK LPKSIYFRRG SLPIALDEVI TDGHKRALIV   480
TDRFCSTTVS DRSLCAERRG VETEVFFEVE AADPTLSVVR KGPELANSFK PDVIIAVGGV   540
PRWTRGEIIG SCTNHPETRL IEERVRFMTS YRIYKFPKMV KAKCSPSTTT SGTGSKLHRL   600
RLCPTTLLPQ KYPLADYAVT PDMAIVDANL VMDMPNTLTR KGPLHRLTHA MERIVSVLAS   660
QSDGQALQAL KEYFPASYHE GKNPVARERL HSAATIAPIA FANAFLGVCH WMAHKLPAQL   720
HIPHGPFNAR YRHSVRRAQS NPTKQVALSQ YLYNFAAHRW PAERSIPRAR TGIRPRKYKL   780
VPVALCHVKG IKADLGIPKS IREAGVQEAD FLAHVDKLSE DAFDDQCTGA NPRYPLMSEL   840
KQILLDTYYG RDFTEGEVAA KKDVVAAPKA EKKAKKSA                           878

SEQ ID NO: 158           moltype = AA   length = 868
FEATURE                  Location/Qualifiers
source                   1..868
                         mol_type = protein
                         organism = Clostridium arbusti
SEQUENCE: 158
MKVSNIDELN VRLEEIREAQ RKFGTYTQEQ VDEIFRQAAM AALDARIPLA KMAAEETGMG    60
LVEDKVIKNH FAAEYIYNQY KDEKTCGVVE TDKSYGITKI AEPIGIVAAV IPTTNPTSTA   120
IFKTLISLKT RNAIMLSPHP RAKKSTIAAA KIILDAAVKA GAPEGIIGWI DEPSIELTQI   180
LMQEADITLA TGGPSMVKSA YSSGKPAIGV GPGNTPVIID ESAHIKMAVS SVILSKTFDN   240
GVICASEQSV IVLDSIYDEV RKEFAERGAY IIKESEIDKV RKTIFINGSI NSKIVGQSAY   300
KIAEMSGIKV PETARILIGE VTSVGKEEPF AHEKLSTVLA MYRAENFDDA LDKAVTLVNL   360
GGLGHTSAIY ADIIKAKDKI DKFSNAMKTV RTFINIPAAQ GASGDLYNFK IAPSFTLGCG   420
SWGGNSVSEN VGPKHLLNIK RVAERRENML WFRVPEKVYF KFGCLQFALR ELKDLNKKRA   480
FIVTDKVLYD LGYADAITKV LEEIGVDFKV FTEVEPDPTL STARKGTEEM MDFKPDTIIS   540
LGGGSAMDAA KIMWVMYEHP EVKFEDLAMR FMDIRKRIYN FPKLGEKAMM IAVATSAGTG   600
SEVTPFAVIT DEKTGVKYPL ADYELTPNMA IVDAELMMNM PKGLTAASGI DALIHGIEAY   660
TSVLASEYTN GLALEAIRLI FKYLPTAYAE GTTNEKAREK MAHASTAGM AFANAFLGVC    720
HSMAHKLGAE HHIAHGTANA LLIEEVIRFN SADNPVKQAA YPQYKYPNAK WRYGKIADYL   780
NLGGNTDDEK VELLIKAIHE LKEKINIPMS IKDAGVSEKN FYATLDKMCE LAFDDQCTGA   840
NPRYPLISEI KQMLITAFDK TEINTEIK                                     868

SEQ ID NO: 159           moltype = AA   length = 891
FEATURE                  Location/Qualifiers
source                   1..891
                         mol_type = protein
                         note = strain K12
                         organism = Escherichia coli
SEQUENCE: 159
MAVTNVAELN ALVERVKKAQ REYASFTQEQ VDKIFRAAAL AAADARIPLA KMAVAESGMG    60
IVEDKVIKNH FASEYIYNAY KDEKTCGVLS EDDTFGTITI AEPIGIICGI VPTTNPTSTA   120
IFKSLISLKT RNAIIFSPHP RAKDATNKAA DIVLQAAIAA GAPKDLIGWI DQPSVELSNA   180
LMHPDINLI LATGGPGMVK AAYSSGKPAI GVGAGNTPVV IDETADIKRA VASVLMSKTF    240
DNGVICASEQ SVVVVDSVYD AVRERFATHG GYLLQGKELK AVQDVILKNG ALNAAIVGQP   300
AYKIAELAGF SVPENTKILI GEVTVVDESE PFAHEKLSPT LAMYRAKDFE DAVEKAEKLV   360
AMGGIGHTSC LYTDQDNQPA RVSYFGQKMK TARILINTPA SQGGIGDLYN FKLAPSLTLG   420
CGSWGGNSIS ENVGPKHLIN KKTVAKRAEN MLWHKLPKSI YFRRGSLPIA LDEVITDGHN   480
RALIVTDRFL FNNGYADQIT SVLKAAGVET EVFFEVEADP TLSIVRKGAE LANSFKPDVI   540
IALGGGSPMD AAKIMWVMYE HPETHFEELA LRFMDIRKRI YKFPKMGVKA KMIAVTTTSG   600
TGSEVTPFAV VTDDATGQKY PLADYALTPD MAIVDANLVM DMPKSLCAFG GLDAVTHAME   660
AYVSVLASEF SDGQALQALK LLKEYLPASY HEGSKNPVAR ERVHSAATIA GIAFANAFLG   720
VCHSMAHKLG SQFHIPHGLA NALLICNVIR YNANDNPTKQ TAFSQYDRPQ ARRRYAEIAD   780
HLGLSAPGDR TAAKIEKLLA WLETKAELG IPKSIREAGV QEADFLANVD KLSEDAFDDQ    840
CTGANPRYPL ISELKQILLD TYYGRDYVEG ETAAKKEAAP AKAEKKAKKS A            891

SEQ ID NO: 160           moltype = AA   length = 336
FEATURE                  Location/Qualifiers
source                   1..336
                         mol_type = protein
                         note = strain K12
                         organism = Escherichia coli
SEQUENCE: 160
MKAAVVTKDH HVDVTYKTLR SLKHGEALLK MECCGVCHTD LHVKNGDFGD KTGVILGHEG    60
```

```
IGVVAEVGPG VTSLKPGDRA SVAWFYEGCG HCEYCNSGNE TLCRSVKNAG YSVDGGMAEE    120
CIVVADYAVK VPDGLDSAAA SSITCAGVTT YKAVKLSKIR PGQWIAIYGL GGLGNLALQY    180
AKNVFNAKVI AIDVNDEQLK LATEMGADLA INSHTEDAAK IVQEKTGGAH AAVVTAVAKA    240
AFNSAVDAVR AGGRVVAVGL PPESMSLDIP RLVLDGIEVV GSLVGTRQDL TEAFQFAAEG    300
KVVPKVALRP LADINTIFTE MEEGKIRGRM VIDFRH                              336

SEQ ID NO: 161           moltype = AA  length = 390
FEATURE                  Location/Qualifiers
source                   1..390
                         mol_type = protein
                         note = strain ATCC 824 / DSM 792 / JCM 1419 / LMG 5710 /
                         VKM B-1787
                         organism = Clostridium acetobutylicum
SEQUENCE: 161
MVDFEYSIPT RIFFGKDKIN VLGRELKKYG SKVLIVYGGG SIKRNGIYDK AVSILEKNSI    60
KFYELAGVEP NPRVTTVEKG VKICRENGVE VVLAIGGGSA IDCAKVIAAA CEYDGNPWDI    120
VLDGSKIKRV LPIASILTIA ATGSEMDTWA VINNMDTNEK LIAAHPDMAP KFSILDPTYT    180
YTVPTNQTAA GTADIMSHIF EVYFSNTKTA YLQDRMAEAL LRTCIKYGGI ALEKPDDYEA    240
RANLMWASSL AINGLLTYGK DTNWSVHLME HELSAYYDIT HGVGLAILTP NWMEYILNND    300
TVYKFVEYGV NVWGIDKEKN HYDIAHQAIQ KTRDYFVNVL GLPSRLRDVG IEEEKLDIMA    360
KESVKLTGGT IGNLRPVNAS EVLQIFKKSV                                     390

SEQ ID NO: 162           moltype = AA  length = 348
FEATURE                  Location/Qualifiers
source                   1..348
                         mol_type = protein
                         note = strain ATCC 204508 / S288c
                         organism = Saccharomyces cerevisiae
SEQUENCE: 162
MSIPETQKAI IFYESNGKLE HKDIPVPKPK PNELLINVKY SGVCHTDLHA WHGDWPLPTK    60
LPLVGGHEGA GVVVGMGENV KGWKIGDYAG IKWLNGSCMA CEYCELGNES NCPHADLSGY    120
THDGSFQEYA TADAVQAAHI PQGTDLAEVA PILCAGITVY KALKSANLRA GHWAAISGAA    180
GGLGSLAVQY AKAMGYRVLG IDGGPGKEEL FTSLGGEVFI DFTKEKDIVS AVVKATNGGA    240
HGIINVSVSE AAIEASTRYC RANGTVVLVG LPAGAKCSSD VFNHVVKSIS IVGSYVGNRA    300
DTREALDFFA RGLVKSPIKV VGLSSLPEIY EKMEKGQIAG RYVVDTSK                 348

SEQ ID NO: 163           moltype = AA  length = 399
FEATURE                  Location/Qualifiers
source                   1..399
                         mol_type = protein
                         note = strain DSM 8691 / JW/SL-YS485
                         organism = Thermoanaerobacterium saccharolyticum
SEQUENCE: 163
MWETKVNPSK IFELRCKNTT YFGVGSIHKI KDILENLKIN GINNVIFITG KGSYKTSGAW    60
DVVRPVLEEL DLKYSLYDKV GPNPTVDMID EAAKIGRESG AKAVIGIGGG SPIDTAKSVA    120
VLLKYTDKNA RELYKQKFIP DDAVPIIAIN LTHGTGTEVD RFAVATIPEK NYKPAIAYDC    180
LYPMFAIDDP SLMTKLDKKQ TIAVTVDALN HITEAATTLV ASPYSILTAK ETVRLIVRYL    240
PAAVNDPLNI VARYYLLYAS ALAGISFDNG LLHLTHALEH PLSAVKPEIA HGLGLGAILP    300
AVIKAIYPAT AEVLADVYSP IVPGLKGLPV EAEYVAEKVQ EWLFSVGCIQ KLSDFGFTKD    360
DIPNLVKLAK TTPSLDGLLS IAPVEATESV IEKIYLKSL                           399

SEQ ID NO: 164           moltype = AA  length = 500
FEATURE                  Location/Qualifiers
source                   1..500
                         mol_type = protein
                         note = strain ATCC 204508 / S288c
                         organism = Saccharomyces cerevisiae
SEQUENCE: 164
MTKLHFDTAE PVKITLPNGL TYEQPTGLFI NNKFMKAQDG KTYPVEDPST ENTVCEVSSA    60
TTEDVEYAIE CADRAFHDTE WATQDPRERG RLLSKLADEL ESQIDLVSSI EALDNGKTLA    120
LARGDVTIAI NCLRDAAAYA DKVNGRTINT GDGYMNFTTL EPIGVCGQII PWNFPIMMLA    180
WKIAPALAMG NVCILKPAAV TPLNALYFAS LCKKVGIPAG VVNIVPGPGR TVGAALTNDP    240
RIRKLAFTGS TEVGKSVAVD SSESNLKKIT LELGGKSAHL VFDDANIKKT LPNLVNGIFK    300
NAGQICSSGS RIYVQEGIYD ELLAAFKAYL ETEIKVGNPF DKANFQGAIT NRQQFDTIMN    360
YIDIGKKEGA KILTGEKVG DKGYFIRPTV FYDVNEDMRI VKEEIFGPVV TVAKFKTLEE    420
GVEMANSSEF GLGSGIETES LSTGLKVAKM LKAGTVWINT YNDFDSRVPF GGVKQSGYGR    480
EMGEEVYHAY TEVKAVRIKL                                                500

SEQ ID NO: 165           moltype = AA  length = 453
FEATURE                  Location/Qualifiers
source                   1..453
                         mol_type = protein
                         organism = Homo sapiens
SEQUENCE: 165
MSKISEAVKR ARAAFSSGRT RPLQFRIQQL EALQRLIQEQ EQELVGALAA DLHKNEWNAY    60
YEEVVYVLEE IEYMIQKLPE WAADEPVEKT PQTQQDELYI HSEPLGVVLV IGTWNYPFNL    120
TIQPMVGAIA AGNSVVLKPS ELSENMASLL ATIIPQYLDK DLYPVINGGV PETTELLKER    180
FDHILYTGST GVGKIIMTAA AKHLTPVTLE LGGKSPCYVD KNCDLDVACR RIAWGKFMNS    240
GQTCVAPDYI LCDPSIQNQI VEKLKKSLKE FYGEDAKKSR DYGRIISARH FQRVMGLIEG    300
```

```
QKVAYGGTGD AATRYIAPTI LTDVDPQSPV MQEEIFGPVL PIVCVRSLEE AIQFINQREK    360
PLALYMFSSN DKVIKKMIAE TSSGGVAAND VIVHITLHSL PFGGVGNSGM GSYHGKKSFE    420
TFSHRRSCLV RPLMNDEGLK VRYPPSPAKM TQH                                453

SEQ ID NO: 166           moltype = AA   length = 316
FEATURE                  Location/Qualifiers
source                   1..316
                         mol_type = protein
                         organism = Escherichia coli
SEQUENCE: 166
MSKRKVAIIG SGNIGTDLMI KILRHGQHLE MAVMVGIDPQ SDGLARARRM GVATTHEGVI    60
GLMNMPEFAD IDIVFDATSA GAHVKNDAAL REAKPDIRLI DLTPAAIGPY CVPVVNLEAN    120
VDQLNVNMVT CGGQATIPMV AAVSRVARVH YAEIIASIAS KSAGPGTRAN IDEFTETTSR    180
AIEVVGGAAK GKAIIVLNPA EPPLMMRDTV YVLSDEASQD DIEASINEMA EAVQAYVPGY    240
RLKQRVQFEV IPQDKPVNLP GVGQFSGLKT AVWLEVEGAA HYLPAYAGNL DVMTSSALAT    300
AEKMAQSLAR KAGEAA                                                   316

SEQ ID NO: 167           moltype = AA   length = 312
FEATURE                  Location/Qualifiers
source                   1..312
                         mol_type = protein
                         organism = Pseudomonas putida
SEQUENCE: 167
MSKKLKVAII GPGNIGTDLM IKVMRNAEHL EMGAMVGIDP ASDGLARAQR MGVATTHEGV    60
EGLINLPEFA DIDFVFDATS ASAHVRNDAL LRRAKPGIRL IDLTPAAIGP YCVPVVNLEE    120
HLAKLNVNMV TCGGQATIPM VAAVSRVAKV HYAEIVASIA SKSAGPGTRA NIDEFTETTS    180
KAIEVIGGAA KGKAIIIMNP AEPPLIMRDT VFVLSEAVDQ AQVEASIEEM ASAVQAYVPG    240
YRLKQKVQFD MIPASAPLHI PGLGTFSGLK TSIYLEVEGA AHYLPAYAGN LDIMTSAALA    300
TAERMAQSLL NA                                                       312

SEQ ID NO: 168           moltype = AA   length = 311
FEATURE                  Location/Qualifiers
source                   1..311
                         mol_type = protein
                         note = 34 E 7
                         organism = Pseudomonas sp.
SEQUENCE: 168
MKKKLKVAIVG SGNIGTDLMI KIMRNAKYLE MGAMVGIDPN SDGLARAARL GVAITHEGVE    60
GLTKLPIFPE IDFVFDATSA GAHVKNDAFL RSIKPGIRLI DLTPAAIGPY CIPVVNLEQN    120
LNALNVNMVT CGGQATIPMV AAVSRVAKVH YAEIVASIAS KSAGPGTRAN IDEFTETTSQ    180
AIEAVGGAAR GKAIIVMNPA EPPLMMRDTV FVLSEAADKA QIEASVEEMV AAVQAYVPGY    240
RLKQKVQFDE ISEQAPLNIP GLGKFHGLKI SIFLEVEGAA HYLPSYAGNL DIMTSAALAT    300
AERMAHSMTS V                                                        311

SEQ ID NO: 169           moltype = AA   length = 306
FEATURE                  Location/Qualifiers
source                   1..306
                         mol_type = protein
                         organism = Pseudomonas fluorescens
SEQUENCE: 169
MNKIKCALIG PGNIGTDLLY KLQRSTVLEP VWMVGVDPTS EGLRRAAAMG LKTTSDGVDG    60
LLPHIATDGI LIAFDATSAY VHAENSRKLN ELGVMMIDLT PAAIGPFCVP PVNLLKHVGQ    120
GEMNVNMVTC GGQATIPMVA AVSRVQPVTY GEIVATTASK SIGPGTRANI DEFTRTTGSA    180
IEIVGGAKKG KAIIIINPAE PPMIMRDTVH CLTETEPDRE RITASVQKMV KEVQKYVPGY    240
KLVNGPVFDG KRISLFLEVE GLGDYLPKYA GNLDIMTAAA VRTAEMFAEE ISSGKLKLGP    300
TIETQK                                                              306

SEQ ID NO: 170           moltype = AA   length = 304
FEATURE                  Location/Qualifiers
source                   1..304
                         mol_type = protein
                         note = strain LB400
                         organism = Paraburkholderia xenovorans
SEQUENCE: 170
MTKKIKCALI GPGNIGTDLL AKLQRSPVLE PIWMVGIDPE SDGLKRAREM GIKTTADGVD    60
GLIPHMQADG VQIVFDATSA YVHADNSRKV NALGALMIDL TPAAIGPFCV PTVNLKEHVG    120
KGEMNVNMVT CGGQATIPMV AAVSRVQPVA YGEIVATVSS KSAGPGTRKN IDEFTRTTAG    180
AVEKVGGAKK GKAIIILNPA EPPLIMRDTV HCLLESEPDQ AKITESIHAM IKEVQKYVPG    240
YKLVNGPVFD GLRSVYLEV EGLGDYLPKY AGNLDIMTAA AARTAEMFAE EILAGQLTLQ    300
PVHA                                                                304

SEQ ID NO: 171           moltype = AA   length = 464
FEATURE                  Location/Qualifiers
source                   1..464
                         mol_type = protein
                         organism = Salmonella typhimurium
SEQUENCE: 171
MNTSELETLI RTILSEQLTT PAQTPVQPQG KGIFQSVSEA IDAAHQAFLR YQQCPLKTRS    60
AIISAMRQEL TPLLAPLAEE SANETGMGNK EDKFLKNKAA LDNTPGVEDL TTTALTGDGG    120
```

```
MVLFEYSPFG VIGSVAPSTN PTETIINNSI SMLAAGNSIY FSPHPGAKKV SLKLISLIEE    180
IAFRCCGIRN LVVTVAEPTF EATQQMMAHP RIAVLAITGG PGIVAMGMKS GKKVIGAGAG    240
NPPCIVDETA DLVKAAEDII NGASFDYNLP CIAEKSLIVV ESVAERLVQQ MQTFGALLLS    300
PADTDKLRAV CLPEGQANKK LVGKSPSAML EAAGIAVPAK APRLLIALVN ADDPWVTSEQ    360
LMPMLPVVKV SDFDSALALA LKVEEGLHHT AIMHSQNVSR LNLAARTLQT SIFVKNGPSY    420
AGIGVGGEGF TTFTIATPTG EGTTSARTFA RSRRCVLTNG FSIR                    464

SEQ ID NO: 172          moltype = AA   length = 469
FEATURE                 Location/Qualifiers
source                  1..469
                        mol_type = protein
                        note = serovar 1/2a (strain ATCC BAA-679 / EGD-e)
                        organism = Listeria monocytogenes
SEQUENCE: 172
MESLELEKLV KKVLLEKLAE QKGIPVKTMT KGAKSGVFDT VDEAVQAAVI AQNSYKEKSL    60
EERRNVVKAI REALYPEIES IAARAVAETG MGNVADKILK NTLAIEKTPG VEDLYTEVAT    120
GDNGMTLYEL SPYGVIGAVA PSTNPTETLI CNTIGMLAAG NAVFYSPHPG AKNISLWLIE    180
KLNTIVRESC GVDNLVVTVE KPSIQAAQEM MNHPKVPLLV ITGGPGVVLQ AMQSGKKVIG    240
AGAGNPPSIV DETANIEKAA ADIVDGASFD HNILCIAEKS VVAVDSIADF LMFQMEKNGA    300
LHVTNPSDIQ KLEKVAVTDK GVTNKKLVGK SASEILKEAG IACDFSPRLI IVETEKTHPF    360
ATVELLMPIV PVVVRVPNFEE ALEVAIELEQ GLHHTATMHS QNISRLNKAA RDMQTSIFVK    420
NGPSFAGLGF RGEGSTTFTI ATPTGEGTTT ARHFARRRRC VLTDGFSIR                469

SEQ ID NO: 173          moltype = AA   length = 469
FEATURE                 Location/Qualifiers
source                  1..469
                        mol_type = protein
                        note = serotype 4a (strain M7)
                        organism = Listeria monocytogenes
SEQUENCE: 173
MESLELEKLV KKVLLEKLAE QKDIPVKTTV KGAKSGVFDT VDEAVQAAVI AQNSYKEKSL    60
EERRNVVKAI REALYPEIES IAARAVAETG MGNVADKILK NTLAIEKTPG VEDLYTEVAT    120
GDNGMTLYEL SPYGVIGAVA PSTNPTETLI CNTIGMLAAG NAVFYSPHPG AKNISLWLIE    180
KLNTIVRESC GVDNLVVTVE KPSIQAAQEM MNHPKVPLLV ITGGPGVVLQ AMQSGKKVIG    240
AGAGNPPSIV DETANIEKAA ADIVDGASFD HNILCIAEKS IVAVDSIADF LMFQMEKNGA    300
LHVTNPSDIQ KLEKVAVTDK GVTNKKLVGK SASEILKEAG IVCDFSPRLI IVETEKTHPF    360
ATVELLMPIV PVVVRVPNFDE ALDVAIELEQ GLHHTATMHS QNISRLNKAA RDMQTSIFVK    420
NGPSFAGLGF RGEGSTTFTI ATPTGEGTTT ARHFARRRRC VLTDGFSIR                469

SEQ ID NO: 174          moltype = AA   length = 462
FEATURE                 Location/Qualifiers
source                  1..462
                        mol_type = protein
                        note = subsp. pneumoniae (strain ATCC 700721 / MGH 78578)
                        organism = Klebsiella pneumoniae
SEQUENCE: 174
MNTAELETLI RTILSEKLAP TPPAPQQEQG IFCDVGSAID AAHQAFLRYQ QCPLKTRSAI    60
ISALRETLAP ELATLAEESA TETGMGNKED KYLKNKAALE NTPGIEDLTT SALTGDGGMV    120
LFEYSPFGVI GAVAPSTNPT ETIINNSISM LAAGNSVYFS PHPGAKKVSL KLIARIEEIA    180
YRCSGIRNLV VTVAEPTFEA TQQMMSHPLI AVLAITGGPG IVAMGMKSGK KVIGAGAGNP    240
PCIVDETADL VKAAEDIISG AAFDYNLPCI AEKSLIVVAS VADRLIQQMQ DFDALLLSVG    300
EADTLRAVCL PDGAANKKLV GKSPAALLAA AGLAVPPRPP RLLIAEVEAN DPWVTCEQLM    360
PVLPIVRVAD FDSALALALR VEEGLHHTAI MHSQNVSRLN LAARTLQTSI FVKNGPSYAG    420
IGVGGEGFTT FTIATPTGEG TTSARTFARL RRCVLTNGFS IR                      462

SEQ ID NO: 175          moltype = AA   length = 488
FEATURE                 Location/Qualifiers
source                  1..488
                        mol_type = protein
                        note = HBS-2
                        organism = Acinetobacter sp.
SEQUENCE: 175
MAKEIYIAGE WRLGRGAVIQ SLFPADQSVN AELSTATLED VNEAIEKADQ AWRQPSWRNS    60
LPHERARILY KVADIIEARV DELAKLQTRD NGKPLTDTRG LVMSAAATAR YVAAACETLN    120
DELTTQRAPD FMTMSVHEPV GVVAAITPWN SPIASEVQKL APALAAGNAV VLKPAEATSL    180
IALELAKIFE EAGLPKGLLS VLVGRGSIIG DAIAQHPLVR KISFTGGTTT GRHLAHIAAD    240
KLITTSLELG GKSPTIVLPD ADVELAAKGV AYGIFSSAGQ ACIAGSRLFI HSSLYDQFLT    300
RLVEITKGLR VGHPEQAGVH LGPLVNDKHL QSVDRYVQLA KSEGGQVLIG GEALTTGDYA    360
KGSYYLPTII TGLNNSAQTC QEEIFGPVLV VMKYDNEQDL IAQANDSCFG LAAGIWTESY    420
RKAWRIARAL EVGTVWINTY KKFSISAPFG GFKDSGIGRE KGRLGILSYM QQKSIYMGLN    480
EQPNPWCD                                                           488

SEQ ID NO: 176          moltype = AA   length = 468
FEATURE                 Location/Qualifiers
source                  1..468
                        mol_type = protein
                        organism = Clostridium beijerinckii
SEQUENCE: 176
MNKDTLIPTT KDLKLKTNVE NINLKNYKDN SSCFGVFENV ENAINSAVHA QKILSLHYTK    60
```

```
EQREKIITEI RKAALENKEV LATMILEETH MGRYEDKILK HELVAKYTPG TEDLTTTAWS    120
GDNGLTVVEM SPYGVIGAIT PSTNPTETVI CNSIGMIAAG NAVVFNGHPG AKKCVAFAIE    180
MINKAIISCG GPENLVTTIK NPTMESLDAI IKHPLIKLLC GTGGPGMVKT LLNSGKKAIG    240
AGAGNPPVIV DDTADIEKAG KSIIEGCSFD NNLPCIAEKE VFVFENVADD LISNMLKNNA    300
VIINEDQVSK LIDLVLQKNN ETQEYFINKK WVGKDAKLFS DEIDVESPSN IKCIVCEVNA    360
NHPFVMTELM MPILPIVRVK DIDEAVKYTK IAEQNRKHSA YIYSKNIDNL NRFEREIDTT    420
IFVKNAKSFA GVGYEAEGFT TFTIAGSTGE GITSARNFTR QRRCVLAG                468

SEQ ID NO: 177          moltype = AA   length = 462
FEATURE                 Location/Qualifiers
source                  1..462
                        mol_type = protein
                        note = strain ATCC 700394 / DSM 18823 / ISDg
                        organism = Lachnoclostridium phytofermentans
SEQUENCE: 177
MTVNEQLVQD IIKNVVASMQ LTQTNKTELG VFDDMNQAIE AAKEAQLVVK KMSMDQREKI     60
ISAIRKKTIE HAETLARMAV EETGMGNVGH KILKHQLVAE KTPGTEDITT TAWSGDRGLT    120
LVEMGPFGVI GAITPCTNPS ETIICNTIGM LAGGNTVVFN PHPAAIKTSN FAVQLINEAS    180
LSAGGPVNIA CSVRKPTLDS SKIMMSHQDI PLIAATGGPG VVTAVLQSGK RGIGAGAGNP    240
PVLVDETADI RKAAEDIING CTFDNNLPCI AEKEVVAIDA IANELMNYMV KEQGCYAITK    300
EQQEKLTNLV ITPKGLNRNC VGKDARTLLG MIGIDVPSNI RCIIFEGEKE HPLISEELMM    360
PILGIVRAKS FDDAVEKAVW LEHGNRHSAH IHSKNVDRIT TYAKAIDTAI LVKNAPSYAA    420
IGFGGEGFCT FTIASRTGEG LTSASTFTKR RRCVMSDSLC IR                      462

SEQ ID NO: 178          moltype = AA   length = 307
FEATURE                 Location/Qualifiers
source                  1..307
                        mol_type = protein
                        organism = Comamonas testosteroni
SEQUENCE: 178
MTQKKIKCAL IGPGNIGTDL LMKLQRSPIL EPVWMVGIDP ESDGLKRARE MGIKTTADGV     60
DGLLPFVKED GIQIAFDATS AYVHAENSRK LNELGVLMID LTPAAIGPYC VPSVNLAEKV    120
AEKAMNVNMV TCGGQATIPM VAAVSRVQAV SYGEIVATVS SRSVGPGTRK NIDEFTRTTS    180
GAVEKIGGAQ KGKAIIVINP AEPPLIMRDT IHCLTVDTPK PAEIEASVHA MIKEVQKYVP    240
GYKLVNGPVI DGNRVSIYME VEGLGDYLPK YAGNLDIMTA AARTAEMFA EEILAGRFEL    300
AEAAVAV                                                             307

SEQ ID NO: 179          moltype = AA   length = 468
FEATURE                 Location/Qualifiers
source                  1..468
                        mol_type = protein
                        note = CAG:12
                        organism = Eubacterium hallii
SEQUENCE: 179
MNIDVELIEK VVKKVLNDVE TGSSESEYGY GIFDTMDEAI EASAKAQKEY MNHSMADRQR     60
YVEGIREVVC TKENLEYMSK LAVEESGMGA YEYKVIKNRL AAVKSPGVED LTTEALSGDD    120
GLTLVEYCPF GVIGAIAPTT NPTETVICNS IAMLAGGNTV VFSPHPRSKG VSIWLIKKLN    180
AKLEELGAPR NLIVTVKEPS IENTNIMMNH PKVRMLVATG GPGIVKAVMS TGKKAIGAGA    240
GNPPVVVDET ADIEKAAKDI VNGCSFDNNL PCIAEKEVIA VDQIADYLIF NMKNNGAYEV    300
KDPEIIEKMV DLVTKDRKKP AVNFGKSAQ YILDKVGIKV GPEVKCIIME APKDHPFVQI    360
ELMMPILPIV RVPNVDEAID FAVEVEHGNR HTAMMHSKNV DKLTKMAKEI ETTIFVKNGP    420
SYAGIGVGGM GYTTFTIAGP TGEGLTSAKS FCRKRRCVLQ DGLHIRMK                468

SEQ ID NO: 180          moltype = AA   length = 481
FEATURE                 Location/Qualifiers
source                  1..481
                        mol_type = protein
                        organism = Lactobacillus collinoides
SEQUENCE: 180
MADQNIEAEI RRILQEELSG NASSSAAGTT TSQPDGLGNR IFTNVNDAIA AAKQAQAIYQ     60
DKPLAFRKKV VQAIKDGFGP YIEYMAKQTR EETGMGTAEA KIAKLKNALY NTPGVELLDP    120
EVETGDGGMV MYEYTPFGVI GAVGPSTNPC ETVLNNSIMM MSAGNALFFG AHPGAKNITR    180
WAVEKLNEFV YKATGLKNLL VSLDTPSIES VQEMMQHPDV AMLAVTGGPA VVHQALTSGK    240
KAVGAGAGNP PAMVDATADI DLAAHNLFTS AKFDNEILCT SEKEIIAEDS IKDELLQKIV    300
AKGACLVTDP KDIKHLADMT IGDNGAPDRK YVGKDATVIL DAAGISYTGD PKLIMMDVDK    360
DNPLVKTEML MPILPIVGCP DFDAVLATAI EVEGGNHHTA SIHSNNILHI NKAAHRMNTS    420
IFVANGPTFA ATGVGDNGYY SGAAALTIAT PTGEGTTTTK TFTRRRRFNC PQGFSLRSWE    480
V                                                                   481

SEQ ID NO: 181          moltype = AA   length = 477
FEATURE                 Location/Qualifiers
source                  1..477
                        mol_type = protein
                        organism = Lactobacillus reuteri
SEQUENCE: 181
MQINDIESAV RKILAEELDN ASSSSANVAA TTDNGHRGIF TNVNDAIAAA KAAQEIYRDK     60
PIAVRQQVID AIKEGFRPYI EKMAKDIKEE TGMGTVEAKI AKLNNALYNT PGPEILEPVV    120
ENGDGGMVMY ERLPYGVIGA VGPSTNPSET VIANAIMMLA GGNTLYFGAH PGAKNVTRWT    180
IEKMNDFIAD ATGLHNLVVS IETPTIESVQ QMMKHPDIAM LAVTGGPAVV HQAMTSGKKA    240
```

```
VGAGPGNPPA MVDATADIDL AAHNIITSAS FDNDILCTAE KEVVAESSIK DELIRKMQDE    300
GAFVVNREQA DKLADMCIQE NGAPDRKFVG KDATYILDQA NIPYTGHPVE IICELPKEHP    360
LVMTEMLMPI LPVVSCPTFD DVLKTAVEVE KGNHHTATIH SNNLKHINNA AHRMQCSIFV    420
VNGPSYVGTG VADNGAHSGA SALTIATPTG EGTCTARTFT RRVRLNSPQG FSVRNWY      477

SEQ ID NO: 182           moltype = AA   length = 303
FEATURE                  Location/Qualifiers
REGION                   44..47
                         note = misc_feature - Xaa can be any naturally occurring
                          amino acid
REGION                   60..67
                         note = misc_feature - Xaa can be any naturally occurring
                          amino acid
REGION                   90..91
                         note = misc_feature - Xaa can be any naturally occurring
                          amino acid
REGION                   101..102
                         note = misc_feature - Xaa can be any naturally occurring
                          amino acid
REGION                   114..115
                         note = misc_feature - Xaa can be any naturally occurring
                          amino acid
source                   1..303
                         mol_type = protein
                         organism = Mycobacterium tuberculosis
SEQUENCE: 182
MPSKAKVAIV GSGNISTDLL YKLLRSEWLE PRWMVGIDPE SDGXXXXAKL GLETTHEGVX    60
XXXXXXXKPD LVFEATSAYV HRDAAPKYAX XGIRAIDLTP XXVGPAVIPP ANLXXHLDAP   120
NVNMITCGGQ ATIPIVYAVS RIVEVPYAEI VASVASVSAG PGTRANIDEF TKTTARGVQT   180
IGGAARGKAI IILNPADPPM IMRDTIFCAI PTDADREAIA ASIHDVVKEV QTYVPGYRLL   240
NEPQFDEPSI NSGGQALVTT FVEVEGAGDY LPPYAGNLDI MTAAATKVGE EIAKETLVVG   300
GAR                                                                  303

SEQ ID NO: 183           moltype = AA   length = 303
FEATURE                  Location/Qualifiers
source                   1..303
                         mol_type = protein
                         note = strain ATCC 25618 / H37Rv
                         organism = Mycobacterium tuberculosis
SEQUENCE: 183
MPSKAKVAIV GSGNISTDLL YKLLRSEWLE PRWMVGIDPE SDGLARAAKL GLETTHEGVD    60
WLLAQPDKPD LVFEATSAYV HRDAAPKYAE AGIRAIDLTP AAVGPAVIPP ANLREHLDAP   120
NVNMITCGGQ ATIPIVYAVS RIVEVPYAEI VASVASVSAG PGTRANIDEF TKTTARGVQT   180
IGGAARGKAI IILNPADPPM IMRDTIFCAI PTDADREAIA ASIHDVVKEV QTYVPGYRLL   240
NEPQFDEPSI NSGGQALVTT FVEVEGAGDY LPPYAGNLDI MTAAATKVGE EIAKETLVVG   300
GAR                                                                  303

SEQ ID NO: 184           moltype = AA   length = 304
FEATURE                  Location/Qualifiers
source                   1..304
                         mol_type = protein
                         note = strain LB400
                         organism = Paraburkholderia xenovorans
SEQUENCE: 184
MTKKIKCALI GPGNIGTDLL AKLQRSPVLE PIWMVGIDPE SDGLKRAREM GIKTTADGVD    60
GLIPHMQADG VQIVFDATSA YVHADNSRKV NALGALMIDL TPAAIGPFCV PTVNLKEHVG   120
KGEMNVNMVT CGGQATIPMV AAVSRVQPVA YGEIVATVSS KSAGPGTRKN IDEFTRTTAG   180
AVEKVGGAKK GKAIIILNPA EPPLIMRDTV HCLLESEPDQ AKITESIHAM IKEVQKYVPG   240
YKLVNGPVFD GLRVSVYLEV EGLGDYLPKY AGNLDIMTAA AARTAEMFAE EILAGQLTLQ   300
PVHA                                                                 304

SEQ ID NO: 185           moltype = AA   length = 533
FEATURE                  Location/Qualifiers
source                   1..533
                         mol_type = protein
                         organism = Rhodobacter capsulatus
SEQUENCE: 185
MKDSDIEDAV ARVLSGYTAP KSLETTVAKA LTDLAKPGTQ GCVWEAPKPA DPIDDIIGGI    60
LTRELGEKNC SCCKAGSCTA PANCLSIPDD QAETLGDGIF ATMDAAVEAA AEAQRQYLFC   120
TMSARKRFID GIREVFLNPA LLDRISRLAV EQTGMGNVAH KIIKNRLAAE KTPGIEDLTT   180
EAQSGDDGLT LVELSAYGVI GAITPTTNPT ETIICNAIGM LAAGNAVVFS PHPRARGVSL   240
LAIKLINRKL AALGAPPNLV VTVQAPSIEN TTAMMAHPKV RMLVATGGPA IVKTVLSSGK   300
KAIGAGAGNP PVVVDETADI PKAAQDIVNG CSFDNNMPCV AEKELIAVAE IADFLTAELV   360
RNGAHRLTDP AQITALEKLV LTDKGGPQTG CVGKSALWLL DKIGIAAAPE TRIILIETGR   420
DHPFVQEELM MPILPLVRVG CVDEAIDLAV ELEHGNRHTA IMHSTNVRKL TKMAKLIQTT   480
IFVKNGPSYA GLGVGGEGYA TFTIAGPTGE GLTSPRSFAR RRKCVMVEAL NVR          533

SEQ ID NO: 186           moltype = AA   length = 300
FEATURE                  Location/Qualifiers
```

```
source                  1..300
                        mol_type = protein
                        note = strain RHA1
                        organism = Rhodococcus jostii
SEQUENCE: 186
MTKASVAIVG SGNISTDLLY KLQRSEWLEP RWMIGIDPES EGLARARKLG LETSAEGVDW    60
LLNQPEKPDL VFEATSAYVH REAAPRYEAA GIRAVDLTPA AVGPAVVPPA NLREHLGAPN   120
VNMITCGGQA TIPIVYAVSR VVDVPYAEIV ASVASVSAGP GTRANIDEFT KTTSRGIETI   180
GGAQRGKAII ILNPADPPMI MRDTIFCAIP EDADRAAITD SIHRVVADIQ QYVPGYRLLN   240
EPQFDDPSVV SGGQATVTTF VEVEGAGDFL PPYAGNLDIM TAAATKVGEE IAQKLLSVEA   300

SEQ ID NO: 187          moltype = AA  length = 464
FEATURE                 Location/Qualifiers
source                  1..464
                        mol_type = protein
                        note = strain BisB18
                        organism = Rhodopseudomonas palustris
SEQUENCE: 187
MVAKAIRDHA GTAQPSGNAA TSSAAVSDGV FETMDAAVEA AALAQQQYLL CSMSDRARFV    60
QGIRDVILNQ DTLEKMSRMA VEETGMGNYE HKLIKNRLAG EKTPGIEDLT TDAFSGDNGL   120
TLVEYSPFGV IGAITPTTNP TETIVCNSIG MLAAGNSVVF SPHPRARQVS LLLVRLINQK   180
LAALGAPENL VVTVEKPSIE NTNAMMAHPK VRMLVATGGP AIVKAVLSTG KKAIGAGAGN   240
PPVVVDETAN IEKAACDIVN GCSFDNNLPC VAEKEIIAVA QIADYLIFNL KKNGAYEIKD   300
PAVLQQLQDL VLTAKGGPQT KCVGKSAVWL LSQIGISVDA SIKIILMEVP REHPFVQEEL   360
MMPILPLVRV ETVDDAIDLA IEVEHDNRHT AIMHSTDVRK LTKMAKLIQT TIFVKNGPSY   420
AGLGAGGEGY STFTIAGPTG EGLTSAKSFA RRRKCVMVEA LNIR                    464

SEQ ID NO: 188          moltype = AA  length = 307
FEATURE                 Location/Qualifiers
source                  1..307
                        mol_type = protein
                        note = strain HB8 / ATCC 27634 / DSM 579
                        organism = Thermus thermophilus
SEQUENCE: 188
MSERVKVAIL GSGNIGTDLM YKLLKNPGHM ELVAVVGIDP KSEGLARARA LGLEASHEGI    60
AYILERPEIK IVFDATSAKA HVRHAKLLRE AGKIAIDLTP AARGPYVVPP VNLKEHLDKD   120
NVNLITCGGQ ATIPLVYAVH RVAPVLYAEM VSTVASRSAG PGTRQNIDEF TFTTARGLEA   180
IGGAKKGKAI IILNPAEPPI LMTNTVRCIP EDEGFDREAV VASVRAMERE VQAYVPGYRL   240
KADPVFERLP TPWGERTVVS MLLEVEGAGD YLPKYAGNLD IMTASARRVG EVFAQHLLGK   300
PVEEVVA                                                             307

SEQ ID NO: 189          moltype = AA  length = 340
FEATURE                 Location/Qualifiers
source                  1..340
                        mol_type = protein
                        note = M-1
                        organism = Acinetobacter sp.
SEQUENCE: 189
MSNHQIRAYA AMQAGEQVVP YQFDAGELKA HQVEVKVEYC GLCHSDLSVI NNEWQSSVYP    60
AVAGHEIIGT IIALGSEAKG LKLGQRVGIG WTAETCQACD PCIGGNQVLC TGEKKATIIG   120
HAGGFADKVR AGWQWVIPLP DDLDPESAGP LLCGGITVLD PLLKHKIQAT HHVGVIGIGG   180
LGHIAIKLLK AWGCEITAFS SNPDKTEELK ANGADQVVNS RDAQAIKGTR WKLIILSTAN   240
GTLNVKAYLN TLAPKGSLHF LGVTLEPIPV SVGAIMGGAK SVTSSPTGSP LALRQLLQFA   300
ARKNIAPQVE LFPMSQLNEA IERLHSGQAR YRIVLKADFD                         340

SEQ ID NO: 190          moltype = AA  length = 268
FEATURE                 Location/Qualifiers
source                  1..268
                        mol_type = protein
                        note = M-1
                        organism = Acinetobacter sp.
SEQUENCE: 190
MRIPQFGLGT FRLKDQAVID SVKTALEVGY RAIDTAQVYE NEAAVGQAIA ESGVARQDLF    60
LTTKIWVDNF AEDKFIPSLK DSLQKLRTDA VDLTLIHWPA PALGVSIPSV MQLLLEAKQQ   120
GLTKQIGISN FNIALTQQAI DSIGIEHIAT NQIELSPYLQ NRNLVNYLRE QNIDVTSYMT   180
LAYGKVLQDP TLIEIAAQHQ ATTAQVALAW ALQNGFAVIP SSTKRENLIS NLKAQDLTLS   240
AEEMQLIAQL ERNGREVSPE PFAPEWDK                                      268

SEQ ID NO: 191          moltype = AA  length = 389
FEATURE                 Location/Qualifiers
source                  1..389
                        mol_type = protein
                        note = strain ATCC 824 / DSM 792 / JCM 1419 / LMG 5710 /
                         VKM B-1787
                        organism = Clostridium acetobutylicum
SEQUENCE: 191
MLSFDYSIPT KVFFGKGKID VIGEEIKKYG SRVLIVYGGG SIKRNGIYDR ATAILKENNI    60
AFYELSGVEP NPRITTVKKG IEICRENNVD LVLAIGGGSA IDCSKVIAAG VYYDGDTWDM   120
VKDPSKITKV LPIASILTLS ATGSEMDQIA VISNMETNEK LGVGHDDMRP KFSVLDPTYT   180
```

```
FTVPKNQTAA GTADIMSHTF ESYFSGVEGA YVQDGIAEAI LRTCIKYGKI AMEKTDDYEA   240
RANLMWASSL AINGLLSLGK DRKWSCHPME HELSAYYDIT HGVGLAILTP NWMEYILNDD   300
TLHKFVSYGI NVWGIDKNKD NYEIAREAIK NTREYFNSLG IPSKLREVGI GKDKLELMAK   360
QAVRNSGGTI GSLRPINAED VLEIFKKSY                                    389

SEQ ID NO: 192         moltype = AA  length = 390
FEATURE                Location/Qualifiers
source                 1..390
                       mol_type = protein
                       note = strain ATCC 824 / DSM 792 / JCM 1419 / LMG 5710 /
                       VKM B-1787
                       organism = Clostridium acetobutylicum
SEQUENCE: 192
MVDFEYSIPT RIFFGKDKIN VLGRELKKYG SKVLIVYGGG SIKRNGIYDK AVSILEKNSI   60
KFYELAGVEP NPRVTTVEKG VKICRENGVE VVLAIGGGSA IDCAKVIAAA CEYDGNPWDI   120
VLDGSKIKRV LPIASILTIA ATGSEMDTWA VINNMDTNEK LIAAHPDMAP KFSILDPTYT   180
YTVPTNQTAA GTADIMSHIF EVYFSNTKTA YLQDRMAEAL LRTCIKYGGI ALEKPDDYEA   240
RANLMWASSL AINGLLTYGK DTNWSVHLME HELSAYYDIT HGVGLAILTP NWMEYILNND   300
TVYKFVEYGV NVWGIDKEKN HYDIAHQAIQ KTRDYFVNVL GLPSRLRDVG IEEEKLDIMA   360
KESVKLTGGT IGNLRPVNAS EVLQIFKKSV                                   390

SEQ ID NO: 193         moltype = AA  length = 345
FEATURE                Location/Qualifiers
source                 1..345
                       mol_type = protein
                       organism = Corynebacterium glutamicum
SEQUENCE: 193
MTTAAPQEFT AAVVEKFGHE VTVKDIDLPK PGPNQALVKV LTSGICHTDL HALEGDWPVK   60
PEPPFVPGHE GVGEVVELGP GEHDVKVGDI VGNAWLWSAC GTCEYCITGR ETQCNEAEYG   120
GYTQNGSFGQ YMLVDTRYAA RIPDGVDYLE AAPILCAGVT VYKALKVSDT RPGQFMVISG   180
VGGLGHIAVQ YAVAMGMRVI AVDIADDKLE LARKHGAEFT VNARNEDPGE AVQKFTDGGA   240
HGVLVTAVHE AAFGQALDMA RRAGTIVFNG LPPGEFPASV FNIVFKGLTI RGSLVGTRQD   300
MAEALDFFAR GLVKPTVSEC SLDDVNDVLD RMRNGKIDGR VAIRY                   345

SEQ ID NO: 194         moltype = AA  length = 345
FEATURE                Location/Qualifiers
source                 1..345
                       mol_type = protein
                       note = strain ATCC 13032 / DSM 20300 / JCM 1318 / LMG 3730
                       / NCIMB 10025
                       organism = Corynebacterium glutamicum
SEQUENCE: 194
MTTAAPQEFT AAVVEKFGHD VTVKDIDLPK PGPHQALVKV LTSGICHTDL HALEGDWPVK   60
PEPPFVPGHE GVGEVVELGP GEHDVKVGDI VGNAWLWSAC GTCEYCITGR ETQCNEAEYG   120
GYTQNGSFGQ YMLVDTRYAA RIPDGVDYLE AAPILCAGVT VYKALKVSET RPGQFMVISG   180
VGGLGHIAVQ YAAAMGMRVI AVDIADDKLE LARKHGAEFT VNARNEDSGE AVQKYTNGGA   240
HGVLVTAVHE AAFGQALDMA RRAGTIVFNG LPPGEFPASV FNIVFKGLTI RGSLVGTRQD   300
LAEALDFFAR GLIKPTVSEC SLDEVNGVLD RMRNGKIDGR VAIRF                   345

SEQ ID NO: 195         moltype = AA  length = 387
FEATURE                Location/Qualifiers
source                 1..387
                       mol_type = protein
                       note = strain K12
                       organism = Escherichia coli
SEQUENCE: 195
MNNFNLHTPT RILFGKGAIA GLREQIPHDA RVLITYGGGS VKKTGVLDQV LDALKGMDVL   60
EFGGIEPNPA YETLMNAVKL VREQKVTFLL AVGGGSVLDG TKFIAAAANY PENIDPWHIL   120
QTGGKEIKSA IPMGCVLTLP ATGSESNAGA VISRKTTGDK QAFHSAHVQP VLDLDPVYT   180
YTLPPRQVAN GVVDAFVHTV EQYVTKPVDA KIQDRFAEGI LLTLIEDGPK ALKEPENYDV   240
RANVMWAATQ ALNGLIGAGV PQDWATHMLG HELTAMHGLD HAQTLAIVLP ALWNEKRDTK   300
RAKLLQYAER VWNITEGSDD ERIDAAIAAT RNFFEQLGVP THLSDYGLDG SSIPALLKKL   360
EEHGMTQLGE NHDITLDVSR RIYEAAR                                      387

SEQ ID NO: 196         moltype = AA  length = 339
FEATURE                Location/Qualifiers
source                 1..339
                       mol_type = protein
                       note = strain K12
                       organism = Escherichia coli
SEQUENCE: 196
MSMIKSYAAK EAGGELEVYE YDPGELRPQD VEVQVDYCGI CHSDLSMIDN EWGFSQYPLV   60
AGHEVIGRVV ALGSAAQDKG LQVGQRVGIG WTARSCGHCD ACISGNQINC EQGAVPTIMN   120
RGGFAEKLRA DWQWVIPLPE NIDIESAGPL LCGGITVFKP LLMHHITATS RVGVIGIGGL   180
GHIAIKLLHA MGCEVTAFSS NPAKEQEVLA MGADKVVNSR DPQALKALAG QFDLIINTVN   240
VSLDWQPYFE ALTYGGNFHT VGAVLTPLSV PAFTLIAGDR SVSGSATGTP YELRKLMRFA   300
ARSKVAPTTE LFPMSKINDA IQHVRDGKAR YRVVLKADF                         339

SEQ ID NO: 197         moltype = AA  length = 336
```

| FEATURE | Location/Qualifiers |
|---|---|
| source | 1..336<br>mol_type = protein<br>note = strain K12<br>organism = Escherichia coli |

SEQUENCE: 197

```
MKAAVVTKDH HVDVTYKTLR SLKHGEALLK MECCGVCHTD LHVKNGDFGD KTGVILGHEG    60
IGVVAEVGPG VTSLKPGDRA SVAWFYEGCG HCEYCNSGNE TLCRSVKNAG YSVDGGMAEE   120
CIVVADYAVK VPDGLDSAAA SSITCAGVTT YKAVKLSKIR PGQWIAIYGL GGLGNLALQY   180
AKNVFNAKVI AIDVNDEQLK LATEMGADLA INSHTEDAAK IVQEKTGGAH AAVVTAVAKA   240
AFNSAVDAVR AGGRVVAVGL PPESMSLDIP RLVLDGIEVV GSLVGTRQDL TEAFQFAAEG   300
KVVPKVALRP LADINTIFTE MEEGKIRGRM VIDFRH                             336
```

| SEQ ID NO: 198 | moltype = AA length = 376 |
|---|---|
| FEATURE | Location/Qualifiers |
| source | 1..376<br>mol_type = protein<br>organism = Propionibacterium freudenreichii |

SEQUENCE: 198

```
MKQFQLATSL ACGPDALTAL DRLGGRRVLV ITDAFMASSA LMDTVRGHLG SAEITVFDQV    60
QPNPDVQAVA RGLRAFLDCA PEALLALGGG SPIDTAKAVR KIALEQGQPL SAGFYVVPTT   120
SGTGSEVSSF AVVTDPEHDA KLPMTSPDMV ADVAILDPDA VRTCPPTLTA DSGMDALSHA   180
VEAYVALDHN DITDALAEKA LRLISANLVA SFRDGNDLAA REHQQNAATM AGIAFENSGL   240
GIVHGLSHAI GGSFHVAHGR LNGILMPHVI GFNAGELGFG AATLSPIAER YAQLAAAIGI   300
DAATRRGLVT GLVDFITAIR RDLDMPASLT DAGVDRAAFR AAIPQLSQTA LRDFCTSGNP   360
RPVTAHELAG LLAHAL                                                   376
```

| SEQ ID NO: 199 | moltype = AA length = 348 |
|---|---|
| FEATURE | Location/Qualifiers |
| source | 1..348<br>mol_type = protein<br>note = strain ATCC 204508 / S288c<br>organism = Saccharomyces cerevisiae |

SEQUENCE: 199

```
MSIPETQKGV IFYESHGKLE YKDIPVPKPK ANELLINVKY SGVCHTDLHA WHGDWPLPVK    60
LPLVGGHEGA GVVVGMGENV KGWKIGDYAG IKWLNGSCMA CEYCELGNES NCPHADLSGY   120
THDGSFQQYA TADAVQAAHI PQGTDLAQVA PILCAGITVY KALKSANLMA GHWVAISGAA   180
GGLGSLAVQY AKAMGYRVLG IDGGEGKEEL FRSIGGEVFI DFTKEKDIVG AVLKATDGGA   240
HGVINVSVSE AAIEASTRYV RANGTTVLVG MPAGAKCCSD VFNQVVKSIS IVGSYVGNRA   300
DTREALDFFA RGLVKSPIKV VGLSTLPEIY EKMEKGQIVG RYVVDTSK                348
```

| SEQ ID NO: 200 | moltype = AA length = 348 |
|---|---|
| FEATURE | Location/Qualifiers |
| source | 1..348<br>mol_type = protein<br>note = strain ATCC 204508 / S288c<br>organism = Saccharomyces cerevisiae |

SEQUENCE: 200

```
MSIPETQKAI IFYESNGKLE HKDIPVPKPK PNELLINVKY SGVCHTDLHA WHGDWPLPTK    60
LPLVGGHEGA GVVVGMGENV KGWKIGDYAG IKWLNGSCMA CEYCELGNES NCPHADLSGY   120
THDGSFQQYA TADAVQAAHI PQGTDLAEVA PILCAGITVY KALKSANLRA GHWAAISGAA   180
GGLGSLAVQY AKAMGYRVLG IDGGPGKEEL FTSLGGEVFI DFTKEKDIVS AVVKATNGGA   240
HGIINVSVSE AAIEASTRYC RANGTVVLVG LPAGAKCSSD VFNHVVKSIS IVGSYVGNRA   300
DTREALDFFA RGLVKSPIKV VGLSSLPEIY EKMEKGQIAG RYVVDTSK                348
```

| SEQ ID NO: 201 | moltype = AA length = 382 |
|---|---|
| FEATURE | Location/Qualifiers |
| source | 1..382<br>mol_type = protein<br>note = strain ATCC 204508 / S288c<br>organism = Saccharomyces cerevisiae |

SEQUENCE: 201

```
MSSVTGFYIP PISFFGEGAL EETADYIKNK DYKKALIVTD PGIAAIGLSG RVQKMLEERD    60
LNVAIYDKTQ PNPNIANVTA GLKVLKEQNS EIVVSIGGGS AHDNAKAIAL LATNGGEIGD   120
YEGVNQSKKA ALPLFAINTT AGTASEMTRF TIISNEEKKI KMAIIDNNVT PAVAVNDPST   180
MFGLPPALTA ATGLDALTHC IEAYVSTASN PITDACALKG IDLINESLVA AYKDGKDKKA   240
RTDMCYAEYL AGMAFNNASL GYVHALAHQL GGFYHLPHGV CNAVLLPHVQ EANMQCPKAK   300
KRLGEIALHF GASQEDPEET IKALHVLNRT MNIPRNLKEL GVKTEDFEIL AEHAMHDACH   360
LTNPVQFTKE QVVAIIKKAY EY                                            382
```

| SEQ ID NO: 202 | moltype = AA length = 360 |
|---|---|
| FEATURE | Location/Qualifiers |
| source | 1..360<br>mol_type = protein<br>note = strain ATCC 204508 / S288c<br>organism = Saccharomyces cerevisiae |

SEQUENCE: 202

```
MSYPEKFEGI AIQSHEDWKN PKKTKYDPKP FYDHDIDIKI EACGVCGSDI HCAAGHWGNM    60
KMPLVVGHEI VGKVVKLGPK SNSGLKVGQR VGVGAQVFSC LECDRCKNDN EPYCTKFVTT   120
```

```
YSQPYEDGYV SQGGYANYVR VHEHFVVPIP ENIPSHLAAP LLCGGLTVYS PLVRNGCGPG   180
KKVGIVGLGG IGSMGTLISK AMGAETYVIS RSSRKREDAM KMGADHYIAT LEEGDWGEKY   240
FDTFDLIVVC ASSLTDIDFN IMPKAMKVGG RIVSISIPEQ HEMLSLKPYG LKAVSISYSA   300
LGSIKELNQL LKLVSEKDIK IWVETLPVGE AGVHEAFERM EKGDVRYRFT LVGYDKEFSD   360

SEQ ID NO: 203          moltype = AA   length = 370
FEATURE                 Location/Qualifiers
source                  1..370
                        mol_type = protein
                        organism = Salmonella typhimurium
SEQUENCE: 203
MNTFSLQTRL YSGQGSLAVL KRFTNKHIWI ICDGFLAHSP LLDTLRNALP ADNRISVFSE    60
ITPDPTIHTV VQGIAQMQAL QPQVVIGFGG GSAMDAAKAI VWFSQQSGIN IETCVAIPTT   120
SGTGSEVTSA CVISDPDKGI KYPLFNNALY PDMAILDPEL VVSVPPQITA NTGMDVLTHA   180
LEAWVSPRAS DFTDALAEKA AKLVFQYLPT AVEKGDCVAT RGKMHNASTL AGMAFSQAGL   240
GLNHAIAHQL GGQFHLPHGL ANALLLTTVI RFNAGVPRAA KRYARLAKAC GFCPAEANDI   300
AAINALIQQI ELLKQRCVLP SLAVALKEGR SDFSARIPAM VQAALADVTL RTNPRPANAE   360
AIRELLEELL                                                         370

SEQ ID NO: 204          moltype = AA   length = 347
FEATURE                 Location/Qualifiers
source                  1..347
                        mol_type = protein
                        note = strain DSM 16993 / JCM 10545 / NBRC 100140 / 7
                        organism = Sulfurisphaera tokodaii
SEQUENCE: 204
MRAMRLVEIG KPLKLEDIPI PKPKGSQVLI KIEAAGVCHS DVHMRQGRFG NLRIVEDLGV    60
KLPVTLGHEI AGRIEEVGDE VVGYSKGDLV AVNPWEGEGN CYYCRIGEEH LCDSPRWLGI   120
NYDGAYAEYV LVPHYKYLYK LRRLSAVEAA PLTCSGVTTY RAVRKASLDP SKTLVVIGAG   180
GGLGTMAIQI AKAVSGATII GVDVREEALE AAKRAGADYV INASSQDPVS EIRRITQGKG   240
ADAVIDLNNS EKTLSIYPYV LAKQGKYVMV GLFGADLKYH APLITLNEVQ FIGSLVGNQS   300
DFLGIMSLAE AGKVKPMVTK TMKLEEANEA IDNLENFKAV GRQVLVP                 347

SEQ ID NO: 205          moltype = AA   length = 336
FEATURE                 Location/Qualifiers
source                  1..336
                        mol_type = protein
                        note = strain PCC 6803 / Kazusa
                        organism = Synechocystis sp.
SEQUENCE: 205
MIKAYAALEA NGKLQPFEYD PGALGANEVE IEVQYCGVCH SDLSMINNEW GISNYPLVPG    60
HEVVGTVAAM GEGVNHVEVG DLVGLGWHSG YCMTCHSCLS GYHNLCATAE STIVGHYGGF   120
GDRVRAKGVS VVKLPKGIDL ASAGPLFCGA ITVFSPMVEL SLKPTAKVAV IGIGGLGHLA   180
VQFLRAWGCE VTAFTSSARK QTEVLELGAH HILDSTNPEA IASAEGKFDY IISTVNLKLD   240
WNLYISTLAP QGHFHFVGVV LEPLDLNLFP LLMGQRSVSA SPVGSPATIA TMLDFAVRHD   300
IKPVVEQFSF DQINEAIAHL ESGKAHYRVV LSHSKN                             336

SEQ ID NO: 206          moltype = AA   length = 337
FEATURE                 Location/Qualifiers
source                  1..337
                        mol_type = protein
                        note = subsp. mobilis (strain ATCC 31821 / ZM4 / CP4]
                        organism = Zymomonas mobilis
SEQUENCE: 206
MKAAVITKDH TIEVKDTKLR PLKYGEALLE MEYCGVCHTD LHVKNGDFGD ETGRITGHEG    60
IGIVKQVGEG VTSLKVGDRA SVAWFFKGCG HCEYCVSGNE TLCRNVENAG YTVDGAMAEE   120
CIVVADYSVK VPDGLDPAVA SSITCAGVTT YKAVKVSQIQ PGQWLAIYGL GGLGNLALQY   180
AKNVFNAKVI AIDVNDEQLA FAKELGADMV INPKNEDAAK IIQEKVGGAH ATVVTAVAKS   240
AFNSAVEAIR AGGRVVAVGL PPEKMDLSIP RLVLDGIEVL GSLVGTREDL KEAFQFAAEG   300
KVKPKVTKRK VEEINQIFDE MEHGKFTGRM VVDFTHH                            337

SEQ ID NO: 207          moltype = AA   length = 461
FEATURE                 Location/Qualifiers
source                  1..461
                        mol_type = protein
                        organism = Corynebacterium glutamicum
SEQUENCE: 207
MSDTPTSALI TTVNRSFDGF DLEEVAADLG VRLTYLPDEE LEVSKVLAAD LLAEGPALII    60
GVGNTFFDAQ VAAALGVPVL LLVDKQGKHV ALARTQVNNA GAVVAAAFTA EQEPMPDKLR   120
KAVRNHSNLE PVMSAELFEN WLLKRARAEH SHIVLPEGDD DRILMAAHQL LDQDICDITI   180
LGDPVKIKER ATELGLHLNT AYLVNPLTDP RLEEFAEQFA ELRKSKSVTI DEAREIMKDI   240
SYFGTMMVHN GDADGMVSGA ANTTAHTIKP SFQIIKTVPE ASVVSSIFLM VLRGRLWAFG   300
DCAVNPNPTA EQLGEIAVVS AKTAAQFGID PRVAILSYST GNSGGGSVDD RAIDALAEAR   360
RLNPELCVDG PLQFDAAVDP GVARKKMPDS DVAGQANVFI FPDLEAGNIG YKTAQRTGHA   420
LAVGPILQGL NKPVNDLSRG ATVPDIVNTV AITAIQAGGR S                       461

SEQ ID NO: 208          moltype = AA   length = 397
FEATURE                 Location/Qualifiers
source                  1..397
```

```
                            mol_type = protein
                            note = strain ATCC 13032 / DSM 20300 / JCM 1318 / LMG 3730
                              / NCIMB 10025
                            organism = Corynebacterium glutamicum
SEQUENCE: 208
MALALVLNSG SSSIKFQLVN PENSAIDEPY VSGLVEQIGE PNGRIVLKIE GEKYTLETPI    60
ADHSEGLNLA FDLMDQHNCG PSQLEITAVG HRVVHGGILF SAPELITDEI VEMIRDLIPL   120
APLHNPANVD GIDVARKILP DVPHAVFDT  GFFHSLPPAA ALYAINKDVA AEHGIRRYGF   180
HGTSHEFVSK RVVEILEKPT EDINTITFHL GNGASMAAVQ GGRAVDTSMG MTPLAGLVMG   240
TRSGDIDPGI VFHLSRTAGM SIDEIDNLLN KKSGVKGLSG VNDFRELREM IDNNDQDAWS   300
AYNIYIHQLR RYLGSYMVAL GRVDTIVFTA GVGENAQFVR EDALAGLEMY GIEIDPERNA   360
LPNDGPRLIS TDASKVKVFV IPTNEELAIA RYAVKFA                            397

SEQ ID NO: 209              moltype = AA   length = 398
FEATURE                     Location/Qualifiers
source                      1..398
                            mol_type = protein
                            note = strain ATCC 204508 / S288c
                            organism = Saccharomyces cerevisiae
SEQUENCE: 209
MSQNVYIVST ARTPIGSFQG SLSSKTAVEL GAVALKGALA KVPELDASKD FDEIIFGNVL    60
SANLGQAPAR QVALAAGLSN HIVASTVNKV CASAMKAIIL GAQSIKCGNA DVVVAGGCES   120
MTNAPYYMPA ARAGAKFGQT VLVDGVERDG LNDAYDGLAM GVHAEKCARD WDITREQQDN   180
FAIESYQKSQ KSQKEGKFDN EIVPVTIKGF RGKPDTQVTK DEEPARLHVE KLRSARTVFQ   240
KENGTVTAAN ASPINDGAAA VILVSEKVLK EKNLKPLAII KGWGEAAHQP ADFTWAPSLA   300
VPKALKHAGI EDINSVDYFE FNEAFSVVGL VNTKILKLDP SKVNVYGGAV ALGHPLGCSG   360
ARVVVTLLSI LQQEGGKIGV AAICNGGGGA SSIVIEKI                           398

SEQ ID NO: 210              moltype = AA   length = 392
FEATURE                     Location/Qualifiers
source                      1..392
                            mol_type = protein
                            note = strain ATCC 824 / DSM 792 / JCM 1419 / LMG 5710 /
                              VKM B-1787
                            organism = Clostridium acetobutylicum
SEQUENCE: 210
MKEVVIASAV RTAIGSYGKS LKDVPAVDLG ATAIKEAVKK AGIKPEDVNE VILGNVLQAG    60
LGQNPARQAS FKAGLPVEIP AMTINKVCGS GLRTVSLAAQ IKAGDADVI  IAGGMENMSR   120
APYLANNARW GYRMGNAKFV DEMITDGLWD AFNDYHMGIT AENIAERWNI SREEQDEFAL   180
ASQKKAEEAI KSGQFKDEIV PVVIKGRKGE TVVDTDEHPR FGSTIEGLAK LKPAFKKDGT   240
VTAGNASGLN DCAAVLVIMS AEKAKELGVK PLAKIVSYGS AGVDPAIMGY GPFYATKAAI   300
EKAGWTVDEL DLIESNEAFA AQSLAVAKDL KFDMNKVNVN GGAIALGHPI GASGARILVT   360
LVHAMQKRDA KKGLATLCIG GGQGTAILLE KC                                 392

SEQ ID NO: 211              moltype = AA   length = 394
FEATURE                     Location/Qualifiers
source                      1..394
                            mol_type = protein
                            note = strain K12
                            organism = Escherichia coli
SEQUENCE: 211
MKNCVIVSAV RTAIGSFNGS LASTSAIDLG ATVIKAAIER AKIDSQHVDE VIMGNVLQAG    60
LGQNPARQAL LKSGLAETVC GFTVNKVCGS GLKSVALAAQ AIQAGQAQSI VAGGMENMSL   120
APYLLDAKAR SGYRLGDGQV YDVILRDGLM CATHGYHMGI TAENVAKEYG ITREMQDELA   180
LHSQRKAAAA IESGAFTAEI VPVNVVTRKK TFVFSQDEFP KANSTAEALG ALRPAFDKAG   240
TVTAGNASGI NDGAAALVIM EESAALAAGL TPLARIKSYA SGGVPPALMG MGPVPATQKA   300
LQLAGLQLAD IDLIEANEAF AAQFLAVGKN LGFDSEKVNV NGGAIALGHP IGASGARILV   360
TLLHAMQARD KTLGLATLCI GGGQGIAMVI ERLN                               394

SEQ ID NO: 212              moltype = AA   length = 391
FEATURE                     Location/Qualifiers
source                      1..391
                            mol_type = protein
                            note = strain ATCC 17699 / H16 / DSM 428 / Stanier 337
                            organism = Cupriavidus necator
SEQUENCE: 212
MAEAYIVAAV RTAGGRKGGK LSGWHPADLA AQVLDALVER TGADPALVED VIMGCVSQVG    60
EQAGVNVARNA ILASRLPESV PGTSVDRQCG SSQALHFAA  QAVMSGAMDI VIAAGVESMT   120
RVPMGLSSQL PAKNGFGVPK SPGIEARYPG VQFSQFTGAE MIARKYDLSR EQLDAYALQS   180
HQRAIAATKS GRFTAEILPV EVRTADGANG EMHTTDEGVR YDATLESIGS VKLIAEGGRV   240
TAASASQICD GAAGLMVVNE AGLKKLGVKP LARVHAMTVI GHDPVVMLEA PLPATEVALK   300
KAGLRIGDID LFEVNEAFAP VPLAWLKATG ADPARLNVHG GAIALGHPLG GSGAKLMTTL   360
VHALHTHGKR YGLQTMCEGG GLANVTIVER L                                  391

SEQ ID NO: 213              moltype = AA   length = 395
FEATURE                     Location/Qualifiers
source                      1..395
                            mol_type = protein
                            note = strain ATCC 51363 / DSM 5348 / JCM 9185 / NBRC 15509
```

```
                      / TH2
                      organism = Metallosphaera sedula
SEQUENCE: 213
MPDVYIVSAV  RTPIGRFGGS  LKSVKPQMLG  AIAIKEALRR  ANTDPSRVEL  TIMGNVLRSG   60
HGQDLARQAA  LLAGIPWEVD  GYCVDMVCSS  GMMGVTNAAQ  MIKSGDADVV  VAGGMESMSQ  120
SMLAVNSEVR  WGVKFLSGKS  LNFIDTMLVD  GLTDPFNLKL  MGQEADMVAR  ERDISRRELD  180
EVAFESHRRA  HQAWEKGLFK  SEVIPVNLDE  GKLERDEGIR  PDTTMEKLSS  LKPAFTENGY  240
HTAGNSSQIS  DGAVAMVLMS  EKAVKEFGVD  PVAKILGYSW  VGIESWRFTE  APLYSVRKLL  300
TRLNMNITQF  DYFENNEAFA  VNNVLFHRYL  GVPYDQLNVF  GGAIALGHPI  GASGARIMVT  360
LLNVLSKMNA  TRGIASICHG  VGGSTAIALE  LLRPL                              395

SEQ ID NO: 214          moltype = AA  length = 403
FEATURE                 Location/Qualifiers
source                  1..403
                        mol_type = protein
                        organism = Arabidopsis thaliana
SEQUENCE: 214
MAHTSESVNP  RDVCIVGVAR  TPMGGFLGSL  SSLPATKLGS  LAIAAALKRA  NVDPALVQEV   60
VFGNVLSANL  GQAPARQAAL  GAGIPNSVIC  TTVNKVCASG  MKAVMIAAQS  IQLGINDVVV  120
AGGMESMSNT  PKYLAEARKG  SRFGHDSLVD  GMLKDGLWDV  YNDCGMGSCA  ELCAEKFQIT  180
REQQDDYAVQ  SFERGIAAQE  AGAFTWEIVP  VEVSGGRGRP  STIVDKDEGL  GKFDAAKLRK  240
LRPSFKENGG  TVTAGNASSI  SDGAAALVLV  SGEKALQLGL  LVLAKIKGYG  DAAQEPEFFT  300
TAPALAIPKA  IAHAGLESSQ  VDYYEINEAF  AVVALANQKL  LGIAPEKVNV  NGGAVSLGHP  360
LGCSGARILI  TLLGILKKRN  GKYGVGGVCN  GGGGASALVL  ELL                    403

SEQ ID NO: 215          moltype = AA  length = 216
FEATURE                 Location/Qualifiers
source                  1..216
                        mol_type = protein
                        note = strain K12
                        organism = Escherichia coli
SEQUENCE: 215
MDAKQRIARR  VAQELRDGDI  VNLGIGLPTM  VANYLPEGIH  ITLQSENGFL  GLGPVTTAHP   60
DLVNAGGQPC  GVLPGAAMFD  SAMSFALIRG  GHIDACVLGG  LQVDEEANLA  NWVVPGKMVP  120
GMGGAMDLVT  GSRKVIIAME  HCAKDGSAKI  LRRCTMPLTA  QHAVHMLVTE  LAVFRFIDGK  180
MWLTEIADGC  DLATVRAKTE  ARFEVAADLN  TQRGDL                             216

SEQ ID NO: 216          moltype = AA  length = 220
FEATURE                 Location/Qualifiers
source                  1..220
                        mol_type = protein
                        note = strain K12
                        organism = Escherichia coli
SEQUENCE: 216
MKTKLMTLQD  ATGFFRDGMT  IMVGGFMGIG  TPSRLVEALL  ESGVRDLTLI  ANDTAFVDTG   60
IGPLIVNGRV  RKVIASHIGT  NPETGRRMIS  GEMDVVLVPQ  GTLIEQIRCG  GAGLGGFLTP  120
TGVGTVVEEG  KQTLTLDGKT  WLLERPLRAD  LALIRAHRCD  TLGNLTYQLS  ARNFNPLIAL  180
AADITLVEPD  ELVETGELQP  DHIVTPGAVI  DHIIVSQESK                         220

SEQ ID NO: 217          moltype = AA  length = 508
FEATURE                 Location/Qualifiers
source                  1..508
                        mol_type = protein
                        organism = Paraburkholderia unamae
SEQUENCE: 217
MDVAKAVEQI  FDGATIALTG  SGGGLLEADA  VLAALEQRFL  ATGHPRDLTI  VHALGIGDGK   60
GSGLGRFAHQ  GMVRRVIGGH  WSWSPAMQQL  AKEEAFEAYS  LPAGAISTLL  REIGAGRPGL  120
ITHVGLRTFV  DPRVEGGKLN  ARATEDLVEL  VELDGREYLR  YKPFKVDFAI  VRGSSADAHG  180
NVTLRREPVD  LDTYAVALAA  HNSGGRVIAQ  VKACMPEGES  VPARLVRIPG  VLVDAVVEAP  240
SQVQCTVADY  DPVLSGETRD  TQCAVEPEVP  TGIRYLIAAR  AARELEGECS  ANFGFGIPGG  300
IPGILAQQGR  LGTFWGSVEQ  GIHNGEMLDG  PMFGTARNAH  AILSGVDQFD  FYSGGGIDVT  360
FLGMGEMDGE  GNINVSKLGP  TVVGPGGFID  ITQGARKIVF  CGAFEAKGLE  VEQHGERVTI  420
TRPGSVPKLV  QRVQQITFSG  AQARIAGQEV  LYVTERAVFR  LERDGVRLIE  VTPGIDIERD  480
VIARMGFRPL  VDAALLARRG  ALSQERAA                                      508

SEQ ID NO: 218          moltype = AA  length = 531
FEATURE                 Location/Qualifiers
source                  1..531
                        mol_type = protein
                        note = O157:H7
                        organism = Escherichia coli
SEQUENCE: 218
MKPVKPPRIN  GRVPVLSAQE  AVNYIPDEAT  LCVLGAGGGI  LEATTLITAL  ADKYKQTQTP   60
RNLSIISPTG  LGDRADRGIS  PLAQEGLVKW  ALCGHWGQSP  RISDLAEQNK  IIAYNYPQGV  120
LTQTLRAAAA  HQPGIISDIG  IGTFVDPRQQ  GGKLNEVTKE  DLIKLVEFDN  KEYLYYKAIA  180
PDIAFIRATT  CDSEGYATFE  DEVMYLDALV  IAQAVHNNGG  IVMMQVQKMV  KKATLHPKSV  240
RIPGYLVDIV  VVDPDQSQLY  GGAPVNRFIS  GDFTLDDSTK  LSLPLNQRKL  VARRALFEMR  300
KGAVGNVGVG  IADGIGLVAR  EEGCADDFIL  TVETGPIGGI  TSQGIAFGAN  VNTRAILDMT  360
SQFDFYHGGG  LDVCYLSFAE  VDQHGNVGVH  KFNGKIMGTG  GFIDISATSK  KIIFCGTLTA  420
```

```
GSLKTEIADG KLNIVQEGRV KKFIRELPEI TFSGKIALER GLDVRYITER AVFTLKEDGL    480
HLIEIAPGVD LQKDILDKMD FTPVISPELK LMDERLFIDA AMGFVLPEAA H             531

SEQ ID NO: 219          moltype = AA  length = 218
FEATURE                 Location/Qualifiers
source                  1..218
                        mol_type = protein
                        note = strain ATCC 824 / DSM 792 / JCM 1419 / LMG 5710 /
                        VKM B-1787
                        organism = Clostridium acetobutylicum
SEQUENCE: 219
MNSKIIRFEN LRSFFKDGMT IMIGGFLNCG TPTKLIDFLV NLNIKNLTII SNDTCYPNTG    60
IGKLISNNQV KKLIASYIGS NPDTGKKLFN NELEVELSPQ GTLVERIRAG GSGLGGVLTK   120
TGLGTLIEKG KKKISINGTE YLLELPLTAD VALIKGSIVD EAGNTFYKGT TKNFNPYMAM   180
AAKTVIVEAE NLVSCEKLEK EKAMTPGVLI NYIVKEPA                           218

SEQ ID NO: 220          moltype = AA  length = 221
FEATURE                 Location/Qualifiers
source                  1..221
                        mol_type = protein
                        note = strain ATCC 824 / DSM 792 / JCM 1419 / LMG 5710 /
                        VKM B-1787
                        organism = Clostridium acetobutylicum
SEQUENCE: 220
MINDKNLAKE IIAKRVAREL KNGQLVNLGV GLPTMVADYI PKNFKITFQS ENGIVGMGAS    60
PKINEADKDV VNAGGDYTTV LPDGTFFDSS VSFSLIRGGH VDVTVLGALQ VDEKGNIANW   120
IVPGKMLSGM GGAMDLVNGA KKVIIAMRHT NKGQPKILKK CTLPLTAKSQ ANLIVTELGV   180
IEVINDGLLL TEINKNTTID EIRSLTAADL LISNELRPMA V                       221

SEQ ID NO: 221          moltype = AA  length = 217
FEATURE                 Location/Qualifiers
source                  1..217
                        mol_type = protein
                        note = DSM 13864
                        organism = Clostridium saccharobutylicum
SEQUENCE: 221
MNKIVKLEDL KHVFKDGMTI MVGGFLDCGT PENIIDMLVD LNIKNLTIIS NDTAFPDKGI    60
GKLIVNGQVS KIIASHIGTN PETGKKMNNG EIEVELSPQG TLIERIRAAG SGLGGVLTPT   120
GLGTIVEEGK RKVTIGGKEY LLELPLCADV SIVKGSVVDE FGNICYRATT KNFNPYMAMA   180
GKIVIVEAEN LVKCEQLKRE NIMTPGVLVN YIVKEAA                            217

SEQ ID NO: 222          moltype = AA  length = 221
FEATURE                 Location/Qualifiers
source                  1..221
                        mol_type = protein
                        note = DSM 13864
                        organism = Clostridium saccharobutylicum
SEQUENCE: 222
MIQDKTIAKK IIAKRVAKEL KEGQLVNLGI GLPSLVANYV PNEMNITFQS ENGIVGMGKI    60
AERDKEDEDI INAGGQCTTL LPHGAFLDSS MSFSLIRGGH VDVAVLGALE VDEKGNLANW   120
IVPNKIVPGM GGAMDLAIGA KRIIVAMQHT GKGKPKILKK CNLPLTAKSQ VDLIVTELGV   180
IKVISDGLLL KEINKDTTID EIKSLTEADL IIPPDIKTMD V                       221

SEQ ID NO: 223          moltype = AA  length = 240
FEATURE                 Location/Qualifiers
source                  1..240
                        mol_type = protein
                        organism = Escherichia coli
SEQUENCE: 223
MRKITTAEAL AAQIQDGATI AISGNGGGMV EADHIMAAIE ARFLQTGHPR DLTLIHSLGI    60
GDRDSKGTNR FAHAEMLKRI IAGHFTWSPK MQALVKNNTI EAYCFPGGVI QALLREIGAG   120
RPGLFTHVGL GSFVDPRNGG GKSNECTTDD LVELIEIDGE TKLRYRPFKV DYAILRGTYA   180
DPRGNVSLEE EAIDMDSYSM ALAAHNSGGK VFVQVRDVLE AGTIEPRRVK ATRNSGRWHR   240

SEQ ID NO: 224          moltype = AA  length = 339
FEATURE                 Location/Qualifiers
source                  1..339
                        mol_type = protein
                        organism = Escherichia coli
SEQUENCE: 224
MRGTYADPRG NVSLEEEAID MDSYSMALAA HNSGGKVFVQ VRDVLEAGAI EPRRVKLPGI    60
LVDGIVEHRE QPQTYLGGYD LTISGQHRRL SSNDAIELVS HPVRRLIARR AARELVAGAS   120
TNFGFGIPGG IPGVALREGV PYQSLWLSVE QGVHNGMMLD DALFGCARNA DAIIPSLDQF   180
EFYSGGGIDI TFLGMGEMDQ YGNVNVSHLN GNLIGPGGFL EIAQNARKVV FCGTFDAKGS   240
KIDVTPDGLH IAQSGQIPKL VTQVEKITFS AAYAQQSGQE VLYITERAVF QLTAEGVELI   300
EIAPSVEIER DILPYMAFRP IIKHPRLMES SLFTPMEDA                          339

SEQ ID NO: 225          moltype = AA  length = 244
FEATURE                 Location/Qualifiers
```

```
source                  1..244
                        mol_type = protein
                        note = strain ATCC 824 / DSM 792 / JCM 1419 / LMG 5710 /
                        VKM B-1787
                        organism = Clostridium acetobutylicum
SEQUENCE: 225
MLKDEVIKQI STPLTSPAFP RGPYKFHNRE YFNIVYRTDM DALRKVVPEP LEIDEPLVRF      60
EIMAMHDTSG LGCYTESGQA IPVSFNGVKG DYLHMMYLDN EPAIAVGREL SAYPKKLGYP     120
KLFVDSDTLV GTLDYGKLRV ATATMGYKHK ALDANEAKDQ ICRPNYMLKI IPNYDGSPRI     180
CELINAKITD VTVHEAWTGP TRLQLFDHAM APLNDLPVKE IVSSSHILAD IILPRAEVIY     240
DYLK                                                                 244

SEQ ID NO: 226          moltype = AA  length = 246
FEATURE                 Location/Qualifiers
source                  1..246
                        mol_type = protein
                        note = strain ATCC 51743 / NCIMB 8052
                        organism = Clostridium beijerinckii
SEQUENCE: 226
MLESEVSKQI TTPLAAPAFP RGPYRFHNRE YLNIIYRTDL DALRKIVPEP LELDRAYVRF      60
EMMAMPDTTG LGSYTECGQA IPVKYNGVKG DYLHMMYLDN EPAIAVGRES SAYPKKLGYP     120
KLFVDSDTLV GTLHGYGTLPV ATATMGYKHE PLDLKEAYAQ IARPNFMLKI IQGYDGKPRI    180
CELICAENTD ITIHGAWTGS ARLQLFSHAL APLADLPVLE IVSASHILTD LTLGTPKVVH     240
DYLSVK                                                               246

SEQ ID NO: 227          moltype = AA  length = 326
FEATURE                 Location/Qualifiers
source                  1..326
                        mol_type = protein
                        organism = Patiria pectinifera
SEQUENCE: 227
MDWFVFFVNS ILFIVPVLLA VALLTLVERK VLGYMQLRKG PNIVGPFGLL QPIADGFKLL      60
IKETLKPSNA SPYLFFFSPV LFLGIALVLW SVIPVKYSVV SVNLSLMLII GLSSLSVYSL    120
LGSGWSSNSN YSFLGAVRAV AQTVSYEISL GLILLGVVLF AGGFNVEVIE SSQSWSWLMF    180
SCFPLFAIWF VSTLAETNRA PFDLTEGESE IVSGYNVEYA GGPFAMFFIA EYANIIFINL    240
LSVLLFLGGS SPMGEFFPVN VLVVSLKAGV LVLLFLWVRA SYPRFRYDQL MYLTWKKYLP    300
LSLSFLVFFV VLLGVLDSLP PSSCFL                                        326

SEQ ID NO: 228          moltype = AA  length = 247
FEATURE                 Location/Qualifiers
source                  1..247
                        mol_type = protein
                        note = strain GMI1000
                        organism = Ralstonia solanacearum
SEQUENCE: 228
MDIDTVRKTA FAMPLTSPAY PPGPYRFINR EFFIITYRTD PARLRAMVPE PLEVPEPLVS      60
YEFIRMADST GFGDYTESGQ VIPVTFEGKP GTYTLAMYLD DHPPLAGGRE MWGFPKKLAT    120
PRLQTSKDTL LGTLDYGPVR VATGTMGYKH KELDLAAQQQ RLARPNFLLK IIPHVDGRTA    180
RICELSRNTM EDIVMKGAWT GPASLELAHH ALAPVADLPV LEIVEARHLI ADLTLGMGEV    240
VFDYLAK                                                              247

SEQ ID NO: 229          moltype = AA  length = 252
FEATURE                 Location/Qualifiers
source                  1..252
                        mol_type = protein
                        note = strain LB400
                        organism = Paraburkholderia xenovorans
SEQUENCE: 229
MDVKSVLSNA FAMPITSPAF PMGPYRFINR EFLIITYRTD PDKLRAVVPE PLEIGEPLVH      60
YEFIRMPDST GFGDYTESGQ VIPVSYKGVA GGYTLAMYLD DHPPIAGGRE LWGFPKKLAN    120
PVLAVHDTL VGTLDYGPVR IATGTMGYKH RQLDLAQQKK RLETPNFLLK VIPHVDTPR      180
ICELVRYYLQ DIDLKGAWTG PAALELAPHA LAPVAALPVL EVVEARHLIA DLTLGLGEVV    240
FDYLGQPQAN AR                                                        252

SEQ ID NO: 230          moltype = AA  length = 246
FEATURE                 Location/Qualifiers
source                  1..246
                        mol_type = protein
                        organism = Paenibacillus polymyxa
SEQUENCE: 230
MNQKDVLSLQ SMPAASGSYG RPPCRFINRE FFIITYESDP AAIRQAVPEP LQPDGSNTVS      60
YEWIKMPDSS GLGSYEESGI VIPCTFQGEP CNFVAQMYLD NAPAILGGRE IWGFPKKWAK    120
PRLVVEDTET LTGTLHYNNV LVAMGTTPFK YNVLDEKETA KAIAKTQVNL KLIPDVDGTP    180
KIAQLVAYNL ENITVKGAWS GPARLSLIPH VNAPVADLPV KTYVGGKHFI ANLTLPYGRV    240
LYDYLQ                                                               246

SEQ ID NO: 231          moltype = AA  length = 132
FEATURE                 Location/Qualifiers
source                  1..132
```

```
                            mol_type = protein
                            note = strain K12
                            organism = Escherichia coli
SEQUENCE: 231
MSTTHNVPQG DLVLRTLAMP ADTNANGDIF GGWLMSQMDI GGAILAKEIA HGRVVTVRVE    60
GMTFLRPVAV GDVVCCYARC VQKGTTSVSI NIEVWVKKVA SEPIGQRYKA TEALFKYVAV   120
DPEGKPRALP VE                                                      132

SEQ ID NO: 232          moltype = AA   length = 139
FEATURE                 Location/Qualifiers
source                  1..139
                        mol_type = protein
                        note = strain ATCC 33305 / BD413 / ADP1
                        organism = Acinetobacter baylyi
SEQUENCE: 232
MLDAHISPEG TLSLQTIAMP ADTNWSGDVF GGWIVSQMDL AGAIHAERFS KGRCATISIN    60
QMTFLVPVKV GDVISCYTKI LKVGNTSIQM QIEVWDSHDS SRPPKRVTEG VFTFVAVDVK   120
GNKRTIAEDL KQQFLQHAS                                               139

SEQ ID NO: 233          moltype = AA   length = 418
FEATURE                 Location/Qualifiers
source                  1..418
                        mol_type = protein
                        note = strain ATCC 204508 / S288c
                        organism = Saccharomyces cerevisiae
SEQUENCE: 233
MSATLFNNIE LLPPDALFGI KQRYGQDQRA TKVDLGIGAY RDDNGKPWVL PSVKAAEKLI    60
HNDSSYNHEY LGITGLPSLT SNAAKIIFGT QSDAFQEDRV ISVQSLSGTG ALHISAKFFS   120
KFFPDKLVYL SKPTWANHMA IFENQGLKTA TYPYWANETK SLDLNGFLNA IQKAPEGSIF   180
VLHSCAHNPT GLDPTSEQWV QIVDAIASKN HIALFDTAYQ GFATGDLDKD AYAVRLGVEK   240
LSTVSPVFVC QSFAKNAGMY GERVGCFHLA LTKQAQNKTI KPAVTSQLAK IIRSEVSNPP   300
AYGAKIVAKL LETPELTEQW HKDMVTMSSR ITKMRHALRD HLVKLGTPGN WDHIVNQCGM   360
FSFTGLTPQM VKRLEETHAV YLVASGRASI AGLNQGNVEY VAKAIDEVVR FYTIEAKL    418

SEQ ID NO: 234          moltype = AA   length = 136
FEATURE                 Location/Qualifiers
source                  1..136
                        mol_type = protein
                        note = strain R
                        organism = Corynebacterium glutamicum
SEQUENCE: 234
MLRTILGSKI HRATVTQADL DYVGSVTIDA DLVHAAGLIE GEKVAIVDIT NGARLETYVI    60
VGDAGTGNIC INGAAAHLIN PGDLVIIMSY LQATDAEAKA YEPKIVHVDA DNRIVALGND   120
LAEALPGSGL LTSRSI                                                  136

SEQ ID NO: 235          moltype = AA   length = 376
FEATURE                 Location/Qualifiers
source                  1..376
                        mol_type = protein
                        note = strain ATCC 204508 / S288c
                        organism = Saccharomyces cerevisiae
SEQUENCE: 235
MTLAPLDASK VKITTTQHAS KPKPNSELVF GKSFTDHMLT AEWTAEKGWG TPEIKPYQNL    60
SLDPSAVVFH YAFELFEGMK AYRTVDNKIT MFRPDMNMKR MNKSAQRICL PTFDPEELIT   120
LIGKLIQQDK CLVPEGKGYS LYIRPTLIGT TAGLGVSTPD RALLYVICCP VGPYYKTGFK   180
AVRLEATDYA TRAWPGGCGD KKLGANYAPC VLPQLQAASR GYQQNLWLFG PNNNITEVGT   240
MNAFFVPKDS KTGKKELVTA PLDGTILEGV TRDSILNLAK ERLEPSEWTI SERYFTIGEV   300
TERSKNGELL EAFGSGTAAI VSPIKEIGWK GEQINIPLLP GEQTGPLAKE VAQWINGIQY   360
GETEHGNWSR VVTDLN                                                  376

SEQ ID NO: 236          moltype = AA   length = 475
FEATURE                 Location/Qualifiers
source                  1..475
                        mol_type = protein
                        organism = Lachancea kluyveri
SEQUENCE: 236
MPSYSVAELY YPDEPTEPKI STSSYPGPKA KQELEKLSNV FDTRAAYLLA DYYKSRGNYI    60
VDQDGNVLLD VYAQISSIAL GYNNPEILKV AKSDAMSVAL ANRPALACFP SNDYGQLLED   120
GLLKAAPQGQ DKIWTALSGS DANETAFKAC FMYQAAKKRN GRSFSTEELE SVMDNQLPGT   180
SEMVICSFEK GFHGRLFGSL STTRSKPIHK LDIPAFNWPK APFPDLKYPL EENKEANKAE   240
ESSCIEKFSQ IVQEWQGKIA AVIIEPIQSE GGDNHASSDF FQKLREITIE NGILMIVDEV   300
QTGVGATGKM WAHEHWNLSN PPDLVTFSKK FQAAGFYYHD PKLQPDQPFR QFNTWCGDPS   360
KALIAKVIYE EIVKHDLVTR TAEVGNYLFN RLEKLFEGKN YIQNLRGKGQ GTYIAFDFGT   420
SSERDSFLSR LRCNGANVAG CGDSAVRLRP SLTFEEKHAD VLVSIFDKTL RQLYG       475

SEQ ID NO: 237          moltype = AA   length = 540
FEATURE                 Location/Qualifiers
source                  1..540
                        mol_type = protein
```

```
                         note = strain K12
                         organism = Escherichia coli
SEQ ID NO: 237
MRVNNGLTPQ  ELEAYGISDV  HDIVYNPSYD  LLYQEELDPS  LTGYERGVLT  NLGAVAVDTG   60
IFTGRSPKDK  YIVRDDTTRD  TFWWADKGKG  KNDNKPLSPE  TWQHLKGLVT  RQLSGKRLFV  120
VDAFCGANPD  TRLSVRFITE  VAWQAHFVKN  MFIRPSDEEL  AGFKPDFIVM  NGAKCTNPQW  180
KEQGLNSENF  VAFNLTERMQ  LIGGTWYGGE  MKKGMFSMMN  YLLPLKGIAS  MHCSANVGEK  240
GDVAVFFGLS  GTGKTTLSTD  PKRRLIGDDE  HGWDDDGVFN  FEGGCYAKTI  KLSKEAEPEI  300
YNAIRRDALL  ENVTVREDGT  IDFDDGSKTE  NTRVSYPIYH  IDNIVKPVSK  AGHATKVVIFL 360
TADAFGVLPP  VSRLTADQTQ  YHFLSGFTAK  LAGTERGITE  PTPTFSACFG  AAFLSLHPTQ  420
YAEVLVKRMQ  AAGAQAYLVN  TGWNGTGKRI  SIKDTRAIID  AILNGSLDNA  ETFTLPMFNL  480
AIPTELPGVD  TKILDPRNTY  ASPEQWQEKA  ETLAKLFIDN  FDKYTDTPAG  AALVAAGPKL  540

SEQ ID NO: 238           moltype = AA  length = 332
FEATURE                  Location/Qualifiers
source                   1..332
                         mol_type = protein
                         note = strain ATCC 204508 / S288c
                         organism = Saccharomyces cerevisiae
SEQUENCE: 238
MVRVAINGFG  RIGRLVMRIA  LSRPNVEVVA  LNDPFITNDY  AAYMFKYDST  HGRYAGEVSH   60
DDKHIIVDGK  KIATYQERDP  ANLPWGSSNV  DIAIDSTGVF  KELDTAQKHI  DAGAKKVVIT  120
APSSTAPMFV  MGVNEEKYTS  DLKIVSNASC  TTNCLAPLAK  VINDAFGIEE  GLMTTVHSLT  180
ATQKTVDGPS  HKDWRGGRTA  SGNIIPSSTG  AAKAVGKVLP  ELQGKLTGMA  FRVPTVDVSV  240
VDLTVKLNKE  TTYDEIKKVV  KAAAEGKLKG  VLGYTEDAVV  SSDFLGDSHS  SIFDASAGIQ  300
LSPKFVKLVS  WYDNEYGYST  RVVDLVEHVA  KA                                 332

SEQ ID NO: 239           moltype = AA  length = 356
FEATURE                  Location/Qualifiers
source                   1..356
                         mol_type = protein
                         organism = Kluyveromyces lactis
SEQUENCE: 239
MPDMTNESSS  KPAQINIGIN  GFGRIGRLVL  RAALTHPEVK  VRLINNPSTT  PEYAAYLFKY   60
DSTHGKYRGE  VEFDDERIII  QNDHVSAHIP  LSHFREPERI  PWASYNVDYV  IDSTGVFKEV  120
DTASRHKGVK  KVIITAPSKT  APMYVYGVNH  VKYNPLTDHV  VSNASCTTNC  LAPLVKALDD  180
EFGIEEALMT  TIHATTASQK  TVDGTSSGGK  DWRGGRSCQG  NIIPSSTGAA  KAVGKILPEL  240
NGKITGMSIR  VPTINISLVD  LTFRTAKKTS  YDDIMKALEQ  RSRSDMKGVL  GVTKDAVVSS  300
DFTSDSRSSI  VDAKAGIELN  DHFFKVLSWY  DNEYGYSSRV  VDLSIFMAQK  DFEAGV      356

SEQ ID NO: 240           moltype = AA  length = 500
FEATURE                  Location/Qualifiers
source                   1..500
                         mol_type = protein
                         note = strain ATCC 204508 / S288c
                         organism = Saccharomyces cerevisiae
SEQUENCE: 240
MSRLERLTSL  NVVAGSDLRR  TSIIGTIGPK  TNNPETLVAL  RKAGLNIVRM  NFSHGSYEYH   60
KSVIDNARKS  EELYPGRPLA  IALDTKGPEI  RTGTTTNDVD  YPIPPNHEMI  FTTDDKYAKA  120
CDDKIMYVDY  KNITKVISAG  RIIYDDGVL   SFQVLEVVDD  KTLKVKALNA  GKICSHKGVN  180
LPGTDVDLPA  LSEKDKEDLR  FGVKNGVHMV  FASFIRTAND  VLTIREVLGE  QGKDVKIIVK  240
IENQQGVNNF  DEILKVTDGV  MVARGDLGIE  IPAPEVLAVQ  KKLIAKSNLA  GKPVICATQM  300
LESMTYNPRP  TRAEVSDVGN  AILDGADCVM  LSGETAKGNY  PINAVTTMAE  TAVIAEQAIA  360
YLPNYDDMRN  CTPKPTSTTE  TVAASAVAAV  FEQKAKAIIV  LSTSGTTPRL  VSKYRPNCPI  420
ILVTRCPRAA  RFSHLYRGVF  PFVFEKEPVS  DWTDDVEARI  NFGIEKAKEF  GILKKGDTYV  480
SIQGFKAGAG  HSNTLQVSTV                                                 500

SEQ ID NO: 241           moltype = AA  length = 422
FEATURE                  Location/Qualifiers
source                   1..422
                         mol_type = protein
                         note = strain ATCC 824 / DSM 792 / JCM 1419 / LMG 5710 /
                         VKM B-1787
                         organism = Clostridium acetobutylicum
SEQUENCE: 241
QKKWGETPIN  ERARIMRKAA  DILDDNAEYI  AKILSNEIAK  DLKSSLSEVK  RTADFIRFTA   60
NEGTHMEGEA  INSDNFPGSK  KDKLSLVERV  PLGIVLAISP  FNYPVNLSGS  KVAPALIAGN  120
SVVLKPSTTG  AISALHLAEI  FNAAGLPAGV  LNTVTGKGSE  IGDYLITHEE  VNFINFTGSS  180
AVGKHISKIA  GMIPMVLELG  GKDAAIVLED  ANLETTAKSI  VSGAYGYSGQ  RCTAVKRVLV  240
MDKVADELVE  LVTKKVKELK  VGNPFDDVTI  TPLIDNKAAD  YVQTLIDDAI  EKGATLIVGN  300
KRKENLMYPT  LFDNVTADMR  IAWEEPFGPV  LPIIRVKSMD  EAIELANRSE  YGLQSAVFTE  360
NMHDAFYIAN  KLDVGTVQVN  NKPERGPDHF  PFLGTKSSGM  GTQGIRYSIE  AMTRHKSIVL  420
NL                                                                     422

SEQ ID NO: 242           moltype = AA  length = 528
FEATURE                  Location/Qualifiers
REGION                   1..528
                         note = Enzyme No. 6
source                   1..528
```

```
                        mol_type = protein
                        organism = synthetic construct
SEQUENCE: 242
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HRYDPGQYLK PGTRLISVTC  300
DPLEAARAPM GDAIVADIGA MASALANLVE ESSRQLPTAA PEPAKVDQDA GRLHPETVFD  360
TLNDMAPEDA IYLNESTSTT AQMWQRLNMR NPGSYYLCAA GGLGFALPAA IGVQLAEPER  420
QVIAVIGDGS ANYSISALWT AAQYNVPTIF VIMNNGTYGT LRWFAGVLEA ENVPGLDVPG  480
IDFRALAKGY GVQALKADNL EQLKGSLQEA LSAKGPVLIE VSTVSPVK             528

SEQ ID NO: 243          moltype = AA   length = 528
FEATURE                 Location/Qualifiers
REGION                  1..528
                        note = Enzyme No. 7
source                  1..528
                        mol_type = protein
                        organism = synthetic construct
SEQUENCE: 243
MASVHGTTYE LLRRQGIDIV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY RQYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLDMR NPGSYYFCAA GGLGFALPAA IGVQLAEPGR  420
QVIAVIGDGS ANYSISALWT AAQYNIPTIF VIMNNGTYGL LRWSAGVLGA ENVPGLDVPG  480
IDFRALAKGY GVQALKADNL EQLKGSLQEA LSAKGPVLIE VSTVSPVK             528

SEQ ID NO: 244          moltype = AA   length = 528
FEATURE                 Location/Qualifiers
REGION                  1..528
                        note = Enzyme No. 8
source                  1..528
                        mol_type = protein
                        organism = synthetic construct
SEQUENCE: 244
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY RQYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLNMR NPGSYYFCAA GGLGFALPAA IGVQLAEPER  420
QVIAVIGDGS ANYSISALWT AAQYNIPTIF VIMNNGTYGG LRWFAGVLEA ENVPGLDVPG  480
IDFRALAKGY GVQALKADNL EQLKGSLQEA LSAKGPVLIE VSTVSPVK             528

SEQ ID NO: 245          moltype = AA   length = 528
FEATURE                 Location/Qualifiers
REGION                  1..528
                        note = Enzyme No. 9
source                  1..528
                        mol_type = protein
                        organism = synthetic construct
SEQUENCE: 245
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HRYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLNMR NPGSYYFCAA GGLGFALPAA IGVQLAEPER  420
QVIAVIGDGS ANYSISALWT AAQYNIPTIF VIMNNGTYGT LRWFAGVLEA ENVPGLDVPG  480
IDFRALAKGY GVQALKADNL EQLKGSLQEA LSAKGPVLIE VSTVSPVK             528

SEQ ID NO: 246          moltype = AA   length = 528
FEATURE                 Location/Qualifiers
REGION                  1..528
                        note = Enzyme No. 10
source                  1..528
                        mol_type = protein
                        organism = synthetic construct
SEQUENCE: 246
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
```

```
PFPTRHPCFR GLMPAGIAAI SQLLEGHDVV LVIGAPVFRY HQYDPGQYLK PGTRLISVTC    300
DPLEAARAPM GDAIVADIGA MASALANLVE ESSRQLPTAA PEPAKVDQDA GRLHPETVFD    360
TLNDMAPENA IYLNESTSTT AQMWQRLNMR NPGSYYACAA GGLGFALPAA IGVQLAEPER    420
QVIAVIGDGS ANYSISALWT AAQYNIPTIF VIMNNGTYGA LRWFAGVLEA ENVPGLDVPG    480
IDFRALAKGY GVQALKADNL EQLKGSLQEA LSAKGPVLIE VSTVSPVK                 528

SEQ ID NO: 247              moltype = AA   length = 528
FEATURE                     Location/Qualifiers
REGION                      1..528
                            note = Enzyme No. 11
source                      1..528
                            mol_type = protein
                            organism = synthetic construct
SEQUENCE: 247
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR    120
PLVKWSYEPA SAAEVPHAMS RAIHMASMAP QGPVYLSVPY DDWDKDADPQ SHHLFDRHVS    180
SSVRLNDQDL DILVKALNSA SNPAIVLGPD VDAANANADC VMLAERLKAP VWVAPSAPRC    240
PFPTRHPCFR GLMPAGIAAI SQLLEGHDVV LVIGAPVFRY HQYDPGQYLK PGTRLISVTC    300
DPLEAARAPM GDAIVADIGA MASALANLVE ESSRQLPTAA PEPAKVDQDA GRLHPETVFD    360
TLNDMAPENA IYLNESTSTT AQMWQRLNMR NPGSYYFCAA GGLGFALPAA IGVQLAEPER    420
QVIAVIGDGS ANYSISALWT AAQYNIPTIF VIMNNGTYGL LRWFAGVLEA ENVPGLDVPG    480
IDFRALAKGY GVQALKADNL EQLKGSLQEA LSAKGPVLIE VSTVSPVK                 528

SEQ ID NO: 248              moltype = AA   length = 528
FEATURE                     Location/Qualifiers
REGION                      1..528
                            note = Enzyme No. 12
source                      1..528
                            mol_type = protein
                            organism = synthetic construct
SEQUENCE: 248
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR    120
PLVKWSYEPA SAAEVPHAMS RAIHMASMAP QGPVYLSVPY DDWDKDADPQ SHHLFDRHVS    180
SSVRLNDQDL DILVKALNSA SNPAIVLGPD VDAANANADC VMLAERLKAP VWVAPSAPRC    240
PFPTRHPCFR GLMPAGIAAI SQLLEGHDVV LVIGAPVFRY RQYDPGQYLK PGTRLISVTC    300
DPLEAARAPM GDAIVADIGA MASALANLVE ESSRQLPTAA PEPAKVDQDA GRLHPETVFD    360
TLNDMAPENA IYLNESTSTT AQMWQRLNMR NPGSYYFCAA GGLGFALPAA IGVQLAEPER    420
QVIAVIGDGS ANYSISALWT AAQYNIPTIF VIMNNGTYGA LRWFAGVLEA ENVPGLDVPG    480
IDFRALAKGY GVQALKADNL EQLKGSLQEA LSAKGPVLIE VSTVSPVK                 528

SEQ ID NO: 249              moltype = AA   length = 528
FEATURE                     Location/Qualifiers
REGION                      1..528
                            note = Enzyme No. 13
source                      1..528
                            mol_type = protein
                            organism = synthetic construct
SEQUENCE: 249
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR    120
PLVKWSYEPA SAAEVPHAMS RAIHMASMAP QGPVYLSVPY DDWDKDADPQ SHHLFDRHVS    180
SSVRLNDQDL DILVKALNSA SNPAIVLGPD VDAANANADC VMLAERLKAP VWVAPSAPRC    240
PFPTRHPCFR GLMPAGIAAI SQLLEGHDVV LVIGAPVFRY RQYDPGQYLK PGTRLISVTC    300
DPLEAARAPM GDAIVADIGA MASALANLVE ESSRQLPTAA PEPAKVDQDA GRLHPETVFD    360
TLNDMAPENA IYLNESTSTT AQMWQRLNMR NPGSYYFCAA GGLGFALPAA IGVQLAEPER    420
QVIAVIGDGS ANYSISALWT AAQYNIPTIF VIMNNGTYGT LRWFAGVLEA ENVPGLDVPG    480
IDFRALAKGY GVQALKADNL EQLKGSLQEA LSAKGPVLIE VSTVSPVK                 528

SEQ ID NO: 250              moltype = AA   length = 528
FEATURE                     Location/Qualifiers
REGION                      1..528
                            note = Enzyme No. 14
source                      1..528
                            mol_type = protein
                            organism = synthetic construct
SEQUENCE: 250
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR    120
PLVKWSYEPA SAAEVPHAMS RAIHMASMAP QGPVYLSVPY DDWDKDADPQ SHHLFDRHVS    180
SSVRLNDQDL DILVKALNSA SNPAIVLGPD VDAANANADC VMLAERLKAP VWVAPSAPRC    240
PFPTRHPCFR GLMPAGIAAI SQLLEGHDVV LVIGAPVFRY HRYDPGQYLK PGTRLISVTC    300
DPLEAARAPM GDAIVADIGA MASALANLVE ESSRQLPTAA PEPAKVDQDA GRLHPETVFD    360
TLNDMAPENA IYLNESTSTT AQMWQRLNMR NPGSYYFCAA GGLGFALPAA IGVQLAEPER    420
QVIAVIGDGS ANYSISALWT AAQYNIPTIF VIMNNGTYGA LRWFAGVLEA ENVPGLDVPG    480
IDFRALAKGY GVQALKADNL EQLKGSLQEA LSAKGPVLIE VSTVSPVK                 528

SEQ ID NO: 251              moltype = AA   length = 528
```

| FEATURE | Location/Qualifiers |
|---|---|
| REGION | 1..528 |
| | note = Enzyme No. 15 |
| source | 1..528 |
| | mol_type = protein |
| | organism = synthetic construct |

SEQUENCE: 251
```
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HRYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLNMR NPGSYYFCAA GGLGFALPAA IGVQLAEPER  420
QVIAVIGDGS ANYSISALWT AAQYNIPTIF VIMNNGTYGL LRWFAGVLEA ENVPGLDVPG  480
IDFRALAKGY GVQALKADNL EQLKGSLQEA LSAKGPVLIE VSTVSPVK              528
```

| SEQ ID NO: 252 | moltype = AA   length = 528 |
|---|---|
| FEATURE | Location/Qualifiers |
| REGION | 1..528 |
| | note = Enzyme No. 16 |
| source | 1..528 |
| | mol_type = protein |
| | organism = synthetic construct |

SEQUENCE: 252
```
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HRYDPGQYLK PGTRLISVTC  300
DPLEAARAPM GDAIVADIGA MASALANLVE ESSRQLPTAA PEPAKVDQDA GRLHPETVFD  360
TLNDMAPEDA IYLNESTSTT AQMWQRLNMR NPGSYYLCAA GGLGFALPAA IGVQLAEPER  420
QVIAVIGDGS ANYSISALWT AAQYNVPTIF VIMNNGTYGL LRWFAGVLEA ENVPGLDVPG  480
IDFRALAKGY GVQALKADNL EQLKGSLQEA LSAKGPVLIE VSTVSPVK              528
```

| SEQ ID NO: 253 | moltype = AA   length = 528 |
|---|---|
| FEATURE | Location/Qualifiers |
| REGION | 1..528 |
| | note = Enzyme No. 17 |
| source | 1..528 |
| | mol_type = protein |
| | organism = synthetic construct |

SEQUENCE: 253
```
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HRYDPGQYLK PGTRLISVTC  300
DPLEAARAPM GDAIVADIGA MASALANLVE ESSRQLPTAA PEPAKVDQDA GRLHPETVFD  360
TLNDMAPEDA IYLNESTSTT AQMWQRLNMR NPGSYYLCAA GGLGFALPAA IGVQLAEPER  420
QVIAVIGDGS ANYSISALWT AAQYNVPTIF VIMNNGTYGG LRWFAGVLEA ENVPGLDVPG  480
IDFRALAKGY GVQALKADNL EQLKGSLQEA LSAKGPVLIE VSTVSPVK              528
```

| SEQ ID NO: 254 | moltype = AA   length = 528 |
|---|---|
| FEATURE | Location/Qualifiers |
| REGION | 1..528 |
| | note = Enzyme No. 18 |
| source | 1..528 |
| | mol_type = protein |
| | organism = synthetic construct |

SEQUENCE: 254
```
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HRYDPGQYLK PGTRLISVTC  300
DPLEAARAPM GDAIVADIGA MASALANLVE ESSRQLPTAA PEPAKVDQDA GRLHPETVFD  360
TLNDMAPEDA IYLNESTSTT AQMWQRLNMR NPGSYYLCAA GGLGFALPAA IGVQLAEPER  420
QVIAVIGDGS ANYSISALWT AAQYNVPTIF VIMNNGTYGT LRWSAGVLEA ENVPGLDVPG  480
IDFRALAKGY GVQALKADNL EQLKGSLQEA LSAKGPVLIE VSTVSPVK              528
```

| SEQ ID NO: 255 | moltype = AA   length = 528 |
|---|---|
| FEATURE | Location/Qualifiers |
| REGION | 1..528 |
| | note = Enzyme No. 19 |
| source | 1..528 |
| | mol_type = protein |
| | organism = synthetic construct |

SEQUENCE: 255

-continued

```
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HRYDPGQYLK PGTRLISVTC  300
DPLEAARAPM GDAIVADIGA MASALANLVE ESSRQLPTAA PEPAKVDQDA GRLHPETVFD  360
TLNDMAPEDA IYLNESTSTT AQMWQRLNMR NPGSYYLCAA GGLGFALPAA IGVQLAEPGR  420
QVIAVIGDGS ANYSISALWT AAQYNVPTIF VIMNNGTYGT LRWSAGVLGA ENVPGLDVPG  480
IDFRALAKGY GVQALKADNL EQLKGSLQEA LSAKGPVLIE VSTVSPVK              528

SEQ ID NO: 256          moltype = AA   length = 528
FEATURE                 Location/Qualifiers
REGION                  1..528
                        note = Enzyme No. 20
source                  1..528
                        mol_type = protein
                        organism = synthetic construct
SEQUENCE: 256
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HRYDPGQYLK PGTRLISVTC  300
DPLEAARAPM GDAIVADIGA MASALANLVE ESSRQLPTAA PEPAKVDQDA GRLHPETVFD  360
TLNDMAPEDA IYLNESTSTT AQMWQRLNMR NPGSYYLCAA GGLGFALPAA IGVQLAEPGR  420
QVIAVIGDGS ANYSISALWT AAQYNIPTIF VIMNNGTYGT LRWSAGVLGA ENVPGLDVPG  480
IDFRALAKGY GVQALKADNL EQLKGSLQEA LSAKGPVLIE VSTVSPVK              528

SEQ ID NO: 257          moltype = AA   length = 528
FEATURE                 Location/Qualifiers
REGION                  1..528
                        note = Enzyme No. 21
source                  1..528
                        mol_type = protein
                        organism = synthetic construct
SEQUENCE: 257
MASVHGTTYE LLRRQGIDIV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY HRYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLDMR NPGSYYFCAA GGLGFALPAA IGVQLAEPGR  420
QVIAVIGDGS ANYSISALWT AAQYNIPTIF VIMNNGTYGL LRWSAGVLGA ENVPGLDVPG  480
IDFRALAKGY GVQALKADNL EQLKGSLQEA LSAKGPVLIE VSTVSPVK              528

SEQ ID NO: 258          moltype = AA   length = 528
FEATURE                 Location/Qualifiers
REGION                  1..528
                        note = Enzyme No. 22
source                  1..528
                        mol_type = protein
                        organism = synthetic construct
SEQUENCE: 258
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY RQYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLNMR NPGSYYNCAA GGLGFALPAA IGVQLAEPER  420
QVIAVIGDGS ANYSISALWT AAQYNIPTIF VIMNNGTYGL LRWFAGVLEA ENVPGLDVPG  480
IDFRALAKGY GVQALKADNL EQLKGSLQEA LSAKGPVLIE VSTVSPVK              528

SEQ ID NO: 259          moltype = AA   length = 528
FEATURE                 Location/Qualifiers
REGION                  1..528
                        note = Enzyme No. 23
source                  1..528
                        mol_type = protein
                        organism = synthetic construct
SEQUENCE: 259
MASVHGTTYE LLRRQGIDTV FGNPGSNELP FLKDFPEDFR YILALQEACV VGIADGYAQA   60
SRKPAFINLH SAAGTGNAMG ALSNAWNSHS PLIVTAGQQT RAMIGVEARL TNVDAANLPR  120
PLVKWSYEPA SAAEVPHAMS RAIHMASMAP QGPVYLSVPY DDWDKDADPQ SHHLFDRHVS  180
SSVRLNDQDL DILVKALNSA SNPAIVLGPD VDAANANADC VMLAERLKAP VWVAPSAPRC  240
PFPTRHPCFR GLMPAGIAAI SQLLEGHDVV LVIGAPVFRY RQYDPGQYLK PGTRLISVTC  300
DPLEAARAPM GDAIVADIGA MASALANLVE ESSRQLPTAA PEPAKVDQDA GRLHPETVFD  360
TLNDMAPENA IYLNESTSTT AQMWQRLNMR NPGSYYWCAA GGLGFALPAA IGVQLAEPER  420
```

```
QVIAVIGDGS ANYSISALWT AAQYNIPTIF VIMNNGTYGA LRWFAGVLEA ENVPGLDVPG   480
IDFRALAKGY GVQALKADNL EQLKGSLQEA LSAKGPVLIE VSTVSPVK               528

SEQ ID NO: 260            moltype = AA  length = 528
FEATURE                   Location/Qualifiers
REGION                    1..528
                          note = Enzyme No. 24
source                    1..528
                          mol_type = protein
                          organism = synthetic construct
SEQUENCE: 260
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWVAPSAPRC   240
PFPTRHPCFR GLMPAGIAAI SQLLEGHDVV LVIGAPVFRY RQYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYRCAA GGVGFALPAA IGVQLAEPER   420
QVIAVIGDGS ANYSISALWT AAQYNIPTIF VIMNNGTYGA LRWFAGVLEA ENVPGLDVPG   480
IDFRALAKGY GVQALKADNL EQLKGSLQEA LSAKGPVLIE VSTVSPVK               528

SEQ ID NO: 261            moltype = AA  length = 528
FEATURE                   Location/Qualifiers
REGION                    1..528
                          note = Enzyme No. 25
source                    1..528
                          mol_type = protein
                          organism = synthetic construct
SEQUENCE: 261
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWVAPSAPRC   240
PFPTRHPCFR GLMPAGIAAI SQLLEGHDVV LVIGAPVFRY RQYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYWCAA GGLGFALPAA IGVQLAEPER   420
QVIAVIGDGS ANYSISALWT AAQYNIPTIF VIMNNGTYGN LRWFAGVLEA ENVPGLDVPG   480
IDFRALAKGY GVQALKADNL EQLKGSLQEA LSAKGPVLIE VSTVSPVK               528

SEQ ID NO: 262            moltype = AA  length = 528
FEATURE                   Location/Qualifiers
REGION                    1..528
                          note = Enzyme No. 26
source                    1..528
                          mol_type = protein
                          organism = synthetic construct
SEQUENCE: 262
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVT   180
SSVRLNDQDL DILVKALNSA SNPVIVLGPD VDAANANADC VMLAERLKAP VWVAPSAPRC   240
PFPTRHPCFR GLMPAGIAAI SQLLEGHDVV LVIGAPVFRY HRYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYFCAA GGLGFALPAA IGVQLAEPER   420
QVIAVIGDGS ANYSISALWT AAQYNIPTIF VIMNNGTYGT LRWFAGVLEA ENVPGLDVPG   480
IDFRALAKGY GVQALKADNL EQLKGSLQEA LSAKGPVLIE VSTVSPVK               528

SEQ ID NO: 263            moltype = AA  length = 528
FEATURE                   Location/Qualifiers
REGION                    1..528
                          note = Enzyme No. 27
source                    1..528
                          mol_type = protein
                          organism = synthetic construct
SEQUENCE: 263
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWVAPSAPRC   240
PFPTRHPCFR GLMPAGIAAI SQLLEGHDVV LVIGAPVFRY HRYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYACAA GGLGFALPAA IGVQLAEPER   420
QVIAVIGDGS ANYSISALWT AAQYNIPTIF VIMNNGTYGT LRWFAGVLEA ENVPGLDVPG   480
IDFRALAKGY GVQALKADNL EQLKGSLQEA LSAKGPVLIE VSTVSPVK               528

SEQ ID NO: 264            moltype = AA  length = 528
FEATURE                   Location/Qualifiers
REGION                    1..528
                          note = Enzyme No. 28
```

|  |  |  |
|---|---|---|
| source | 1..528<br>mol_type = protein<br>organism = synthetic construct | |
| SEQUENCE: 264 | | |
| MASVHGTTYE | LLRRQGIDTV FGNPGSNELP FLKDFPEDFR YILALQEACV VGIADGYAQA | 60 |
| SRKPAFINLH | SAAGTGNAMG ALSNAWNSHS PLIVTAGQQT RAMIGVEARL TNVDAANLPR | 120 |
| PLVKWSYEPA | SAAEVPHAMS RAIHMASMAP QGPVYLSVPY DDWDKDADPQ SHHLFDRHVS | 180 |
| SSVRLNDQDL | DILVKALNSA SNPAIVLGPD VDAANANADC VMLAERLKAP VWVAPSAPRC | 240 |
| PFPTRHPCFR | GLMPAGIAAI SQLLEGHDVV LVIGAPVFRY HRYDPGQYLK PGTRLISVTC | 300 |
| DPLEAARAPM | GDAIVADIGA MASALANLVE ESSRQLPTAA PEPAKVDQDA GRLHPETVFD | 360 |
| TLNDMAPENA | IYLNESTSTT AQMWQRLNMR NPGSYYLCAA GGLGFALPAA IGVQLAEPER | 420 |
| QVIAVIGDGS | ANYSISALWT AAQYNIPTIF VIMNNGTYGT LRWFAGVLEA ENVPGLDVPG | 480 |
| IDFRALAKGY | GVQALKADNL EQLKGSLQEA LSAKGPVLIE VSTVSPVK | 528 |

| SEQ ID NO: 265<br>FEATURE<br>REGION | moltype = AA length = 528<br>Location/Qualifiers<br>1..528<br>note = Enzyme No. 29 | |
|---|---|---|
| source | 1..528<br>mol_type = protein<br>organism = synthetic construct | |
| SEQUENCE: 265 | | |
| MASVHGTTYE | LLRRQGIDTV FGNPGSNELP FLKDFPEDFR YILALQEACV VGIADGYAQA | 60 |
| SRKPAFINLH | SAAGTGNAMG ALSNAWNSHS PLIVTAGQQT RAMIGVEARL TNVDAANLPR | 120 |
| PLVKWSYEPA | SAAEVPHAMS RAIHMASMAP QGPVYLSVPY DDWDKDADPQ SHHLFDRHVS | 180 |
| SSVRLNDQDL | DILVKALNSA SNPAIVLGPD VDAANANADC VMLAERLKAP VWVAPSAPRC | 240 |
| PFPTRHPCFR | GLMPAGIAAI SQLLEGHDVV LVIGAPVFRY HRYDPGQYLK PGTRLISVTC | 300 |
| DPLEAARAPM | GDAIVADIGA MASALANLVE ESSRQLPTAA PEPAKVDQDA GRLHPETVFD | 360 |
| TLNDMAPEDA | IYLNESTSTT AQMWQRLNMR NPGSYYRCAA GGVGFALPAA IGVQLAEPER | 420 |
| QVIAVIGDGS | ANYSISALWT AAQYNVPTIF VIMNNGTYGA LRWFAGVLEA ENVPGLDVPG | 480 |
| IDFRALAKGY | GVQALKADNL EQLKGSLQEA LSAKGPVLIE VSTVSPVK | 528 |

| SEQ ID NO: 266<br>FEATURE<br>REGION | moltype = AA length = 528<br>Location/Qualifiers<br>1..528<br>note = Enzyme No. 30 | |
|---|---|---|
| source | 1..528<br>mol_type = protein<br>organism = synthetic construct | |
| SEQUENCE: 266 | | |
| MASVHGTTYE | LLRRQGIDTV FGNPGSNELP FLKDFPEDFR YILALQEACV VGIADGYAQA | 60 |
| SRKPAFINLH | SAAGTGNAMG ALSNAWNSHS PLIVTAGQQT RAMIGVEARL TNVDAANLPR | 120 |
| PLVKWSYEPA | SAAEVPHAMS RAIHMASMAP QGPVYLSVPY DDWDKDADPQ SHHLFDRHVS | 180 |
| SSVRLNDQDL | DILVKALNSA SNPAIVLGPD VDAANANADC VMLAERLKAP VWVAPSAPRC | 240 |
| PFPTRHPCFR | GLMPAGIAAI SQLLEGHDVV LVIGAPVFRY HRYDPGQYLK PGTRLISVTC | 300 |
| DPLEAARAPM | GDAIVADIGA MASALANLVE ESSRQLPTAA PEPAKVDQDA GRLHPETVFD | 360 |
| TLNDMAPEDA | IYLNESTSTT AQMWQRLNMR NPGSYYRCAA GGVGFALPAA IGVQLAEPER | 420 |
| QVIAVIGDGS | ANYSISALWT AAQYNVPTIF VIMNNGTYGG LRWFAGVLEA ENVPGLDVPG | 480 |
| IDFRALAKGY | GVQALKADNL EQLKGSLQEA LSAKGPVLIE VSTVSPVK | 528 |

| SEQ ID NO: 267<br>FEATURE<br>REGION | moltype = AA length = 528<br>Location/Qualifiers<br>1..528<br>note = Enzyme No. 31 | |
|---|---|---|
| source | 1..528<br>mol_type = protein<br>organism = synthetic construct | |
| SEQUENCE: 267 | | |
| MASVHGTTYE | LLRRQGIDTV FGNPGSNELP FLKDFPEDFR YILALQEACV VGIADGYAQA | 60 |
| SRKPAFINLH | SAAGTGNAMG ALSNAWNSHS PLIVTAGQQT RAMIGVEARL TNVDAANLPR | 120 |
| PLVKWSYEPA | SAAEVPHAMS RAIHMASMAP QGPVYLSVPY DDWDKDADPQ SHHLFDRHVS | 180 |
| SSVRLNDQDL | DILVKALNSA SNPAIVLGPD VDAANANADC VMLAERLKAP VWVAPSAPRC | 240 |
| PPPTRHPCFR | GLMPAGIAAI SQLLEGHDVV LVIGAPVFRY HRYDPGQYLK PGTRLISVTC | 300 |
| DPLEAARAPM | GDAIVADIGA MASALANLVE ESSRQLPTAA PEPAKVDQDA GRLHPETVFD | 360 |
| TLNDMAPEDA | IYLNESTSTT AQMWQRLNMR NPGSYYWCAA GGSGFALPAA IGVQLAEPER | 420 |
| QVIAVIGDGS | ANYSISALWT AAQYNVPTIF VIMNNGTYGN LRWFAGVLEA ENVPGLDVPG | 480 |
| IDFRALAKGY | GVQALKADNL EQLKGSLQEA LSAKGPVLIE VSTVSPVK | 528 |

| SEQ ID NO: 268<br>FEATURE<br>REGION | moltype = AA length = 528<br>Location/Qualifiers<br>1..528<br>note = Enzyme No. 32 | |
|---|---|---|
| source | 1..528<br>mol_type = protein<br>organism = synthetic construct | |
| SEQUENCE: 268 | | |
| MASVHGTTYE | LLRRQGIDTV FGNPGSNELP FLKDFPEDFR YILALQEACV VGIADGYAQA | 60 |
| SRKPAFINLH | SAAGTGNAMG ALSNAWNSHS PLIVTAGQQT RAMIGVEARL TNVDAANLPR | 120 |
| PLVKWSYEPA | SAAEVPHAMS RAIHMASMAP QGPVYLSVPY DDWDKDADPQ SHHLFDRHVS | 180 |

```
SSVRLNDQDL DILVKALNSA SNPAIVLGPD VDAANANADC VMLAERLKAP VWVAPSAPRC   240
PFPTRHPCFR GLMPAGIAAI SQLLEGHDVV LVIGAPVFRY RQYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYWCAA GGLGFALPAA IGVQLAEPER   420
QVIAVIGDGS ANYSISALWT AAQYNIPTIF VIMNNGTYGL LRWFAGVLEA ENVPGLDVPG   480
IDFRALAKGY GVQALKADNL EQLKGSLQEA LSAKGPVLIE VSTVSPVK               528

SEQ ID NO: 269          moltype = AA   length = 528
FEATURE                 Location/Qualifiers
REGION                  1..528
                        note = Enzyme No. 33
source                  1..528
                        mol_type = protein
                        organism = synthetic construct
SEQUENCE: 269
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWVAPSAPRC   240
PFPTRHPCFR GLMPAGIAAI SQLLEGHDVV LVIGAPVFRY RQYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYRCAA GGLGFALPAA IGVQLAEPER   420
QVIAVIGDGS ANYSISALWT AAQYNIPTIF VIMNNGTYGL LRWFAGVLEA ENVPGLDVPG   480
IDFRALAKGY GVQALKADNL EQLKGSLQEA LSAKGPVLIE VSTVSPVK               528

SEQ ID NO: 270          moltype = AA   length = 528
FEATURE                 Location/Qualifiers
REGION                  1..528
                        note = Enzyme No. 34
source                  1..528
                        mol_type = protein
                        organism = synthetic construct
SEQUENCE: 270
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWVAPSAPRC   240
PFPTRHPCFR GLMPAGIAAI SQLLEGHDVV LVIGAPVFRY HRYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYWCAA GGLGFALPAA IGVQLAEPER   420
QVIAVIGDGS ANYSISALWT AAQYNIPTIF VIMNNGTYGT LRWFAGVLEA ENVPGLDVPG   480
IDFRALAKGY GVQALKADNL EQLKGSLQEA LSAKGPVLIE VSTVSPVK               528

SEQ ID NO: 271          moltype = AA   length = 528
FEATURE                 Location/Qualifiers
REGION                  1..528
                        note = Enzyme No. 35
source                  1..528
                        mol_type = protein
                        organism = synthetic construct
SEQUENCE: 271
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWVAPSAPRC   240
PFPTRHPCFR GLMPAGIAAI SQLLEGHDVV LVIGAPVFRY HRYDPGQYLK PGTRLISVTC   300
DPLEAARAPM GDAIVADIGA MASALANLVE ESSRQLPTAA PEPAKVDQDA GRLHPETVFD   360
TLNDMAPENA IYLNESTSTT AQMWQRLNMR NPGSYYRCAA GGLGFALPAA IGVQLAEPER   420
QVIAVIGDGS ANYSISALWT AAQYNIPTIF VIMNNGTYGT LRWFAGVLEA ENVPGLDVPG   480
IDFRALAKGY GVQALKADNL EQLKGSLQEA LSAKGPVLIE VSTVSPVK               528

SEQ ID NO: 272          moltype = AA   length = 528
FEATURE                 Location/Qualifiers
REGION                  1..528
                        note = 36
source                  1..528
                        mol_type = protein
                        organism = synthetic construct
SEQUENCE: 272
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWVAPSAPRC   240
PFPTRHPCFR GLMPAGIAAI SQLLEGHDVV LVIGAPVFRY HRYDPGQYLK PGTRLISVTC   300
DPLEAARAPM GDAIVADIGA MASALANLVE ESSRQLPTAA PEPAKVDQDA GRLHPETVFD   360
TLNDMAPEDA IYLNESTSTT AQMWQRLNMR NPGSYYRCAA GGVGFALPAA IGVQLAEPER   420
QVIAVIGDGS ANYSISALWT AAQYNVPTIF VIMNNGTYGT LRWFAGVLEA ENVPGLDVPG   480
IDFRALAKGY GVQALKADNL EQLKGSLQEA LSAKGPVLIE VSTVSPVK               528
```

| | |
|---|---|
| SEQ ID NO: 273 | moltype = AA length = 528 |
| FEATURE | Location/Qualifiers |
| REGION | 1..528 |
| | note = Enzyme No. 37 |
| source | 1..528 |
| | mol_type = protein |
| | organism = synthetic construct |

SEQUENCE: 273
```
MASVHGTTYE LLRRQGIDTV FGNPGSNELP FLKDFPEDFR YILALQEACV VGIADGYAQA    60
SRKPAFINLH SAAGTGNAMG ALSNAWNSHS PLIVTAGQQT RAMIGVEARL TNVDAANLPR   120
PLVKWSYEPA SAAEVPHAMS RAIHMASMAP QGPVYLSVPY DDWDKDADPQ SHHLFDRHVS   180
SSVRLNDQDL DILVKALNSA SNPAIVLGPD VDAANANADC VMLAERLKAP VWVAPSAPRC   240
PPPTRHPCFR GLMPAGIAAI SQLLEGHDVV LVIGAPVFRY HRYDPGQYLK PGTRLISVTC   300
DPLEAARAPM GDAIVADIGA MASALANLVE ESSRQLPTAA PEPAKVDQDA GRLHPETVFD   360
TLNDMAPEDA IYLNESTSTT AQMWQRLNMR NPGSYYWCAA GGSGFALPAA IGVQLAEPER   420
QVIAVIGDGS ANYSISALWT AAQYNVPTIF VIMNNGTYGT LRWFAGVLEA ENVPGLDVPG   480
IDFRALAKGY GVQALKADNL EQLKGSLQEA LSAKGPVLIE VSTVSPVK                528
```

| | |
|---|---|
| SEQ ID NO: 274 | moltype = AA length = 528 |
| FEATURE | Location/Qualifiers |
| REGION | 1..528 |
| | note = amino acid sequence of the enzymes able to catalyze thedecarboxylation of oxaloacetate into malonic semi-aldehyde |
| VARIANT | 19 |
| | note = Xaa in position 19 is selected from the group consisting ofthreonine and isoleucine |
| VARIANT | 109 |
| | note = Xaa in position 109 is selected from the group consisting ofleucine, lysine, arginine and valine |
| VARIANT | 110 |
| | note = Xaa in position 110 is selected from the group consisting ofleucine and lysine |
| VARIANT | 180 |
| | note = Xaa in position 180 is selected from the group consisting ofserine and threonine |
| VARIANT | 204 |
| | note = Xaa in position 204 is selected from the group consisting ofalanine and valine |
| VARIANT | 281 |
| | note = Xaa in position 281 is selected from the group consisting ofhistidine and arginine |
| VARIANT | 282 |
| | note = Xaa in position 282 is selected from the group consisting ofglutamine and arginine |
| VARIANT | 369 |
| | note = Xaa in position 369 is selected from the group consisting ofasparagine and aspartic acid |
| VARIANT | 377 |
| | note = Xaa in position 377 is selected from the group consisting ofthreonine and serine |
| VARIANT | 388 |
| | note = Xaa in position 388 is selected from the group consisting ofasparagine and aspartic acid |
| VARIANT | 397 |
| | note = Xaa in position 397 is selected from the group consisting ofphenylalanine, asparagine, alanine, isoleucine, valine, leucine,tryptophan and arginine |
| VARIANT | 398 |
| | note = Xaa in position 398 is selected from the group consisting ofcysteine and arginine |
| VARIANT | 403 |
| | note = Xaa in position 403 is selected from the group consisting ofleucine, asparagine, alanine, valine and serine |
| VARIANT | 419 |
| | note = Xaa in position 419 is selected from the group consisting ofglutamic acid and glycine |
| VARIANT | 446 |
| | note = Xaa in position 446 is selected from the group consisting ofisoleucine and valine |
| VARIANT | 460 |
| | note = Xaa in position 460 is selected from the group consisting ofalanine, leucine, threonine, glycine and asparagine |
| VARIANT | 464 |
| | note = Xaa in position 464 is selected from the group consisting ofphenylalanine and serine |
| VARIANT | 469 |

```
                        note = Xaa in position 469 is selected from the group
                         consisting ofglutamic acid and glycine
source                  1..528
                        mol_type = protein
                        organism = synthetic construct
SEQUENCE: 274
MASVHGTTYE LLRRQGIDXV FGNPGSNELP FLKDFPEDFR YILALQEACV VGIADGYAQA   60
SRKPAFINLH SAAGTGNAMG ALSNAWNSHS PLIVTAGQQT RAMIGVEAXX TNVDAANLPR  120
PLVKWSYEPA SAAEVPHAMS RAIHMASMAP QGPVYLSVPY DDWDKDADPQ SHHLFDRHVX  180
SSVRLNDQDL DILVKALNSA SNPXIVLGPD VDAANANADC VMLAERLKAP VWVAPSAPRC  240
PPFPTRHPCFR GLMPAGIAAI SQLLEGHDVV LVIGAPVFRY XXYDPGQYLK PGTRLISVTC  300
DPLEAARAPM GDAIVADIGA MASALANLVE ESSRQLPTAA PEPAKVDQDA GRLHPETVFD  360
TLNDMAPEXA IYLNESXSTT AQMWQRLXMR NPGSYYXXAA GGXGFALPAA IGVQLAEPXR  420
QVIAVIGDGS ANYSISALWT AAQYNXPTIF VIMNNGTYGX LRWXAGVLXA ENVPGLDVPG  480
IDFRALAKGY GVQALKADNL EQLKGSLQEA LSAKGPVLIE VSTVSPVK              528

SEQ ID NO: 275          moltype = AA    length = 540
FEATURE                 Location/Qualifiers
source                  1..540
                        mol_type = protein
                        organism = Tribolium castaneum
SEQUENCE: 275
MPATGEDQDL VQDLIEEPAT FSDAVLSSDE ELFHQKCPKP APIYSPVSKP VSFESLPNRR   60
LHEEFLRSSV DVLLQEAVFE GTNRKNRVLQ WREPEELRRL MDFGVRSAPS THEELLEVLK  120
KVVTYSVKTG HPYFVNQLFS AVDPYGLVAQ WATDALNPSV YTYEVSPVFV LMEEVVLREM  180
RAIVGFEGGK GDGIFCPGGS IANGYAISCA RYRFMPDIKK KGLHSLPRLV LFTSEDAHYS  240
IKKLASFQGI GTDNVYLIRT DARGRMDVSH LVEEIERSLR EGAAPFMVSA TAGTTVIGAF  300
DPIEKIADVC QKYKLWLHVD AAWGGGALVS AKHRHLLKGI ERADSVTWNP HKLLTAPQQC  360
STLLLRHEGV LAEAHSTNAA YLFQKDKFYD TKYDTGDKHI QCGRRADVLK FWFMWKAKGT  420
SGLEKHVDKV FENARFFTDC IKNREGFEMV IAEPEYTNIC FWYVPKSLRG RKDEADYKDK  480
LHKVAPRIKE RMMKEGSMMV TYQAQKGHPN FFRIVFQNSG LDKADMVHLV EEIERLGSDL  540

SEQ ID NO: 276          moltype = AA    length = 608
FEATURE                 Location/Qualifiers
source                  1..608
                        mol_type = protein
                        organism = Arabidopsis thaliana
SEQUENCE: 276
MTATTTLKSF NYLSLINHRL NHNSYAILSS PLLPRSHPAS TSFSNSGFRF FQSNHLFSSQ   60
SGSLMEVFKA AFSEASNSCD RIAIKADGKS YSYGQLTSSA LRISKLFLKD DTTNGGQETK  120
KYEGFGSLKG ARIGIVAKPS AEFVAGVLGT WFSGGVAVPL ALSYPEAELL HVMNDSDISL  180
LLSTEDHSET MKTIAAKSGA RFHLIPPVVN STSETVACNQ FQDDSFEAEG KFLDDPALIV  240
YTSGTTGKPK GVVHTHNSIN SQVRMLTEAW EYTSADHFLH CLPLHHVHGL FNALFAPLYA  300
RSLVEFLPKF SVSGIWRRWR ESYPVNDEKT NDSITVFTGV PTMYTRLIQG YEAMDKEMQD  360
SSAFAARKLR LMMSGSSALP RPVMHQWESI TGHRLLERYG MTEFVMAMSN PLRGARNAGT  420
VGKPLPGVEA KIKEDENDAN GVGEICVKSP SLFKEYWNLP EVTKESFTED GYFKTGDAGR  480
VDEDGYYVIL GRNSADIMKV GGYKLSALEI ESTLLEHPTV AECCVLGLTD NDYGEAVTAI  540
IIAESAAKKR REDESKPVIT LEELCGWAKD KLAPYKLPTR LLIWESLPRN AMGKVNKKEL  600
KKSLENQE                                                         608

SEQ ID NO: 277          moltype = AA    length = 576
FEATURE                 Location/Qualifiers
source                  1..576
                        mol_type = protein
                        organism = Homo sapiens
SEQUENCE: 277
MLPHVVLTFR RLGCALASCR LAPARHRGSG LLHTAPVARS DRSAPVFTRA LAFGDRIALV   60
DQHGRHTYRE LYSRSLRLSQ EICRLCGCVG GDLREERVSF LCANDASYVV AQWASWMSGG  120
VAVPLYRKHP AAQLEYVICD SQSSVVLASQ EYLLELLSPVV RKLGVPLLPL TPAIYTGAVE  180
EPAEVPVPEQ GWRNKGAMII YTSGTTGRPK GVLSTHQNIR AVVTGLVHKW AWTKDDVILH  240
VLPLHHVHGV VNALLCPLWV GATCVMMPEF SPQQVWEKFL SSETPRINVF MAVPTIYTKL  300
MEYYDRHFTQ PHAQDFLRAV CEEKIRLMVS GSAALPLPVL EKWKNITGHT LLERYGMTEI  360
GMALSGPLTT AVRLPGSVGT PLPGVQVRIV SENPQREACS YTIHAEGDER GTKVTPGFEE  420
KEGELLVRGP SVFREYWNKP EETKSAFTLD GWFKTGDTVV FKDGQYWIRG RTSVDIIKTG  480
GYKVSALEVE WHLLAHPSIT DVAVIGVPDM TWGQRVTAVV TLREGHSLSH RELKEWARNV  540
LAPYAVPSEL VLVEEIPRNQ MGKIDKKALI RHFHPS                           576

SEQ ID NO: 278          moltype = AA    length = 1220
FEATURE                 Location/Qualifiers
source                  1..1220
                        mol_type = protein
                        organism = Chloroflexus aurantiacus
SEQUENCE: 278
MSGTGRLAGK IALITGGAGN IGSELTRRFL AEGATVIISG RNRAKLTALA ERMQAEAGVP   60
AKRIDLEVMD GSDPVAVRAG IEAIVARHGQ IDILVNNAGS AGAQRRLAEI PLTEAELGPG  120
AEETLHASIA NLLGMGWHLM RIAAPHMPVG SAVINVSTIF SRAEYYGRIP YVTPKAALNA  180
LSQLAARELG ARGIRVNTIF PGPIESDRIR TVFQRMDQLK GRPEGDTAHH FLNTMRLCRA  240
NDQGALERRF PSVGDVADAA VFLASAESAA LSGETIEVTH GMELPACSET SLLARTDLRT  300
IDASGRTTLI CAGDQIEEVM ALTGMLRTCG SEVIIGFRSA AALAQFEQAV NESRRLAGAD  360
```

```
FTPPIALPLD PRDPATIDAV FDWGAGENTG GIHAAVILPA TSHEPAPCVI EVDDERVLNF    420
LADEITGTIV IASRLARYWQ SQRLTPGARA RGPRVIFLSN GADQNGNVYG RIQSAAIGQL    480
IRVWRHEAEL DYQRASAAGD HVLPPVWANQ IVRFANRSLE GLEFACAWTA QLLHSQRHIN    540
EITLNIPANI SATTGARSAS VGWAESLIGL HLGKVALITG GSAGIGGQIG RLLALSGARV    600
MLAARDRHKL EQMQAMIQSE LAEVGYTDVE DRVHIAPGCD VSSEAQLADL VERTLSAFGT    660
VDYLINNAGI AGVEEMVIDM PVEGWRHTLF ANLISNYSLM RKLAPLMKKQ GSGYILNVSS    720
YFGGEKDAAI PYPNRADYAV SKAGQRAMAE VFARFLGPEI QINAIAPGPV EGDRLRGTGE    780
RPGLFARRAR LILENKRLNE LHAALIAAAR TDERSMHELV ELLLPNDVAA LEQNPAAPTA    840
LRELARRFRS EGDPAASSSS ALLNRSIAAK LLARLHNGGY VLPADIFANL PNPPDPFFTR    900
AQIDREARKV RDGIMGMLYL QRMPTEFDVA MATVYYLADR NVSGETFHPS GGLRYERTPT    960
GGELFGLPSP ERLAELVGST VYLIGEHLTE HLNLLARAYL ERYGARQVVM IVETETGAET   1020
MRRLLHDHVE AGRLMTIVAG DQIEAAIDQA ITRYGRPGPV VCTPFRPLPT VPLVGRKDSD   1080
WSTVLSEAEF AELCEHQLTH HFRVARKIAL SDGASLALVT PETTATSTTE QFALANFIKT   1140
TLHAFTATIG VESERTAQRI LINQVDLTRR ARAEEPRDPH ERQQELERFI EAVLLVTAPL   1200
PPEADTRYAG RIHRGRAITV                                              1220

SEQ ID NO: 279         moltype = AA   length = 493
FEATURE                Location/Qualifiers
source                 1..493
                       mol_type = protein
                       organism = Homo sapiens
SEQUENCE: 279
MRGFGPGLTA RRLLPLRLPP RPPGPRLASG QAAGALERAM DELLRRAVPP TPAYELREKT     60
PAPAEGQCAD FVSFYGGLAE TAQRAELLGR LARGFGVDHG QVAEQSAGVL HLRQQQREAA    120
VLLQAEDRLR YALVPRYRGL FHHISKLDGG VRFLVQLRAD LLEAQALKLV EGPDVREMNG    180
VLKGMLSEWF SSGFLNLERV TWHSPCEVLQ KISEAEAVHP VKNWMDMKRR VGPYRRCYFF    240
SHCSTPGEPL VVLHVALTGD ISSNIQAIVK EHPPSETEEK NKITAAIFYS ISLTQQGLQG    300
VELGTFLIKR VVKELQREFP HLGVFSSLSP IPGFTKWLLG LLNSQTKEHG RNELFTDSEC    360
KEISEITGGP INETLKLLLS SSEWVQSEKL VRALQTPLMR LCAWYLYGEK HRGYALNPVA    420
NPHLQNGAVL WRINWMADVS LRGITGSCGL MANYRYFLEE TGPNSTSYLG SKIIKASEQV    480
LSLVAQFQKN SKL                                                      493

SEQ ID NO: 280         moltype = AA   length = 548
FEATURE                Location/Qualifiers
source                 1..548
                       mol_type = protein
                       organism = Lactococcus lactis
SEQUENCE: 280
MYTVGDYLLD RLHELGIEEI FGVPGDYNLQ FLDQIISRKD MKWVGNANEL NASYMADGYA     60
RTKKAAAFLT TFGVGELSAV NGLAGSYAEN LPVVEIGSP TSKVQNEGKF VHHTLADGDF    120
KHFMKMHEPV TAARTLLTAE NATVEIDRVL SALLKERKPV YINLPVDVAA AKAEKPSLPL    180
KKENPTSNTS DQEILNKIQE SLKNAKKPIV ITGHEIISFG LENTVTQFIS KTKLPITTLN    240
FGKSSVDETL PSFLGIYNGK LSEPNLKEFV ESADFILMLG VKLTDSSTGA FTHHLNENKM    300
ISLNIDEGKI FNESIQNFDF ESLISSLLDL SGIEYKGKYI DKKQEDFVPS NALLSQDRLW    360
QAVENLTQSN ETIVAEQGTS FFGASSIFLK PKSHFIGQPL WGSIGYTFPA ALGSQIADKE    420
SRHLLFIGDG SLQLTVQELG LAIREKINPI CFIINNDGYT VEREIHGPNQ SYNDIPMWNY    480
SKLPESFGAT EERVVSKIVR TENEFVSVMK EAQADPNRMY WIELVLAKED APKVLKKMGK    540
LFAEQNKS                                                            548

SEQ ID NO: 281         moltype = AA   length = 547
FEATURE                Location/Qualifiers
source                 1..547
                       mol_type = protein
                       organism = Lactococcus lactis
SEQUENCE: 281
MYTVGDYLLD RLHELGIEEI FGVPGDYNLQ FLDQIISRED MKWIGNANEL NASYMADGYA     60
RTKKAAAFLT TFGVGELSAI NGLAGSYAEN LPVVEIGSP TSKVQNDGKF VHHTLADGDF    120
KHFMKMHEPV TAARTLLTAE NATYEIDRVL SQLLKERKPV YINLPVDVAA AKAEKPALSL    180
EKESSTTNTT EQVILSKIEE SLKNAQKPVV IAGHEVISFG LEKTVTQFVS ETKLPITTLN    240
FGKSAVDESL PSFLGIYNGK LSEISLKNFV ESADFILMLG VKLTDSSTGA FTHHLDENKM    300
ISLNIDEGII FNKVVEDFDF RAVVSSLSEL KGIEYEGQYI DKQYEEFIPS SAPLSQDRLW    360
QAVESLTQSN ETIVAEQGTS FFGASTIFLK SNSRFIGQPL WGSIGYTFPA ALGSQIADKE    420
SRHLLFIGDG SLQLTVQELG LSIREKLNPI CFIINNDGYT VEREIHGPTQ SYNDIPMWNY    480
SKLPETFGAT EDRVVSKIVR TENEFVSVMK EAQADVNRMY WIELVLEKED APKLLKKMGK    540
LFAEQNK                                                             547

SEQ ID NO: 282         moltype = AA   length = 635
FEATURE                Location/Qualifiers
source                 1..635
                       mol_type = protein
                       organism = Saccharomyces cerevisiae
SEQUENCE: 282
MAPVTIEKFV NQEERHLVSN RSATIPFGEY IFKRLLSIDT KSVFGVPGDF NLSLLEYLYS     60
PSVESAGLRW VGTCNELNAA YAADGYSRYS NKIGCLITTY GVGELSALNG IAGSFAENVK    120
VLHIVGVAKS IDSRSSNFSD RNLHHLVPQL HDSNFKGPNH KVYHDMVKDR VACSVAYLED    180
IETACDQVDN VIRDIYKSK PGYIFVPADF ADMSVTCDNL VNVPRISQQD CIVYPSENQL    240
SDIINKITSW IYSSKTPAIL GDVLTDRYGV SNFLNKLICK TGIWNFSTVM GKSVIDESNP    300
TYMGQYNGKE GLKQVYEHFE LCDLVLHFGV DINEINNGHY TFTYKPNAKI IQFHPNYIRL    360
VDTRQGNEQM FKGINFAPIL KELYKRIDVS KLSLQYDSNV TQYTNETMRL EDPTNGQSSI    420
```

```
ITQVHLQKTM PKFLNPGDVV VCETGSFQFS VRDFAFPSQL KYISQGFFLS IGMALPAALG    480
VGIAMQDHSN AHINGGNVKE DYKPRLILFE GDGAAQMTIQ ELSTILKCNI PLEVIIWNNN    540
GYTIERAIMG PTRSYNDVMS WKWTKLFEAF GDFDGKYTNS TLIQCPSKLA LKLEELKNSN    600
KRSGIELLEV KLGELDFPEQ LKCMVEAAAL KRNKK                               635

SEQ ID NO: 283          moltype = AA  length = 491
FEATURE                 Location/Qualifiers
source                  1..491
                        mol_type = protein
                        organism = Saccharomyces cerevisiae
SEQUENCE: 283
MKLSTKLCWC GIKGRLRPQK QQQLHNTNLQ MTELKKQKTA EQKTRPQNVG IKGIQIYIPT    60
QCVNQSELEK FDGVSQGKYT IGLGQTNMSF VNDREDIYSM SLTVLSKLIK SYNIDTNKIG   120
RLEVGTETLI DKSKSVKSVL MQLFGENTDV EGIDTLNACY GGTNALFNSL NWIESNAWDG   180
RDAIVVCGDI AIYDKGAARP TGGAGTVAMW IGPDAPIVFD SVRASYMEHA YDFYKPDFTS   240
EYPYVDGHFS LTCYVKALDQ VYKSYSKKAI SKGLVSDPAG SDALNVLKYF DYNVFHVPTC   300
KLVTKSYGRL LYNDFRANPQ LFPEVDAELA TRDYDESLTD KNIEKTFVNV AKPFHKERVA   360
QSLIVPTNTG NMYTASVYAA FASLLNYVGS DDLQGKRVGL FSYGSGLAAS LYSCKIVGDV   420
QHIIKELDIT NKLAKRITET PKDYEAAIEL RENAHLKKNF KPQGSIEHLQ SGVYYLTNID   480
DKFRRSYDVK K                                                        491

SEQ ID NO: 284          moltype = AA  length = 299
FEATURE                 Location/Qualifiers
source                  1..299
                        mol_type = protein
                        organism = Bacillus subtilis
SEQUENCE: 284
MPYPKKVTIK EVGPRDGLQN EPVWIATEDK ITWINQLSRT GLSYIEITSF VHPKWIPALR    60
DAIDVAKGID REKGVTYAAL VPNQRGLENA LEGGINEACV FMSASETHNR KNINKSTSES   120
LHILKQVNND AQKANLTTRA YLSTVFGCPY EKDVPIEQVI RLSEALFEFG ISELSLGDTI   180
GAANPAQVET VLEALLARFP ANQIALHFHD TRGTALANMV TALQMGITVF DGSAGGLGGC   240
PYAPGSSGNA ATEDIVYMLE QMDIKTNVKL EKLLSAAKWI EEKMGKPLPS RNLQVFKSS    299

SEQ ID NO: 285          moltype = AA  length = 329
FEATURE                 Location/Qualifiers
source                  1..329
                        mol_type = protein
                        organism = Streptomyces sp.
SEQUENCE: 285
MTDVRFRIIG TGAYVPERIV SNDEVGAPAG VDDDWITRKT GIRQRRWAAD DQATSDLATA    60
AGRAALKAAG ITPEQLTVIA VATSTPDRPQ PPTAAYVQHH LGATGTAAFD VNAVCSGTVF   120
ALSSVAGTLV YRGGYALVIG ADLYSRILNP ADRKTVVLFG DGAGAMVLGP TSTGTGPIVR   180
RVALHTFGGL TDLIRVPAGG SRQPLDTDGL DAGLQYFAMD GREVRRFVTE HLPQLIKGFL   240
HEAGVDAADI SHFVPHQANG VMLDEVFGEL HLPRATMHRT VETYGNTGAA SIPITMDAAV   300
RAGSFRPGEL VLLAGFGGGM AASFALIEW                                     329
```

CO-PRODUCTION PATHWAY FOR 3-HPA AND ACETYL-COA DERIVATIVES FROM MALONATE SEMIALDEHYDE

CROSS-REFERENCE TO RELATED APPLICATION

This application claims priority to U.S. patent application Ser. No. 16/719,833 filed Dec. 18, 2019, which claims priority to U.S. Provisional Application No. 62/781,511 filed Dec. 18, 2018, the contents of which are incorporated by reference in their entirety herein.

BACKGROUND OF THE DISCLOSURE

The disclosure relates generally to the production of commodity and specialty chemicals, and, more specifically, an integrated bioprocess for producing 3-hydroxypropionic acid (3-TP or 3-HPA) and acetyl-CoA derivatives from malonate semialdehyde (MSA).

Derivatives of 3-HP include acrylic acid, 1-propanol, propene, polypropylene, etc. Derivatives of acetyl-CoA include acetone, 2-propanol, propene, polypropylene, etc. Many of these molecules are produced via synthetic chemistry along with considerable amounts of chemical waste.

There exists a need to minimize chemical waste produced from production of these molecules to seek a more environmentally friendly and cost-effective approach for processes and molecules that utilize these 3-HP and acetyl-CoA derivatives.

As set forth herein, the disclosure provides methods and compositions for the fermentative co-production of 3-HP and acetyl-CoA derivatives.

STATEMENT REGARDING SEQUENCE LISTING

The sequence listing associated with this application is provided in text format in lieu of a paper copy, and is hereby incorporated by reference into the specification. The name of the XLM file containing the Sequence Listing is 127125-5015-US01_Sequence_Listing.xml. The text file is about 468,041 bytes, was created on or about Sep. 7, 2022, and is being submitted electronically via EFS-Web.

SUMMARY OF THE DISCLOSURE

This disclosure provides a recombinant microorganism capable of co-producing 3-hydroxypropionic acid (3-HP) and acetyl-CoA, and/or derivatives thereof, from a feedstock comprising one or more carbon sources, wherein the recombinant microorganism comprises one or more of the following: (a) at least one endogenous and/or exogenous nucleic acid molecule encoding a 3-hydroxypropionic acid dehydrogenase that catalyzes the production of 3-HP from malonate semialdehyde; (b) at least one endogenous and/or exogenous nucleic acid molecule encoding a (i) malonate semialdehyde dehydrogenase that catalyzes the production of acetyl-CoA from malonate semialdehyde, and/or (ii) malonyl-CoA reductase and/or 2-keto acid decarboxylase that catalyzes the conversion of malonate semialdehyde into malonyl-CoA, and malonyl-CoA decarboxylase that catalyzes the production of acetyl-CoA from malonyl-CoA; (c) at least one endogenous and/or exogenous nucleic acid molecule encoding an enzyme that is able to catalyze the decarboxylation of oxaloacetate into malonate semialdehyde.

In some embodiments, the recombinant microorganism is capable of producing 1-propanol, wherein the recombinant microorganism comprises one or more of the following: (a) at least one endogenous and/or exogenous nucleic acid molecule encoding a propionyl-CoA synthase that catalyzes the conversion of 3-HP into propionyl-CoA; (b) at least one endogenous and/or exogenous nucleic acid molecule encoding a 3-hydroxypropionyl-CoA synthetase/CoA transferase, 3-hydroxypropionyl-CoA dehydratase, and acrylyl-CoA reductase that catalyzes the conversion of 3-HP into propionyl-CoA; (c) at least one endogenous and/or exogenous nucleic acid molecule encoding an alcohol/aldehyde dehydrogenase that catalyzes the conversion of propionyl-CoA from (a) or (b) into 1-propanol, or an aldehyde dehydrogenase (acetylating) and alcohol dehydrogenase that catalyzes together the production of 1-propanol from propionyl-CoA.

In some embodiments, the derivatives of 3-HP are selected from the group consisting of: acrylic acid, 1-propanol, propene, and polypropylene. In some embodiments, the derivatives of acetyl-CoA are selected from the group consisting of: acetone, 2-propanol, propene, and polypropylene. In some embodiments, at least a portion of excess NAD(P)H generated in the production of acetyl-CoA is utilized as a source of reducing equivalents in the production of 3-HP and/or 3-HP derivatives.

In some embodiments, the recombinant microorganism produces 3-hydroxypropionic acid (3-HP), acetyl-CoA, 1-propanol and/or 2-propanol, in an aerobic or anaerobic production process, preferably an anaerobic process.

In some embodiments, the microorganism is selected from a bacterium, a fungus, or a yeast. In some embodiments, the recombinant microorganism is derived from a parental microorganism selected from the group consisting of: *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Candida* sp., *Clostridium formicoaceticum*, *Clostridium scatologenes*, *Moorella thermautotrophicus*, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Candida krusei*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema azotonutricium*, *Escherichia coli*, *Saccharomyces cerevisiae*, *Pseudomonas putida*, *Bacillus* sp., *Corynebacterium* sp., *Yarrowia lipolytica*, *Scheffersomyces stipitis*, and *Terrisporobacter glycolicus*. In some embodiments, the recombinant microorganism is a yeast. In some embodiments, the yeast is *Saccharomyces cerevisiae*.

In some embodiments, the endogenous and/or exogenous nucleic acid molecule encoding a 3-hydroxypropionic acid dehydrogenase encodes an amino acid sequence comprising MCR-Nterm.Cau (SEQ ID NO: 105), ADH.Ae (SEQ ID NO: 106), MMSB.Bce (SEQ ID NO: 107), YDFG-0.Ec (SEQ ID NO: 108), YMR226C (YDF1) (SEQ ID NO: 109), or HPD1 (SEQ ID NO: 110). In some embodiments, the endogenous and/or exogenous nucleic acid molecule encoding a 3-hydroxypropionic acid dehydrogenase encodes an amino acid sequence comprising YMR226C (YDF1) (SEQ ID NO: 109). In some embodiments, the endogenous and/or exogenous nucleic acid molecule encoding a 3-hydroxypropionic acid dehydrogenase encodes an amino acid sequence comprising HPD1 (SEQ ID NO: 110).

In some embodiments, the endogenous and/or exogenous nucleic acid molecule encoding a malonate semialdehyde dehydrogenase encodes an amino acid sequence comprising MSD.Pa (SEQ ID NO: 111), MSD.Cal (SEQ ID NO: 112), iolA (SEQ ID NO: 113), iolA (SEQ ID NO: 114), iolA (SEQ ID NO: 115), mmsA (SEQ ID NO: 116), dddC (SEQ ID NO: 117), or iolA (SEQ ID NO: 118). In some embodiments, the endogenous and/or exogenous nucleic acid molecule encoding a malonate semialdehyde dehydrogenase encodes an amino acid sequence comprising MSD.Pa (SEQ ID NO: 111). In some embodiments, the endogenous and/or exogenous nucleic acid molecule encoding a malonate semialdehyde dehydrogenase encodes an amino acid sequence comprising MSD.Cal (SEQ ID NO: 112).

In some embodiments, the endogenous and/or exogenous nucleic acid molecule encoding a malonyl-CoA reductase and/or 2-keto acid decarboxylase encodes an amino acid sequence comprising mcr (SEQ ID NO: 278), matA, MLYCD (SEQ ID NO: 279), kivD (SEQ ID NO: 280), kdcA (SEQ ID NO: 281), ARO10 (SEQ ID NO: 282). In some embodiments, the endogenous and/or exogenous nucleic acid molecule encoding a malonyl-CoA reductase and/or 2-keto acid decarboxylase encodes an amino acid sequence comprising mcr (SEQ ID NO: 278). In some embodiments, the endogenous and/or exogenous nucleic acid molecule encoding a malonyl-CoA reductase and/or 2-keto acid decarboxylase encodes an amino acid sequence comprising kivD (SEQ ID NO: 280). In some embodiments, the endogenous and/or exogenous nucleic acid molecule encoding a malonyl-CoA reductase and/or 2-keto acid decarboxylase encodes an amino acid sequence comprising ARO10 (SEQ ID NO: 282).

In some embodiments, the at least one endogenous and/or exogenous nucleic acid molecule encoding an enzyme that is able to catalyze the decarboxylation of oxaloacetate into malonate semialdehyde encodes an amino acid sequence comprising (SEQ ID NO: 1) or (SEQ ID NO: 274). In some embodiments, the at least one endogenous and/or exogenous nucleic acid molecule encoding an enzyme that is able to catalyze the decarboxylation of oxaloacetate into malonate semialdehyde encodes an amino acid sequence comprising (SEQ ID NO: 1). In some embodiments, the at least one endogenous and/or exogenous nucleic acid molecule encoding an enzyme that is able to catalyze the decarboxylation of oxaloacetate into malonate semialdehyde encodes an amino acid sequence comprising (SEQ ID NO: 274).

In some embodiments, the recombinant microorganism comprises one or more of the following: (a) at least one endogenous and/or exogenous nucleic acid molecule encoding a thiolase or an acetyl-CoA acetyltransferase that catalyzes the production of acetoacetyl-CoA from acetyl-CoA; (b) at least one endogenous and/or exogenous nucleic acid molecule encoding an acetoacetyl-CoA synthase that catalyzes the production of acetoacetyl-CoA from malonyl-CoA; (c) at least one endogenous and/or exogenous nucleic acid molecule encoding an acetoacetyl-CoA transferase that catalyzes the production of acetoacetate from acetoacetyl-CoA; (d) at least one endogenous and/or exogenous nucleic acid molecule encoding a (i) hydroxymethylglutaryl-CoA synthase that catalyzes the production of HMG-CoA from acetoacetyl-CoA, and (ii) hydroxymethylglutaryl-CoA lyase that catalyzes the production of acetoacetate from HMG-CoA; and (e) at least one endogenous and/or exogenous nucleic acid molecule encoding an acetoacetate decarboxylase that catalyzes the production of acetone from acetoacetate.

In some embodiments, the endogenous and/or exogenous nucleic acid molecule encoding a thiolase or an acetyl-CoA acetyltransferase encodes an amino acid sequence comprising ERG10 (SEQ ID NO: 209), thlA (SEQ ID NO: 210), atoB (SEQ ID NO: 211), H16_B0759 (SEQ ID NO: 212), Msed_0656 (SEQ ID NO: 213), or AAT1 (SEQ ID NO: 214). In some embodiments, the endogenous and/or exogenous nucleic acid molecule encoding a thiolase or an acetyl-CoA acetyltransferase encode an amino acid sequence comprising ERG10 (SEQ ID NO: 209). In some embodiments, the endogenous and/or exogenous nucleic acid molecule encoding a acetoacetyl-CoA synthase encodes an amino acid sequence comprising nphT7 (SEQ ID NO: 285).

In some embodiments, the endogenous and/or exogenous nucleic acid molecule encoding a acetoacetyl-CoA transferase encodes an amino acid sequence comprising atoA/atoD (SEQ ID NO: 215 and 216), ctfA/ctfB (SEQ ID NO: 219 and 220), ctfA/ctfB (SEQ ID NO:221 and 222) or ctfA/ctfB (SEQ ID NO:223 and 224). In some embodiments, the endogenous and/or exogenous nucleic acid molecule encoding an acetoacetyl-CoA transferase encodes an amino acid sequence comprising atoA/atoD (SEQ ID NO: 215 and 216)

In some embodiments, the endogenous and/or exogenous nucleic acid molecule encoding a hydroxymethylglutaryl-CoA synthase and a hydroxymethylglutaryl-CoA lyase encode an amino acid sequence comprising ERG13 (SEQ ID NO: 283) and yngG (SEQ ID NO: 284). In some embodiments, the endogenous and/or exogenous nucleic acid molecule encoding a acetoacetate decarboxylase encodes an amino acid sequence comprising Adc.Ca (SEQ ID NO: 225), Adc.Cbe (SEQ ID NO: 226), Adc (SEQ ID NO: 227), Adc (SEQ ID NO: 228), Adc (SEQ ID NO: 229) or Adc.Pp (SEQ ID NO: 230). In some embodiments, the endogenous and/or exogenous nucleic acid molecule encoding a acetoacetate decarboxylase encodes an amino acid sequence comprising Adc.Pp (SEQ ID NO: 230).

The disclosure provides a method of co-producing 3-HP, and/or derivatives thereof and Acetyl-CoA and/or derivatives thereof by contacting the recombinant microorganism of any of the claim 1 or 2 with a fermentable carbon source under conditions and for a sufficient period of time to produce 3-HP, or derivatives and Acetyl-CoA or derivatives. In some embodiments, the carbon source is selected from sugars, glycerol, alcohols, organic acids, alkanes, fatty acids, lignocellulose, proteins, carbon dioxide, and carbon monoxide. In some embodiments, the recombinant microorganism produces 3-hydroxypropionic acid (3-HP), acetyl-CoA, 1-propanol and/or 2-propanol, in an aerobic or anaerobic production process, preferably an anaerobic process.

DETAILED DESCRIPTION OF THE DISCLOSURE

Figure 1:
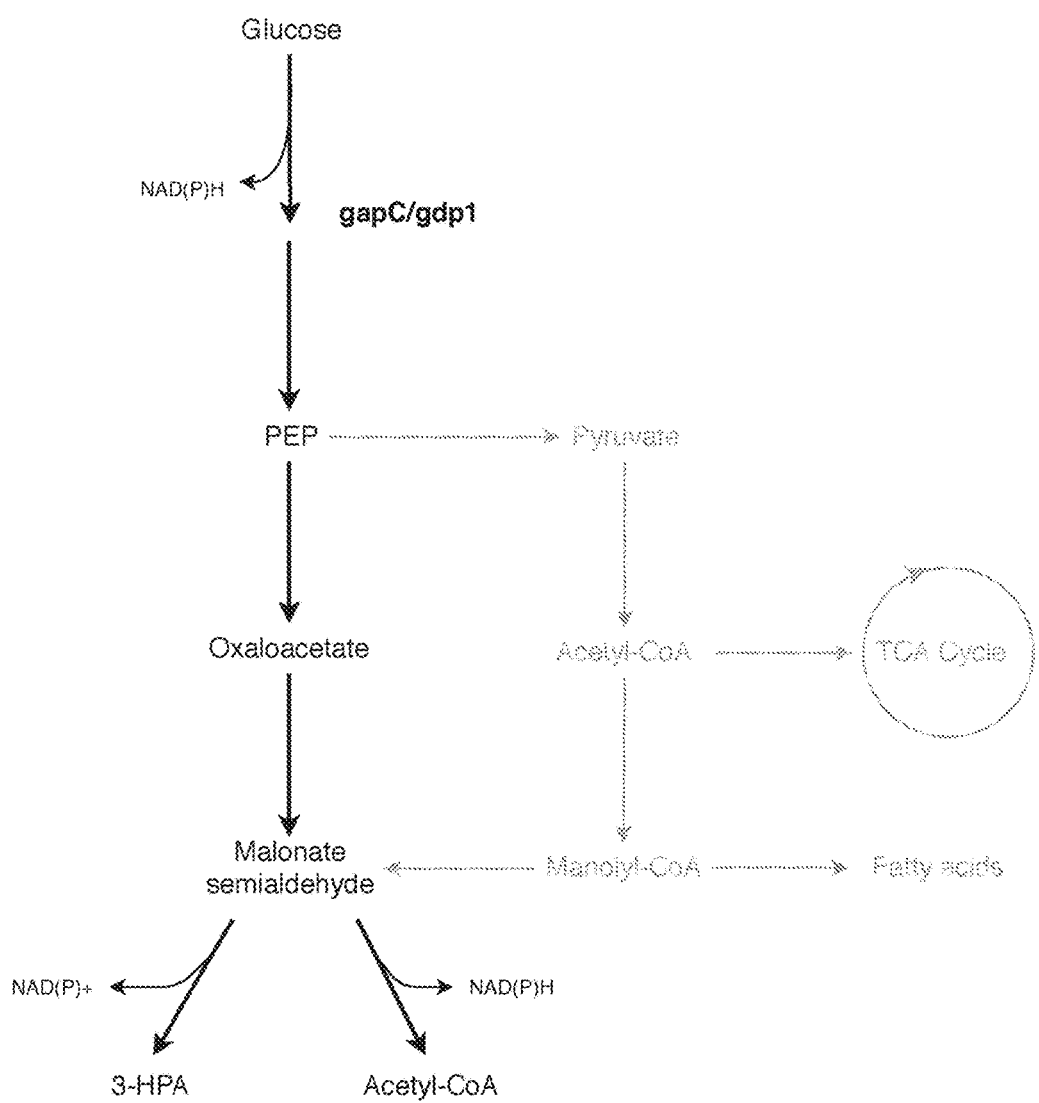
FIG. 1 depicts a novel combined pathway for 3-HP and acetyl-CoA production with malonate semialdehyde as a common single intermediate. The shaded offshoot identifies the usual pathway for malonate semialdehyde production with malonyl-CoA as an intermediate, which is replaced by a malonate semialdehyde in the present pathway.

The present disclosure is generally drawn to methods for utilizing genetically modified microbes to co-produce 3-hydroxypropionic acid (3-HP) and acetyl-CoA derivatives from malonate semialdehyde as a common single intermediate. The disclosure further provides modified microbe that co-produce the 3-HP and acetyl-CoA derivatives from malonate semialdehyde.

The co-production of 3-HP and acetyl-CoA, and derivatives thereof from malonate semialdehyde is novel, and the co-production results in a redox balanced set of pathways that co-produces the products at a high yield.

As used herein and in the appended claims, the singular forms "a," "an," and "the" include plural referents unless the context clearly dictates otherwise. Thus, for example, reference to "an enzyme" includes a plurality of such enzymes and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "about" is used synonymously with the term "approximately." Illustratively, the use of the term "about" with regard to an amount indicates that values slightly outside the cited values, e.g., plus or minus 0.1% to 10%.

The term "biologically pure culture" or "substantially pure culture" refers to a culture of a microbe species described herein containing no other microbe species in quantities sufficient to interfere with the replication of the culture or be detected by normal microbiological techniques.

As used herein, a "control sequence" refers to an operator, promoter, silencer, or terminator.

As used herein, "introduced" refers to the introduction by means of modern biotechnology, and not a naturally occurring introduction.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development.

As used herein, a "non-constitutive promoter" is a promoter which is active under certain conditions, in certain types of cells, and/or during certain development stages. For example, inducible promoters, and promoters under development control are non-constitutive promoters. As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

The term "signal sequence" as used herein refers to an amino acid sequence that targets peptides and polypeptides to cellular locations or to the extracellular environment. Signal sequences are typically at the N-terminal portion of a polypeptide and are typically removed enzymatically. Polypeptides that have their signal sequences are referred to as being full-length and/or unprocessed. Polypeptides that have had their signal sequences removed are referred to as being mature and/or processed.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature. On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene.

Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one aspect, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Michigan), AlignX, and Vector NTI (Invitrogen, Carlsbad, CA). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one aspect, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

Genes of the present disclosure may be referenced with their common names, their nucleic acid sequences, and the amino acid sequences that are translated from the nucleic acid sequences. Using the references given in accession numbers for known genes, a practitioner is able to determine equivalent genes in other organisms, bacterial strains, yeast, fungi, mammals, plants, etc. This work is performed utilizing consensus sequences that can be determined by carrying out sequence alignments with genes derived from other microorganisms and designing degenerated probes to clone the corresponding gene in another organism.

As used herein, "overexpression" means that the expression of a gene or of an enzyme is increased as compared to the non-modified microorganism. Increasing the expression of an enzyme is obtained by increasing the expression of a gene encoding said enzyme. When a non-modified microorganism did not express a given gene, modifying said microorganism in order to express this gene is thus also considered as being an increase expression of said gene, and thus as an overexpression. Increasing the expression of a gene may be carried out by all techniques known by the one skilled in the art. In this regard, it may be notably cited the implementation of a strong promoter upstream the nucleic acid intended to be overexpressed or the introduction of a plurality of copies of the said nucleic acid between a promoter, especially a strong promoter, and a terminator.

As used herein, "inducible" promoter" means a promoter whose activity is induced, i.e. increased (1) in the presence of one or more particular metabolite(s)—the higher the metabolite concentration in the medium, the stronger the promoter activity; or (2) in the presence of a low concentration, or in the absence, of one or more metabolite(s). These metabolites are different from those whose increasing presence induces the activity of the promoter. The lower the metabolite concentration in the medium, the stronger the promoter activity.

As used herein, enzyme/protein "activity" and "function" are used interchangeably and designates, in the context of the disclosure, the capacity of (1) an enzyme to catalyze a desired reaction or (2) a protein to act in a certain manner.

As used herein, "aerobic conditions" refer to concentrations of oxygen in the culture medium that are sufficient for an aerobic or facultative anaerobic microorganism to use oxygen as a terminal electron acceptor.

As used herein, "anaerobic conditions" refer to culture or growth conditions with regard to the concentration of oxygen, which is intended to mean that the amount of oxygen is less than about 0% saturation of dissolved oxygen in liquid media. The term is also intended to include sealed chambers of liquid or solid media maintained with an atmosphere of less than about 0% oxygen.

As used herein, "microaerobic conditions" refer to concentrations of oxygen in the culture medium in which the concentration of oxygen is less than that in air under standard temperature and pressure, i.e., an oxygen concentration of up to ~6% of the total gas present.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting aspect, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference enzyme. In some aspects, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed enzymes of the present disclosure. In some aspects, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed enzymes of the present disclosure.

As used herein the terms "microorganism" or "microbe" should be taken broadly. These terms, used interchangeably, include but are not limited to, the two prokaryotic domains, Bacteria and Archaea.

As used herein, "isolate," "isolated," "isolated microbe," and like terms, are intended to mean that the one or more microorganisms has been separated from at least one of the materials with which it is associated in a particular environment (for example media, water, reaction chamber, etc.). Thus, an "isolated microbe" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain). In aspects, the isolated microbe may be in association with an acceptable carrier, which may be a commercially or industrial acceptable carrier.

In certain aspects of the disclosure, the isolated microbes exist as "isolated and biologically pure cultures." It will be appreciated by one of skill in the art that an isolated and biologically pure culture of a particular microbe, denotes that said culture is substantially free of other living organisms and contains only the individual microbe in question. The culture can contain varying concentrations of said microbe. The present disclosure notes that isolated and biologically pure microbes often "necessarily differ from less pure or impure materials." See, e.g. In re Bergstrom, 427 F.2d 1394, (CCPA 1970) (discussing purified prostaglandins), see also, In re Bergy, 596 F.2d 952 (CCPA 1979) (discussing purified microbes), see also, Parke-Davis & Co. v. H.K. Mulford & Co., 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain aspects, is a further attribute that distinguishes the presently disclosed microbes from those microbes existing in a natural state. See, e.g., Merck & Co. v. Olin Mathieson Chemical Corp., 253 F.2d 156 (4th Cir. 1958) (discussing purity limitations for vitamin B12 produced by microbes), incorporated herein by reference.

Microbes of the present disclosure may include spores and/or vegetative cells. In some aspects, microbes of the present disclosure include microbes in a viable but non-culturable (VBNC) state. As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconducive to the survival or growth of vegetative cells.

As used herein, "microbial composition" refers to a composition comprising one or more microbes of the present disclosure.

As used herein, "carrier," "acceptable carrier," "commercially acceptable carrier," or "industrial acceptable carrier" refers to a diluent, adjuvant, excipient, or vehicle with which the microbe can be administered, stored, or transferred, which does not detrimentally effect the microbe.

The term "yield potential" as used herein refers to a yield of a product from a biosynthetic pathway. In one aspect, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway. If a specific pathway towards a product has a lower yield than the thermodynamic maximum yield, then it loses mass and can most likely be improved upon or substituted with a more efficient pathway towards the product.

The term "redox balanced" refers to a set of reactions, which taken together produce as much redox cofactors as they consume. Designing metabolic pathways and engineering an organism such that the redox cofactors are balanced or close to being balanced usually results in a more efficient, higher yield production of the desired compounds. Redox reactions always occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one aspect, the redox reactions take place in a biological system. Biological energy is frequently stored and released by means of redox reactions. Photosynthesis involves the reduction of carbon dioxide into sugars and the oxidation of water into molecular oxygen. The reverse reaction, respiration, oxidizes sugars to produce carbon dioxide and water. As intermediate steps, the reduced carbon compounds are used to reduce nicotinamide adenine dinucleotide (NAD+), which then contributes to the creation of a proton gradient, which drives the synthesis of adenosine triphosphate (ATP) and is maintained by the reduction of oxygen. The term redox state is often used to describe the balance of GSH/GSSG, NAD+/NADH and NADP+/NADPH in a biological system such as a cell or organ. The redox state is reflected in the balance of several sets of metabolites (e.g., lactate and pyruvate, beta-hydroxybutyrate, and acetoacetate), whose interconversion is dependent on these ratios. An abnormal redox state can develop in a variety of deleterious situations, such as hypoxia, shock, and sepsis.

As used herein, the term "productivity" refers to the total amount of bioproduct (the products described herein) produced per hour.

As used herein "malonate semialdehyde," "malonic semialdehyde," and "3-oxopropanoic acid are used interchangeably to describe the C3H4O3 molecule of the present disclosure.

As used herein, "enhanced activity" of an enzyme designates either an increased specific catalytic activity of the enzyme, and/or an increased quantity/availability of the enzyme in the cell, obtained, for example, by overexpression of the gene encoding the enzyme.

The present application generally relates to methods of utilizing modified microbes for co-producing 3-hydroxypropionic acid (3-TIP) and acetyl-CoA, and/or derivatives thereof, and further related to the modified microbes per se.

In some aspects, the present disclosure is drawn to a recombinant microorganism capable of co-producing 3-hydroxypropionic acid (3-HP) and acetyl-CoA, and/or derivatives thereof, from a feedstock comprising one or more carbon sources, wherein the recombinant microorganism comprises one or more of the following: (a) at least one endogenous and/or exogenous nucleic acid molecule encoding an 3-hydroxypropionic acid dehydrogenase that catalyzes the production of 3-HP from malonate semialdehyde; (b) at least one endogenous and/or exogenous nucleic acid molecule encoding a (i) malonate semialdehyde dehydrogenase that catalyzes the production of acetyl-CoA from malonate semialdehyde, and/or (ii) malonyl-CoA reductase and/or 2-keto acid decarboxylase that catalyzes the conversion of malonate semialdehyde into malonyl-CoA, and malonyl-CoA decarboxylase that catalyzes the production of acetyl-CoA from malonyl-CoA, and/or (iii) malonyl-CoA synthetase that catalyzes the conversion of oxaloacetate to malonyl-CoA, and malonyl-CoA decarboxylase that catalyzes the production of acetyl-CoA from malonyl-CoA; (c) at least one endogenous and/or exogenous nucleic acid molecule encoding an enzyme that is able to catalyze the decarboxylation of oxaloacetate into malonate semialdehyde.

In some aspects, the recombinant microorganism is capable of producing 1-propanol. In some aspects, the recombinant microorganism comprises one or more of the following: (a) at least one endogenous and/or exogenous nucleic acid molecule encoding a propionyl-CoA synthase that catalyzes the production of propionyl-CoA from 3-HP; (b) at least one endogenous and/or exogenous nucleic acid molecule encoding a 3-hydroxypropionyl-CoA synthetase/transferase, 3-hydroxypropionyl-CoA dehydratase, and acrylyl-CoA reductase that catalyzes the production of propionyl-CoA from 3-HP; (c) at least one endogenous and/or exogenous nucleic acid molecule encoding an alcohol/aldehyde dehydrogenase that catalyzes the production of 1-propanol from propionyl-CoA; (d) at least one endogenous and/or exogenous nucleic acid molecule encoding an aldehyde dehydrogenase (acetylating) that catalyzes the production of propionaldehyde from propionyl-CoA and alcohol dehydrogenase that catalyzes the production of 1-propanol from propionaldehyde.

In some aspects, the recombinant microorganism is capable of producing acetone. In some aspects, the recombinant microorganism comprises one or more of the following: (a) at least one endogenous and/or exogenous nucleic acid molecule encoding a thiolase or an acetyl-CoA acetyltransferase that catalyzes the production of acetoacetyl-CoA from acetyl-CoA; (b) at least one endogenous and/or exogenous nucleic acid molecule encoding an acetoacetyl-CoA synthase that catalyzes the production of acetoacetyl-CoA from malonyl-CoA; (c) at least one endogenous and/or exogenous nucleic acid molecule encoding an acetoacetyl-CoA transferase that catalyzes the production of acetoacetate from acetoacetyl-CoA; (d) at least one endogenous and/or exogenous nucleic acid molecule encoding a (i) hydroxymethylglutaryl-CoA synthase that catalyzes the production of HMG-CoA from acetoacetyl-CoA, and (ii) hydroxymethylglutaryl-CoA lyase that catalyzes the production of acetoacetate from HMG-CoA; and (e) at least one endogenous and/or exogenous nucleic acid molecule encoding an acetoacetate decarboxylase that catalyzes the production of acetone from acetoacetate.

In some aspects, the recombinant microorganism catalyzes malonate semialdehyde for the production of both 3-HP and acetyl-CoA, and/or derivatives thereof. In some aspects, the recombinant microorganism comprises a decarboxylase capable of acting on oxaloacetate to produce malonate semialdehyde. In some aspects, the derivatives of 3-HP are selected from the group consisting of: acrylic acid, 1-propanol, propene, and polypropylene. In some aspects, the derivatives of acetyl-CoA are selected from the group consisting of: acetone, 2-propanol, propene, and polypropylene.

In some aspects, at least a portion of excess NAD(P)H produced by the recombinant microorganism in the production of acetyl-CoA is utilized as a source of reducing equivalents in the production of 3-HP.

In some aspects, the microorganism is selected from a bacterium, a fungus, or a yeast. In some aspects, the recombinant microorganism is a yeast. In some aspects, the yeast is *Saccharomyces cerevisiae*. In some aspects, the yeast is capable of aerobic and anaerobic growth.

In some aspects, the recombinant microorganism is derived from a parental microorganism selected from the group consisting of: *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella* thermoautotrophica, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema azotonutricium*, *Escherichia coli*, *Saccharomyces cerevisiae*, *Pseudomonas putida*, *Bacillus* sp, *Candida* sp., *Candida Krusei*, *Corynebacterium* sp., *Yarrowia lipolytica*, *Scheffersomyces stipitis*, and Terri *Sporobacter glycolicus*.

In some aspects, the disclosure is drawn to a method of producing 3-hydroxypropionic acid (3-TIP) and acetyl-CoA, and/or derivatives thereof, the method comprising culturing the recombinant microorganism in a culture medium containing a feedstock comprising a carbon source until the 3-hydroxypropionic acid (3-THP) and acetyl-CoA, and/or derivatives thereof, are produced.

In some aspects, the disclosure is drawn to a method of producing a recombinant microorganism capable of co-producing 3-hydroxypropionic acid (3-TIP) and acetyl-CoA, and/or derivatives thereof, from a feedstock comprising one or more carbon sources, the method comprising introducing into and/or overexpressing in the recombinant microorganism one or more of the following: (a) at least one endogenous and/or exogenous nucleic acid molecule encoding an 3-hydroxypropionic acid dehydrogenase that catalyzes the production of 3-HP from malonate semialdehyde; (b) at least one endogenous and/or exogenous nucleic acid molecule encoding a (i) malonate semialdehyde dehydrogenase that catalyzes the production of acetyl-CoA from malonate semialdehyde, and/or or (ii) malonyl-CoA reductase and/or 2-keto acid decarboxylase that catalyzes the conversion of malonate semialdehyde into malonyl- CoA, and malonyl-CoA decarboxylase that catalyzes the production of acetyl-CoA from malonyl-CoA, and/or (iii) malonyl-CoA synthetase that catalyzes the conversion of oxaloacetate to malonyl-CoA, and malonyl-CoA decarboxylase that catalyzes the production of acetyl-CoA from malonyl-CoA; (c) at least one endogenous and/or exogenous nucleic acid molecule encoding an enzyme that is able to catalyze the decarboxylation of oxaloacetate into malonate semialdehyde.

In some aspects, the recombinant microorganism is capable of producing 1-propanol.

In some aspects, the method further comprises introducing into and/or overexpressing in the recombinant microorganism one or more of the following: (a) at least one endogenous and/or exogenous nucleic acid molecule encoding a propionyl-CoA synthase that catalyzes the production of propionyl-CoA from 3-HP; (b) at least one endogenous and/or exogenous nucleic acid molecule encoding a 3-hydroxypropionyl-CoA synthetase/transferase, 3-hydroxypropionyl-CoA dehydratase, and acrylyl-CoA reductase that catalyzes the production of propionyl-CoA from 3-HP; (c) at least one endogenous and/or exogenous nucleic acid molecule encoding an alcohol/aldehyde dehydrogenase that catalyzes the production of 1-propanol from propionyl-CoA; (d) at least one endogenous and/or exogenous nucleic acid molecule encoding an aldehyde dehydrogenase (acetylating) that catalyzes the production of propionaldehyde from propionyl-CoA and alcohol dehydrogenase that catalyzes the production of 1-propanol from propionaldehyde. In some aspects, the recombinant microorganism is capable of producing acetone. In some aspects, the method further comprises introducing into and/or overexpressing in the recombinant microorganism one or more of the following: (a) at least one endogenous and/or exogenous nucleic acid molecule encoding a thiolase or an acetyl-CoA acetyltransferase that catalyzes the production of acetoacetyl-CoA from acetyl-CoA; (b) at least one endogenous and/or exogenous nucleic acid molecule encoding an acetoacetyl-CoA synthase that catalyzes the production of acetoacetyl-CoA from malonyl-CoA; (c) at least one endogenous and/or exogenous nucleic acid molecule encoding an acetoacetyl-CoA transferase that catalyzes the production of acetoacetate from acetoacetyl-CoA; (d) at least one endogenous and/or exogenous nucleic acid molecule encoding a (i) hydroxymethylglutaryl-CoA synthase that catalyzes the production of HMG-CoA from acetoacetyl-CoA, and (ii) hydroxymethylglutaryl-CoA lyase that catalyzes the production of acetoacetate from HMG-CoA; and (e) at least one endogenous and/or exogenous nucleic acid molecule encoding an acetoacetate decarboxylase that catalyzes the production of acetone from acetoacetate.

In some aspects, the recombinant microorganism catalyzes malonate semialdehyde for the production of both 3-HP and acetyl-CoA, and/or derivatives thereof. In some aspects, the derivatives of 3-TIP are selected from the group consisting of: acrylic acid, 1-propanol, propene, and polypropylene. In some aspects, the derivatives of acetyl-CoA are selected from the group consisting of: acetone, 2-propanol, propene, and polypropylene. In some aspects, at least a portion of excess NAD(P)H produced by the recombinant microorganism in the production of acetyl-CoA is utilized as a source of reducing equivalents in the production of 3-HP. In some aspects, the recombinant microorganism comprises a decarboxylase capable of acting on oxaloacetate to produce malonate semialdehyde.

In some aspects, the microorganism is selected from a bacterium, a fungus, or a yeast. In some aspects, the recombinant microorganism is a yeast. In some aspects, the yeast is capable of aerobic and anaerobic growth. In some aspects, the yeast is *Saccharomyces cerevisiae*.

In some aspects, the recombinant microorganism is derived from a parental microorganism selected from the group consisting of: *Clostridium* sp., *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Clostridium acetobutylicum, Clostridium beijerinckii, Oxobacter pfennigii, Thermoanaerobacter kivui, Sporomusa ovata, Thermoacetogenium phaeum, Acetobacterium carbinolicum, Sporomusa termitida, Moorella glycerini, Eubacterium aggregans, Treponema azotonutricium, Escherichia coli, Saccharomyces cerevisiae, Pseudomonas putida, Bacillus* sp, *Candida* sp., *Candida krusei, Corynebacterium* sp., *Yarrowia lipolytica, Scheffersomyces stipitis,* and Terri *Sporobacter glycolicus.*

Generation of Microbial Populations
Genetic Modification

The genetic modification introduced into one or more microbes of the present disclosure may alter or abolish a regulatory sequence of a target gene. In some aspects, the genetic modification introduced into one or more microbes of the present disclosure may introduce a new trait or phenotype into the one or more microbes. One or more regulatory sequences may also be inserted, including heterologous regulatory sequences and regulatory sequences found within a genome of an animal, plant, fungus, yeast, bacteria, or virus corresponding to the microbe into which the genetic variation is introduced. Moreover, regulatory sequences may be selected based on the expression level of a gene in a microbial culture. The genetic variation may be a pre-determined genetic variation that is specifically introduced to a target site. In some aspects the genetic variation is a nucleic acid sequence that is introduced into one or more microbial chromosomes. In some aspects, the genetic variation is a nucleic acid sequence that is introduced into one or more extrachromosomal nucleic acid sequence. The genetic variation may be a random mutation within the target site. The genetic variation may be an insertion or deletion of one or more nucleotides. In some cases, a plurality of different genetic variations (e.g. 2, 3, 4, 5, 10, or more) are introduced into one or more of the isolated bacteria. The plurality of genetic variations can be any of the above types, the same or different types, and in any combination. In some cases, a plurality of different genetic variations are introduced serially, introducing a first genetic variation after a first isolation step, a second genetic variation after a second isolation step, and so forth so as to accumulate a plurality of desired modifications in the microbes.

In general, the term "genetic variation" refers to any change introduced into a polynucleotide sequence relative to a reference polynucleotide, such as a reference genome or portion thereof, or reference gene or portion thereof. A genetic variation may be referred to as a "mutation," and a sequence or organism comprising a genetic variation may be referred to as a "genetic variant" or "mutant". Genetic variations can have any number of effects, such as the increase or decrease of some biological activity, including gene expression, metabolism, and cell signaling. Genetic variations can be specifically introduced to a target site, or introduced randomly. A variety of molecular tools and methods are available for introducing genetic variation. For example, genetic variation can be introduced via polymerase chain reaction mutagenesis, oligonucleotide-directed mutagenesis, saturation mutagenesis, fragment shuffling mutagenesis, homologous recombination, recombineering, lambda red mediated recombination, CRISPR/Cas9 systems, chemical mutagenesis, and combinations thereof. Chemical methods of introducing genetic variation include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethylsulfate, benzopyrene, cyclophosphamide bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic variation can also be introduced into a nucleic acid using, e.g., trimethylpsoralen with ultraviolet light. Random or targeted insertion of a mobile DNA element, e.g., a transposable element, is another suitable method for generating genetic variation. Genetic variations can be introduced into a nucleic acid during amplification in a cell-free in vitro system, e.g., using a polymerase chain reaction (PCR) technique such as error-prone PCR. Genetic variations can be introduced into a nucleic acid in vitro using DNA shuffling techniques (e.g., exon shuffling, domain swapping, and the like). Genetic variations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic variations are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

In some aspects, recombinant microbes of the present disclosure may comprise any one or more of the disclosed nucleic acid sequence listings. In some aspects, recombinant microbes of the present disclosure may comprise any one or more nucleic acid sequences that share at least 80%, at least 85%, at least 90%, at least 95%, at least 96%, at least 97%, at least 98%, or at least 99% sequence identity with any one or more of the disclosed nucleic acid sequence listings. In some aspects, recombinant microbes of the present disclosure may comprise any one or more nucleic acid sequence that shares at least about 80%, at least about 85%, at least about 90%, at least about 95%, at least about 96%, at least about 97%, at least about 98%, or at least about 99% sequence identity with any one or more of the disclosed nucleic acid sequence listings.

In some aspects, recombinant microbes of the present disclosure may comprise one or more nucleic acid sequences that encode one or more amino acid sequences of the present disclosure. In some aspects, recombinant microbes of the present disclosure may comprise one or more nucleic acid sequences that encode one or more amino acid sequences that share at least 80%, at least 85%, at least 90%, at least 95%, at least 96%, at least 97%, at least 98%, or at least 99% sequence identity with any one or more of the disclosed amino acid sequence listings. In some aspects, recombinant microbes of the present disclosure may comprise one or more nucleic acid sequences that encode one or more amino acid sequences that share at least about 80%, at least about 85%, at least about 90%, at least about 95%, at least about 96%, at least about 97%, at least about 98%, or at least about 99% sequence identity with any one or more of the disclosed amino acid sequence listings.

Genetic variations introduced into microbes may be classified as transgenic, cisgenic, intragenomic, intrageneric, intergeneric, synthetic, evolved, rearranged, or SNPs. CRISPR/Cas9 (Clustered regularly interspaced short palindromic repeats)/CRISPR-associated (Cas) systems can be used to introduce desired mutations. CRISPR/Cas9 provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on the association of the protein with two naturally occurring or synthetic RNA molecules called crRNA and tracrRNA (also called guide RNAs). In some cases, the two molecules are covalently link to form a single molecule (also called a single guide RNA ("sgRNA"). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-stranded break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic variation can be found in, e.g. US879596 and Di Carlo et al. (2013. *Nucl. Acids Res.*, 7(41):4336-4343).

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic variations can be introduced using error-prone PCR. In this technique, the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosoguanidine or ethyl methanesulfonate (Nestmann, Mutat Res 1975 June; 28(3):323-30), and the vector containing the gene is then isolated from the host.

Homologous recombination mutagenesis involves recombination between an exogenous DNA fragment and the targeted polynucleotide sequence. After a double-stranded break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional. Typically, a recombination template is also provided. A recombination template may be a component of another vector, contained in a separate vector, or provided as a separate polynucleotide. In some aspects, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some aspects, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some aspects, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US20140301990.

Introducing genetic variation may be an incomplete process, such that some bacteria in a treated population of bacteria carry a desired mutation while others do not. In some cases, it is desirable to apply a selection pressure so as to enrich for bacteria carrying a desired genetic variation. Traditionally, selection for successful genetic variants involved selection for or against some functionality imparted or abolished by the genetic variation, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic variation need be introduced (e.g. without also requiring a selectable marker). In this case, the selection pressure can comprise cleaving genomes lacking the genetic variation introduced to a target site, such that selection is effectively directed against the reference sequence into which the genetic variation is sought to be introduced. Typically, cleavage occurs within 100 nucleotides of the target site (e.g. within 75, 50, 25, 10, or fewer nucleotides from the target site, including cleavage at or within the target site). Cleaving may be directed by a site-specific nuclease selected from the group consisting of a Zinc Finger nuclease, a CRISPR nuclease, a TALE nuclease (TALEN), or a meganuclease. Such a process is similar to processes for enhancing homologous recombination at a target site, except that no template for homologous recombination is provided. As a result, bacteria lacking the desired genetic variation are more likely to undergo cleavage that, left unrepaired, results in cell death. Bacteria surviving selection may then be isolated for assessing conferral of an improved trait.

A CRISPR nuclease may be used as the site-specific nuclease to direct cleavage to a target site. An improved selection of mutated microbes can be obtained by using Cas9 to kill non-mutated cells. Microbes can then be re-isolated from tissues. CRISPR nuclease systems employed for selection against non-variants can employ similar elements to those described above with respect to introducing genetic variation, except that no template for homologous recombination is provided. Cleavage directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double stranded breaks. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. Meganucleases (homing endonuclease) are endodeoxyribonucleases characterized by a large recognition site (double-stranded DNA sequences of 12 to 40 base pairs. Meganucleases can be used to replace, eliminate or modify sequences in a highly targeted way. By modifying their recognition sequence through protein engineering, the targeted sequence can be changed. Meganucleases can be used to modify all genome types, whether bacterial, plant or animal and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

In some aspects, methods of enhancing expression of endogenous or exogenous genes is to introduce one or more supplementary copies of the gene into a chromosome or plasmid. In some aspects, another way of enhancing expression of endogenous or exogenous genes is to replace the endogenous promoter of a gene with, or to use an exogenous promoter of a gene, a stronger promoter. In some aspects, the promoters are homologous or heterologous.

In some aspects, the microbes of the present disclosure are modified such that they comprise one or more selectable markers useful for the selection of transformed microbial cells. In some aspects, the selectable markers are introduced via DNA constructs comprising the genes, polynucleotides, oligonucleotides, and/or pathways of the present disclosure.

In some aspects, the selectable marker is an antibiotic resistance marker. Illustrative examples of antibiotic resistance markers include, but are not limited to, the, NAT1, AUR1-C, HPH, DSDA, KAN<R>, and SH BLE gene products. The NAT 1 gene product from *S. noursei* confers resistance to nourseothricin; the AUR1-C gene product from *Saccharomyces cerevisiae* confers resistance to Aureobasidin A (AbA); the HPH gene product of *Klebsiella pneumonia* confers resistance to Hygromycin B; the DSDA gene product of *E. coli* allows cells to grow on plates with D-serine as the sole nitrogen source; the KAN<R> gene of the Tn903 transposon confers resistance to G418; and the SH BLE gene product from *Streptoalloteichus hindustanus* confers resistance to Zeocin (bleomycin). In some aspects, the antibiotic resistance marker is deleted after the genetically modified microbial cell of the present disclosure is isolated.

In some aspects, the selectable marker rescues an auxotrophy (e.g., a nutritional auxotrophy) in the genetically modified microbial cell. In such aspects, a parent microbial cell comprises a functional disruption in one or more gene products that function in an amino acid or nucleotide biosynthetic pathway, such as, for example, the HIS3, LEU2, LYS1, LYS2, MET 15, TRP1, ADE2, and URA3 gene products in yeast, which renders the parent microbial cell incapable of growing in media without supplementation with one or more nutrients (auxotrophic phenotype). The auxotrophic phenotype can then be rescued by transforming the parent microbial cell with a chromosomal integration encoding a functional copy of the disrupted gene product (NB: the functional copy of the gene can originate from close species, such as *Kluyveromyces, Candida* etc.), and the genetically modified microbial cell generated can be selected for based on the loss of the auxotrophic phenotype of the parent microbial cell.

When a gene from a different type of microorganism is introduced into a cell (yeast gene to bacteria, bacterial gene to yeast, viral gene to yeast, etc), the gene may be transcoded (codon-optimized) such that the genes are synthesized with an optimal codon usage for expression in the host to which the gene is being introduced. In some aspects, the nucleotide sequence (and not the amino acid sequence) of some genes may be transcoded to minimize recombination with an endogenous copy of the same gene or homolog. In some aspects, the gene may be rendered inducible by deleting the endogenous copy of the gene, if necessary, and placing a new copy of the gene under the control of an inducible promoter.

In some aspects, the disclosure is drawn to a nucleic acid sequence encoding an enzyme capable of catalyzing the decarboxylation of oxaloacetate into malonate semialdehyde, or one of its salts, and can be expressed in a microbe using to types of non-mutually exclusive manners: (1) overexpression, i.e., one or a plurality of copies is/are introduced into the microorganism; and/or (2) the at least one nucleic acid is placed under the control of a strong or inducible promoter.

Promoters

In some aspects, various promoters may be used for the desired expression of the coding sequences of interest, which include (i) constitutive strong promoters (sometimes referred to as strong promoters), and (ii) inducible promoters.

In some aspects, the promoters are yeast promoters. A list of yeast promoters with their relative activities in different media can be found in Keren et al. (2013. Molecular Systems Biology, 9:701). Promoters allowing the constitutive over-expression of a given gene, may be found in Velculescu et al. (1997. Cell, 88:243-251).

In some aspects, strong promoters may be selected from the following: pTDH3 (SEQ ID NO: 13), pENO2 (SEQ ID NO: 14), pTEF KI (SEQ ID NO: 15), pTEF3 (SEQ ID NO: 16), pTEF1 (SEQ ID NO: 17), pADH1 (SEQ ID NO: 18), pGMP1 (SEQ ID NO: 19), pFBA1 (SEQ ID NO: 20), pPDC1 (SEQ ID NO: 21), pCCW12 (SEQ ID NO: 22), and pGK1 (SEQ ID NO: 23).

In some aspects, the strong promoter according to the disclosure is, independently, selected from the group consisting of pTDH3, pENO2, pTEF-KI, pTEF3, pTEF1, pADH1, pGMP1, pFBA1, pPDC1, pCCW12 and pGK1.

As described herein, inducible promoters are promoters whose activity is controlled by the presence or absence of biotic or abiotic factors, and also by the quantity of said factor. Accordingly, their activity will be induced and thus increased when the quantity of a given factor increases or is increased.

In some aspects, increasing the quantity of methionine in a culture medium of a recombinant yeast comprising a pSAM4 promoter will induce and thus increase transcription of the gene under the control of this promoter. In some aspects, reducing the quantity of copper in a culture medium of a recombinant yeast comprising a pCTR1 promoter will lead to an induced, and thus an increased, transcription of the gene under the control of this promoter.

For this reason, the following promoters are referred to in the present text as being "inducible promoters."

In some aspects, inducible promoters may be selected from the group comprising promoters inducible with copper, promoters inducible with methionine and promoters inducible with threonine, and may be selected from the group consisting of: pSAM4—methionine inducible (SEQ ID NO: 24), pCUP1-1—copper inducible (SEQ ID NO: 25), pCUP1.cg1a—copper inducible (SEQ ID NO: 26), pCUP1.sba—copper inducible (SEQ ID NO: 27), pACU1—copper inducible (SEQ ID NO: 28), pACU2—copper inducible (SEQ ID NO: 29), pACU3p—copper inducible (SEQ ID NO: 30), pACU4p—copper inducible (SEQ ID NO: 31), pACU5—copper inducible (SEQ ID NO: 32), pACU6—copper inducible (SEQ ID NO: 33), pACU7—copper inducible (SEQ ID NO: 34), pACU8—copper inducible (SEQ ID NO: 35), pACU9—copper inducible (SEQ ID NO: 36), pACU10p—copper inducible (SEQ ID NO: 37), pACU11—copper inducible (SEQ ID NO: 38), pACU12—copper inducible (SEQ ID NO: 39), pACU13—copper inducible (SEQ ID NO: 40), pACU14—copper inducible (SEQ ID NO: 41), pACU15—copper inducible (SEQ ID NO: 42), pGAL/CUP1p—copper inducible (SEQ ID NO: 43), pCRS5—copper inducible (SEQ ID NO: 44), and pCHA1—threonine inducible (SEQ ID NO: 45).

In some aspects, the inducible promoter(s) may be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, and pCHA1. The activity of these promoters is thus induced by the increasing presence of methionine, copper or threonine as indicated above.

In some aspects, inducible promoters may be selected from: (1) promoters inducible due to the absence of copper (i.e. promoter's activity is increased by the absence of copper—the fewer copper there is in the medium, the higher the activity of these promoters); (2) promoters inducible due to the absence of lysine (i.e. promoter's activity is increased by the absence of lysine—the fewer lysine there is in the medium, the higher the activity of these promoters); and (3) promoters inducible due to the absence of methionine (i.e.

promoter's activity is increased by the absence of methionine—the fewer methionine there is in the medium, the higher the activity of these promoters). In some aspects, the inducible promoters are selected from the group consisting of: pCTR1—copper inducible (SEQ ID NO: 46), pCTR3—copper inducible (SEQ ID NO: 47), pCUR1—copper inducible (SEQ ID NO: 48), pCUR2—copper inducible (SEQ ID NO: 49), pCUR3—copper inducible (SEQ ID NO: 50), pCUR4—copper inducible (SEQ ID NO: 51), pCUR5p—copper inducible (SEQ ID NO: 52), pCUR6—copper inducible (SEQ ID NO: 53), pCUR7—copper inducible (SEQ ID NO: 54), pCUR8—copper inducible (SEQ ID NO: 55), pCUR9—copper inducible (SEQ ID NO: 56), pCUR10—copper inducible (SEQ ID NO: 57), pCUR11—copper inducible (SEQ ID NO: 58), pCUR12—copper inducible (SEQ ID NO: 59), pCUR13—copper inducible (SEQ ID NO: 60), pCUR14—copper inducible (SEQ ID NO: 61), pCUR15—copper inducible (SEQ ID NO: 62), pCUR16—copper inducible (SEQ ID NO: 63), pCUR17—copper inducible (SEQ ID NO: 64), pLYS1—lysine inducible (SEQ ID NO: 65), pLYS4—lysine inducible (SEQ ID NO: 66), pLYS9—lysine inducible (SEQ ID NO: 67), pLYR1p—lysine inducible (SEQ ID NO: 68), pLYR2p—lysine inducible (SEQ ID NO: 69), pLYR3p—lysine inducible (SEQ ID NO: 70), pLYR4p—lysine inducible (SEQ ID NO: 71), pLYR5p—lysine inducible (SEQ ID NO: 72), pLYR6p—lysine inducible (SEQ ID NO: 73), pLYR7p—lysine inducible (SEQ ID NO: 74), pLYR8—lysine inducible (SEQ ID NO: 75), pLYR9—lysine inducible (SEQ ID NO: 76), pLYR10—lysine inducible (SEQ ID NO: 77), pLYR11—lysine inducible (SEQ ID NO: 78), pMET17—methionine inducible (SEQ ID NO: 79), pMET6—methionine inducible (SEQ ID NO: 80), pMET14—methionine inducible (SEQ ID NO: 81), pMET3—methionine inducible (SEQ ID NO: 82), pSAM1—methionine inducible (SEQ ID NO: 83), pSAM2—methionine inducible (SEQ ID NO: 84), pMDH2—glucose inducible (SEQ ID NO: 85), pJEN1—glucose inducible (SEQ ID NO: 86), pICL1—glucose inducible (SEQ ID NO: 87), pADH2—glucose inducible (SEQ ID NO: 88), and pMLS1—glucose inducible (SEQ ID NO: 89).

In some aspects, the inducible promoter(s) may be selected from the group consisting of pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2, and pMLS1.

In some aspects, inducible promoters may be selected from the group comprising promoters inducible with copper, promoters inducible due to the absence of copper, promoters inducible due to the absence of glucose, promoters inducible due to the absence of lysine, promoters inducible with methionine, promoters inducible due to the absence of methionine, and promoters inducible with threonine.

In some aspects, inducible promoter may be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, pCHA1, pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

In some aspects, the inducible promoters, identical or different, may be preferably characterized by a sequence of nucleic acids selected from the group consisting of sequences having at least 80/85/90/95/96/97/98/99/100% identity with sequences SEQ ID NOs: 13-89.

In some aspects, synthetic promoters, as described in Blazeck & Alper (2013) Biotechnol. J. 8 46-58, can also be used.

The strong and inducible or repressible promoters of the disclosure can originate from any organism from Saccharomycetes class and can in particular originate, independently, from an organism selected from the group consisting of *Saccharomyces cerevisiae, Saccharomyces boulardii, Saccharomyces castelii, Saccharomyces bayanus, Saccharomyces arboricola, Saccharomyces kudriavzevii, Ashbya gossypii, Kluveromyces lactis, Pichia pastoris, Candida glabrata, Candida tropicalis, Debaryomyces castelii, Yarrowia lipolytica,* and *Cyberlindnera jadinii*.

In some aspects, strong, weak, and inducible promoters may originate from an organism selected from the group consisting of *Saccharomyces cerevisiae, Saccharomyces castelii, Saccharomyces bayanus, Saccharomyces arboricola, Saccharomyces kudriavzevii,* and *Kluveromyces lactis*.

Terminators

In some aspects, the recombinant microbes comprise appropriate transcription terminator sequences that are functional in yeast cells, including in *Saccharomyces cerevisiae*. In some aspects, the transcription terminators, identical or different, may be found in Yamanishi et al., (2013) ACS synthetic biology 2, 337-347.

In some aspects, terminators may be selected from the group comprising:
  tTDH2 from the gene coding for Glyceraldehyde-3-phosphate dehydrogenase, isozyme 2 (TDH2 gene=Sequence SEQ ID NO: 90),
  tCYC1 (=Sequence SEQ ID NO: 91),
  tTDH3 (=Sequence SEQ ID NO: 92),
  tADH1 from gene coding for the alcohol dehydrogenase (ADH1 gene=Sequence SEQ ID NO: 93),
  tADH2 from gene coding for the alcohol dehydrogenase (ADH2 gene=Sequence SEQ ID NO: 94),
  tTPI1 from the gene encoding for the Triose Phosphate Isomerase (TPI1 gene=Sequence SEQ ID NO: 95),
  tMET17 from the gene encoding for the O-acetyl homoserine-O-acetyl serine sulfhydrylase (Met17 gene=Sequence SEQ ID NO: 96),
  tENO2 from the gene coding for Enolase II (ENO2 gene=Sequence SEQ ID NO: 97),
  tMET3 (=Sequence SEQ ID NO: 98),
  tPGK1 from the gene encoding for the 3-phosphoglycerate kinase (PGK1 gene=Sequence SEQ ID NO: 99),
  tDIT1 (=Sequence SEQ ID NO: 100)
  tRPL3 (=Sequence SEQ ID NO: 101)
  tRPL41B (=Sequence SEQ ID NO: 102)
  tRPL15 A (=Sequence SEQ ID NO: 103)
  tIDP1 (=Sequence SEQ ID NO: 104)

In some aspects, the terminator, identical or different, may be preferably characterized by a sequence of nucleic acid selected from the group consisting of sequences having at least 80/85/90/95/96/97/98/99/100% identity with SEQ ID NOs: 90-104.

Malonate Semialdehyde, Salts Thereof, and Derivatives Thereof

Malonate semialdehyde and its salts thereof are a key intermediate for the production of valuable compounds.

These compounds of economic interest include those produced directly from malonate semialdehyde or its salts, such as acrylate, 1-propanol, isopropanol, 3-hydroxypropionate, and propionate, but also those derived from malonyl-CoA, mostly produced by polyketides synthases such as phloroglucinol and flavonoids, and the fatty acids synthase, or those derived from the mevalonate such as farnesyl-PP, squalene and derivatives or the 3-hydroxy-3-methyl-butyrate pathways.

Malonate semialdehyde and its salts are naturally produced in yeast from malonyl-CoA and beta-alanine. However, production of malonyl-CoA and its salts is in competition with the ethanol biosynthesis pathway, thus rendering difficult the flux derivation to malonate semialdehyde.

Moreover, production from beta-alanine requires the amination of oxaloacetate followed by the deamination of beta-alanine, involving a great number of enzymes.

In order to facilitate the production of malonate semialdehyde and its salts in yeasts, it has been proposed to obtain malonate semialdehyde in one step by decarboxylation of oxaloacetate (US2010/0021978). However, no natural enzyme is known as being able to perform this transformation in a natural pathway efficiently. The enzymatic activity of the decarboxylation of oxaloacetate into malonate semialdehyde is herein referred to as oxaloacetate 1-decarboxylase (MSA forming), and is not to be confused with oxaloacetate decarboxylase (EC 4.1.1.3) which yields pyruvate.

US2010/0021978 proposes the use of a promiscuous decarboxylase such as the benzoylformate decarboxylase, the alpha-ketoglutarate decarboxylase, the alpha-ketoisovalerate decarboxylase or the pyruvate decarboxylase to perform this decarboxylation of oxaloacetate in malonate semialdehyde or one of its salts. This document exemplifies the use of benzoylformate decarboxylase in *Escherichia coli* to produce 3 hydroxypropionate through malonate semialdehyde.

US2018/032830 proposes and exemplifies the use of a decarboxylase such as pyruvate decarboxylase to perform this decarboxylation of oxaloacetate in 3-oxopropanoate (malonate semialdehyde) to produce 3-hydroxipropionate.

U.S. Pat. No. 8,809,027 proposes and exemplifies the use of pyruvate decarboxylase, 2-oxoglutarate decarboxylase and alpha-ketoglutarate decarboxylase to perform the decarboxylation of oxaloacetate in malonate semialdehyde to produce 3-hydroxipropionate.

The inventors in the aforementioned pre-grant publication could detect carboxylase activity both in cellulo and in vitro on their cognate substrate, the inventors were unable to detect any activity of all these enzymes on oxaloacetate.

Accordingly, there is still a need in the art for enzymes able to efficiently catalyze the transformation of oxaloacetate into malonate semialdehyde, or one of its salts, when expressed in a yeast, and in particular in the yeast *Saccharomyces cerevisiae*.

Malonate semialdehyde is a compound having the following structure:

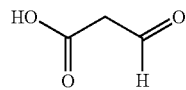

In some aspects, the compound may exist in the form of a base or of a salt. In some aspects, the salt can be malonate semialdehyde having the following structure:

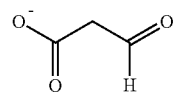

In some aspects, organic cation salts such as ammonium, sodium, potassium, phosphonium, or sulfonium salts may also be concerned.

In some aspects, malonate semialdehyde derivatives are compounds that may be obtained from malonate semialdehyde, or from one of its salts, after modification by at least one enzyme naturally or artificially present in the microorganism producing the malonate semialdehyde, or one of its salts.

In some aspects, derivatives of malonate semialdehyde include propanol, propanal, acrylic acid, acrylyl-CoA, acetyl-CoA, 3-HP, acrylate, acetone, isopropanol, propionate, propionyl-CoA, 3-hydroxypropionate, 3-hydroxypropionyl-CoA, 3-hydroxy-3-methyl-butyrate, phloroglucinol, flavonoids, cannabinoids, farnesyl-PP, and squalene.

Figure 11:
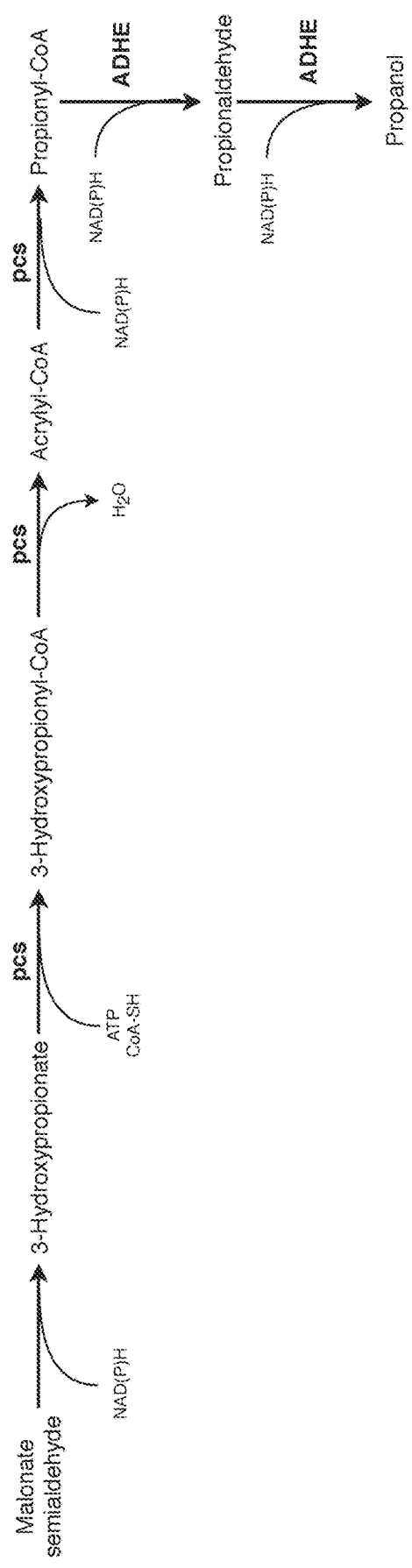
FIG. 11 depicts a pathway from malonate semialdehyde to propanol, including catalytic enzymes and corresponding malonate semialdehyde intermediates.

In some aspects, 3-hydroxypropionate, Acrylyl-CoA, Propionyl-CoA, propanal and propanol can be obtained from malonate semialdehyde or from one of its salts through the steps detailed in FIG. 11 PCS represents a propionyl-CoA synthase, such as the PCS of *Chloroflexus aggregans, Roseiflexus castenholzii,* or *Chloroflexus aurantiacus*. This reaction can be catalyzed by enzymes with, but not restricted to, EC number 6.2.1.17/6.2.1.36 such as listed in Table 3. ADHE represents an alcohol dehydrogenase E, such as the ADHE from *Clostridium beijerinckii* or *Clostridium arbusti*. This reaction can be catalyzed by enzymes with, but not restricted to, EC number 1.1.1.1/1.2.1.4/1.2.1.5 such as those listed in Table 7.

Figure 12:
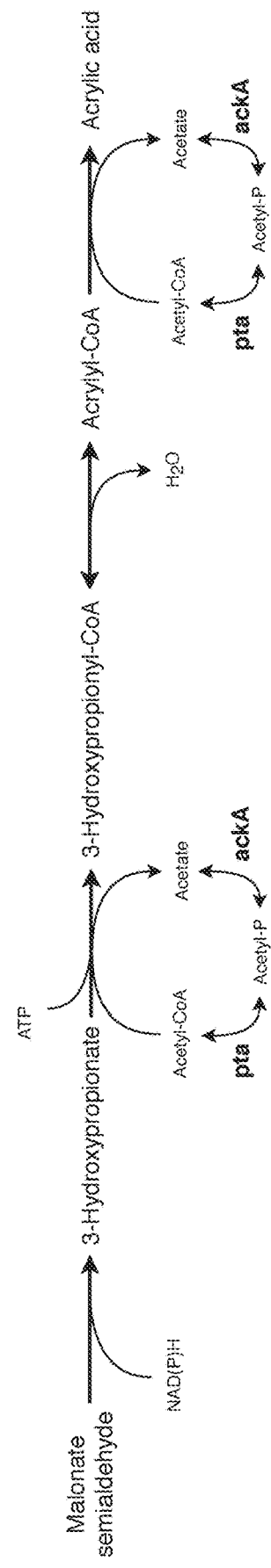
FIG. 12 depicts a pathway from malonate semialdehyde to acrylic acid, including malonate semialdehyde intermediates and corresponding cofactors.

In some aspects, acrylic acid and acrylate can be obtained from malonate semialdehyde or from one of its salts by multi-step enzymatic reactions involving the CoA attachment to 3-HP, dehydration of 3-HP-CoA to acrylyl-CoA as depicted in FIG. 12 and detachment of CoA from acrylyl-CoA as a synthetic pathway already demonstrated in the literature (Chu et al. Direct fermentation route for the production of acrylic acid. Metabolic Engineering, 32 (2015), 23-29). The steps from malonate semialdehyde to acrylyl-CoA can be catalyzed by 3-hydroxypropionic acid dehydrogenase with, but not restricted to, EC number 1.1.1.381 such as those listed in Table 1; 3-hydroxypropionyl-CoA synthetase/CoA transferases that can be used have, but are not restricted to, EC numbers 2.8.3.1/6.2.1.17/6.2.1.36 such as those listed in Table 4; 3-hydroxypropionyl-CoA dehydratase/enoyl-CoA hydratases that can be used have, but are not restricted to, EC numbers 4.2.1.116/4.2.1.55/4.2.1.150/4.2.1.17 such as those listed in Table 5 and acyl-CoA hydrolase or thioesterase (Table 14). Acrylic acid can be derived chemically via a dehydration reaction. Dehydration methods of 3-hydroxypropionic acid are well known in the art. For example, incorporated herein for its teachings of conversion of 3-HP, U.S. Pat. No. 8,846,353 B2 describes a method where 3-HP present in a fermentation broth can be dehydrated in a vapor phase reaction in the presence of an acid catalyst like but not limited to NaH2PO4-silica gel, H3PO4-silica gel, CuSO4-silica gel and zeolite H-β-H3PO4. The U.S. Pat. No. 2,469,701 describes other example for the reaction by adding 3-hydroxypropionic acid gradually to a concentrated dehydration catalyst, such as phosphoric acid or sulfuric acid maintained at a temperature of about 150-190° C. under reduced pressure, in the presence of powdered metallic copper and separating the aqueous acrylic acid formed from the catalyst by distillation. An aqueous phase containing 3-HP can also be dehydrated via reactive distillation to give a fluid acrylic acid solution that may proceed to an optional purification step by a suspension crystallization or a layer crystallization as described in U.S. Pat. No. 8,198,481 B2.

Figure 9:
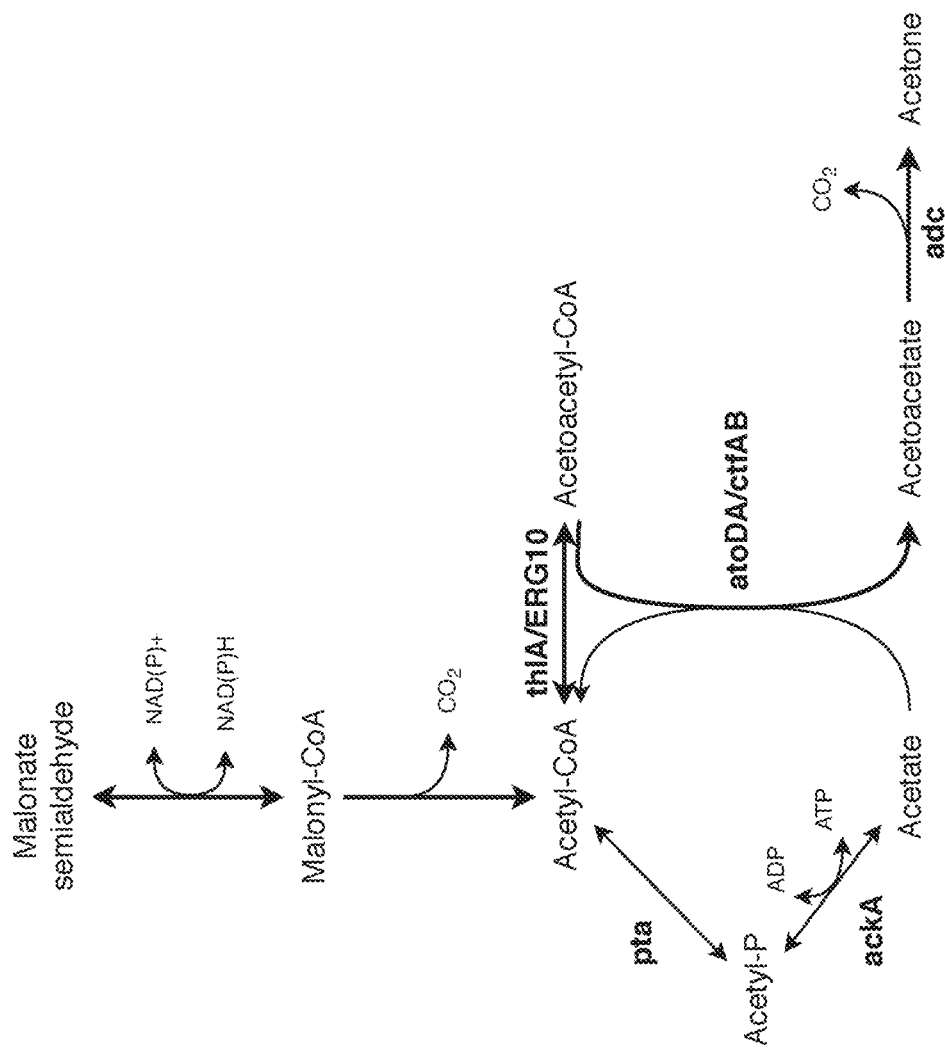
FIG. 9 depicts a pathway from malonate semialdehyde to acetone, including catalytic enzymes and corresponding malonate semialdehyde intermediates.
Figure 10:
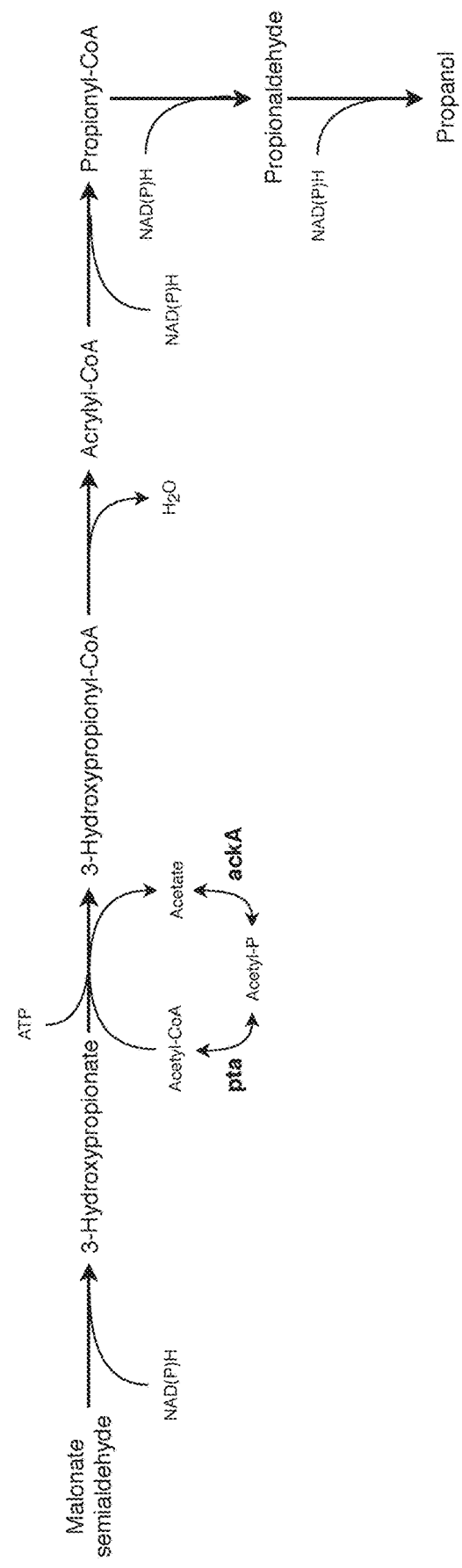
FIG. 10 depicts a pathway from malonate semialdehyde to propanol, including malonate semialdehyde intermediates and corresponding cofactors.

In some aspects, malonate semialdehyde can be transformed into acetyl-CoA by a malonate semialdehyde dehydrogenase (acetylating (E.C. 1.2.1.18), such as KES23460 from *Pseudomonas putida* described in Wilding et al. (2016. Appl. Microbiol Biotechnol, 82:3846-3856). See FIG. 9 Acetyl-CoA is then a starting point to produce isopropanol as described in Tamakawa et al. Appl Microbiol Biotechnol (2013) 97:6231-6239.

In some aspects, propionyl-CoA is obtained from malonate semialdehyde. Propionyl-CoA can then be transformed into propionate through the successive catalysis of phosphotransacetylase (E.C. 2.3.1) and an acetate kinase (E.C. 2.7.2.1), described in Erbilgin et al. (2016) PLoS Biol 14(3): e1002399.doi:10.1371/journal.pbio.1002399 and Reinscheid et al. (1999) Microbiology 145,503-513

Figure 4:
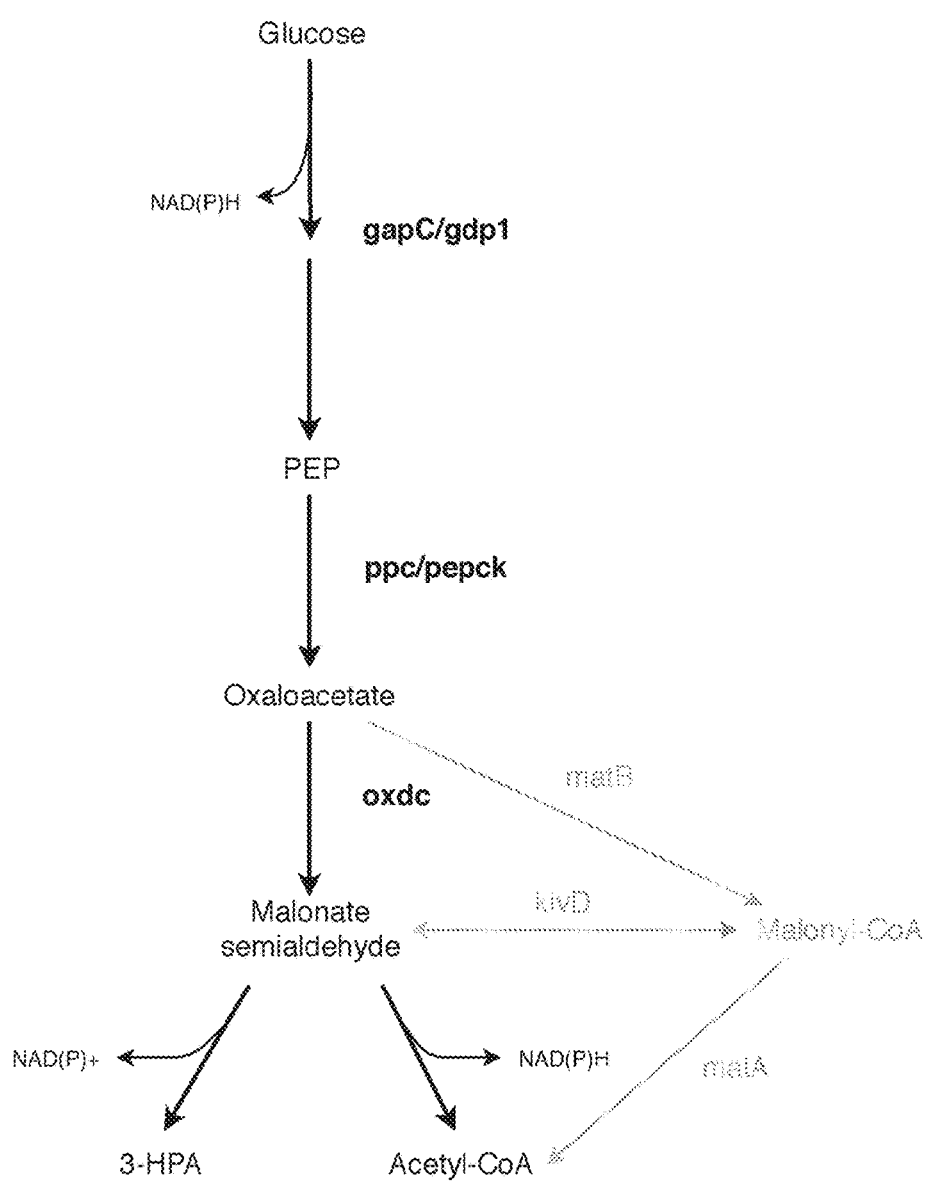
FIG. 4 depicts the two pathways for the production of acetyl-CoA, through malonyl-CoA as an intermediate (standard route) and directly with malonate semialdehyde (new route).

In some aspects, malonate semialdehyde can be transformed into malonyl-CoA by a malonyl-CoA reductase (E.C. 1.2.1.75) as described in Alber et al. (2006) Journal of bacteriology 188, 8551-8559. See FIG. 4 Malonyl-CoA is then the starting point to synthetize phloroglucinol and derivatives using a phloroglucinol synthase (E.C.2.3.1.253) as described in Yang and Cao (2012) Appl Microbiol Biotechnol93:487-495.

Malonyl-CoA is a major building block and often a bottleneck required for flavonoids biosynthesis (Johnson et al. (2017) Metabolic Engineering 44: 253-264). Malonate semialdehyde can be transformed into malonyl-CoA by a malonyl-CoA reductase (E.C. 1.2.1.75) as described in Alber et al. (2006) Journal of bacteriology 188, 8551-8559. Malonyl-CoA can then be used to fuel flavonoids synthesis as described in Batra, Priya, and Anil K. Sharma. (2013) 3 Biotech 6: 439-59; and in Mou, et al. (2015) PLoS ONE 10(6).

Acetyl-CoA is also a major building block and often a bottleneck required for farnesyl-PP and derivatives biosynthesis, as for example squalene. As mentioned above, malonate semialdehyde can be transformed into acetyl-CoA by a malonate semialdehyde dehydrogenase (acetylating) (E.C 1.2.1.18) as for example KES23460 from *Pseudomonas putida* described in Wilding et al. (2016) Appl.Env.Microbiology, 82, 3846-3856. Acetyl-CoA is then a starting point to produce Farnesyl PP and derivatives as described in Wang, J.; Li, Y.; Liu, D. Cloning and Characterization of Farnesyl Diphosphate Synthase Gene Involved in Triterpenoids Biosynthesis from *Poria cocos*. Int. J. Mol. Sci. 2014, 15, 22188-22202.

In some aspects, cannabinoids can be obtained from malonate semialdehyde or from one of its salts from acetyl-CoA which is the precursor of all cannabinoids. Malonate semialdehyde can be transformed into acetyl-CoA by a malonate semialdehyde dehydrogenase (acetylating) (E.C 1.2.1.18) as for example KES23460 from *Pseudomonas putida* described in Wilding et al. Acetyl-CoA is then a starting point to produce cannabinoids as described in Carvalho et al. (2017) FEMS Yeast Research, 17, fox037. doi: 10.1093/femsyr/fox037.

In some aspects, 3-hydroxy-3-methyl-butyrate can be obtained from malonic semialdehyde or from one of its salts as follows. Malonate semialdehyde can, as mentioned above, be transformed into acetyl-CoA by a malonate semialdehyde dehydrogenase (acetylating) (E.C 1.2.1.18) as for example KES23460 from *Pseudomonas putida* described in Wilding et al. Acetyl-CoA is then the starting point for 3-hydroxy-3-methyl-butyrate biosynthesis as described in Gogerty and Bobic (2010) Appl Microbiol Biotechnol 76: 8004-8010.

In some aspects, a recombinant microbe of the present disclosure may comprise one or more nucleic acid sequences encoding the enzymes mentioned above in order to obtain the malonate semialdehyde and/or derivatives of interest. The one or more nucleic acid sequences encoding the enzymes performing the necessary transformations of malonate semialdehyde, or one of its salts, to the malonate semialdehyde derivative of interest can be naturally present in the microbe (endogenous) and/or can be incorporated into the microbe as transgenes according to methods well known to the man skilled in the art.

In some aspects, a recombinant microbe of the present disclosure may comprise, in addition to a nucleic acid sequence encoding an enzyme able to catalyze the decarboxylation of oxaloacetate into malonate semialdehyde as defined above, at least one nucleic acid encoding a 3-hydroxy acid dehydrogenase and/or a malonyl-CoA reductase.

In some aspects, the 3-hydroxy acid dehydrogenase and/or malonyl-CoA reductase according to this embodiment can be, but not limited to, the 3-hydroxy acid dehydrogenase with EC number 1.1.1.381 such as those listed in Table 1.

In some aspects, a recombinant microbe of the present disclosure may comprise, in addition to a nucleic acid gene encoding an enzyme able to catalyze the decarboxylation of oxaloacetate into malonate semialdehyde as defined above, (i) at least one nucleic acid encoding a 3-hydroxy acid dehydrogenase or a malonyl-CoA reductase and (ii) at least one nucleic acid encoding a propionyl-CoA synthase.

In some aspects, the 3-hydroxy acid dehydrogenase and/or malonyl-CoA reductase according to this embodiment can be, but not limited to, the 3-hydroxy acid dehydrogenase with EC number 1.1.1.381 such as those listed in Table 1. The propionyl-coA synthase (PCS) that can be used has, but is not restricted to, EC numbers 6.2.1.17/6.2.1.36 as those listed in Table 3.

In some aspects, a recombinant microbe of the disclosure may comprise, in addition to a nucleic acid gene encoding an enzyme able to catalyze the decarboxylation of oxaloacetate into malonate semialdehyde as defined above, (i) at least one nucleic acid encoding a 3-hydroxy acid dehydrogenase or a malonyl-CoA reductase, (ii) at least one nucleic acid encoding a propionyl-CoA synthase or 3-hydroxypropionyl-CoA synthetase/transferase, 3-hydroxypropionyl-CoA dehydratase, and acrylyl-CoA reductase and (iii) at least one alcohol dehydrogenase E or aldehyde dehydrogenase and alcohol dehydrogenase.

In some aspects, the 3-hydroxy acid dehydrogenase and/or malonyl-CoA reductase of the disclosure may be the 3-hydroxy acid dehydrogenase with, but not restricted to, EC number 1.1.1.381 such as those listed in Table 1. In some aspects, the propionyl-CoA synthase (PCS) of the disclosure may be the PCS with, but not limited to, EC numbers 6.2.1.17/6.2.1.36 such as those listed in Table 3.

In some aspects, the ADHE of the disclosure that can be used, but is not restricted to, is a enzyme with EC numbers 1.1.1.1/1.2.1.4/1.2.1.5 such as those listed in Table 7. In some aspects, it is possible to use two enzymes to convert propanol from propionyl-CoA. Can be used, but are not restricted to, enzymes with EC numbers 1.2.1.10/1.2.1.87 such as those listed in Table 8 or enzymes with EC numbers 2.3.1.8/2.7.2.1 such as those listed in Table 10 and enzymes with EC numbers 1.1.1.1/1.1.1.2 such as those listed in Table 9.

In some aspects, the recombinant microbe may comprise, in addition to a nucleic acid sequence encoding an enzyme able to catalyze the decarboxylation of oxaloacetate into malonate semialdehyde as defined above, (i) at least one nucleic acid encoding a 3-hydroxy acid dehydrogenase or a malonyl-CoA reductase and (ii) at least one nucleic acid encoding a propionate-CoA transferase.

In some aspects, a propionate-CoA transferase may be, but not restricted to, the enzyme with the reference E.C.2.8.3.1.

In some aspects, the 3-hydroxy acid dehydrogenase and/or malonyl-CoA reductase may be, but not limited to, the 3-hydroxy acid dehydrogenase or the malonyl-CoA reductase with EC number 1.1.1.381 such as those listed in Table 1. In some aspects, the propionate-CoA transferase may be, but not limited to, the propionate-CoA transferases or 3-hydroxypropionyl-CoA synthetases with EC number 2.8.3.1/6.2.1.17/6.2.1.36 such as those listed in Table 4.

In some aspects, a recombinant microbe may comprise, in addition to a nucleic acid gene encoding an enzyme able to catalyze the decarboxylation of oxaloacetate into malonate semialdehyde as defined above, (i) at least one nucleic acid encoding a 3-hydroxy acid dehydrogenase or a malonyl-CoA reductase, (ii) at least one nucleic acid encoding a propionate-CoA transferase and (iii) at least one 3-hydroxypropionyl coenzyme A dehydratase.

In some aspects, the 3-hydroxy acid dehydrogenase and/or malonyl-CoA reductase may be, but are not restricted to enzymes with EC number 1.1.1.381 such as those listed in Table 1. In some aspects, the propionate-CoA transferase or 3-hydroxypropionyl-CoA synthetase that can be used has, but is not restricted to, EC number 2.8.3.1/6.2.1.17/6.2.1.36 such as those listed in Table 4. In some aspects, the 3-hydroxypropionyl coenzyme A dehydratase may be, but is not restricted to enzymes with EC numbers 4.2.1.116/4.2.1.55/4.2.1.150/4.2.1.17 such as those listed in Table 5.

In some aspects, the disclosure is drawn to a recombinant microbial organism, a microbe in some aspects, able to catalyze the decarboxylation of oxaloacetate into malonate semialdehyde. In some aspects, these enzymes are characterized by SEQ ID NO: 1, as follows.

```
                                          (SEQ ID NO: 1)
MASVHGTTYELLRRQGIDTVFGNPGSNELPFLKDFPEDFRYILALQEA

CVVGIADGYAQASRKPAFINLHSAAGTGNAMGALSNAWNSHSPLIVTA

GQQTRAMIGVEAX₁X₂TNVDAANLPRPLVKWSYEPASAAEVPHAMSRAI

HMASMAPQGPVYLSVPYDDWDKDADPQSHHLFDRHVSSSVRLNDQDLD

ILVKALNSASNPAIVLGPDVDAANANADCVMLAERLKAPVWVAPSAPR

CPFPTRHPCFRGLMPAGIAAISQLLEGHDVVLVIGAPVFRYHQYDPGQ

YLKPGTRLISVTCDPLEAARAPMGDAIVADIGAMASALANLVEESSRQ

LPTAAPEPAKVDQDAGRLHPETVFDTLNDMAPENAIYLNESX₃STTAQ

MWQRLNMRNPGSYYX₄X₅AAGGX₆FALPAAIGVQLAEPERQVIAVIGDG

SANYSISALWTAAQYNIPTIFVIMNNGTYGX₇LRWFAGVLEAENVPGL

DVPGIDFRALAKGYGVQALKADNLEQLKGSLQEALSAKGPVLIEVSTV

SPVK;
``` wherein:

$X_1$ represents an amino acid selected from the group consisting of leucine, lysine, arginine and valine;

$X_2$ represents an amino acid selected from the group consisting of leucine and lysine;

$X_3$ represents an amino acid selected from the group consisting of threonine and serine; $X_4$ represents an amino acid selected from the group consisting of phenylalanine, asparagine, alanine, isoleucine and valine;

$X_5$ represents an amino acid selected from the group consisting of cysteine and arginine; $X_6$ represents an amino acid selected from the group consisting of leucine, asparagine and alanine; and $X_7$ represents an amino acid selected from the group consisting of alanine and leucine, with the proviso that the enzyme cannot have the sequence SEQ ID NO: 1 wherein $X_1$ represents leucine; $X_2$ represents leucine; $X_3$ represents threonine; $X_4$ represents phenylalanine; $X_5$ represents cysteine; $X_6$ represents leucine; and $X_7$ represents alanine.

In some aspects, $X_1$ represents an amino acid selected from the group consisting of lysine, arginine and valine. In some aspects, $X_1$ represents an amino acid selected from the group consisting of arginine and valine. In some aspects, $X_1$ is arginine.

In some aspects, an enzyme of the disclosure is that of SEQ ID NO: 1 as defined above, with $X_1$ being arginine.

In some aspects, $X_2$ represents leucine.

In some aspects, $X_1$ represents valine and $X_2$ represents lysine.

In some aspects, $X_3$ represents threonine.

In some aspects, $X_1$ is arginine, $X_2$ represents leucine and $X_3$ represents threonine.

In some aspects, $X_4$ represents phenylalanine or asparagine.

In some aspects, an enzyme of sequence of SEQ ID NO: 1 is such that:

$X_1$ is arginine or lysine, $X_2$ represents leucine, $X_3$ represents threonine and $X_4$ represents phenylalanine; or $X_1$ is arginine or lysine, $X_2$ represents leucine, $X_3$ represents threonine and $X_4$ represents asparagine.

In some aspects, $X_5$ represents cysteine.

In some aspects, an enzyme of sequence SEQ ID NO: 1 is such that:

$X_1$ is arginine or lysine, $X_2$ represents leucine, $X_3$ represents threonine, $X_4$ represents phenylalanine and $X_5$ represents cysteine; or $X_1$ is arginine or lysine, $X_2$ represents leucine, $X_3$ represents threonine, $X_4$ represents asparagine, and $X_5$ represents cysteine.

In some aspects, $X_6$ represents an amino acid selected from the group consisting of leucine and asparagine. In some aspects, $X_6$ is leucine.

In some aspects, $X_1$ represents valine, $X_2$ represents lysine and $X_6$ represents asparagine.

In some aspects, an enzyme of sequence SEQ ID NO: 1 is such that:

$X_1$ is arginine or lysine, $X_2$ represents leucine, $X_3$ represents threonine, $X_4$ represents phenylalanine, $X_5$ represents cysteine and $X_6$ is leucine; or $X_1$ is arginine or lysine, $X_2$ represents leucine, $X_3$ represents threonine, $X_4$ represents asparagine, $X_5$ represents cysteine and $X_6$ is leucine.

In some aspects, $X_7$ represents alanine.

In some aspects, an enzyme of sequence SEQ ID NO: 1 is such that:

$X_1$ is arginine or lysine, $X_2$ represents leucine, $X_3$ represents threonine, $X_4$ represents phenylalanine, $X_5$ represents cysteine, $X_6$ is leucine and $X_7$ is alanine; or $X_1$ is arginine or lysine, $X_2$ represents leucine, $X_3$ represents threonine, $X_4$ represents asparagine, $X_5$ represents cysteine, $X_6$ is leucine and $X_7$ is alanine.

In some aspects, an enzyme of the disclosure is selected from the group consisting of:
(i) an enzyme of sequence SEQ ID NO: 1 wherein $X_1$ represents arginine; $X_2$ represents leucine; $X_3$ represents threonine; $X_4$ represents phenylalanine; $X_5$ represents cysteine; $X_6$ represents leucine; and $X_7$ represents alanine; (i.e. an enzyme of amino acid sequence SEQ ID NO: 2)
(ii) an enzyme of sequence SEQ ID NO: 1 wherein $X_1$ represents arginine; $X_2$ represents leucine; $X_3$ represents threonine; $X_4$ represents asparagine; $X_5$ represents cysteine; $X_6$ represents leucine; and $X_7$ represents alanine; (i.e. an enzyme of amino acid sequence SEQ ID NO: 3)
(iii) an enzyme of sequence SEQ ID NO: 1 wherein $X_1$ represents arginine; $X_2$ represents leucine; $X_3$ represents threonine; $X_4$ represents asparagine; $X_5$ represents cysteine; $X_6$ represents leucine; and $X_7$ represents alanine; (i.e. an enzyme of amino acid sequence SEQ ID NO: 4)
(iv) an enzyme of sequence SEQ ID NO: 1 wherein $X_1$ represents arginine; $X_2$ represents leucine; $X_3$ represents threonine; $X_4$ represents asparagine; $X_5$ represents cysteine; $X_6$ represents leucine; and $X_7$ represents leucine; (i.e. an enzyme of amino acid sequence SEQ ID NO: 5), and
(v) an enzyme of sequence SEQ ID NO: 1 wherein $X_1$ represents valine; $X_2$ represents lysine; $X_3$ represents threonine; $X_4$ represents asparagine; $X_5$ represents cysteine; $X_6$ represents asparagine; and $X_7$ represents alanine. (i.e. an enzyme of amino acid sequence SEQ ID NO: 6)

In some aspects, the disclosure is drawn to a recombinant microbial organism, a microbe in some aspects, able to catalyze the decarboxylation of oxaloacetate into malonate semialdehyde. In some aspects, these enzymes are characterized by an amino acid sequence comprising:

(SEQ ID NO: 274)
MASVHGTTYELLRRQGIDX$_8$VFGNPGSNELPFLKDFPEDFRYILALQE

ACVVGIADGYAQASRKPAFINLHSAAGTGNAMGALSNAWNSHSPLIVT

AGQQTRAMIGVEAX$_1$X$_2$TNVDAANLPRPLVKWSYEPASAAEVPHAMSRA

IHMASMAPQGPVYLSVPYDDWDKDADPQSHHLFDRHVX$_9$SSVRLNDQDL

DILVKALNSASNPX$_{10}$IVLGPDVDAANANADCVMLAERLKAPVWVAPSA

PRCPFPTRHPCFRGLMPAGIAAISQLLEGHDVVLVIGAPVFRYX$_{11}$X$_{12}$Y

DPGQYLKPGTRLISVTCDPLEAARAPMGDAIVADIGAMASALANLVEES

SRQLPTAAPEPAKVDQDAGRLHPETVFDTLNDMAPEX$_{13}$AIYLNESX$_3$ST

TAQMWQRLX$_{14}$MRNPGSYYX$_4$X$_5$AAGGX$_6$GFALPAAIGVQLAEPX$_{15}$RQVI

-continued

AVIGDGSANYSISALWTAAQYNX$_{16}$PTIFVIMNNGTYGX$_7$LRWX$_{17}$AGVL

X$_{18}$AENVPGLDVPGIDFRALAKGYGVQALKADNLEQLKGSLQEALSAKG

PVLIEVSTVSPVK wherein:
$X_1$ represents an amino acid selected from the group consisting of leucine, lysine, arginine and valine;
$X_2$ represents an amino acid selected from the group consisting of leucine and lysine;
$X_3$ represents an amino acid selected from the group consisting of threonine and serine;
$X_4$ represents an amino acid selected from the group consisting of phenylalanine, asparagine, alanine, isoleucine, valine, leucine, tryptophan and arginine;
$X_5$ represents an amino acid selected from the group consisting of cysteine and arginine;
$X_6$ represents an amino acid selected from the group consisting of leucine, asparagine, alanine, valine and serine;
$X_7$ represents an amino acid selected from the group consisting of alanine, leucine, threonine, glycine and asparagine;
$X_8$ represents an amino acid selected from the group consisting of threonine or isoleucine;
$X_9$ represents an amino acid selected from the group consisting of serine or threonine;
$X_{10}$ represents an amino acid selected from the group consisting of alanine or valine;
$X_{11}$ represents an amino acid selected from the group consisting of histidine or arginine;
$X_{12}$ represents an amino acid selected from the group consisting of glutamine or arginine;
$X_{13}$ represents an amino acid selected from the group consisting of asparagine or aspartic acid;
$X_{14}$ represents an amino acid selected from the group consisting of asparagine or aspartic acid;
$X_{15}$ represents an amino acid selected from the group consisting of glutamic acid or glycine;
$X_{16}$ represents an amino acid selected from the group consisting of isoleucine or valine;
$X_{17}$ represents an amino acid selected from the group consisting of phenylalanine or serine; and
$X_{18}$ represents an amino acid selected from the group consisting of glutamic acid or glycine;
with the proviso that the enzyme cannot have the sequence SEQ ID NO: 274 wherein $X_1$ represents leucine; $X_2$ represents leucine; $X_3$ represents threonine; $X_4$ represents phenylalanine; $X_5$ represents cysteine; $X_6$ represents leucine; $X_7$ represents alanine, $X_8$ represents threonine; $X_9$ represents serine; $X_{10}$ represents alanine; $X_{11}$ represents histidine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine and $X_{18}$ represents glutamic acid.

An enzyme according to the invention can in particular be selected from the group consisting of:
(i) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents alanine; $X_8$ represents threonine; $X_9$ represents serine; $X_{10}$ represents alanine; $X_{11}$ represents histidine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 2);

(ii) an enzyme of sequence SEQ ID NO: 274 wherein $X_1$ represents arginine; $X_2$ represents leucine; $X_3$ represents threonine; $X_4$ represents leucine; $X_5$ represents cysteine; $X_6$ represents leucine; $X_7$ represents threonine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glutamic acid; $X_{16}$ represents valine; $X_{17}$ represents phenylalanine; and $X_{18}$ represents glutamic acid (i.e. an enzyme of amino acid sequence SEQ ID NO: 242);

(iii) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents leucine; $X_8$ represents isoleucine; $X_9$ represents serine; $X_{10}$ represents alanine; $X_{11}$ represents arginine; $X_{12}$ represents glutamine; $X_{13}$ represents asparagine; $X_{14}$ represents aspartic acid; $X_{15}$ represents glycine; $X_{16}$ represents isoleucine; $X_{17}$ represents serine; and $X_{18}$ represents glycine (i.e. an enzyme of amino acid sequence SEQ ID NO: 243);

(iv) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents glycine; $X_8$ represents threonine; $X_9$ represents serine; $X_{10}$ represents alanine; $X_{11}$ represents arginine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 244);

(v) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents threonine; $X_8$ represents threonine; $X_9$ represents serine; $X_{10}$ represents alanine; $X_{11}$ represents histidine; $X_{12}$ represents arginine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 245);

(vi) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents leucine; $X_8$ represents threonine; $X_9$ represents serine; $X_{10}$ represents alanine; $X_{11}$ represents histidine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 247);

(vii) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents alanine; $X_8$ represents threonine; $X_9$ represents serine; $X_{10}$ represents alanine; $X_{11}$ represents arginine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 248);

(viii) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents threonine; $X_8$ represents threonine; $X_9$ represents serine; $X_{10}$ represents alanine; $X_{11}$ represents arginine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 249);

(ix) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents alanine; $X_8$ represents threonine; $X_9$ represents serine; $X_{10}$ represents alanine; $X_{11}$ represents histidine; $X_{12}$ represents arginine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 250);

(x) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents leucine; $X_8$ represents threonine; $X_9$ represents serine; $X_{10}$ represents alanine; $X_{11}$ represents histidine; $X_{12}$ represents arginine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 251);

(xi) an enzyme of sequence SEQ ID NO: 274 wherein $X_1$ represents arginine; $X_2$ represents leucine; $X_3$ represents threonine; $X_4$ represents leucine; $X_5$ represents cysteine; $X_6$ represents leucine; $X_7$ represents leucine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glutamic acid; $X_{16}$ represents valine; $X_{17}$ represents phenylalanine; and $X_{18}$ represents glutamic acid (i.e. an enzyme of amino acid sequence SEQ ID NO: 252);

(xii) an enzyme of sequence SEQ ID NO: 274 wherein $X_1$ represents arginine; $X_2$ represents leucine; $X_3$ represents threonine; $X_4$ represents leucine; $X_5$ represents cysteine; $X_6$ represents leucine; $X_7$ represents glycine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glutamic acid; $X_{16}$ represents valine; $X_{17}$ represents phenylalanine; and $X_{18}$ represents glutamic acid (i.e. an enzyme of amino acid sequence SEQ ID NO: 253);

(xiii) an enzyme of sequence SEQ ID NO: 274 wherein $X_1$ represents arginine; $X_2$ represents leucine; $X_3$ represents threonine; $X_4$ represents leucine; $X_5$ represents cysteine; $X_6$ represents leucine; $X_7$ represents threonine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glutamic acid; $X_{16}$ represents valine; $X_{17}$ represents serine; and $X_{18}$ represents glutamic acid (i.e. an enzyme of amino acid sequence SEQ ID NO: 254);

(xiv) an enzyme of sequence SEQ ID NO: 274 wherein $X_1$ represents arginine; $X_2$ represents leucine; $X_3$ represents threonine; $X_4$ represents leucine; $X_5$ represents cysteine; $X_6$ represents leucine; $X_7$ represents threonine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glycine; $X_{16}$ represents valine; $X_{17}$ represents serine; and $X_{18}$ represents glycine (i.e. an enzyme of amino acid sequence SEQ ID NO: 255);

(xv) an enzyme of sequence SEQ ID NO: 274 wherein $X_1$ represents arginine; $X_2$ represents leucine; $X_3$ represents threonine; $X_4$ represents leucine; $X_5$ represents cysteine; $X_6$ represents leucine; $X_7$ represents threonine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glycine; $X_{16}$ represents isoleucine; $X_{17}$ represents serine; and $X_{18}$ represents glycine (i.e. an enzyme of amino acid sequence SEQ ID NO: 256);

(xvi) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents leucine; $X_8$ represents isoleucine; $X_9$ represents serine; $X_{10}$ represents alanine; $X_{11}$ represents histidine; $X_{12}$ represents arginine; $X_{13}$ represents asparagine; $X_{14}$ represents aspartic acid; $X_{15}$ represents glycine; $X_{16}$ represents isoleucine; $X_{17}$ represents serine; and $X_{18}$ represents glycine (i.e. an enzyme of amino acid sequence SEQ ID NO: 257);

(xvii) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents leucine; $X_8$ represents isoleucine; $X_9$ represents serine; $X_{10}$ represents alanine; $X_{11}$ represents histidine; $X_{12}$ represents arginine; $X_{13}$ represents asparagine; $X_{14}$ represents aspartic acid; $X_{15}$ represents glycine; $X_{16}$ represents isoleucine; $X_{17}$ represents serine; and $X_{18}$ represents glycine (i.e. an enzyme of amino acid sequence SEQ ID NO: 258);

(xviii) an enzyme of sequence SEQ ID NO: 274 wherein $X_1$ represents arginine; $X_2$ represents leucine; $X_3$ represents threonine; $X_4$ represents tryptophan; $X_5$ represents cysteine; $X_6$ represents leucine; $X_7$ represents alanine; $X_8$ represents threonine; $X_9$ represents serine; $X_{10}$ represents alanine; $X_{11}$ represents arginine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 259);

(xix) an enzyme of sequence SEQ ID NO: 274 wherein $X_1$ represents arginine; $X_2$ represents leucine; $X_3$ represents threonine; $X_4$ represents arginine; $X_5$ represents cysteine; $X_6$ represents valine; $X_7$ represents alanine; $X_8$ represents threonine; $X_9$ represents serine; $X_{10}$ represents alanine; $X_{11}$ represents arginine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 260);

(xx) an enzyme of sequence SEQ ID NO: 274 wherein $X_1$ represents arginine; $X_2$ represents leucine; $X_3$ represents threonine; $X_4$ represents tryptophan; $X_5$ represents cysteine; $X_6$ represents leucine; $X_7$ represents asparagine; $X_8$ represents isoleucine; $X_9$ represents serine; $X_{10}$ represents alanine; $X_{11}$ represents histidine; $X_{12}$ represents arginine; $X_{13}$ represents asparagine; $X_{14}$ represents aspartic acid; $X_{15}$ represents glycine; $X_{16}$ represents isoleucine; $X_{17}$ represents serine; and $X_{18}$ represents glycine (i.e. an enzyme of amino acid sequence SEQ ID NO: 261);

(xxi) an enzyme of sequence SEQ ID NO: 274 wherein $X_1$ represents arginine; $X_2$ represents leucine; $X_3$ represents threonine; $X_4$ represents phenylalanine; $X_5$ represents cysteine; $X_6$ represents leucine; $X_7$ represents threonine; $X_8$ represents threonine; $X_9$ represents threonine; $X_{10}$ represents valine; $X_{11}$ represents histidine; $X_{12}$ represents arginine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 262);

(xxii) an enzyme of sequence SEQ ID NO: 274 wherein $X_1$ represents arginine; $X_2$ represents leucine; $X_3$ represents threonine; $X_4$ represents alanine; $X_5$ represents cysteine; $X_6$ represents leucine; $X_7$ represents threonine; $X_8$ represents threonine; $X_9$ represents serine; $X_{10}$ represents alanine; $X_{11}$ represents histidine; $X_{12}$ represents arginine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 263);

(xxiii) an enzyme of sequence SEQ ID NO: 274 wherein $X_1$ represents arginine; $X_2$ represents leucine; $X_3$ represents threonine; $X_4$ represents leucine; $X_5$ represents cysteine; $X_6$ represents leucine; $X_7$ represents threonine; $X_8$ represents threonine; $X_9$ represents serine; $X_{10}$ represents alanine; $X_{11}$ represents histidine; $X_{12}$ represents arginine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 264);

(xxiv) an enzyme of sequence SEQ ID NO: 274 wherein $X_1$ represents arginine; $X_2$ represents leucine; $X_3$ represents threonine; $X_4$ represents arginine; $X_5$ represents cysteine; $X_6$ represents valine; $X_7$ represents alanine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glutamic acid; $X_{16}$ represents valine; $X_{17}$ represents phenylalanine; and $X_{18}$ represents glutamic acid (i.e. an enzyme of amino acid sequence SEQ ID NO: 265);

(xxv) an enzyme of sequence SEQ ID NO: 274 wherein $X_1$ represents arginine; $X_2$ represents leucine; $X_3$ represents threonine; $X_4$ represents arginine; $X_5$ represents cysteine; $X_6$ represents valine; $X_7$ represents glycine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glutamic acid; $X_{16}$ represents valine; $X_{17}$ represents phenylalanine; and $X_{18}$ represents glutamic acid (i.e. an enzyme of amino acid sequence SEQ ID NO: 266);

(xxvi) an enzyme of sequence SEQ ID NO: 274 wherein $X_1$ represents arginine; $X_2$ represents leucine; $X_3$ represents threonine; $X_4$ represents tryptophan; $X_5$ represents cysteine; $X_6$ represents serine; $X_7$ represents asparagine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glutamic acid; $X_{16}$ represents valine; $X_{17}$ represents phenylalanine; and $X_{18}$ represents glutamic acid (i.e. an enzyme of amino acid sequence SEQ ID NO: 267);

(xxvii) an enzyme of sequence SEQ ID NO: 274 wherein $X_1$ represents arginine; $X_2$ represents leucine; $X_3$ represents threonine; $X_4$ represents tryptophan; $X_5$ represents cysteine; $X_6$ represents leucine; $X_7$ represents glycine; $X_8$ represents threonine; $X_9$ represents serine; $X_{10}$ represents alanine; $X_{11}$ represents arginine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 268);

(xxviii) an enzyme of sequence SEQ ID NO: 274 wherein $X_1$ represents arginine; $X_2$ represents leucine; $X_3$ represents threonine; $X_4$ represents arginine; $X_5$ represents cysteine; $X_6$ represents leucine; $X_7$ represents glycine; $X_8$ represents threonine; $X_9$ represents serine; $X_{10}$ represents alanine; $X_{11}$ represents arginine; $X_{12}$ represents glutamine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 269);

(xxix) an enzyme of sequence SEQ ID NO: 274 wherein $X_1$ represents arginine; $X_2$ represents leucine; $X_3$ represents threonine; $X_4$ represents tryptophan; $X_5$ represents cysteine; $X_6$ represents leucine; $X_7$ represents threonine; $X_8$ represents threonine; $X_9$ represents serine; $X_{10}$ represents alanine; $X_{11}$ represents histidine; $X_{12}$ represents arginine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 270);

(xxx) an enzyme of sequence SEQ ID NO: 274 wherein $X_1$ represents arginine; $X_2$ represents leucine; $X_3$ represents threonine; $X_4$ represents arginine; $X_5$ represents cysteine; $X_6$ represents leucine; $X_7$ represents threonine; $X_8$ represents threonine; $X_9$ represents serine; $X_{10}$ represents alanine; $X_{11}$ represents histidine; $X_{12}$ represents arginine; $X_{13}$ represents asparagine; $X_{14}$ represents asparagine; $X_{15}$ represents glutamic acid; $X_{16}$ represents isoleucine; $X_{17}$ represents phenylalanine; and $X_{18}$ represents glutamic acid (i.e. an enzyme of amino acid sequence SEQ ID NO: 271);

(xxxi) an enzyme of sequence SEQ ID NO: 274 wherein $X_1$ represents arginine; $X_2$ represents leucine; $X_3$ represents threonine; $X_4$ represents arginine; $X_5$ represents cysteine; $X_6$ represents valine; $X_7$ represents threonine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glutamic acid; $X_{16}$ represents valine; $X_{17}$ represents phenylalanine; and $X_{18}$ represents glutamic acid (i.e. an enzyme of amino acid sequence SEQ ID NO: 272); and (xxxii) an enzyme of sequence SEQ ID NO: 274 wherein $X_1$ represents arginine; $X_2$ represents leucine; $X_3$ represents threonine; $X_4$ represents tryptophan; $X_5$ represents cysteine; $X_6$ represents serine; $X_7$ represents threonine; $X_8$ represents threonine; $X_9$ represents serine; $X_{10}$ represents alanine; $X_{11}$ represents histidine; $X_{12}$ represents arginine; $X_{13}$ represents aspartic acid; $X_{14}$ represents asparagine; $X_{15}$ represents glutamic acid; $X_{16}$ represents valine; $X_{17}$ represents phenylalanine; and $X_{18}$ represents glutamic acid (i.e. an enzyme of amino acid sequence SEQ ID NO: 273).

3-HP and Derivatives Thereof

3-HP derivatives include, but are not limited to acrylic acid, 1-propanol, propene, acrylyl-CoA, and polypropylene.

Acetyl-CoA and Derivatives Thereof

Acetyl-CoA derivatives include, but are not limited to acetone, 2-propanol, propene, and polypropylene.

Co-Production of 3-HP and Acetyl-CoA, Salts Thereof, and Derivatives Thereof

The combination of the 3-HP pathway with the acetyl-CoA pathway is adopted here to create a redox balanced pathway resulting in high yield. Between 3-HP derivatives, is possible to cite acrylic acid, 1-propanol, propene, and polypropylene. Between acetyl-CoA derivatives, is possible to cite acetone, 2-propanol, propene, and polypropylene.

Looking for a solution for the loss of yield for production of 3-HP and acetyl-CoA derivatives, we identify a novel pathway combination of 3-HP derivative production with acetyl-CoA derivative production in a recombinant yeast. 1-propanol biosynthesis from glucose is highly dependent on the availability of reducing power cofactors for the conversion of malonate semialdehyde into 1-propanol: 4 NAD(P)H cofactors are required to convert 1 molecule of malonate semialdehyde into 1 molecule of 1-propanol. Although the biosynthesis of malonate semialdehyde from glucose generates some NAD(P)H cofactors, there is not enough NAD(P)H being formed though to sustain such malonate semialdehyde conversion into 1-propanol. The remaining NAD(P)H cofactors required for the biosynthesis of 1-propanol itself should be provided burning some glucose under aerobic conditions, but reducing so its overall yield potential. The current invention overcomes such redox unbalance and yield potential restriction by combining the biosynthesis of 1-propanol with the biosynthesis of acetone. As acetone is a highly oxidized molecule, its biosynthesis from glucose is linked to the net production of reducing power NAD(P)H cofactors. So, the co-production of both 1-propanol and acetone is redox balanced under certain carbon flow ratio to the target products, since the NAD(P)H required for 1-propanol biosynthesis would come from both glycolysis and acetone biosynthesis.

Figure 15:
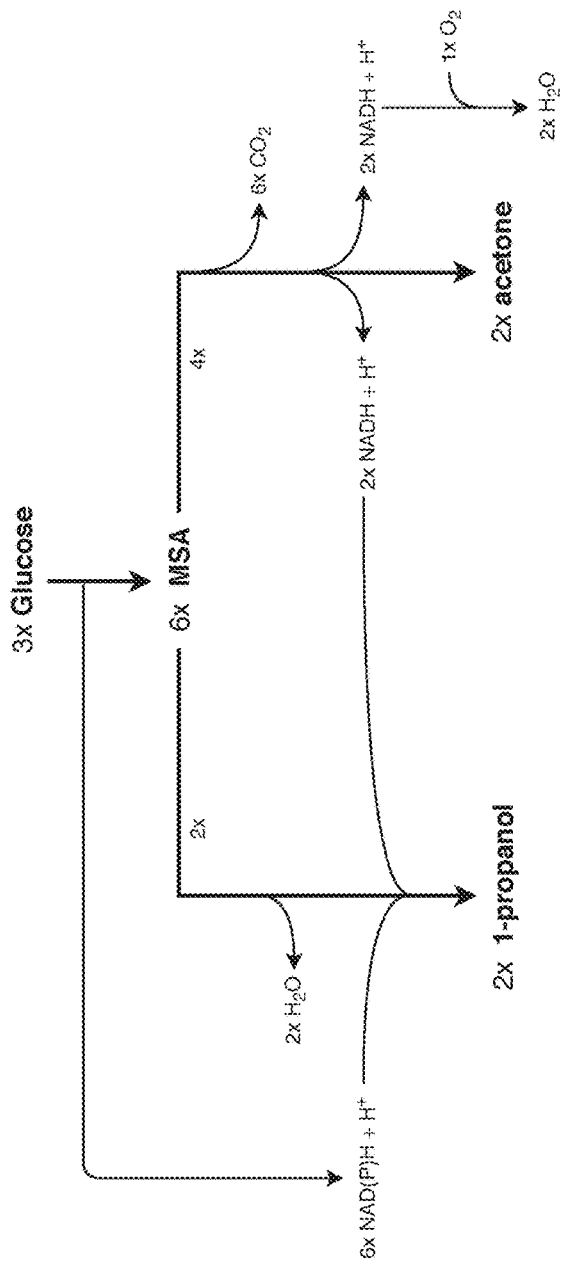
FIG. 15 depicts the stoichiometry of co-production of 1-propanol and acetone in aerobic conditions.
Figure 16:
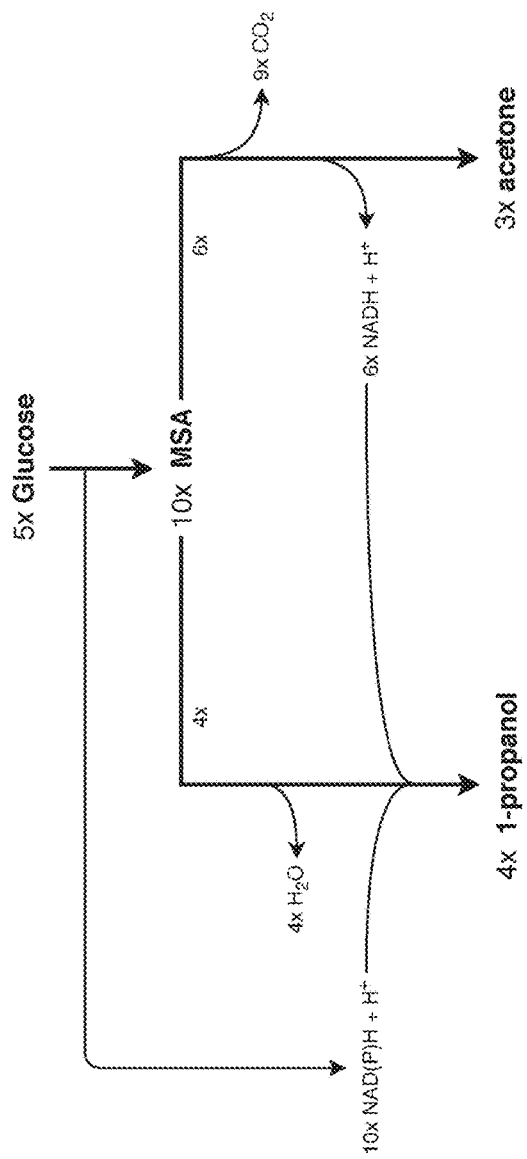
FIG. 16 depicts the stoichiometry of co-production of 1-propanol and acetone in anaerobic conditions.

As described on FIG. 15 and FIG. 16, the co-production of 1-propanol and acetone is redox balanced under both aerobic and anaerobic fermentation conditions, with a yield potential increase under anaerobic condition. The stoichiometry of 1-propanol and acetone co-production pathway under aerobic fermentation condition is: 1 Glucose+0.33 O2→0.67 acetone+0.67 1-propanol+1.33H2O+2 CO2 with a maximum theoretical yield of 0.437 g/g products per glucose. As shown on FIG. 15, 6 molecules of malonate semialdehyde is produced from 3 molecules of glucose, wherein 4 molecules of malonate semialdehyde goes to the acetone biosynthesis and 2 molecules goes to the 1-propanol biosynthesis adjusting the NAD(P)H cofactors net to a neutral redox balance.

Figure 14:
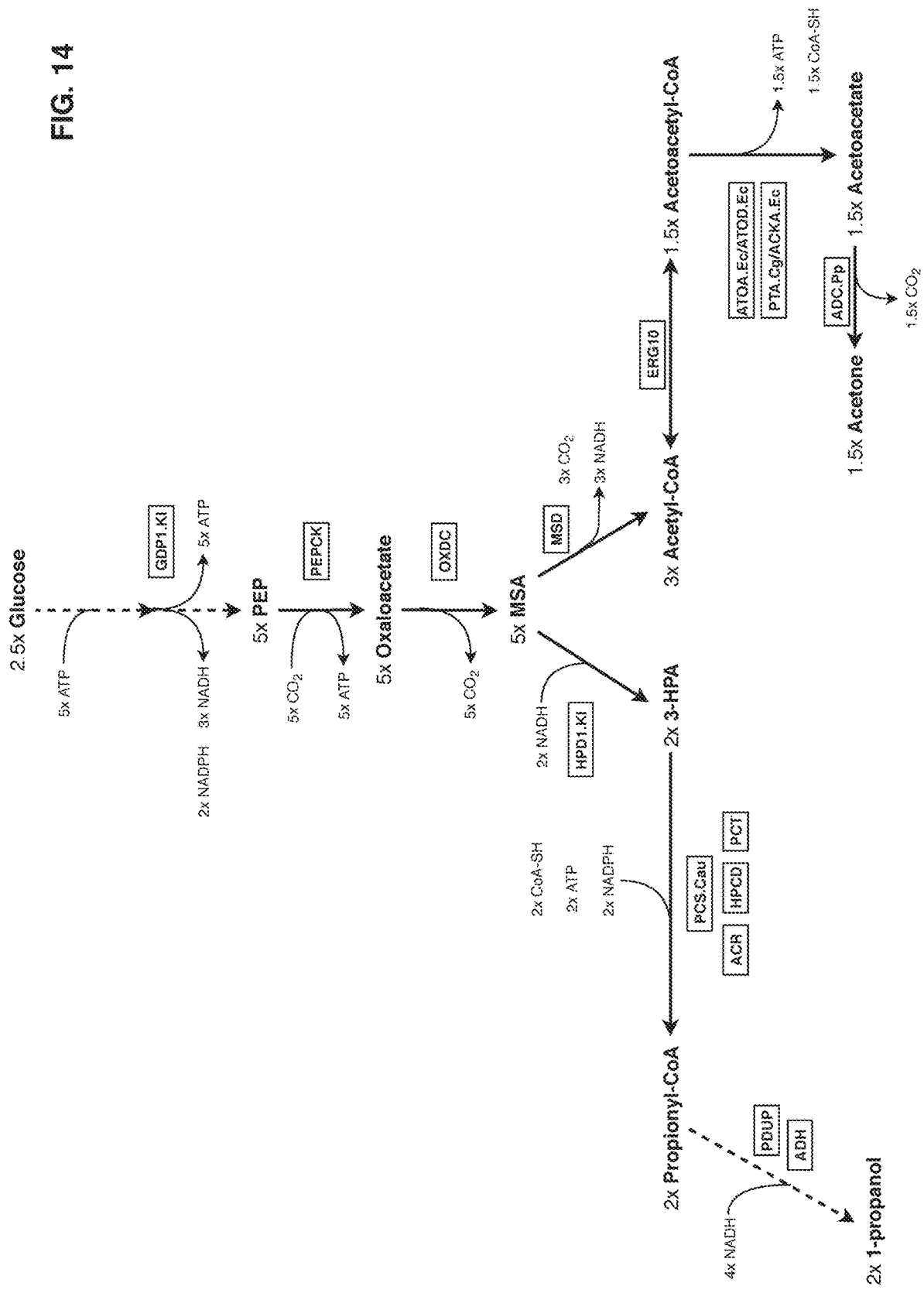
FIG. 14 depicts a co-production pathway of 1-propanol and acetone that shows a neutral redox balance using selected enzymes.

In contrast, the stoichiometry of 1-propanol and acetone co-production pathway under anaerobic fermentation condition is: 1 Glucose→0.6 acetone+0.8 1-propanol+0.8H2O+ 1.8 CO2 with a maximum theoretical yield of 0.46 g/g products per glucose. As shown on FIG. 16, 10 molecules of malonate semialdehyde is produced from 5 molecules of glucose, wherein 6 molecules of malonate semialdehyde goes to acetone biosynthesis and 4 goes to 1-propanol biosynthesis in order to have a neutral redox balance. An example of redox balanced 1-propanol and acetone co-production pathway is shown in the FIG. 14 wherein cofactors NADH and NADPH are perfectly equilibrated: the 6 NADH cofactors generated in the upper glycolysis and acetone biosynthesis are consumed in the 1-propanol biosynthesis, and the 2 NADPH cofactors generated in the upper glycolysis are used in the 1-propanol biosynthesis, considering 2.5 molecules of glucose consumed for the production of 2 molecules of 1-propanol and 1.5 molecules of acetone. This can be achieved by using specific enzymes described and listed in the current invention. More precisely, a glyceraldehyde 3-phosphate dehydrogenase enzyme candidate (GAPDH) from *Kluyveromyces lactis* can be used, which show high activity either with NAD+ and NADP+ (and so generating NADH and NADPH), instead of using the native genes from *Saccharomyces cerevisiae* (TDH1, TDH2 and TDH3), which display a strict requirement for NAD+ (generating NADH only). Besides, malonate semialdehyde dehydrogenase enzyme candidates from *Pseudomonas aeruginosa* or *Candida albicans* can convert malonate semialdehyde into acetyl-CoA displaying a strict requirement for NAD+ as cofactor. A highly active NADH-dependent 3-hydroxypropionic acid dehydrogenase enzyme from *Candida albicans* (encoded by the gene HPD1) can be used to convert malonate semialdehyde into 3-HP. Finally, the conversion of 3-HP into propionyl-CoA shall be done by using NADPH-dependent enzymes, while 1-propanol production from propionyl-CoA can be performed by NADH-dependent dehydrogenase enzymes. This co-production pathway is redox neutral and with a small excess of ATP, resulting in a more efficient and higher yield production of the desired compounds. Furthermore, the balanced pathway has the potential to be performed under anaerobic conditions, which brings several process advantages when compared with an aerobic process with the same yield. Like for example no air needs to be supplied to the production fermenters, so there is a CAPEX reduction with air compressors and an OPEX reduction with the utilities consumed by these equipment. Another significant advantage is that anaerobic fermenters can have larger maximum sizes than aerobic fermenters, mainly because in aerobic fermenters the oxygen transfer from gas to liquid phase gets more difficult as the size of the fermenter increase, limiting its size to a maximum value, so for the same annual production anaerobic process can have a smaller number of larger fermenters than an aerobic process, which at the end represents a smaller CAPEX with fermenters and its accessories for the anaerobic process. Besides that, there is an improvement of yield in anaerobic conditions, where co-production of 1-propanol and acetone leads to a higher total yield of 0.46 g of solvents/g of glucose, assuming these products are produced in a 3:4 ratio (acetone:1-propanol).

Under anaerobic conditions, the proposed pathway, which includes acetyl-CoA generation from malonate semialdehyde, avoids some of the biggest pathway engineering challenges for acetyl-CoA derivative production, which is acetyl-CoA availability in anaerobic conditions.

Furthermore, the new route for acetyl-CoA production is independent of pyruvate, which is distinct from the typical acetyl-CoA production pathways. In addition, the pathway for 3-HP derivatives is also distinct from the typical 3-HP production pathways, being independent of malonyl-CoA.

In some aspects, the recombinant microorganism is capable of producing acetone from malonate semialdehyde via acetyl-CoA. The proposed acetone pathway relies on the conversion of malonate semialdehyde to acetyl-CoA that is independent of pyruvate, and differs from the typical acetyl-CoA production pathways, mitigating the yield loss by pyruvate deviation to the TCA cycle. Also, malonate semialdehyde is produced by the decarboxylation of oxaloacetate or by the β-alanine pathway, which differs from the naturally malonate semialdehyde produced from malonyl-CoA in yeast. The natural production of malonyl-CoA and its salts is in competition with the ethanol biosynthesis, thus rendering difficult the flux derivation to malonate semialdehyde.

In some aspects, the native glyceraldehyde-3-phosphate dehydrogenase of the microbe is replaced by an exogenous version. The native yeast glyceraldehyde-3-phosphate dehydrogenase catalyzes glyceraldehyde-3-phosphate conversion to 1,3-bisphosphoglycerate resulting in the oxidation of an aldehyde with conversion of $NAD^+$ to NADH. Other versions of this enzyme are described in literature where the enzyme activity results in conversion of $NADP^+$ to NADPH. See Martinez et al. (2008. Metabolic Engineering, 10(6): 352-359). Replacement of the native NAD-dependent enzyme with a NADP-dependent enzyme provides a better balanced pathway favoring production of desired compounds. In some aspects, one or more non-native glyceraldehyde-3-phosphate dehydrogenases replace the native enzyme. In some aspects, the glyceraldehyde-3-phosphate dehydrogenase is selected from a fungi, yeast, bacterium, insect, animal, plant, or flagellate. In some aspects, the glyceraldehyde-3-phosphate dehydrogenase that can be used has, but is not restricted to, EC number 1.2.1.12, such as from *Clostridium acetobutylicum* (gapC) or *Kluyveromyces lactis* (gdp1).

The novel combined pathway for 3-HP and acetyl-CoA production has malonate semialdehyde as a common single intermediate. The usual pathway for malonate semialdehyde production has malonyl-CoA as intermediate (Suyama et al., 2017). Otherwise, in the instant pathway, malonate semialdehyde has oxaloacetate as intermediate. See FIG. 1.

The aforementioned issues relating to the traditional pathways of the producing the products, as described above, depress the availability of intermediates and result in enzymes with low activity. As indicated in FIG. 1, the traditional route to malonyl-CoA is from acetyl-CoA, but a considerable portion of the acetyl-CoA is directed towards the TCA cycle. Thus a limited amount of malonyl-CoA is formed (0.01-0.023 nmolmg—1 cell dry weight, which is only 0.5% of the total CoA pool) (Rathnasingh et al., 2012). In addition, malonyl-CoA is an important intermediate in fatty acid metabolism, and it is difficult to redirect this compound into the pathway for the products described herein. Furthermore, the conversion of malonyl-CoA into malonate semialdehyde is performed by a reductase with low activity at 37° C. (maximum activity at 50° C., decrease of 65% at 37° C.) and high $K_m$ value for malonyl-CoA (30 μM) (Rathnasingh et al., 2012). The instant pathway is able to clear these issues by utilizing oxaloacetate as an intermediate for malonate semialdehyde production.

Figure 2:
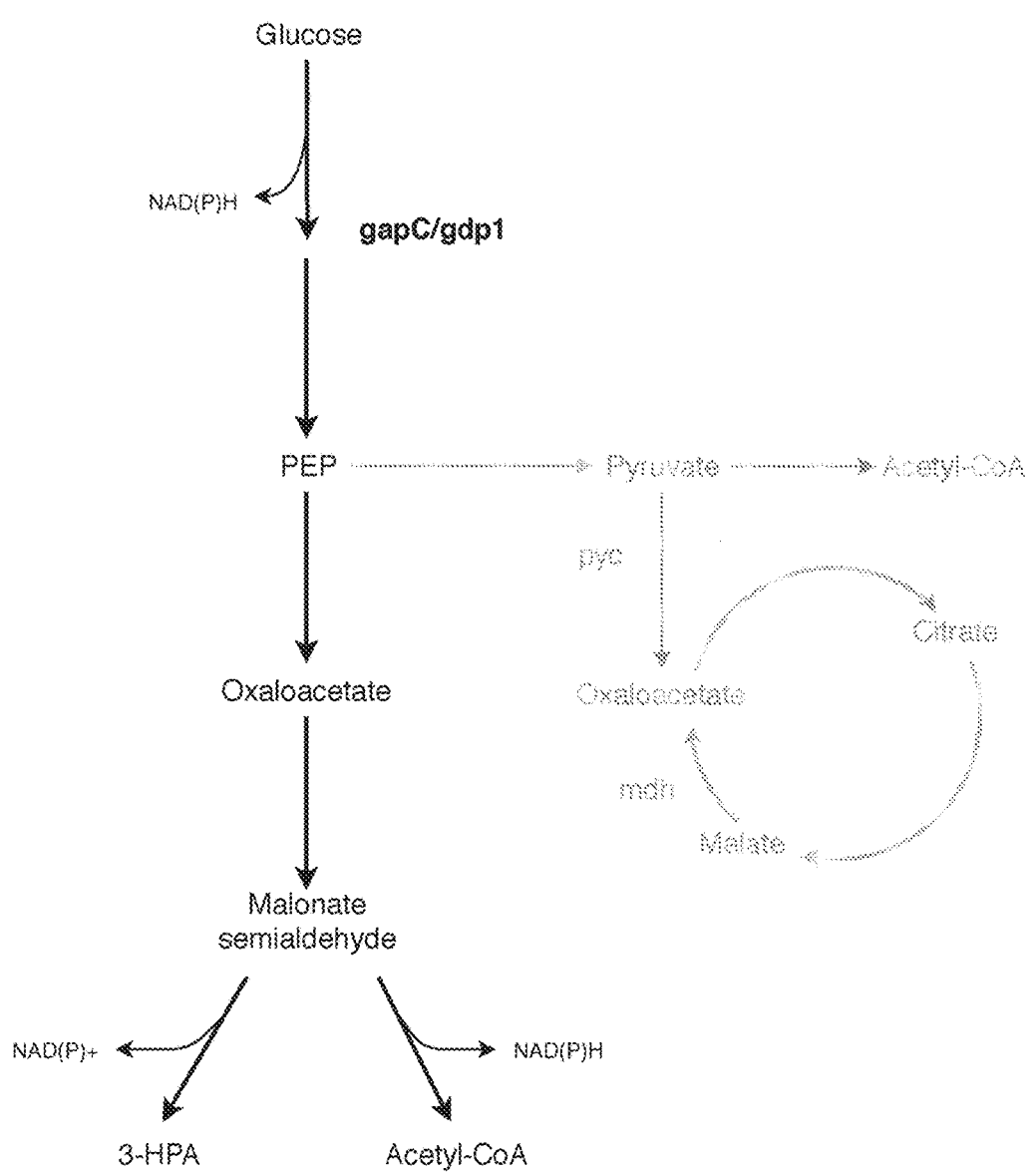
FIG. 2 depicts the two routes for oxaloacetate generation in yeast cells, through pyruvate carboxylase (pyc gene) or malate dehydrogenase (mdh gene) activity.

As depicted in FIG. 2, yeast cells have two routes for oxaloacetate generation; through pyruvate carboxylase (pyc gene) or malate dehydrogenase (mdh gene) activity. As the pyruvate carboxylase is a biotin-dependent enzyme with low catalytic activity, its catalytic turnover is not sufficient to provide high levels of oxaloacetate. Furthermore, oxaloacetate generated by the TCA cycle was found not to be useful to fuel high carbon fluxes. The instant pathway is able to clear these issues by producing oxaloacetate from phosphoenol pyruvate (PEP) instead of from pyruvate. To achieve a high concentration of oxaloacetate, the bacterial enzyme phosphoenol pyruvate carboxylase and/or phosphoenol pyruvate carboxykinase is utilized in the recombinant microbe. In some aspects, the microbe of interest is modified by introduction of one or more phosphoenol pyruvate carboxylase (ppc) and/or one or more phosphoenol pyruvate carboxykinase (pepck). In some aspects, the one or more phosphoenol pyruvate carboxylase (ppc) and/or one or more phosphoenol pyruvate carboxykinase (pepck) are selected from a fungi, yeast, bacterium, insect, animal, plant, or flagellate. In some aspects, the one or more phosphoenol pyruvate carboxylase (ppc) and/or one or more phosphoenol pyruvate carboxykinase (pepck) are from E. coli.

Figure 3:
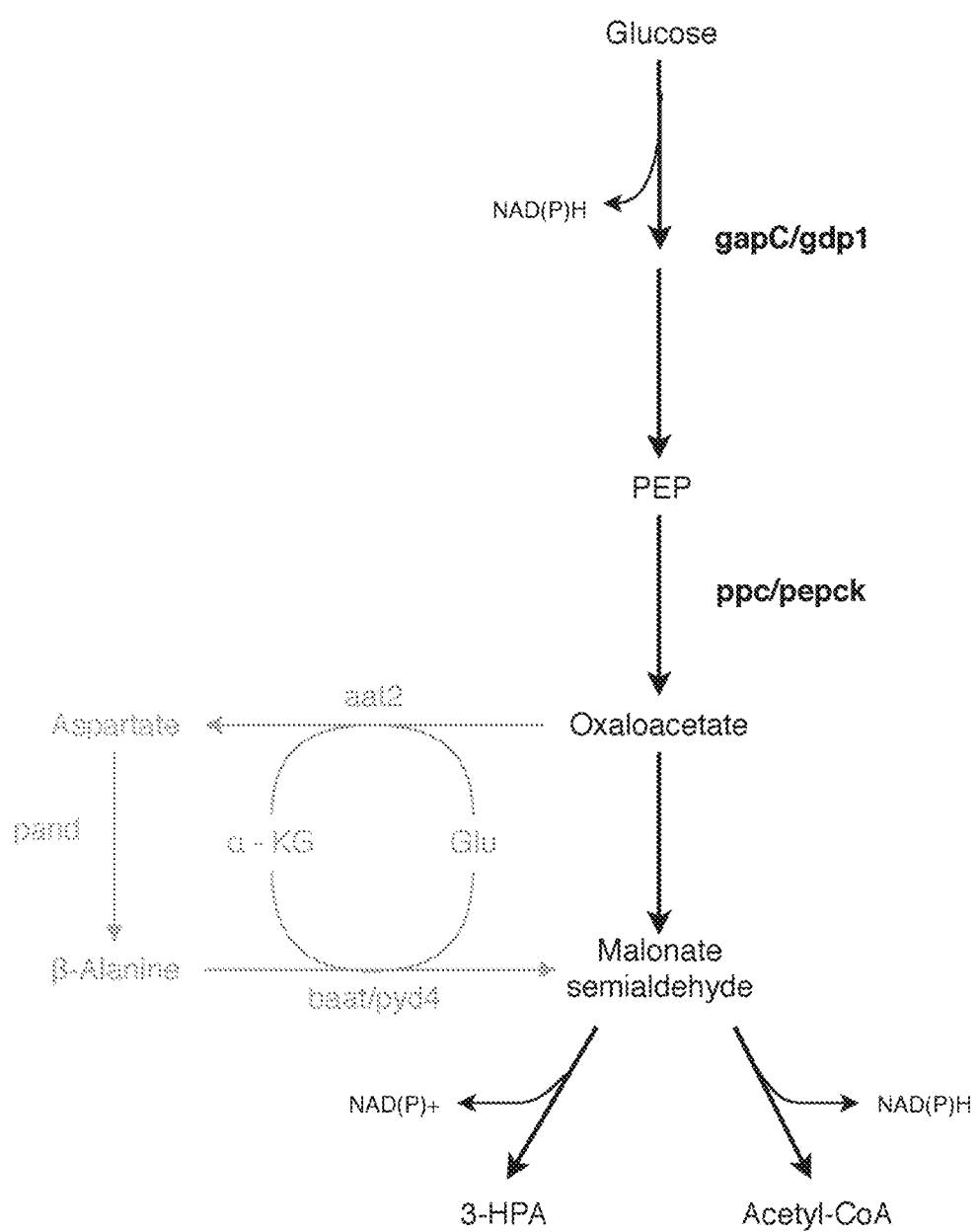
FIG. 3 depicts the pathways from oxaloacetate to malonate semialdehyde. The typical pathway utilizes aspartate and beta-alanine as intermediates, and the new route utilizes a decarboxylase (oxdc) to directly produce malonate semialdehyde from oxaloacetate.

Once oxaloacetate is formed, the molecule can be converted to malonate semialdehyde directly from oxaloacetate or through the intermediary formation of β-alanine, as depicted in FIG. 3.

In some aspects, the malonate semialdehyde directed production from oxaloacetate is performed by a decarboxylase, such as an alpha-ketoisovalerate decarboxylase, benzoylformate decarboxylase, or a 2-oxoglutarate decarboxylase. In some aspects, the recombinant microbe comprises one or more alpha-ketoisovalerate decarboxylase (kdca), benzoylformate decarboxylase (mdlc), and/or 2-oxoglutarate decarboxylase (oxdc). In some aspects, the one or more alpha-ketoisovalerate decarboxylase, benzoylformate decarboxylase, and/or 2-oxoglutarate decarboxylase are selected from a fungi, yeast, bacterium, insect, animal, plant, or flagellate. In some aspects, the alpha-ketoisovalerate decarboxylase is from *Lactococcus lactis*. In some aspects, the benzoylformate decarboxylase is from *Pseudomonas putida*. In some aspects, the 2-oxoglutarate decarboxylase is from *Oenococcus oeni* or *Euglena gracilis*.

The malonate semialdehyde production through β-alanine involved oxaloacetate transamination to aspartate by an aspartate amino transferase (aat2), aspartate conversion to β-alanine by an aspartate decarboxylase (pand) and β-alanine conversion to malonate semialdehyde by a β-alanine pyruvate amino transferase (baat) and/or β-alanine transaminase (pyd4). In some aspects, the recombinant microbe comprises one or more aspartate amino transferase, aspartate decarboxylase, β-alanine pyruvate amino transferase, and/or β-alanine transaminase. In some aspects, the aspartate amino transferase, aspartate decarboxylase, β-alanine pyruvate amino transferase, and/or β-alanine transaminase are selected from a fungi, yeast, bacterium, insect, animal, plant, or flagellate. In some aspects, the aspartate amino transferase is from *S. cerevisiae*. In some aspects, the aspartate decarboxylase is from *Tribolium castaneum*. In some aspects, the aspartate decarboxylase is from *Corynebacterium glutamicum*. In some aspects, the beta-alanine pyruvate amino transferase is from *Bacillus cereus*. In some aspects, the beta-alanine transaminase is from *Lachancea kluyveri* (Table 16).

Malonate semialdehyde can be converted to 3-HP by a 3-hydroxypropionic acid dehydrogenase. In some aspects, the recombinant microbe comprises one or more 3-hydroxypropionic acid dehydrogenases that can be, but are not restricted to, enzymes with EC number 1.1.1.381 such as those listed in Table 1. In some aspects, the 3-hydroxypropionic acid dehydrogenase is from a fungi, yeast, bacterium, insect, animal, plant, or flagellate. In some aspects, the 3-hydroxypropionic acid dehydrogenase (mcr-1) is from *Chloroflexus aurantiacus*. In some aspects, the 3-hydroxypropionic acid dehydrogenase (adh) is from *Arthrobacter enclensis*. In some aspects, the 3-hydroxypropionic acid dehydrogenase (mmsb) is from *Bacillus cereus*. In some aspects, the 3-hydroxypropionic acid dehydrogenase (ydfg-0) is from *E. coli*. In some aspects, the 3-hydroxypropionic acid dehydrogenase (YDFI) is from *Saccharomyces cerevisiae*. In some aspects, the 3-hydroxypropionic acid dehydrogenase is preferentially (HPD1) from *Candida albicans*,

TABLE 1

Enzymes candidates for conversion to 3-HP from malonate semialdehyce.

| Enzymes | Origin | UniProt number | EC Number | SEQ ID NO |
|---|---|---|---|---|
| MCR-Nterm.Cau | *Chloroflexus aurantiacus* | YP_001636209.1 (NCBI ref seq) | — | 105 |
| ADH.Ae | *Arthrobacter enclensis* | WP_058267460.1 (NCBI ref seq) | — | 106 |
| MMSB.Bce | *Bacillus cereus* | NP_833760.1 (NCBI ref seq) | — | 107 |
| YDFG-0.Ec | *Escherichia coli* | BAA15241.1 (seq nucleotideo) | — | 108 |
| YMR226C (YDF1) | *Saccharomyces cerevisiae* | Q05016 | 1.1.1.381 | 109 |
| HPD1 | *Candida albicans* | A0A1D8PQ07 | | 110 |

Malonate semialdehyde can be converted to acetyl-CoA by a one-step reaction using a malonate semialdehyde dehydrogenase or by a two-step reaction through malonyl-CoA including a malonyl-CoA synthetase or a malonyl-CoA reductase and a malonyl-CoA decarboxylase. In some aspects, a plurality or majority of the malonate semialdehyde is produced from oxaloacetate. In some aspects, a plurality or majority of the malonate semialdehyde is not produced from malonyl-CoA. The enzymes candidates to this step can be, but are not restricted to, enzymes with EC number 1.2.1.18/1.2.1.27 such as those listed in Table 2.

TABLE 2

Enzymes candidates for conversion to acetyl-CoA from malonate semialdehyde

| Genes | Origin | UniProt number | EC Number | SEQ ID NO |
|---|---|---|---|---|
| MSD.Pa | *Pseudomonas aeruginosa* | Q9I702 | 1.2.1.18 | 111 |
| MSD.Cal | *Candida albicans* | A0A1D8PM94 | 1.2.1.18 | 112 |
| iolA | *Listeria monocytogenes* | Q8Y9Y4 | 1.2.1.27 | 113 |
| iolA | *Bacillus subtilis* | A7BJC4 | 1.2.1.27 | 114 |
| iolA | *Cupriavidus necator* | F8GGV48 | 1.2.1.18 | 115 |
| mmsA | *Bacillus cereus* | A0A2C1ZL92 | 1.2.1.27 | 116 |
| dddC | *Halomonas* sp. HTNK1 | C8YX90 | — | 117 |
| iolA | *Lactobacillus casei* | A5YBJ3 | 1.2.1.27 | 118 |

Alternatively, another option to produce acetyl-CoA is a two-step pathway from oxaloacetate and through malonyl-CoA including a 2-keto acid decarboxylase and a malonyl-CoA decarboxylase. See FIG. 4 None of the routes presented utilizes pyruvate as an intermediate, being different from usual pathways and an interesting solution for acetyl-CoA generation in anaerobic conditions, where the availability of cytosolic acetyl-CoA is compromised.

In some aspects, the recombinant microbe comprises one or more malonate semialdehyde dehydrogenase, malonyl- CoA synthetase, malonyl-CoA reductase, malonyl-CoA decarboxylase, and/or 2-keto acid decarboxylase. In some aspects, one or more malonate semialdehyde dehydrogenase, malonyl-CoA synthetase, malonyl-CoA reductase, malonyl-CoA decarboxylase, and/or 2-keto acid decarboxylase are from a fungi, yeast, bacterium, insect, animal, plant, or flagellate. In some aspects, the malonate semialdehyde dehydrogenase that can be used has, but is not restricted to, EC number 1.2.1.18/1.2.1.27 such as those listed in Table 2, preferentially MSD from *Candida albicans* or *Pseudomonas aeruginosa*.

In some aspects, the malonyl-CoA synthetase (MatB) is from *Rhizobium trifolii*. In some aspects, the malonyl-CoA synthetase (AAE13) is from *Arabidopsis thaliana*. In some aspects, the malonyl-CoA synthetase (ACSF3B) is from *Homo sapiens*. In some aspects, the malonyl-CoA reductase (mcr) is from *Chloroflexus aurantiacus*.

In some aspects, the malonyl-CoA decarboxylase (MatA) is from *Rhizobium trifolii*. In some aspects, the malonyl-CoA decarboxylase (MLYCD) is from *Homo sapiens*. In some aspects, the 2-keto acid decarboxylase (kivd) is from *Lactococcus lactis*. In some aspects, the 2-keto acid decarboxylase (KdcA) is from *Lactococcus lactis*. In some aspects, the 2-keto acid decarboxylase (ARO10) is from *Saccharomyces cerevisiae*.

Figure 5:
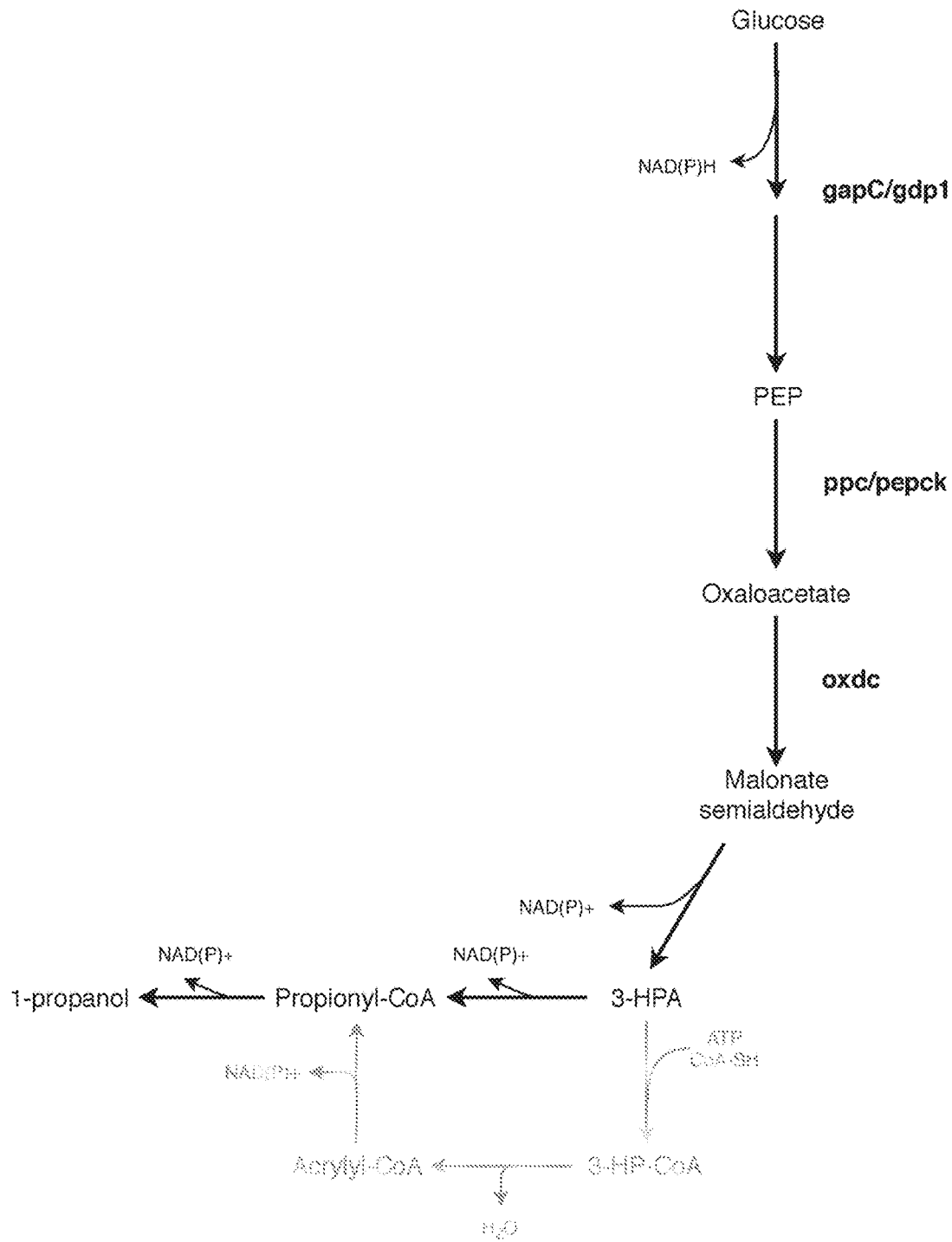
FIG. 5 depicts the pathways for production of 1-propanol from 3-HP by a four-step process and by a 2-step process.

From 3-HP, several compound can be produced, including 1-propanol as an example. For 1-propanol production, 3-HP needs to be converted to propionyl-CoA by a single-step reaction performed by a propionyl-CoA synthase or by multi-step reactions involving a 3-hydroxypropionyl-CoA synthetase, 3-hydroxypropionyl-CoA dehydratase, and acrylyl-CoA reductase. Then propionyl-CoA needs to be converted to 1-propanol by a bifunctional alcohol/aldehyde dehydrogenase (EC number 1.1.1.1/1.2.1.4/1.2.1.5 such as listed in Table 7) or by an aldehyde dehydrogenase (acetylating) (table 8) and an alcohol dehydrogenase (EC number 1.2.1.10/1.2.1.87 such as listed in Table 9). As depicted in FIG. 5, 1-propanol production has a high demand for NAD(P)H, with there being no balanced pathway.

In some aspects, the recombinant microbe comprises one or more propionyl-CoA synthase, 3-hydroxypropionyl-CoA synthetase, 3-hydroxypropionyl-CoA dehydratase, acrylyl-CoA reductase, alcohol/aldehyde dehydrogenase, alcohol dehydrogenase and/or aldehyde dehydrogenase from a fungi, yeast, bacterium, insect, animal, plant, or flagellate. In some aspects, the one or more propionyl-CoA synthase that can be used are enzymes with, but not limited to, EC number 6.2.1.17/6.2.1.36 such as those listed in Table 3. In some aspects, the 3-hydroxypropionyl-CoA synthetase/transferase that can be used, but is not restricted to, is an enzyme with EC number 2.8.3.1/6.2.1.17/6.2.1.36 such as those listed in Table 4. In some aspects, the 3-hydroxypropionyl-CoA dehydratase that can be used, but is not restricted to, is an enzyme with EC number 4.2.1.116/4.2.1.55/4.2.1.150/4.2.1.17 such as those listed in Table 5. In some aspects, the acrylyl-CoA reductase is from, but not limited to, the organisms and/or correspond to the genes indicated in Table 6. In some aspects, the alcohol/aldehyde dehydrogenase, that can be used, but is not restricted to, is an enzyme with EC number 1.1.1.1/1.2.1.4/1.2.1.5 such as listed in Table 7. In some aspects, other candidates to convert propionyl-CoA to propanol are used (EC number: 1.2.1.10/1.2.1.87 such as listed in Table 8, EC number 2.3.1.8/2.7.2.1 such as listed in Table 9 and EC number 2.3.1.8/2.7.2.1 such as listed in Table 10).

TABLE 47

Enzymes candidates for the conversion of oxaloacetate to acetyl-CoA trough malonyl-CoA

| Genes | Origin | Uniprot number | EC number | SEQ ID NO |
|---|---|---|---|---|
| AAE13 | *Arabidopsis thaliana* | Q8H151 | 6.2.1.- | 276 |
| matB | *Rhizobium trifolii* | — | — | — |
| ACSF3 | *Homo sapiens* | Q4G176 | 6.2.1.- | 277 |
| mcr | *Chloroflexus aurantiacus* | Q6QQP7 | 1.1.1.298 | 278 |
| mata | *Rhizobium trifolii* | — | — | — |
| MLYCD | *Homo sapiens* | O95822 | 4.1.1.9 | 279 |
| kivD | *Lactococcus lactis* | D2BR82 | — | 280 |
| kdcA | *Lactococcus lactis* | Q6QBS4 | — | 281 |
| ARO10 | *Saccharomyces cerevisiae* | Q06408 | — | 282 |

TABLE 3

Enzymes candidates for trifunctional propionyl-CoA synthase.

| Genes | Origin | Uniprot number | EC number | SEQ ID NO |
|---|---|---|---|---|
| PCS.Cau | *Chloroflexus aurantiacus* | Q8VRG6 | 6.2.1.17 | 119 |
| PCS.Cag | *Chloroflexus aggregans* | B8G4K4 | 6.2.1.17 | 120 |
| PCS.Rca | *Roseiflexus castenholzii* | WP_012121416.1 (genebank) | 6.2.1.17 | 121 |
| PCS.No | *Natronococcus occultus* | WP_015322855.1 (NCBI ref Seq) | 6.2.1.17 | 122 |
| PCS.Hj | *Halioglobus japonicus* | — | 6.2.1.17 | — |
| NAP1_02725 | *Erythrobacter* sp NAP1 | A3WE14 | 6.2.1.36 4.2.1.116 1.3.1.84 | 123 |
| AP017312.1 | *Aneurinibacillus soli* | | | — |
| CP0022600.1 | *Porphyrobacter HT-58-2* | | | — |
| CP017057.1 | *Erythrobacter litoralis* | | | — |
| CP020083.1 | *Blasromonas fulva* | | | — |
| CP003929.1 | *Natronococcus occultus* | | | — |
| CP007793.1 | *Azospirillum brasilense* | | | — |
| CP019450.1 | *Halioglobus japonicus* | | | — |

TABLE 4

Enzymes candidates for conversion to 3-hydroxypropionyl-CoA from 3-HP (3-hydroxypropionyl-CoA synthetase/CoA transferase).

| Genes | Organism | Uniprot number | EC number | SEQ ID NO |
|---|---|---|---|---|
| PCT-0.Cne (pct) | *Cupriavidus necator* | Q0K874 | 2.8.3.1 | 124 |
| PCT-0.Cp (pct) | *Clostridium propionicum* | Q9L3F7 | 2.8.3.1 | 125 |
| PCT or YdiF | *Megasphaera elsdenii* | G0VND6 | 2.8.3.1 | 126 |
| PrpE | *Salmonella enterica* | P55912 | 6.2.1.17 | 127 |
| Nmar_1309 | *Nitrosopumilus maritimus* | A9A2G6 | — | 128 |
| Msed_1456 | *Metallosphaera sedula* | A4YGR1 | 6.2.1.36 | 129 |
| PrpE | *Escherichia coli* | P77495 | 6.2.1.17 | 130 |
| YdiF | *Cupriavidus necator* | Q0K874 | 2.8.3.1 | 131 |

TABLE 4-continued

Enzymes candidates for conversion to 3-hydroxypropionyl-CoA from 3-HP (3-hydroxypropionyl-CoA synthetase/CoA transferase).

| Genes | Organism | Uniprot number | EC number | SEQ ID NO |
|---|---|---|---|---|
| STK_07830 | Sulfolobus tokodaii | Q973W5 | 6.2.1.36 | 132 |

TABLE 5

Enzymes candidates for conversion to acrylyl-CoA from 3-Hydroxypropionyl-CoA (3-hydroxypropionyl-coA dehydratase/enoyl-CoA hydratase)

| Genes | Organism | Uniprot number | EC number | SEQ ID NO |
|---|---|---|---|---|
| HPCD.Mse | Metallosphaera sedula | A4YI89 | 4.2.E116 | 133 |
| HPDC.Bsp | Bacillus sp. | A0A1B9ACR9 | — | 134 |
| HPCD.Sac | Sporanaerobacter acetigenes | A0A1M5Y529 | — | 135 |
| ENCD.Rp | Ruegeria pomeroyi | Q5LMB7 | — | 136 |
| 3HPCD | Sulfolobus tokodaii | F9VNG3 | 4.2.1.116 | 137 |
| Nmar_1308 | Nitrosopumilus maritimus | A9A2G5 | 4.2.1.116 | 138 |
| Hpcd | Chloroflexus aurantiacus | — | 4.2.1.116 | — |
| crt | Clostridium acetobutylicum | P52046 | 4.2.1.55/ 4.2.1.150 | 139 |
| 3-hydrobutyryl-coa dehydratase | Clostridium pasteuranum | L7EP14 | 4.2.1.55 | 140 |
| crt | Clostridium pasteuranum | P81357 | 4.2.1.150 | 141 |
| MELS_1449 | Megasphaera elsdenii | G0VQE2 | 4.2.1.55 | 142 |
| Aflv_0566 | Anoxybacillus flavithermus | B7GGZ2 | 4.2.1.17 | 143 |

TABLE 6

Enzymes candidates for conversion to Propionyl-CoA from Acrylyl-CoA (acrylyl-CoA reductase).

| Genes | Organism | Uniprot number | EC number | SEQ ID NO |
|---|---|---|---|---|
| ACR-0.Rp | Ruegeria pomeroyi | Q5LS56 | 1.3.1.84 | 144 |
| ACR-0.Ec | Escherichia coli | P26646 | 1.3.1.84 | 145 |
| ACR-0.Rs | Rhodobacter sphaeroides | Q3J6K9 | 1.3.1.84 | 146 |

TABLE 6-continued

Enzymes candidates for conversion to Propionyl-CoA from Acrylyl-CoA (acrylyl-CoA reductase).

| Genes | Organism | Uniprot number | EC number | SEQ ID NO |
|---|---|---|---|---|
| acuI | Ruegeria pomeroyi | Q5LS56 | 1.3.1.84 | 147 |
| acuI | Rhodobacter sphaeroids | Q3J6K9 | 1.3.1.84 | 148 |
| β-ETF, α-ETF and Propionyl-coA dehydrogenase | Clostridium propionicum | G3KIM6, G3KIM7 and G3KIM8 | 1.3.1.95 | 149 |
| acuI | Alcaligenes faecalis | A0A3G6HCN9 | 1.3.1.95 | 150 |
| ACR | Sulfurisphaera tokodaii | Q975C8 | 1.3.1.84 | 151 |
| AcuI | Escherichia coli | P26646 | 1.3.1.84 | 152 |
| Acr | Metallosphaera sedula | A4YGN2 | 1.3.1.84 | 153 |
| Nmar_1565 | Nitrosopumilus maritimus | A9A5Y3 | — | 154 |

TABLE 7

Enzymes candidates for conversion to Propanol from Propionyl-CoA (alcohol/aldehyde dehydrogenase)

| Genes | Origin | UniProt number | EC number | SEQ ID NO |
|---|---|---|---|---|
| ADHE.Ca | Clostridium acetobutylicum | Q9ANR5 | — | 155 |
| ADHE.Cbe | Clostridium beijerinckii | A0A1S8PSK3 | — | 156 |
| ADHE.St | Salmonella typhimurium | P74880 | — | 157 |
| ADHE.Car | Clostridium arbusti | WP_010241373.1 (NCBI Ref Seq) | — | 158 |
| adhE | Escherichia coli | P0A9Q7 | 1.1.1.1 | 159 |
| adhP | Escherichia coli | P39451 | 1.1.1.1 | 160 |
| bdhB | Clostridium acetobutylicum | Q04945 | 1.1.1.1 | 161 |
| ADH2 | Saccharomyces cerevisiae | P00331 | 1.1.1.1 | 162 |
| adhE | Clostridium roseum | — | — | — |
| adhA | Thermoanaerobacterium saccharolyticum | I3VX46 | — | 163 |
| ald6 | Saccharomyces cerevisiae | P54115 | 1.2.1.4 | 164 |
| aldh3A1 | Homo sapiens | P30838 | 1.2.1.5 | 165 |

TABLE 8

Enzymes candidates for conversion of propionyl-CoA to propionaldehyde (aldehyde dehydrogenase (acetylating))

| Genes | Origin | UniProt number | EC number | SEQ ID NO |
|---|---|---|---|---|
| MHPF.Ec | Escherichia coli | WP_097337838.1 (NCBI ref seq) | 1.2.1.10 | 166 |
| MHPF.Ppu | Pseudomonas putida | YP_003617188.1 (NCBI ref seq) | 1.2.1.10 | 167 |
| MHPF.Pse | Pseudomonas sp. | CRM99844.1 (NCBI ref Seq) | 1.2.1.10 | 168 |
| MHPF.Pf | Pseudomonas fluorescens | BAA09693.1 (gene Bank) | 1.2.1.10 | 169 |
| MHPF.Px | Paraburkholderia xenovorans | Q79AF6 | 1.2.1.10 | 170 |
| PDUP.Sen | Salmonella enterica | AAD39015.1 (H9L4I6) | — | 171 |
| PDUP1.Lmo | listeria monocytogenes | NP_464690.1 (Q8Y7V4) | — | 172 |

TABLE 8-continued

Enzymes candidates for conversion of propionyl-CoA to propionaldehyde (aldehyde dehydrogenase (acetylating))

| Genes | Origin | UniProt number | EC number | SEQ ID NO |
|---|---|---|---|---|
| PDUP2.Lmo | listeria monocytogenes | A0A0E0UUX4 | — | 173 |
| PDUP.Kp | Klebsiella pneumoniae | YP_001336844.1 | — | 174 |
| aldH | Acinetobacter sp. | A5JT11 | 1.2.1.10 | 175 |
| Ald | Clostridium beijerinckii | Q9X681 | 1.2.1.10 | 176 |
| Cphy1178 | Clostridium phytofermentans | A9KN57 | — | 177 |
| tesF | Comamonas testosteroni | Q83VZ4 | 1.2.1.10 | 178 |
| BN476_01309 | Eubacterium hallii | R6G856 | — | 179 |
| PduP | Lactobacillus collinoides | Q845A7 | — | 180 |
| EutE | Lactobacillus reuteri | A0A1B7LQN5 | — | 181 |
| HsaG | Mycobacterium tuberculosis | A0A2I7WCV7 | 1.2.1.10 | 182 |
| MhpF | Mycobacterium tuberculosis | P9WQH3 | 1.2.1.10 | 183 |
| bphJ | Paraburkholderia xenovorans | Q79AF6 | 1.2.1.10 1.2.1.87 | 184 |
| SAMN04244550_00489 | Rhodobacter capsulatus | A0A1G7D6K3 | — | 185 |
| hsaG | Rhodococcus jostii | Q0S816 | 1.2.1.10 | 186 |
| RPC_1174 | Rhodopseudomonas palustris | Q21A49 | — | 187 |
| TTHB247 | Thermus thermophilus | Q53WH9 | 1.2.1.10 1.2.1.87 | 188 |

TABLE 9

Enzymes candidates for conversion to propanol from propionaldehyde

| Genes | Origin | UniProt number | EC number | SEQ ID NO |
|---|---|---|---|---|
| alrA | Acinetobacter sp | Q9F1R1 | 1.1.1.2 | 189 |
| Aldehyde reductase | Acinetobacter sp. | Q9F1Q8 | 1.1.1.2 | 190 |
| bdhI | Clostridium acetobutylicum | Q04944 | 1.1.1.- | 191 |
| bdhII | Clostridium acetobutylicum | Q04945 | 1.1.1.- | 192 |
| adhA | Corynebacterium glutamicum | A0A169S5A7 Q8NLX9 | 1.1.1.1 | 193 194 |
| yqhD | Escherichia coli | Q46856 | 1.1.1.2 | 195 |
| yjgB | Escherichia coli | P27250 | 1.1.1.2 | 196 |
| adhP | Escherichia coli | P39451 | 1.1.1.1 | 197 |
| PduQ | Propionibacterium freudenreichii | A0A2C8A2U1 | — | 198 |
| ADH1 | Saccharomyces cerevisiae | P00330 | 1.1.1.1 | 199 |
| ADH2 | Saccharomyces cerevisiae | P00331 | 1.1.1.1 | 200 |
| ADH4 | Saccharomyces cerevisiae | P10127 | 1.1.1.1 | 201 |
| ADH6 | Saccharomyces cerevisiae | Q04894 | 1.1.1.2 | 202 |
| PduQ (adhE_2) | Salmonella enterica | H9L4H8 | — | 203 |
| Adh | Sulfolobus tokodaii | Q96XE0 | 1.1.1.1 | 204 |
| adhA | Synechocystis sp | P74721 | — | 205 |
| adhA | Zymomonas mobilis | P20368 | 1.1.1.1 | 206 |

TABLE 10

Enzymes candidates for conversion to propionaldehyde from propionyl-CoA

| Genes | Origin | UniProt number | EC number | SEQ ID NO |
|---|---|---|---|---|
| PTA.Cg | Corynebacterium glutamicum | WP_011015350 (NCBI ref seq) | 2.3.1.8 | 207 |
| ACKA.Cg | Corynebacterium glutamicum | P77845 | 2.7.2.1 | 208 |

Figure 6:
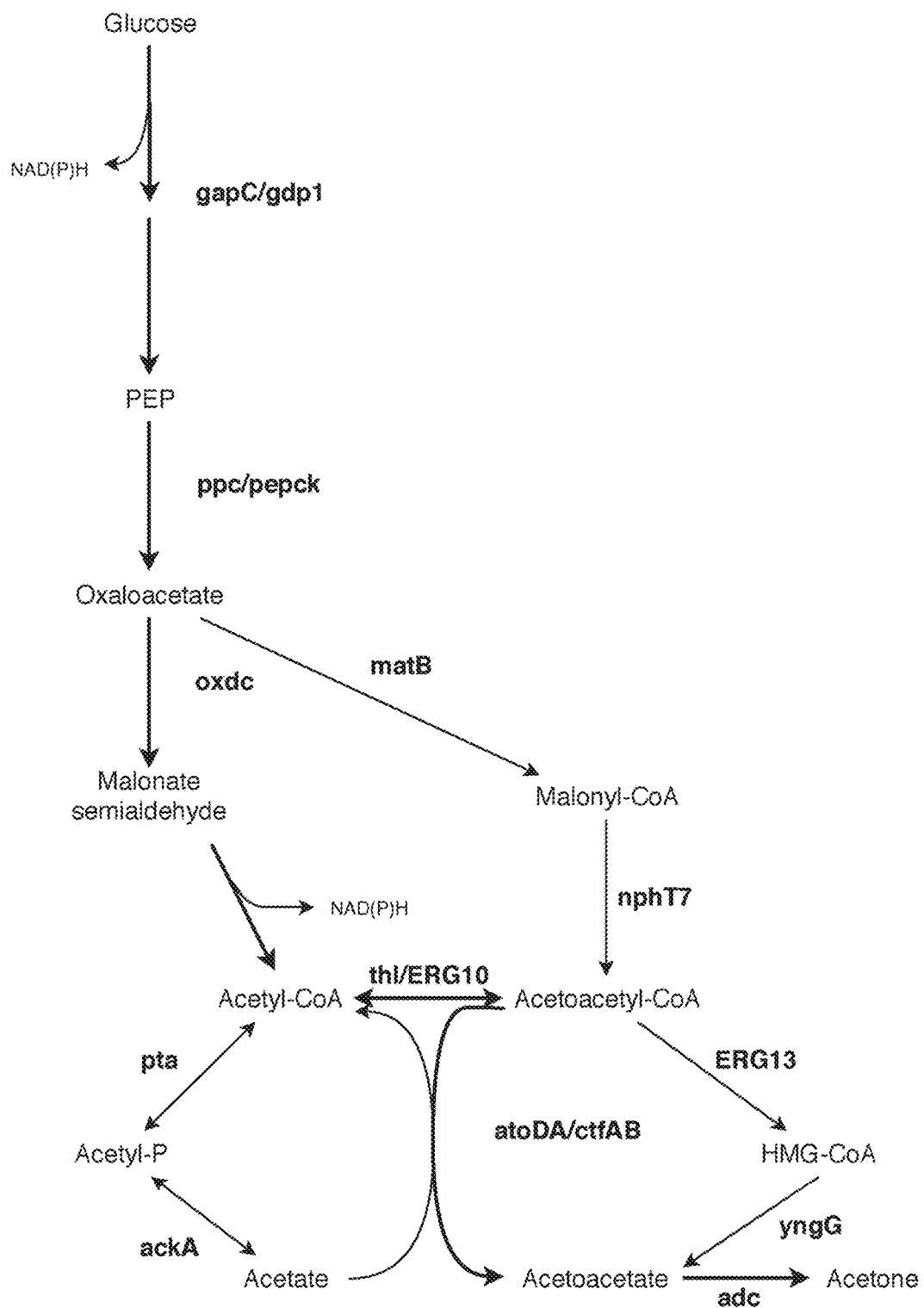
FIG. 6 the pathways to acetone production from glucose, and the excess of NAD(P)H produced in the pathways.

From acetyl-CoA, several compound can be produced, being possible to cite acetone as an example. For acetone production, acetyl-CoA needs to be converted to acetoacetyl-CoA by a thiolase or an acetyl-CoA acetyltransferase. Alternatively, acetoacetyl-CoA can be formed through malonyl-CoA by acetoacetyl-CoA synthase. Once acetoacetyl-CoA is formed, its conversion to acetoacetate can be done by an acetoacetyl-CoA transferase or through HMG-CoA by hydroxymethylglutaryl-CoA synthase and hydroxymethylglutaryl-CoA lyase. Acetoacetate conversion to acetone is done by an acetoacetate decarboxylase. As depicted in FIG. 6, acetone production has an excess of NAD(P)H, being also a no balanced pathway.

In some aspects, the recombinant microbe comprises one or more thiolase, acetyl-CoA acetyltransferase, acetoacetyl CoA synthase, acetoacetyl-CoA transferase, hydroxymethylglutaryl-CoA synthase, hydroxymethylglutaryl-CoA lyase, and/or acetoacetate decarboxylase from a fungi, yeast, bacterium, insect, animal, plant, or flagellate. In some aspects, the one or more thiolase or acetyl-CoA acetyltransferase that can be used has, but is not restricted to, EC number 2.3.1.9 such as those listed in Table 11 and acetoacetyl-CoA transferase that can be used has, but is not restricted to, EC number 2.8.3.8/2.8.3.9 such as those listed in Table 12, hydroxymethylglutaryl-CoA synthase, hydroxymethylglutaryl-CoA lyase, and/or acetoacetate decarboxylase that can be used has, but is not restricted to, an enzyme with EC number 4.1.1.4 such as those listed in Table 13.

TABLE 11

Enzymes candidates for conversion to acetoacetyl-CoA from acetyl-CoA (acetyltransferase)

| Genes | Origin | UniProt number | EC number | SEQ ID NO |
|---|---|---|---|---|
| ERG10 | Saccharomyces cerevisiae | P41338 | 2.3.1.9 | 209 |
| thlA | Clostridium acetobutylicum | P45359 | 2.3.1.9 | 210 |
| atoB | Escherichia coli | P76461 | 2.3.1.9 | 211 |
| H16_B0759 | Cupriviadus necator | Q0K368 | 2.3.1.9 | 212 |
| Msed_0656 | Metallosphaera sedula | A4YEH9 | 2.3.1.9 | 213 |
| AAT1 | Arabidopsis thaliana | Q8S4Y1 | 2.3.1.9 | 214 |

TABLE 12

Enzymes candidates for conversion to acetoacetate from acetoacetyl-CoA (acetoacetyl-CoA transferase/synthase)

| Genes | Origin | UniProt number | EC number | SEQ ID NO |
|---|---|---|---|---|
| ATOA.Ec/ ATOD.Ec | Escherichia coli | P76459 P76458 | 2.8.3.8 | 215 216 |
| C7401_123119 | Paraburkholderia unamae | A0A328X8N5 | 2.8.3.8 | 217 |
| YdiF | Escherichia coli | Q8X5X6 | 2.8.3.8 | 218 |
| ctfA.Ca/ctfB | Clostridium acetobutylicum | P33752 P23673 | 2.8.3.9 | 219 220 |
| ctfA./ctfB | Clostridium saccharobutylicum | U5MXH7 U5MUQ0 | 2.8.3.9 | 221 222 |
| ctfA/ctfB | Escherichia coli | A0A2X1MWL8 A0A0K5TTP4 | 2.8.3.9 | 223 224 |
| ERG13 | Saccharomyces cerevisiae | P54839 | 2.3.3.10 | 283 |
| yngG | Bacillus subtilis | O34873 | 4.1.3.4 | 284 |
| nphT7 | Streptomyces sp. | D7URV0 | 2.3.1.194 | 285 |

TABLE 13

Enzymes candidates for conversion to acetone from acetoacetate (acetoacetate decarboxylase)

| Genes | Origin | UniProt number | EC number | SEQ ID NO |
|---|---|---|---|---|
| Adc.Ca | Clostridium acetobutylicum | P23670 | 4.1.1.4 | 225 |
| Adc.Cbe | Clostridium beijerinckii | A6M020 | 4.1.1.4 | 226 |
| Adc | Clostridium pasteurianum | P23650 | 4.1.1.4 | 227 |
| Adc | Pseudomonas solanacearum | Q8XR10 | 4.1.1.4 | 228 |
| Adc | Paraburkholderia xenovorans | Q141C9 | 4.1.1.4 | 229 |
| Adc.Pp | Paenibacillus polymyxa | A0A378XWA9 | — | 230 |

Figure 7:
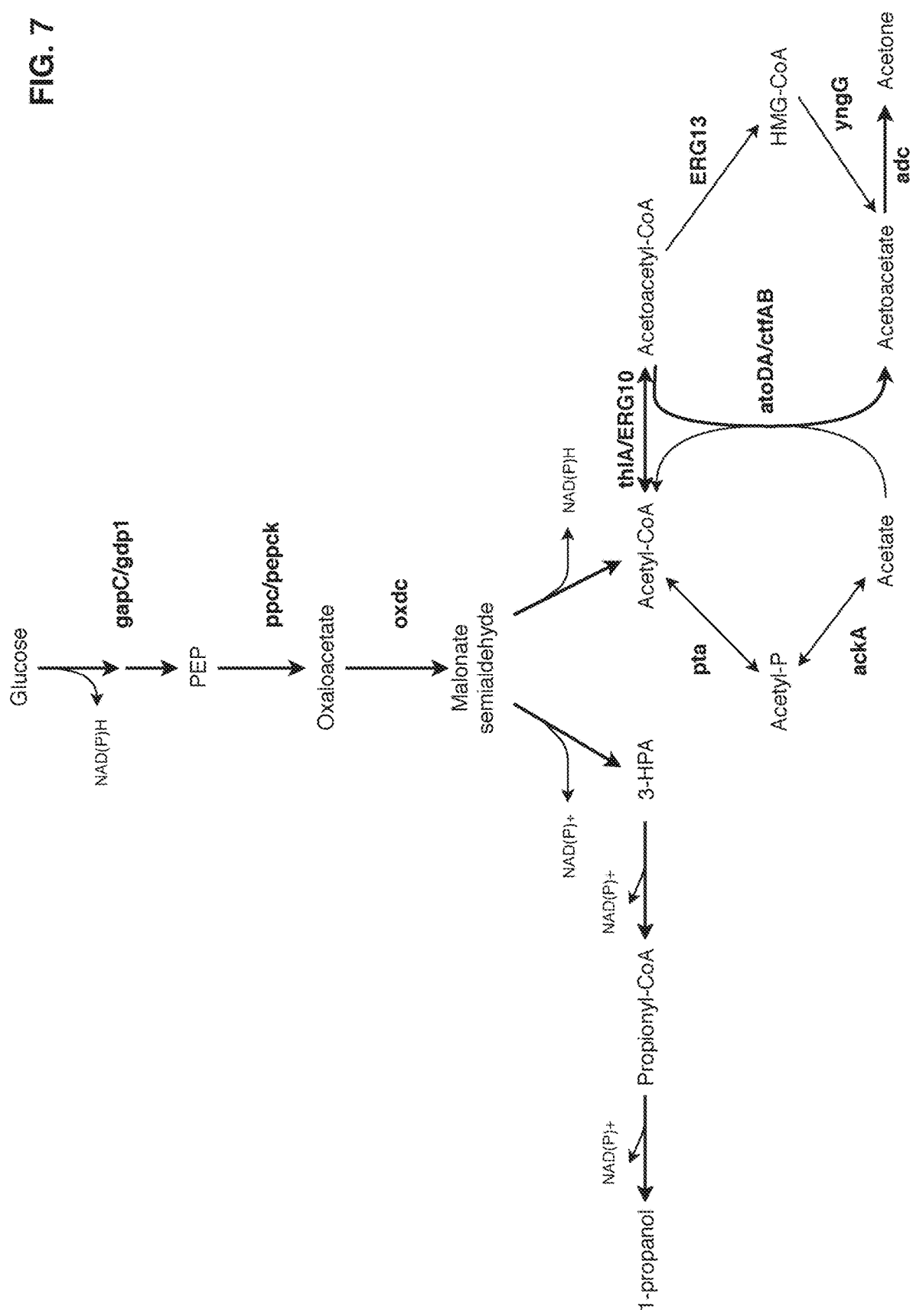
FIG. 7 depicts the combined pathways from oxaloacetate to malonate semialdehyde to 1-propanol and acetone, and the redox neutral status of the combined pathways.
Figure 8:
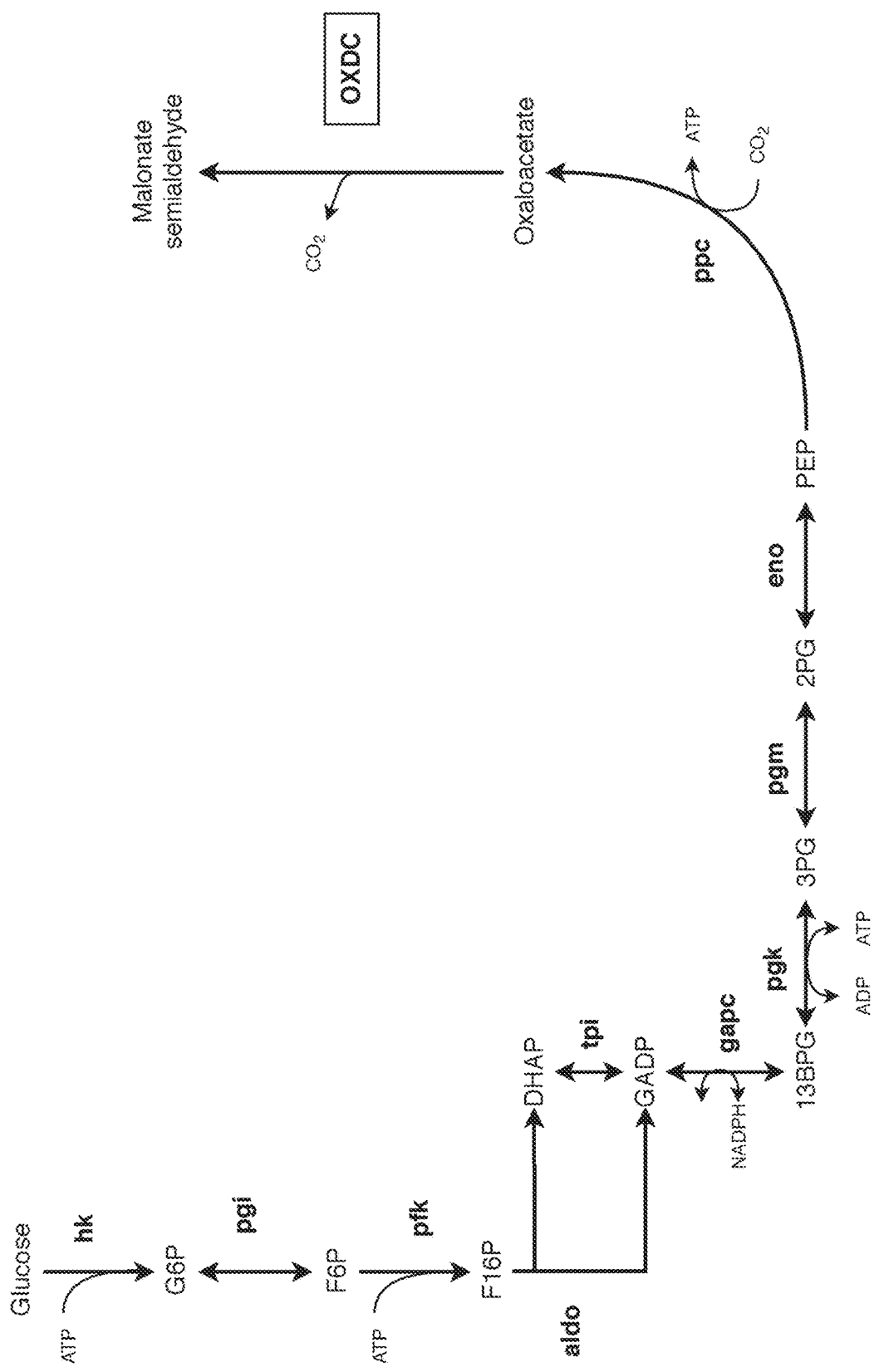
FIG. 8 depicts a pathway from glucose to malonate semialdehyde, including catalytic enzymes and corresponding malonate semialdehyde intermediates, particularly identifying the oxaloacetate decarboxylase utilized to produce malonate semialdehyde from oxaloacetate.

To solve high demand of NAD(P)H related to 3-HP derivatives production and excess of NADH related to acetyl-CoA derivatives production, we are suggesting the combination of both pathways to result in a balanced pathway. As depicted in FIG. 7, combination of these pathways for 1-propanol and acetone, for example, leads to a high total yield of 0.437 g of solvents/g of glucose, assuming these products are produced in a 1:1 ratio (acetone:1-propanol) in aerobic conditions (FIG. 15). The proposed co-production pathway is redox neutral and with a small excess of ATP, results in a more efficient and high yield production of the desired compounds. Furthermore, balanced pathway has potential to be performed in an anaerobic condition, which may represent a potential for a lower production cost process, due to advantages already mentioned, like CAPEX and OPEX reduction with air compressors, and CAPEX decrease with production fermenters. Besides that, there is an improvement of yield in anaerobic conditions, where co-production of 1-propanol and acetone leads to a higher total yield of 0.46 g of solvents/g of glucose, assuming these products are produced in a ratio 3:4 (acetone:1-propanol) (FIG. 16).

Figure 17:
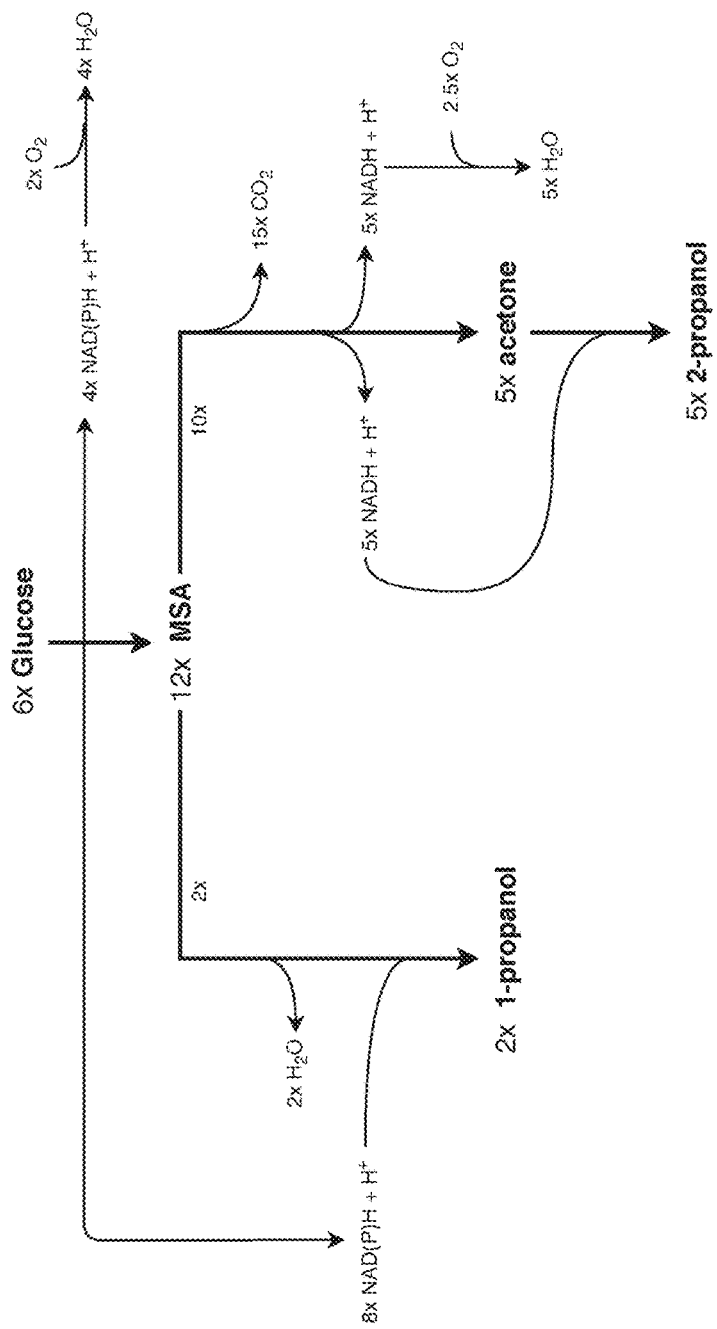
FIG. 17 depicts the stoichiometry of co-production of 1-propanol and 2-propanol in aerobic conditions.

In some aspects, 2-propanol can be obtained by dehydrogenation of acetone and can be coproduced with 1-propanol. The NADPH/NADH requirements in the 3-HPA derivative pathway complements the NADPH/NADH excess from the acetyl-CoA derivative pathway. The combination of these pathways for the production of 1-propanol and 2-propanol, leads to a high total yield of 0.39 g of solvents/g of glucose, assuming these products are produced in a 2:5 ratio (1-propanol:2-propanol), in aerobic conditions, according to FIG. 17.

Figure 18:
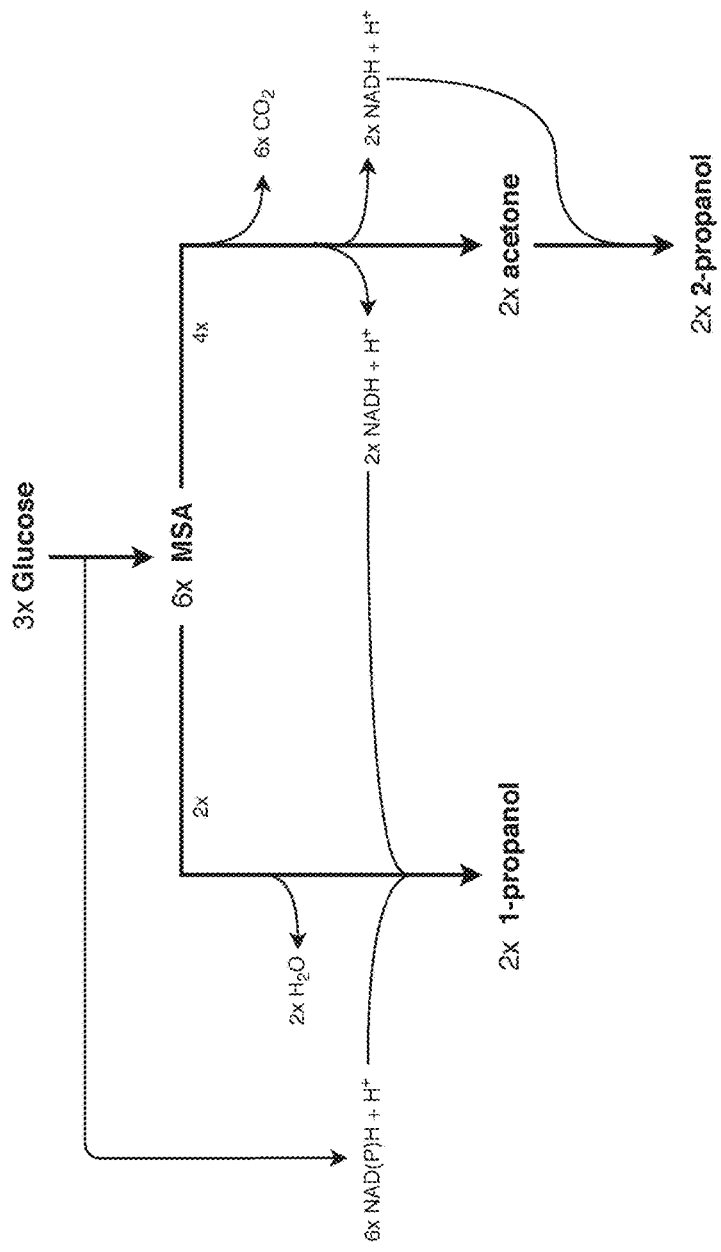
FIG. 18 depicts the stoichiometry of co-production of 1-propanol and 2-propanol in anaerobic conditions.
Figure 19:
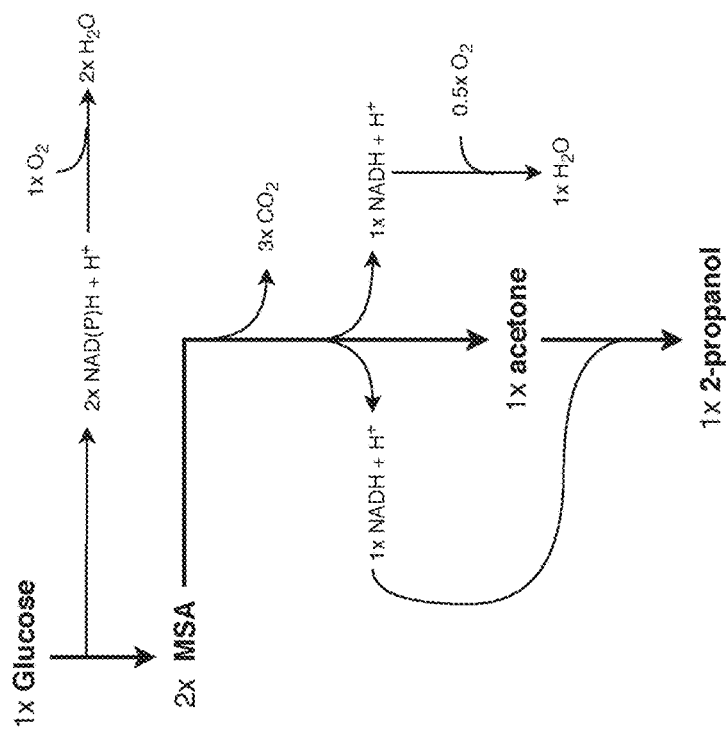
FIG. 19 depicts the stoichiometry of production of 2-propanol in aerobic conditions.

In some aspects, 2-propanol can be obtained by enzymatic dehydrogenation of acetone and can be coproduced with 1-propanol in anaerobic conditions, that leads to a higher total yield of 0.44 g of solvents/g of glucose, assuming these products are produced in a 1:1 ratio (1-propanol:2-propanol), in anaerobic conditions, according to FIG. 18. This process may represent a potential for a lower cost process, in relation to an aerobic process.

TABLE 14

Enzymes to convert acrylyl-CoA to acrylic acid (acyl-CoA hydrolase or thioesterase)

| Genes | Origin | UniProt number | EC number | SEQ ID NO |
|---|---|---|---|---|
| yciA | Escherichia coli | P0A8Z0 | — | 231 |
| ACIAD3139 | Escherichia coli | Q6F7Y5 | — | 232 |

TABLE 15

Enzymes candidates to 2-propanol dehydrogenase

| Genes | Origin | UniProt number | EC number |
|---|---|---|---|
| PRDH.Dr | Devosia riboflavina | — | — |
| PRDH.Sp | Sporotrichum pulverulentum | — | — |

TABLE 16

Genes involved on malonate semialdehyde production by β-alanine pathway

| Genes | Origin | UniProt number | EC number | SEQ ID NO |
|---|---|---|---|---|
| aat2 | Saccharomyces cerevisiae | P23542 | 2.6.1.1 | 233 |
| PAND | Corynebacterium glutamicum | A4QAD0 | 4.1.1.11 | 234 |

TABLE 16-continued

Genes involved on malonate semialdehyde production by β-alanine pathway

| Genes | Origin | UniProt number | EC number | SEQ ID NO |
|---|---|---|---|---|
| PAND. Tca | *Tribolium castaneum* | A7U8C7 | 4.1.1.11 | 275 |
| Baat | *Saccharomyces cerevisiae* | P47176 | 2.6.1.42 | 235 |
| PYD4.Lk | *Lachancea kluyveri* | A5H0J5 | 2.6.1.19 | 236 |

TABLE 17

Genes of glycolysis

| Genes | Origin | UniProt Number | EC number | SEQ ID |
|---|---|---|---|---|
| PEPCK | *Escherichia coli* | P22259 | 4.1.1.49 | 237 |
| GAPDH | *Saccharomyces cerevisiae* | P00359 | 1.2.1.13 | 238 |
| GDP1.K1 | *Kluyveromyces lactis* | Q8J0C9 | 1.2.1.13 | 239 |
| PYK1 | *Saccharomyces cerevisiae* | P00549 | 2.7.1.40 | 240 |
| gapC | *Clostridium acetobutylicum* | Q97D25 | 1.2.1.13 | 241 |

Methods of Detecting Genetic Modification

The present disclosure teaches primers, probes, and assays that are useful for detecting the microbes taught herein. In some aspects, the disclosure provides for methods of detecting the WT parental strains. In other aspects, the disclosure provides for methods of detecting the engineered or modified microbes derived from parent strains or WT strains. In some aspects, the present disclosure provides methods of identifying genetic alterations in a microbe.

In some aspects, the genomic engineering methods of the present disclosure lead to the creation of non-natural nucleotide "junction" sequences in the modified microbes. These non-naturally occurring nucleotide junctions can be used as a type of diagnostic that is indicative of the presence of a particular genetic alteration in a microbe taught herein.

The present techniques are able to detect these non-naturally occurring nucleotide junctions via the utilization of specialized quantitative PCR methods, including uniquely designed primers and probes. In some aspects, the probes of the disclosure bind to the non-naturally occurring nucleotide junction sequences. In some aspects, traditional PCR is utilized. In other aspects, real-time PCR is utilized. In some aspects, quantitative PCR (qPCR) is utilized. In some aspects, the PCR methods are used to identify heterologous sequences that have been inserted into the genomic DNA or extra-genomic DNA of the microbes.

Thus, the disclosure can cover the utilization of two common methods for the detection of PCR products in real-time: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence. In some aspects, only the non-naturally occurring nucleotide junction will be amplified via the taught primers, and consequently can be detected via either a non-specific dye, or via the utilization of a specific hybridization probe. In other aspects, the primers of the disclosure are chosen such that the primers flank either side of a junction sequence, such that if an amplification reaction occurs, then said junction sequence is present.

Aspects of the disclosure involve non-naturally occurring nucleotide junction sequence molecules per se, along with other nucleotide molecules that are capable of binding to said non-naturally occurring nucleotide junction sequences under mild to stringent hybridization conditions. In some aspects, the nucleotide molecules that are capable of binding to said non-naturally occurring nucleotide junction sequences under mild to stringent hybridization conditions are termed "nucleotide probes."

In some aspects, genomic DNA can be extracted from samples and used to quantify the presence of microbes of the disclosure by using qPCR. The primers utilized in the qPCR reaction can be primers designed by Primer Blast (www.ncbi.nlm.nih.gov) to amplify unique regions of the wild-type genome or unique regions of the engineered non-intergeneric mutant strains. The qPCR reaction can be carried out using the SYBR GreenER qPCR SuperMix Universal (Thermo Fisher P/N 11762100) kit, using only forward and reverse amplification primers; alternatively, the Kapa Probe Force kit (Kapa Biosystems P/N KK4301) can be used with amplification primers and a TaqMan probe containing a FAM dye label at the 5' end, an internal ZEN quencher, and a minor groove binder and fluorescent quencher at the 3' end (Integrated DNA Technologies).

Quantitative polymerase chain reaction (qPCR) is a method of quantifying, in real time, the amplification of one or more nucleic acid sequences. The real time quantification of the PCR assay permits determination of the quantity of nucleic acids being generated by the PCR amplification steps by comparing the amplifying nucleic acids of interest and an appropriate control nucleic acid sequence, which may act as a calibration standard.

TaqMan probes are often utilized in qPCR assays that require an increased specificity for quantifying target nucleic acid sequences. TaqMan probes comprise an oligonucleotide probe with a fluorophore attached to the 5' end and a quencher attached to the 3' end of the probe. When the TaqMan probes remain as is with the 5' and 3' ends of the probe in close contact with each other, the quencher prevents fluorescent signal transmission from the fluorophore. TaqMan probes are designed to anneal within a nucleic acid region amplified by a specific set of primers. As the Taq polymerase extends the primer and synthesizes the nascent strand, the 5' to 3' exonuclease activity of the Taq polymerase degrades the probe that annealed to the template. This probe degradation releases the fluorophore, thus breaking the close proximity to the quencher and allowing fluorescence of the fluorophore. Fluorescence detected in the qPCR assay is directly proportional to the fluorophore released and the amount of DNA template present in the reaction.

The features of qPCR allow the practitioner to eliminate the labor-intensive post-amplification step of gel electrophoresis preparation, which is generally required for observation of the amplified products of traditional PCR assays. The benefits of qPCR over conventional PCR are considerable, and include increased speed, ease of use, reproducibility, and quantitative ability.

Microbes

As described herein, in some aspects, the recombinant microorganisms are prokaryotic microorganism. In some aspects, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus,* Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces;* (6) *Bacteroides,* Flavobacteria; (7) *Chlamydia;* (8) Green sulfur bacteria; (9) Green non-sulfur bacteria (also anaerobic phototrophs); (10) Radioresistant micrococci and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema,* and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces.*

In some aspects, the microorganisms of the present disclosure are fungi or yeasts.

In some aspects, the recombinant microorganism is a eukaryotic microorganism. In some aspects, the eukaryotic microorganism is a yeast. In exemplary aspects, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula,* and *Myxozyma.*

In some aspects, the recombinant microorganism is a prokaryotic microorganism. In exemplary aspects, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium,* and *Brevibacterium.*

In some aspects, microorganism for use in the methods of the present disclosure can be selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula, Myxozyma, Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium,* and *Brevibacterium.*

In some aspects, a microbe resulting from the methods described herein may be a species selected from any of the following genera: *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, Fusobacterium, Actinomyces, Bacillus, Clostridium, Corynebacterium, Erysipelothrix, Lactobacillus, Listeria, Mycobacterium, Myxococcus, Nocardia, Staphylococcus, Streptococcus, Streptomyces, Saccharomyces, Pichia,* and *Aspergillus.*

In some aspects, microorganisms for use in the methods of the present disclosure include *Clostridium* sp., *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Clostridium acetobutylicum, Clostridium beijerinckii, Candida krusei, Oxobacter pfennigii, Thermoanaerobacter kivui, Sporomusa ovata, Thermoacetogenium phaeum, Acetobacterium carbinolicum, Sporomusa termitida, Moorella glycerini, Eubacterium aggregans, Treponema azotonutricium, Escherichia coli, Saccharomyces cerevisiae, Pseudomonas putida, Bacillus sp, Corynebacterium sp., Yarrowia lipolytica, Scheffersomyces stipitis,* and *Terrisporobacter glycolicus.* In some aspects, the recombinant microorganisms are derived from a parental microorganism selected from any one of the microorganisms disclosed herein.

In some aspects, yeast can be cultivated more rapidly and at a higher density than bacteria, and does not require an aseptic environment in the commercial/industrial setting. In some aspects, yeast cells can be more easily separated from the culture medium than can bacteria, simplifying the process for product extraction and purification.

In some aspects, the microorganism(s) used in the methods of the present disclosure include yeasts selected from genus *Saccharomyces, Candida, Ashbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus,* or *Malassezia.*

In some aspects, the yeast may be a Crabtree-positive yeast selected from genus *Saccharomyces, Dekkera, Schizosaccharomyces, Kluyveromyces, Torulaspora Zigosaccharomyces,* or Brettanomycces.

In some aspects, the yeast may be selected from *Saccharomyces cerevisiae, Saccharomyces boulardii, Saccharomyces douglasii, Saccharomyces bayanus, Zigosaccharomyces bailii, Schizosaccharomyces pombe, Dekkera brucelensis, Dekkera intermedia,* Brettanomycces custersii, Brettanomycces intermedius, *Kluyveromyces themotolerens, Torulaspora globosa,* and *Torulaspora* glabrata.

In some aspects, the yeast may be from genus *Saccharomyces.* In some aspects, the yeast may be *Saccharomyces cerevisiae.*

In some aspects, a recombinant yeast of the present disclosure is able to decarboxylate oxaloacetate into malonate semialdehyde due to the insertion of at least one nucleic acid sequence or gene described herein. In some aspects, a recombinant yeast of the present disclosure is further able to co-produce one or more 3-HP and acetyl-CoA derivatives. In some aspects the malonate semialdehyde is the substrate for the co-production of the one or more 3-HP and acetyl-CoA derivatives.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but also to the progeny or potential progeny of such a microorganism. Because certain modifications may occur in succeeding generations due to either mutation or environmental influences, such progeny may not, in fact, be identical to the parent cell, but are still included within the scope of the term as used herein.

Culture Conditions

Culturing of the microorganisms used in the methods of the disclosure may be conducted using any number of processes known in the art for culturing and fermenting substrates using the microorganisms of the present disclosure.

The fermentation may be carried out in any suitable bioreactor, such as Continuous Stirred Tank Bioreactor, Bubble Column Bioreactor, Airlift Bioreactor, Fluidized Bed Bioreactor, Packed Bed Bioreactor, Photo-Bioreactor, Immobilized Cell Reactor, Trickle Bed Reactor, Moving Bed Biofilm Reactor, Bubble Column, Gas Lift Fermenter, Membrane Reactors such as Hollow Fiber Membrane Bioreactor. In some aspects, the bioreactor comprises a first, growth reactor in which the microorganisms are cultured, and a second, fermentation reactor, to which fermentation broth from the growth reactor is fed and in which most of the fermentation product is produced. In some aspects, the bioreactor simultaneously accomplishes the culturing of microorganism and the producing the fermentation product from carbon sources such substrates and/or feedstocks provided.

In some aspects, the present disclosure relates to the use of a recombinant microbe, for the production of (1) malonate semialdehyde, one of its salts, or a malonate semialdehyde derivative; (2) 3-HP, one of its salts, or a 3-HP derivative; and (3) acetyl-CoA, one of its salts, or a acetyl-CoA derivative. In some aspects, the recombinant microorganism is a yeast.

In some aspects, the present disclosure further relates to a method for producing (1) malonate semialdehyde, one of its salts, or a malonate semialdehyde derivative; (2) 3-HP, one of its salts, or a 3-HP derivative; and (3) acetyl-CoA, one of its salts, or a acetyl-CoA derivative; the method comprising the steps of:
  (a) culturing a recombinant microorganism described herein in a culture medium; and
  (b) recovering the (2) 3-HP, one of its salts, or a 3-HP derivative; and (3) acetyl-CoA, one of its salts, or an acetyl-CoA derivative from the culture medium. In some aspects, the recombinant microorganism is a yeast.

In some aspects, microorganisms described herein are grown at a temperature in the range of about 20° C. to about 37° C., preferably at a temperature ranging from 27 to 34° C., in an appropriate culture medium.

In some aspects, the recombinant yeast of the present disclosure belongs to the *S. cerevisiae* species, the temperature may range from 27 to 34° C., in an appropriate culture medium.

In some aspects, suitable growth media for yeast are common commercially prepared media such as broth that includes yeast nitrogen base, ammonium sulfate, and dextrose as the carbon/energy source) or YPD Medium, a blend of peptone, yeast extract, and dextrose in optimal proportions for growing most. In some aspects, other defined or synthetic growth media may also be used and the appropriate medium for growth of the particular microorganism will be known by one skilled in the art of microbiology or fermentation science.

Examples of culture media for a recombinant yeast of the present disclosure are described by D. Burke et al., Methods in yeast Genetics—A cold spring harbor laboratory course Manual (2000).

In some aspects, suitable pH ranges for the fermentation may be between pH 3.0 to pH 7.5, where pH 4.5 to pH 6.5 is preferred as the initial condition.

In some aspects, fermentations may be performed under aerobic conditions, microaerobic conditions, or anaerobic conditions.

In some aspects, the amount of product(s) in the fermentation medium can be determined using a number of methods known in the art, for example, high performance liquid chromatography (HPLC) or gas chromatography (GC).

In some aspects, the present process may employ a batch method of fermentation. A classical batch fermentation is a closed system where the composition of the medium is set at the beginning of the fermentation and not subject to artificial alterations during the fermentation. Thus, at the beginning of the fermentation, the medium is inoculated with the desired organism or organisms, and fermentation is permitted to occur without adding anything to the system. Typically, however, a "batch" fermentation is batch with respect to the addition of carbon source and attempts are often made at controlling factors such as temperature, pH and oxygen concentration. In batch systems, the metabolite and biomass compositions of the system change constantly up to the time when the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

In some aspects, a fed-batch system may also be used. A fed-batch system is similar to a typical batch system with the exception that the carbon source substrate is added in increments as the fermentation progresses. Fed-batch systems are useful when catabolite repression (e.g. glucose repression) is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$.

A variety of fermentations are described in Sunderland et al., (1992), herein incorporated by reference. In some aspects, the fermentation is performed in batch mode it is contemplated that the method would be adaptable to continuous fermentation.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

In some aspects, the methods may be practiced using either batch, fed-batch, or continuous processes and that any known mode of fermentation would be suitable. Additionally, it is contemplated that cells may be immobilized on a substrate as whole cell catalysts and subjected to fermentation conditions for production.

In order to still improve the production of (1) malonate semialdehyde, (2) 3-HP, and acetyl-CoA; one of their salts, or derivatives thereof, a particular embodiment may consist of culturing the recombinant yeast cells in an appropriate culture medium, such as above-mentioned, wherein the said culture medium comprises an optimal amount of carbon source, especially glucose.

In some aspects, the cells are cultured in such an optimal culture medium during only a part of the whole culture duration. In some aspects, the yeast cells are incubated in the said optimal culture medium 10 hours or more after initiation of the culture, which encompasses 11, 12, 13, 14, 15 or 16 hours or more after initiation of the culture.

In some aspects, the cells are cultured in such an optimal culture medium during a time period ranging from 5 hours to 15 hours, which includes from 6 hours to 10 hours, e.g. 8 hours after initiation of the culture.

In some aspects, the carbon source comprised in said optimal culture medium consists of glucose. In preferred embodiments, the said optimal culture medium comprises 12% w/w or more glucose, including 15% w/w or more glucose. In preferred embodiments, the said optimal culture medium comprises at most 40% w/w glucose, which includes at most 35% w/w glucose.

In some aspects, a method for producing (1) malonate semialdehyde, (2) 3-HP, and (3) acetyl-CoA; one of their salts, or derivatives thereof may further comprise, between steps (a) and (c), an intermediate step (b) consisting of cultivating the yeast cells in the said optimal culture medium.

Product Isolation/Purification

In some aspects, the method of producing (1) malonate semialdehyde, one of its salts, or a malonate semialdehyde derivative; (2) 3-HP, one of its salts, or a 3-HP derivative; and (3) acetyl-CoA, one of its salts, or a acetyl-CoA derivative comprises one or more steps of isolation of at least the (2) 3-HP, one of its salts, or a 3-HP derivative; and (3) acetyl-CoA, one of its salts, or a acetyl-CoA derivative. In some aspects, the method comprises, in a first reaction, producing and isolating/purifying malonate semialdehyde, one of its salts, or a malonate semialdehyde derivative in one fermentation to add the purified/isolated product to a second reaction (fermentation/bioreactor) to drive the production of (2) 3-HP, one of its salts, or a 3-HP derivative; and (3) acetyl-CoA, one of its salts, or a acetyl-CoA derivative.

In some aspects, recovering one or more of (1) malonate semialdehyde, one of its salts, or a malonate semialdehyde derivative; (2) 3-HP, one of its salts, or a 3-HP derivative; and (3) acetyl-CoA, one of its salts, or a acetyl-CoA derivative from a culture medium may be achieved by a number of techniques, including, but not limited to, distillation, gas-stripping, pervaporation, selective precipitation, or liquid extraction.

In some aspects, the recombinant microorganism exports (1) malonate semialdehyde, one of its salts, or a malonate semialdehyde derivative; (2) 3-HP, one of its salts, or a 3-HP derivative; and (3) acetyl-CoA, one of its salts, or a acetyl-CoA derivative into the culture medium, thus simplifying the culture process.

In some aspects, the products are referred to as one or more of (1) malonate semialdehyde, one of its salts, or a malonate semialdehyde derivative; (2) 3-HP, one of its salts, or a 3-HP derivative; and (3) acetyl-CoA, one of its salts, or a acetyl-CoA derivative.

In some aspects, the products are collected from the medium by distillation. In some aspects, distillation may involve a component different from the culture medium in order to facilitate the isolation of the products by forming azeotrope and notably with water. This component is an organic solvent such as cyclohexane, pentane, butanol, benzene, toluene, trichloroethylene, octane, diethylether, or a mixture thereof.

In some aspects, gas stripping is achieved with a stripping gas chosen among helium, argon, carbon dioxide, hydrogen, nitrogen, or mixtures thereof. In some aspects, liquid extraction is achieved with an organic solvent as the hydrophobic phase such as pentane, hexane, or dodecane.

In some aspects, once a desired number of microbes have been achieved, the spent media is subjected to a process for isolating the products. In some aspects, once a desired density of microbes has been achieved, the spent media is subject to a process for isolating the products. In some aspects, the microbes are lysed and the cellular debris is pelleted out of solution in a centrifuge. In some aspects, the products collected from the cell pellet fraction or the liquid fraction with the aid of a solvent extraction process or a gradient ultra-centrifugation process.

Microbial Compositions

In some aspects, the microbes of the disclosure are combined into microbial compositions.

In some aspects, the microbial compositions of the present disclosure are solid. Where solid compositions are used, it may be desired to include one or more carrier materials including, but not limited to: mineral earths such as silicas, talc, kaolin, limestone, chalk, clay, dolomite, diatomaceous earth; calcium sulfate; magnesium sulfate; magnesium oxide; zeolites, calcium carbonate; magnesium carbonate; trehalose; chitosan; shellac; albumins; starch; skim milk powder; sweet whey powder; maltodextrin; lactose; inulin; dextrose; and products of vegetable origin such as cereal meals, tree bark meal, wood meal, and nutshell meal.

In some aspects, the microbial compositions of the present disclosure are liquid. In further aspects, the liquid comprises a solvent that may include water or an alcohol or a saline or carbohydrate solution. In some aspects, the microbial compositions of the present disclosure include binders such as polymers, carboxymethylcellulose, starch, polyvinyl alcohol, and the like.

In some aspects, microbial compositions of the present disclosure comprise saccharides (e.g., monosaccharides, disaccharides, trisaccharides, polysaccharides, oligosaccharides, and the like), polymeric saccharides, lipids, polymeric lipids, lipopolysaccharides, proteins, polymeric proteins, lipoproteins, nucleic acids, nucleic acid polymers, silica, inorganic salts and combinations thereof. In further aspect, microbial compositions comprise polymers of agar, agarose, gelrite, gellan gum, and the like. In some aspects, microbial compositions comprise plastic capsules, emulsions (e.g., water and oil), membranes, and artificial membranes. In some aspects, emulsions or linked polymer solutions may comprise microbial compositions of the present disclosure. See Harel and Bennett (U.S. Pat. No. 8,460,726 B2).

In some aspects, microbial compositions of the present disclosure occur in a solid form (e.g., dispersed lyophilized spores) or a liquid form (microbes interspersed in a storage medium). In some aspects, microbial compositions of the present disclosure are added in dry form to a liquid to form a suspension immediately prior to use.

In some aspects, the microbial composition of the present disclosure possesses a water activity (aw) of less than 0.750, 0.700, 0.650, 0.600, 0.550, 0.500, 0.475, 0.450, 0.425, 0.400, 0.375, 0.350, 0.325, 0.300, 0.275, 0.250, 0.225, 0.200, 0.190, 0.180, 0.170, 0.160, 0.150, 0.140, 0.130, 0.120, 0.110, 0.100, 0.095, 0.090, 0.085, 0.080, 0.075, 0.070, 0.065, 0.060, 0.055, 0.050, 0.045, 0.040, 0.035, 0.030, 0.025, 0.020, 0.015, 0.010, or 0.005.

In some aspects, the microbial composition of the present disclosure possesses a water activity (aw) of less than about 0.750, about 0.700, about 0.650, about 0.600, about 0.550, about 0.500, about 0.475, about 0.450, about 0.425, about 0.400, about 0.375, about 0.350, about 0.325, about 0.300, about 0.275, about 0.250, about 0.225, about 0.200, about 0.190, about 0.180, about 0.170, about 0.160, about 0.150, about 0.140, about 0.130, about 0.120, about 0.110, about 0.100, about 0.095, about 0.090, about 0.085, about 0.080, about 0.075, about 0.070, about 0.065, about 0.060, about 0.055, about 0.050, about 0.045, about 0.040, about 0.035, about 0.030, about 0.025, about 0.020, about 0.015, about 0.010, or about 0.005.

The water activity values are determined by the method of Saturated Aqueous Solutions (Multon, "Techniques d'Analyse E De Controle Dans Les Industries Agroalimentaires" APRIA (1981)) or by direct measurement using a viable Robotronic BT hygrometer or other hygrometer or hygroscope.

Feedstock

In some aspects, the disclosure is drawn to a method of producing and/or recovering/isolating a 3-HP and acetyl-CoA derivative. The recovery/collection/isolation can be by methods known in the art, such as distillation, membrane-based separation gas stripping, solvent extraction, and expanded bed adsorption.

In some aspects, the feedstock comprises a carbon source. In some aspects, the carbon source may be selected from sugars, glycerol, alcohols, organic acids, alkanes, fatty acids, lignocellulose, proteins, carbon dioxide, and carbon monoxide. In one aspect, the carbon source is a sugar. In one aspect, the sugar is glucose or oligomers of glucose thereof. In one aspect, the oligomers of glucose are selected from fructose, sucrose, starch, cellobiose, maltose, lactose and cellulose. In one aspect, the sugar is a five carbon sugar. In one aspect, the sugar is a six carbon sugar. In some aspects, the feedstock comprises one or more five carbon sugars and/or one or more six carbon sugars. In some aspects, the feedstock comprises one or more of xylose, glucose, arabinose, galactose, maltose, fructose, mannose, sucrose, and/or combinations thereof. In some aspects, the feedstock comprises one or more of xylose and/or glucose. In some aspects, the feedstock comprises one or more of arabinose, galactose, maltose, fructose, mannose, sucrose, and/or combinations thereof.

In some aspects, the microbes utilize one or more five carbon sugars (pentoses) and/or one or more six carbon sugars (hexoses). In some aspects, the microbes utilize one or more of xylose and/or glucose. In some aspects, the microbes utilize one or more of arabinose, galactose, maltose, fructose, mannose, sucrose, and/or combinations thereof. In some aspects, the microbes utilize one or more of xylose, glucose, arabinose, galactose, maltose, fructose, mannose, sucrose, and/or combinations thereof. The carbon source(s) utilized may encompass a wide variety of carbon-containing substrates and will generally only be limited by the choice of microorganism.

In some aspects, hexoses may be selected from D-allose, D-altrose, D-glucose, D-mannose, D-gulose, D-idose, D-galactose, D-talose, D-tagtose, D-sorbose, D-fructose, D-psicose, and other hexoses known in the art. In some aspects, pentoses may be selected from D-xylose, D-ribose, D-arabinose, D-lyxose, D-xylulose, D-ribulose, and other pentoses known in the art. In some aspects, the hexoses and pentoses may be selected from the levorotary or dextrorotary enantiomer of any of the hexoses and pentoses disclosed herein.

In some aspects, a fermentation is generally conducted in fermenters/bioreactors with an appropriate culture medium adapted to the microorganism(s) being cultivated. In some aspects, the medium contains at least one simple carbon source. In some aspects, the medium contains additional substrates.

In some aspects, additional substrates may include any one or more of the carbon sources described herein; polysaccharides such as start or cellulose, or mixtures thereof, unpurified mixtures from renewable feedstocks such as cheese whey permeate, corn steep liquor, sugar beet molasses, and barley malt.

In some aspects, the media may further contain suitable minerals, salts, cofactors, buffers, and other components suitable for the growth of the cultures and promotion of the enzymatic pathway necessary for the production of the desired product.

In some aspects, total amount of C5 and/or C6 carbohydrates fed to a bioreactor/growth medium during the growth phase is at least 5 kg carbohydrate/m3, at least 10 kg carbohydrate/m3, at least 20 kg carbohydrate/m3, at least 30 kg carbohydrate/m3, at least 40 kg carbohydrate/m3, at least 50 kg carbohydrate/m3, at least 60 kg carbohydrate/m3, at least 70 kg carbohydrate/m3, at least 80 kg carbohydrate/m3, at least 90 kg carbohydrate/m3, at least 100 kg carbohydrate/m3, at least 150 kg carbohydrate/m3, at least 200 kg carbohydrate/m3, at least 250 kg carbohydrate/m3, at least 300 kg carbohydrate/m3, at least 400 kg carbohydrate/m3 at least 500 kg carbohydrate/m3, at least 600 kg carbohydrate/m3, at least 700 kg carbohydrate/m3, up to 800 kg carbohydrate/m3. In some aspects, total amount of C5 and/or C6 carbohydrates fed to the bioreactor/growth medium during the growth phase ranges from about 10 kg carbohydrate/m3 up to 500 kg carbohydrate/m3.

In some aspects, time required for the growth phase varies between 1 to 200 hours. In further aspects, the time of the growth phase is between 5 to 50 hours. The time is dependent on carbohydrate feeds and/or feedstocks.

As used herein, an "appropriate culture medium" means a medium, such as a sterile liquid medium, comprising nutrients essential or beneficial to the maintenance and/or growth of the microbial cells such as carbon sources or carbon substrate, nitrogen sources, for example, peptone, yeast extracts, meat extracts, malt extracts, urea, ammonium sulfate, ammonium chloride, ammonium nitrate, and ammonium phosphate; phosphorus sources, for example, monopotassium phosphate or dipotassium phosphate; trace elements (e.g., metal salts), for example magnesium salts, cobalt salts, and/or manganese salts; as well as growth factors such as amino acids, vitamins, growth promoters, and the like. The term "carbon source" or "carbon substrate" or "source of carbon" according to the present disclosure denotes any source of carbon that can be used by those skilled in the art to support the normal growth of a microorganism, including hexoses (such as glucose, galactose or lactose), pentoses, monosaccharides, oligosaccharides, disaccharides (such as sucrose, cellobiose or maltose), molasses, starch or its derivatives, cellulose, hemicelluloses and combinations thereof.

In some aspects, the total amount of C5 and/or C6 carbohydrates fed to the bioreactor/growth medium during the production phase is at least 50 kg carbohydrate/m3, at least 60 kg carbohydrate/m3, at least 70 kg carbohydrate/m3, at least 80 kg carbohydrate/m3, at least 90 kg carbohydrate/m3, at least 100 kg carbohydrate/m3, at least 150 kg carbohydrate/m3, at least 200 kg carbohydrate/m3, at least 250 kg carbohydrate/m3, at least 300 kg carbohydrate/m3, at least 400 kg carbohydrate/m3, at least 500 kg carbohydrate/m3, at least 600 kg carbohydrate/m3, at least 700 kg carbohydrate/m3, at least 800 kg carbohydrate/m3, at least 900 kg carbohydrate/m3 up to 1000 kg carbohydrate/m3. In some aspects, total amount of C5 and/or C6 carbohydrates fed to the bioreactor/growth medium during the production phase ranges from about 100 kg carbohydrate/m3 up to 800 kg carbohydrate/m3.

In some aspects, time required for the production phase varies between 5 to 500 hours. In further aspects, the time for the production phase varies from 10 to 300 hours for batch and fed-batch operations. In other aspects, the time of the production phase is up to 300 hours with continuous fermentation.

In some aspects, the total amount of C5 and/or C6 carbohydrates fed to the bioreactor/growth medium for one-phase process is at least 50 kg carbohydrate/m3, at least 60 kg carbohydrate/m3, at least 70 kg carbohydrate/m3, at least 80 kg carbohydrate/m3, at least 90 kg carbohydrate/m3, at least 100 kg carbohydrate/m3, at least 150 kg carbohydrate/m3, at least 200 kg carbohydrate/m3, at least 250 kg carbohydrate/m3, at least 300 kg carbohydrate/m3, at least 400 kg carbohydrate/m3, at least 500 kg carbohydrate/m3, at least 600 kg carbohydrate/m3, at least 700 kg carbohydrate/m3, at least 800 kg carbohydrate/m3, at least 900 kg carbohydrate/m3 up to 1000 kg carbohydrate/m3. In some aspects, total amount of C5 and/or C6 carbohydrates fed to the bioreactor/growth medium during the production phase ranges from about 100 kg carbohydrate/m3 up to 800 kg carbohydrate/m3.

In some aspects, time required for the production phase in the one-phase process varies between 5 to 500 hours. In further aspects, the time required for production phase in the one-phase process varies between 5 to 300 hours.

In some aspects, the one-phase or multi-phase production processes take about 5, about 10, about 25, about 50, about 75, about 100, about 125, about 150, about 175, about 200, about 225, about 250, about 275, about 300 about 325, about 350, about 375, about 400, about 425, about 450, about 475, or about 500 hours.

In some aspects, the one-phase or multi-phase production processes take 5, 10, 25, 50, 75, 100, 125, 150, 175, 200, 225, 250, 275, 300 325, 350, 375, 400, 425, 450, 475, or 500 hours.

EXAMPLES

Example 1: Creating Recombinant *S. cerevisiae* Strain to Produce Malonate Semialdehyde Recombinant *Saccharomyces cerevisiae* strains were constructed from standard strains using standard yeast molecular genetics procedure (Methods in yeast Genetics—A cold spring harbor laboratory course Manual (2000) by D. Burke, D. Dawson, T. Stearns CSHL Press).

The following genes were integrated in recombinant yeast using the ability of yeast to efficiently recombine free DNA ends sharing sequence homology.

More particularly, the coding sequences to be cloned were artificially synthesized. For heterologous sequences (non-yeast), the nucleic sequences were modified in order to obtain a synonymous coding sequence using the yeast codon usage. Using restriction enzyme and classical cloning technology, each synthetic sequence was cloned in between a transcription promoter and a transcription terminator. Each promoter sequence is preceded by a 50 to 200 nucleotides sequence homologous to the sequence of the terminator of the upstream gene. Similarly, the terminator of each gene (a gene comprising the promoter-coding sequence-terminator) is followed by sequences homologous to the gene immediately following. So that each of the unit to be integrated have a 50-200 nucleotide overlap with both the unit upstream and the unit downstream. For the first unit, the promoter is preceded by 50-200 nucleotides homologous to the yeast chromosome nucleotide for the locus in which it will be integrated. Similarly, for the last unit, the terminator is followed by 50-200 nucleotides homologous to the yeast chromosome nucleotide for the locus in which it will be integrated.

Each unit are then PCR amplified from the plasmids constructs, yielding X unit of linear DNA having overlapping sequences. At least one of this gene is an auxotrophic marker, in order to select for recombination event. All the linear fragments are transformed in the yeast at once, and recombinant yeast are selected for the auxotrophy related to the marker used. The integrity of the sequence is then verified by PCR and sequencing. Aspects of synthetic biology utilized described in Tian J. et al., Mol. Biosyst. 2009; 5(7):714-22.

Example 2: Method of Modifying a Yeast

The recombinant yeasts are mutant yeasts (Δfms1) which are impaired for β-alanine synthesis. As a consequence, the yeast is auxotroph for panthothenate and cannot grow on a medium deprived of pantothenate. In the same yeasts is expressed PYD4 from *Lachancea kluyveri*, a gene which encodes a β-alanine aminotransferase activity absent from *Saccharomyces cerevisiae*.

Figure 13:
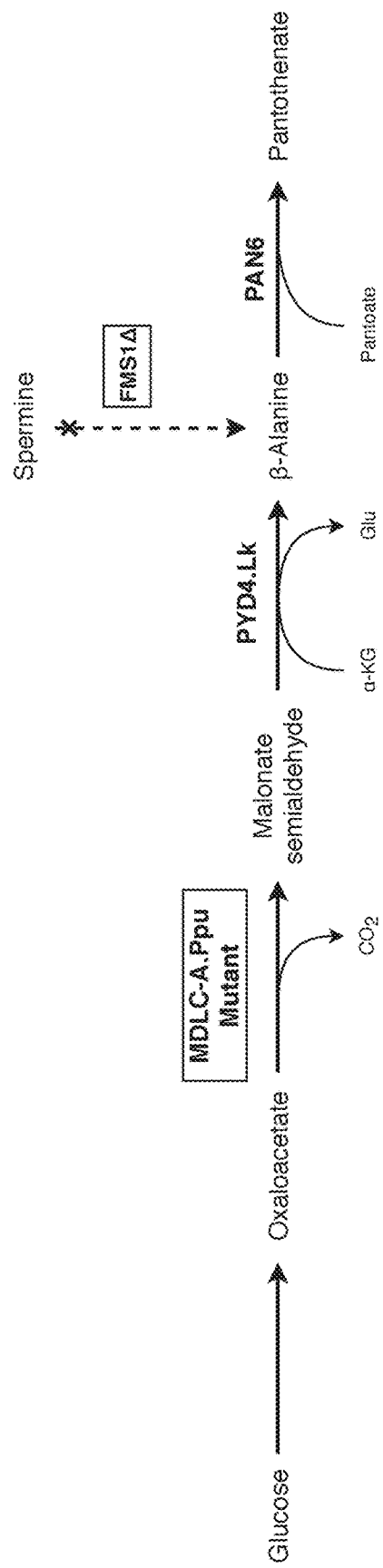
FIG. 13 depicts a pathway and yeast genotype relating to the mutants relating to Example 2.

This enzyme is able to transform Malonic semialdehyde into β-alanine (Andersen et al. 2007 FEBS Journal 274, 1804-1817). This yeast then lacks an activity able to produce malonyl semialdehyde to be able to grow in absence of pantothenate in the medium. See FIG. 13.

This yeast is still unable to grow on a pantothenate free medium upon expression of the benzoylformate decarboxylase from *P. putida*. Indeed, benzoylformate decarboxylase is not able to catalyze the transformation of oxaloacetate into malonate semialdehyde.

The following enzymes have been tested in vivo, in separate yeasts.

```
Enzyme No 1:
                                                   (SEQ ID NO: 2)
MASVHGTTYELLRRQGIDTVFGNPGSNELPFLKDFPEDFRYILALQEACVVGIA

DGYAQASRKPAFINLHSAAGTGNAMGALSNAWNSHSPLIVTAGQQTRAMIGVEARLTN

VDAANLPRPLVKWSYEPASAAEVPHAMSRAIHMASMAPQGPVYLSVPYDDWDKDADP

QSHHLFDRHVSSSVRLNDQDLDILVKALNSASNPAIVLGPDVDAANANADCVMLAERL

KAPVWVAPSAPRCPFPTRHPCFRGLMPAGIAAISQLLEGHDVVLVIGAPVFRYHQYDPG

QYLKPGTRLISVTCDPLEAARAPMGDAIVADIGAMASALANLVEESSRQLPTAAPEPAK

VDQDAGRLHPETVFDTLNDMAPENAIYLNESTSTTAQMWQRLNMRNPGSYYFCAAGG

LGFALPAAIGVQLAEPERQVIAVIGDGSANYSISALWTAAQYNIPTIFVIMNNGTYGALR

WFAGVLEAENVPGLDVPGIDFRALAKGYGVQALKADNLEQLKGSLQEALSAKGPVLIE

VSTVSPVK

Enzyme No 2:
                                                   (SEQ ID NO: 3)
MASVHGTTYELLRRQGIDTVFGNPGSNELPFLKDFPEDFRYILALQEACVVGIA

DGYAQASRKPAFINLHSAAGTGNAMGALSNAWNSHSPLIVTAGQQTRAMIGVEARLTN

VDAANLPRPLVKWSYEPASAAEVPHAMSRAIHMASMAPQGPVYLSVPYDDWDKDADP

QSHHLFDRHVSSSVRLNDQDLDILVKALNSASNPAIVLGPDVDAANANADCVMLAERL

KAPVWVAPSAPRCPFPTRHPCFRGLMPAGIAAISQLLEGHDVVLVIGAPVFRYHQYDPG

QYLKPGTRLISVTCDPLEAARAPMGDAIVADIGAMASALANLVEESSRQLPTAAPEPAK

VDQDAGRLHPETVFDTLNDMAPENAIYLNESTSTTAQMWQRLNMRNPGSYYNCAAGG

LGFALPAAIGVQLAEPERQVIAVIGDGSANYSISALWTAAQYNIPTIFVIMNNGTYGALR

WFAGVLEAENVPGLDVPGIDFRALAKGYGVQALKADNLEQLKGSLQEALSAKGPVLIE

VSTVSPVK

Enzyme No 3:
                                                   (SEQ ID NO: 4)
MASVHGTTYELLRRQGIDTVFGNPGSNELPFLKDFPEDFRYILALQEACVVGIA

DGYAQASRKPAFINLHSAAGTGNAMGALSNAWNSHSPLIVTAGQQTRAMIGVEAKLTN

VDAANLPRPLVKWSYEPASAAEVPHAMSRAIHMASMAPQGPVYLSVPYDDWDKDADP

QSHHLFDRHVSSSVRLNDQDLDILVKALNSASNPAIVLGPDVDAANANADCVMLAERL

KAPVWVAPSAPRCPFPTRHPCFRGLMPAGIAAISQLLEGHDVVLVIGAPVFRYHQYDPG

QYLKPGTRLISVTCDPLEAARAPMGDAIVADIGAMASALANLVEESSRQLPTAAPEPAK

VDQDAGRLHPETVFDTLNDMAPENAIYLNESTSTTAQMWQRLNMRNPGSYYNCAAGG

LGFALPAAIGVQLAEPERQVIAVIGDGSANYSISALWTAAQYNIPTIFVIMNNGTYGALR

WFAGVLEAENVPGLDVPGIDFRALAKGYGVQALKADNLEQLKGSLQEALSAKGPVLIE

VSTVSPVK

Enzyme No 4:
                                                   (SEQ ID NO: 5)
MASVHGTTYELLRRQGIDTVFGNPGSNELPFLKDFPEDFRYILALQEACVVGIA

DGYAQASRKPAFINLHSAAGTGNAMGALSNAWNSHSPLIVTAGQQTRAMIGVEARLTN
```

-continued

```
VDAANLPRPLVKWSYEPASAAEVPHAMSRAIHMASMAPQGPVYLSVPYDDWDKDADP

QSHHLFDRHVSSSVRLNDQDLDILVKALNSASNPAIVLGPDVDAANANADCVMLAERL

KAPVWVAPSAPRCPFPTRHPCFRGLMPAGIAAISQLLEGHDVVLVIGAPVFRYHQYDPG

QYLKPGTRLISVTCDPLEAARAPMGDAIVADIGAMASALANLVEESSRQLPTAAPEPAK

VDQDAGRLHPETVFDTLNDMAPENAIYLNESTSTTAQMWQRLNMRNPGSYYNCAAGG

LGFALPAAIGVQLAEPERQVIAVIGDGSANYSISALWTAAQYNIPTIFVIMNNGTYGLLR

WFAGVLEAENVPGLDVPGIDFRALAKGYGVQALKADNLEQLKGSLQEALSAKGPVLIE

VSTVSPVK

Enzyme No 5:
                                                    (SEQ ID NO: 6)
MASVHGTTYELLRRQGIDTVFGNPGSNELPFLKDFPEDFRYILALQEACVVGIA

DGYAQASRKPAFINLHSAAGTGNAMGALSNAWNSHSPLIVTAGQQTRAMIGVEAVKT

NVDAANLPRPLVKWSYEPASAAEVPHAMSRAIHMASMAPQGPVYLSVPYDDWDKDA

DPQSHHLFDRHVSSSVRLNDQDLDILVKALNSASNPAIVLGPDVDAANANADCVMLAE

RLKAPVWVAPSAPRCPFPTRHPCFRGLMPAGIAAISQLLEGHDVVLVIGAPVFRYHQYD

PGQYLKPGTRLISVTCDPLEAARAPMGDAIVADIGAMASALANLVEESSRQLPTAAPEP

AKVDQDAGRLHPETVFDTLNDMAPENAIYLNESTSTTAQMWQRLNMRNPGSYYNCAA

GGNGFALPAAIGVQLAEPERQVIAVIGDGSANYSISALWTAAQYNIPTIFVIMNNGTYGA

LRWFAGVLEAENVPGLDVPGIDFRALAKGYGVQALKADNLEQLKGSLQEALSAKGPVL

IEVSTVSPVK

Enzyme No 6:
                                                    (SEQ ID NO: 242)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYLCAAGGLGFALPAAIGVQLAEP

ERQVIAVIGDGSANYSISALWTAAQYNVPTIFVIMNNGTYGTLRWFAGVLEAENVPGLDV

PGIDFRALAKGYGVQALKADNLEQLKGSLQEALSAKGPVLIEVSTVSPVK

Enzyme No 7:
                                                    (SEQ ID NO: 243)
MASVHGTTYELLRRQGIDIVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLDMRNPGSYYFCAAGGLGFALPAAIGVQLAEP

GRQVIAVIGDGSANYSISALWTAAQYNIPTIFVIMNNGTYGLLRWSAGVLGAENVPGLDV

PGIDFRALAKGYGVQALKADNLEQLKGSLQEALSAKGPVLIEVSTVSPVK
```

-continued

Enzyme No 8:
(SEQ ID NO: 244)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYFCAAGGLGFALPAAIGVQLAEP

ERQVIAVIGDGSANYSISALWTAAQYNIPTIFVIMNNGTYGGLRWFAGVLEAENVPGLDVP

GIDFRALAKGYGVQALKADNLEQLKGSLQEALSAKGPVLIEVSTVSPVK

Enzyme No 9:
(SEQ ID NO: 245)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYFCAAGGLGFALPAAIGVQLAEP

ERQVIAVIGDGSANYSISALWTAAQYNIPTIFVIMNNGTYGTLRWFAGVLEAENVPGLDVP

GIDFRALAKGYGVQALKADNLEQLKGSLQEALSAKGPVLIEVSTVSPVK

Enzyme No 10:
(SEQ ID NO: 246)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYACAAGGLGFALPAAIGVQLAEP

ERQVIAVIGDGSANYSISALWTAAQYNIPTIFVIMNNGTYGALRWFAGVLEAENVPGLDVP

GIDFRALAKGYGVQALKADNLEQLKGSLQEALSAKGPVLIEVSTVSPVK

Enzyme No 11:
(SEQ ID NO: 247)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYFCAAGGLGFALPAAIGVQLAEP

ERQVIAVIGDGSANYSISALWTAAQYNIPTIFVIMNNGTYGLLRWFAGVLEAENVPGLDVP

GIDFRALAKGYGVQALKADNLEQLKGSLQEALSAKGPVLIEVSTVSPVK

-continued

Enzyme No 12:
(SEQ ID NO: 248)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYFCAAGGLGFALPAAIGVQLAEP

ERQVIAVIGDGSANYSISALWTAAQYNIPTIFVIMNNGTYGALRWFAGVLEAENVPGLDVP

GIDFRALAKGYGVQALKADNLEQLKGSLQEALSAKGPVLIEVSTVSPVK

Enzyme No 13:
(SEQ ID NO: 249)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYFCAAGGLGFALPAAIGVQLAEP

ERQVIAVIGDGSANYSISALWTAAQYNIPTIFVIMNNGTYGTLRWFAGVLEAENVPGLDVP

GIDFRALAKGYGVQALKADNLEQLKGSLQEALSAKGPVLIEVSTVSPVK

Enzyme No 14:
(SEQ ID NO: 250)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYFCAAGGLGFALPAAIGVQLAEP

ERQVIAVIGDGSANYSISALWTAAQYNIPTIFVIMNNGTYGALRWFAGVLEAENVPGLDVP

GIDFRALAKGYGVQALKADNLEQLKGSLQEALSAKGPVLIEVSTVSPVK

Enzyme No 15:
(SEQ ID NO: 251)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYFCAAGGLGFALPAAIGVQLAEP

ERQVIAVIGDGSANYSISALWTAAQYNIPTIFVIMNNGTYGLLRWFAGVLEAENVPGLDVP

GIDFRALAKGYGVQALKADNLEQLKGSLQEALSAKGPVLIEVSTVSPVK

Enzyme No 16:
(SEQ ID NO: 252)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYLCAAGGLGFALPAAIGVQLAEP

ERQVIAVIGDGSANYSISALWTAAQYNVPTIFVIMNNGTYGLLRWFAGVLEAENVPGLDV

PGIDFRALAKGYGVQALKADNLEQLKGSLQEALSAKGPVLIEVSTVSPVK

Enzyme No 17:
(SEQ ID NO: 253)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYLCAAGGLGFALPAAIGVQLAEP

ERQVIAVIGDGSANYSISALWTAAQYNVPTIFVIMNNGTYGGLRWFAGVLEAENVPGLDV

PGIDFRALAKGYGVQALKADNLEQLKGSLQEALSAKGPVLIEVSTVSPVK

Enzyme No 18:
(SEQ ID NO: 254)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYLCAAGGLGFALPAAIGVQLAEP

ERQVIAVIGDGSANYSISALWTAAQYNVPTIFVIMNNGTYGTLRWSAGVLEAENVPGLDV

PGIDFRALAKGYGVQALKADNLEQLKGSLQEALSAKGPVLIEVSTVSPVK

Enzyme No 19:
(SEQ ID NO: 255)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYLCAAGGLGFALPAAIGVQLAEP

GRQVIAVIGDGSANYSISALWTAAQYNVPTIFVIMNNGTYGTLRWSAGVLGAENVPGLDV

PGIDFRALAKGYGVQALKADNLEQLKGSLQEALSAKGPVLIEVSTVSPVK

-continued

Enzyme No 20:
(SEQ ID NO: 256)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYLCAAGGLGFALPAAIGVQLAEP

GRQVIAVIGDGSANYSISALWTAAQYNIPTIFVIMNNGTYGTLRWSAGVLGAENVPGLDV

PGIDFRALAKGYGVQALKADNLEQLKGSLQEALSAKGPVLIEVSTVSPVK

Enzyme No 21:
(SEQ ID NO: 257)
MASVHGTTYELLRRQGIDIVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLDMRNPGSYYFCAAGGLGFALPAAIGVQLAEP

GRQVIAVIGDGSANYSISALWTAAQYNIPTIFVIMNNGTYGLLRWSAGVLGAENVPGLDV

PGIDFRALAKGYGVQALKADNLEQLKGSLQEALSAKGPVLIEVSTVSPVK

Enzyme No 22:
(SEQ ID NO: 258)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYNCAAGGLGFALPAAIGVQLAEP

ERQVIAVIGDGSANYSISALWTAAQYNIPTIFVIMNNGTYGLLRWFAGVLEAENVPGLDVP

GIDFRALAKGYGVQALKADNLEQLKGSLQEALSAKGPVLIEVSTVSPVK

Enzyme No 23:
(SEQ ID NO: 259)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYWCAAGGLGFALPAAIGVQLAEP

ERQVIAVIGDGSANYSISALWTAAQYNIPTIFVIMNNGTYGALRWFAGVLEAENVPGLDVP

GIDFRALAKGYGVQALKADNLEQLKGSLQEALSAKGPVLIEVSTVSPVK

Enzyme No 24:
(SEQ ID NO: 260)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYRCAAGGVGFALPAAIGVQLAEP

ERQVIAVIGDGSANYSISALWTAAQYNIPTIFVIMNNGTYGALRWFAGVLEAENVPGLDVP

GIDFRALAKGYGVQALKADNLEQLKGSLQEALSAKGPVLIEVSTVSPVK

Enzyme No 25:
(SEQ ID NO: 261)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYWCAAGGLGFALPAAIGVQLAEP

ERQVIAVIGDGSANYSISALWTAAQYNIPTIFVIMNNGTYGNLRWFAGVLEAENVPGLDVP

GIDFRALAKGYGVQALKADNLEQLKGSLQEALSAKGPVLIEVSTVSPVK

Enzyme No 26:
(SEQ ID NO: 262)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VTSSVRLNDQDLDILVKALNSASNPVIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYFCAAGGLGFALPAAIGVQLAEP

ERQVIAVIGDGSANYSISALWTAAQYNIPTIFVIMNNGTYGTLRWFAGVLEAENVPGLDVP

GIDFRALAKGYGVQALKADNLEQLKGSLQEALSAKGPVLIEVSTVSPVK

Enzyme No 27:
(SEQ ID NO: 263)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPATVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYACAAGGLGFALPAAIGVQLAEP

ERQVIAVIGDGSANYSISALWTAAQYNIPTIFVIMNNGTYGTLRWFAGVLEAENVPGLDVP

GIDFRALAKGYGVQALKADNLEQLKGSLQEALSAKGPVLIEVSTVSPVK

```
Enzyme No 28:
                                                       (SEQ ID NO: 264)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYLCAAGGLGFALPAAIGVQLAEP

ERQVIAVIGDGSANYSISALWTAAQYNIPTIFVIMNNGTYGTLRWFAGVLEAENVPGLDVP

GIDFRALAKGYGVQALKADNLEQLKGSLQEALSAKGPVLIEVSTVSPVK

Enzyme No 29:
                                                       (SEQ ID NO: 265)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYRCAAGGVGFALPAAIGVQLAEP

ERQVIAVIGDGSANYSISALWTAAQYNVPTIFVIMNNGTYGALRWFAGVLEAENVPGLDV

PGIDFRALAKGYGVQALKADNLEQLKGSLQEALSAKGPVLIEVSTVSPVK

Enzyme No 30:
                                                       (SEQ ID NO: 266)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYRCAAGGVGFALPAAIGVQLAEP

ERQVIAVIGDGSANYSISALWTAAQYNVPTIFVIMNNGTYGGLRWFAGVLEAENVPGLDV

PGIDFRALAKGYGVQALKADNLEQLKGSLQEALSAKGPVLIEVSTVSPVK

Enzyme No 31:
                                                       (SEQ ID NO: 267)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYWCAAGGSGFALPAAIGVQLAEP

ERQVIAVIGDGSANYSISALWTAAQYNVPTIFVIMNNGTYGNLRWFAGVLEAENVPGLDV

PGIDFRALAKGYGVQALKADNLEQLKGSLQEALSAKGPVLIEVSTVSPVK
```

-continued

Enzyme No 32:
(SEQ ID NO: 268)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYWCAAGGLGFALPAAIGVQLAEP

ERQVIAVIGDGSANYSISALWTAAQYNIPTIFVIMNNGTYGLLRWFAGVLEAENVPGLDVP

GIDFRALAKGYGVQALKADNLEQLKGSLQEALSAKGPVLIEVSTVSPVK

Enzyme No 33:
(SEQ ID NO: 269)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYRQYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYRCAAGGLGFALPAAIGVQLAEP

ERQVIAVIGDGSANYSISALWTAAQYNIPTIFVIMNNGTYGLLRWFAGVLEAENVPGLDVP

GIDFRALAKGYGVQALKADNLEQLKGSLQEALSAKGPVLIEVSTVSPVK

Enzyme No 34:
(SEQ ID NO: 270)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRHRYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYWCAAGGLGFALPAAIGVQLAEP

ERQVIAVIGDGSANYSISALWTAAQYNIPTIFVIMNNGTYGTLRWFAGVLEAENVPGLDVP

GIDFRALAKGYGVQALKADNLEQLKGSLQEALSAKGPVLIEVSTVSPVK

Enzyme No 35:
(SEQ ID NO: 271)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPENAIYLNESTSTTAQMWQRLNMRNPGSYYRCAAGGLGFALPAAIGVQLAEP

ERQVIAVIGDGSANYSISALWTAAQYNIPTIFVIMNNGTYGTLRWFAGVLEAENVPGLDVP

GIDFRALAKGYGVQALKADNLEQLKGSLQEALSAKGPVLIEVSTVSPVK

-continued

Enzyme No 36:
(SEQ ID NO: 272)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRYHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYRCAAGGVGFALPAAIGVQLAEP

ERQVIAVIGDGSANYSISALWTAAQYNVPTIFVIMNNGTYGTLRWFAGVLEAENVPGLDV

PGIDFRALAKGYGVQALKADNLEQLKGSLQEALSAKGPVLIEVSTVSPVK

Enzyme No 37:
(SEQ ID NO: 273)
MASVHGTTYELLRRQGIDTVFGNPGSNELPFLKDFPEDFRYILALQEACVVGIADGYAQAS

RKPAFINLHSAAGTGNAMGALSNAWNSHSPLIVTAGQQTRAMIGVEARLTNVDAANLPR

PLVKWSYEPASAAEVPHAMSRAIHMASMAPQGPVYLSVPYDDWDKDADPQSHHLFDRH

VSSSVRLNDQDLDILVKALNSASNPAIVLGPDVDAANANADCVMLAERLKAPVWVAPSA

PRCPFPTRHPCFRGLMPAGIAAISQLLEGHDVVLVIGAPVFRHRYDPGQYLKPGTRLISVT

CDPLEAARAPMGDAIVADIGAMASALANLVEESSRQLPTAAPEPAKVDQDAGRLHPETVF

DTLNDMAPEDAIYLNESTSTTAQMWQRLNMRNPGSYYWCAAGGSGFALPAAIGVQLAEP

ERQVIAVIGDGSANYSISALWTAAQYNVPTIFVIMNNGTYGTLRWFAGVLEAENVPGLDV

PGIDFRALAKGYGVQALKADNLEQLKGSLQEALSAKGPVLIEVSTVSPVK

When one of the enzymes of the invention of sequence SEQ ID NO:274 as described herein was expressed in the Δfms1-Pyd4lk strain, this yeast was able to grow on a pantothenate free medium.

These in vivo results show that the enzymes of the disclosure catalyze the transformation of oxaloacetate into malonic semialdehyde or one of its derivatives, such as for example malonate semialdehyde.

Example 3: 3-HP Production from MSA

3-HP Dehydrogenase

Most 3-HP dehydrogenase enzymes (Table 1) accept NADPH as a cofactor to convert malonate semialdehyde to 3-hydroxypropionic acid, but the use of NADH is desirable to get a redox balanced pathway. To contemplate this issue, the 3-HP dehydrogenase encoded by the HPD1 gene from the yeast *Candida albicans*, also active in *Saccharomyces* cells was identified and characterized as a 3-HP dehydrogenase working in the Propionyl-CoA degradation pathway and it was demonstrated to sustain efficient 3-HP synthesis from malonate semialdehyde, while using preferentially NADH as cofactor. The full-length HPD1.Cal gene was therefore cloned and expressed on a plasmid under the control of a strong promoter in *Saccharomyces cerevisiae* cells and compared with other enzymes. On the assay, it was used 20 mM of malonate semialdehyde and 2 mM of cofactor (NADPH or NADH). 3-HP was measured by GC-MS/MS after derivatization with BSTFA (data not shown).

TABLE 18

Constructed strain to test the 3-HP dehydrogenase.

| Strain | Genotype |
| --- | --- |
| YA3542-3 | MAT-α, ade2, adh1::[ADH1-4-URA3.Kl-loxP], adh3::RS, adh4::RS, adh5::RS, can1-100, his3, leu2, pdc1::HIS5.Sp-loxP, pdc6::LEU2.Kl-loxP, trp1, ura3 |

TABLE 19

Plasmids constructed with different 3-HP dehydrogenases.

| Plasmid | Description |
| --- | --- |
| pAD4003 | pRS314-pCCW12-YDFG.Ec-tRPL15A |
| pAD4042 | pRS314-pCCW12-YDF1-tRPL15A |
| pAD4287 | pRS314-pCCW12-YDF1-11-tRPL15A |
| pAD4346 | pRS314-pCCW12-HPD1.Cal-tRPL15A |

TABLE 20

Activity of 3-HP dehydrogenases based on cofactor consuming (in-vitro).

| Strain | Relevant genotype | Activity (nmol · min$^{-1}$ · mg$^{-1}$) NADPH | Activity (nmol · min$^{-1}$ · mg$^{-1}$) NADH |
|---|---|---|---|
| YA3542-3 | WT | Not detected | |
| YA3542-3 + pAD4003 | pRS314-pSTRONG-YDFG-0.Ec | 50 | Not detected |
| YA3542-3 + pAD4042 | pRS316-pSTRONG-YDF1 | 2750 (+/−250) | 2 (+/−1) |
| YA3542-3 + pAD4287 | pRS316-pSTRONG-YDF1 – 11 (S22N + A47D + R48F) | 50 | 48 (+/−2) |
| YA3542-3 + pAD4346 | pRS316-pSTRONG-HPD1.Cal | 200 | 2500 |

It was demonstrated that HPD1.Cal is highly active in the catalysis of 3-1HP formation from MSA and further displays a preferential use of NADH as cofactor.

Example 4: 3-HP Production from Glucose—Carbon Flux Rewiring from PEP to Oxaloacetate This example describes enzymatic conversion of malonate semialdehyde to 3-HP. The MSA was produced by the β-alanine pathway (FIG. 3).

The redirection of the carbon flow towards oxaloacetate can be achieved through the implementation of the Oxaloacetate shunt, based on the strong expression of phosphoenolpyruvate carboxykinase from *E. coli* (PEPCK.Ec), while the yeast pyruvate kinase activity is strongly attenuated by (i) expressing the PYK1 gene from a weak promoter (pNUP57 or pMET25ΔF) and (ii) decreasing the half-life of the protein itself by its fusion to a specific degron (PYK1-7). Such strategy is described in WO2019011945A1 and WO2019011948A1.

Figure 20:
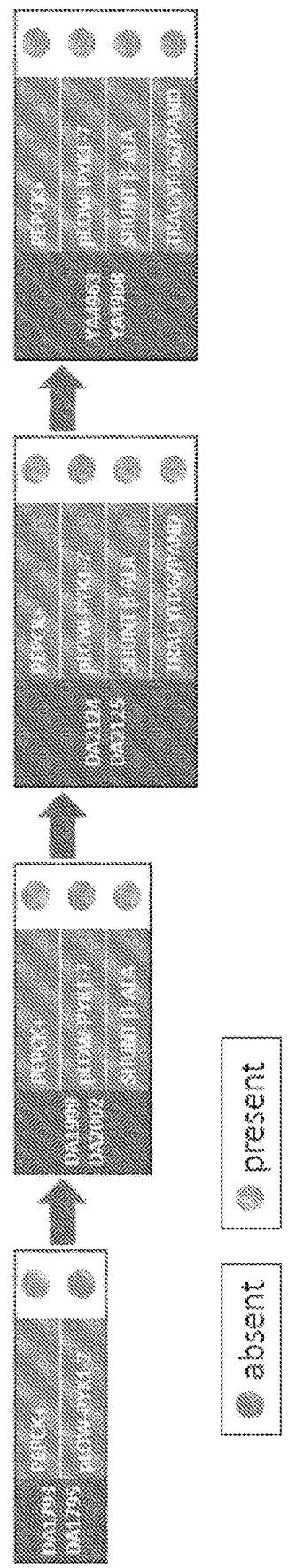
FIG. 20 depicts the workflow for engineering an organism to produce 3-HP from glucose.
Figure 21:
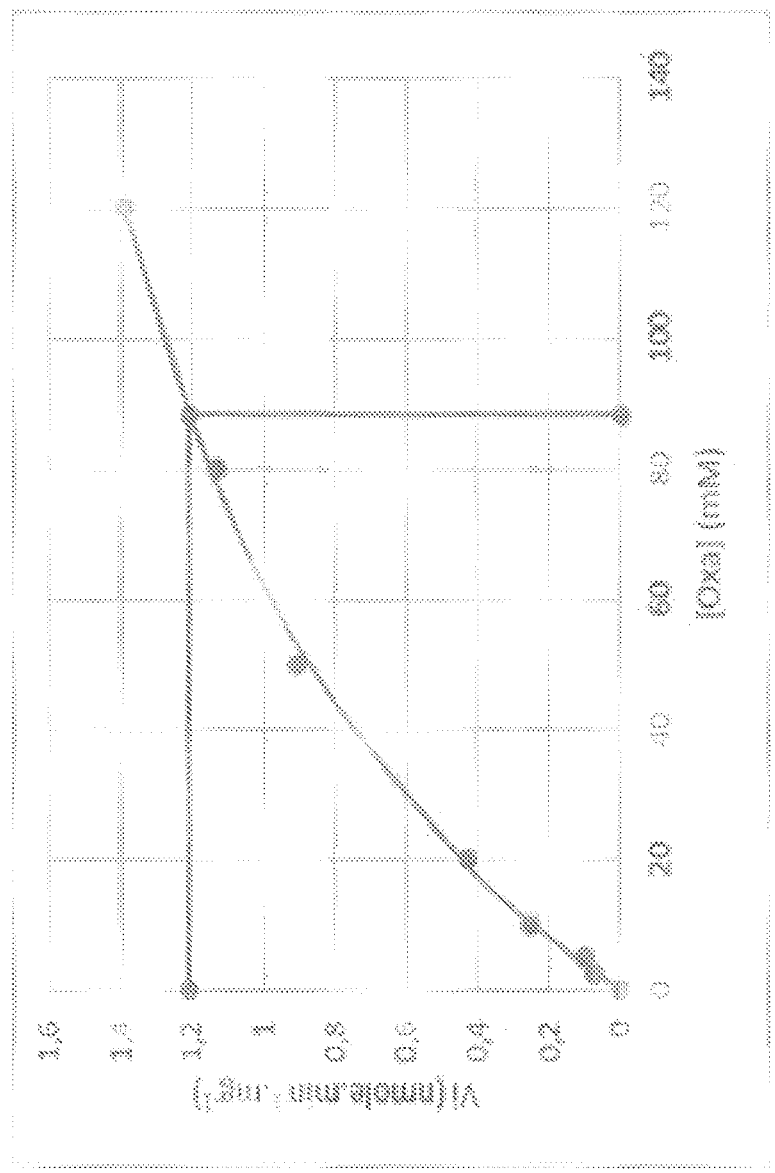
FIG. 21 is a plot and values demonstrating kinetic parameters for Enzyme N° 1.
Figure 22:
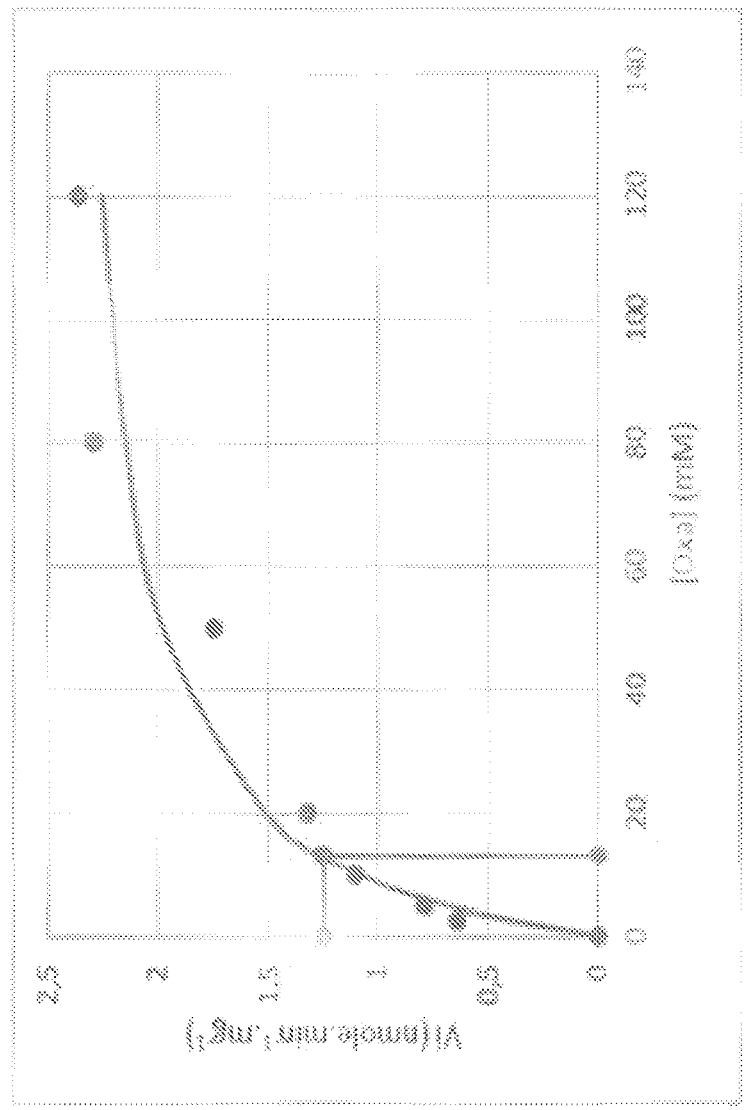
FIG. 22 is a plot and values demonstrating kinetic parameters for Enzyme N° 6.
Figure 23:
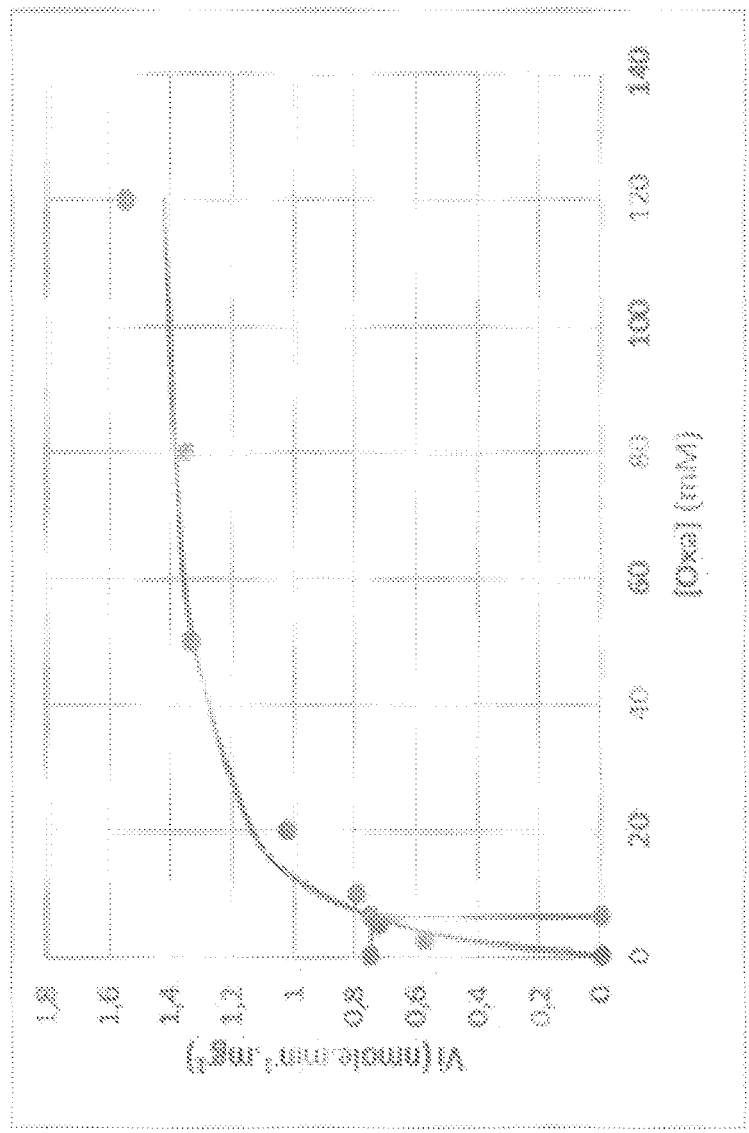
FIG. 23 is a plot and values demonstrating kinetic parameters for Enzyme N° 7.
Figure 24:
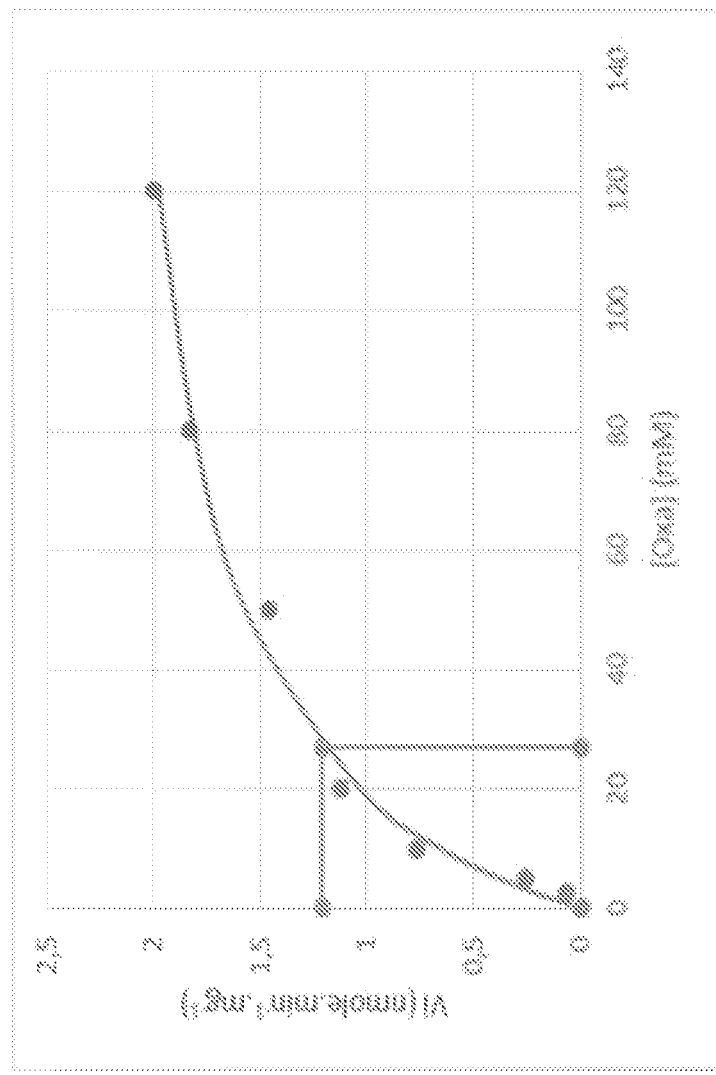
FIG. 24 is a plot and values demonstrating kinetic parameters for Enzyme N° 8.
Figure 25:
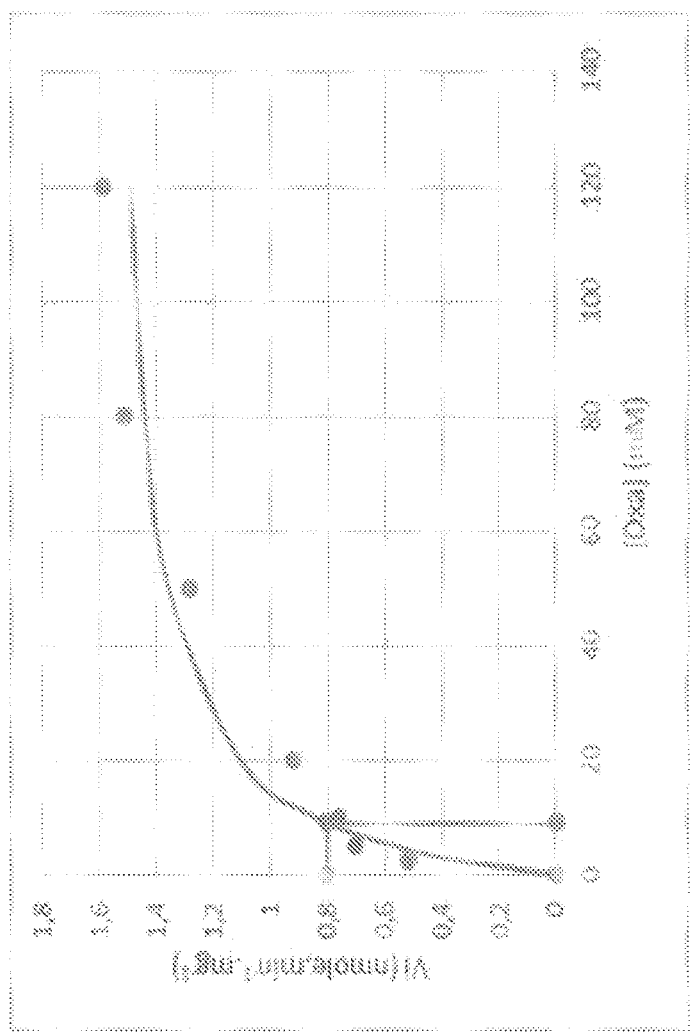
FIG. 25 is a plot and values demonstrating kinetic parameters for Enzyme N° 9

The engineering workflow (FIG. 20) starts with diploid strains that comprise an inactive oxaloacetate shunt, as the pLow-PYK1-7 is present in only one chromosome, and it ends by a sporulation step allowing the oxaloacetate shunt activation. The final haploid strains are YA4963 and YA4968 (Table 21).

Strains were thus assayed for 3-HP production in anaerobic growth conditions: 10 mL of rich medium in the presence of 8% glucose in 50 mL closed Falcon tubes. Stirring at 135 rpm (50 mm shaking diameter). The 3-HP analysis was done after 48 h of growth using GC/FID (after 3-HP extraction in presence of 1-butanol).

TABLE 21

Strains constructed to improve carbon flux rewiring from PEP.

| Strain | Genotype |
|---|---|
| DA2124-14 | MAT-a/MAT-α, can1-100/can1-100, his3/his3, JLP1/jlp1::[TRP1.Kl-loxP-PYK1-7], leu2/leu2, MET14/met14::[HIS3.Sba-RS-PAND.Tca-PYD4.Lk-YDFG-0.Ec], PYK1/pyk1::[LEU2.Kl-loxP-PEPCK-1.Ec-AAT2-PEPCK-1.Ec], trp1/trp1, ura3/ura3::[PAND.Tca-YDFG-0.Ec-URA3]x9 |
| YA4963-25A | jlp1::[TRP1.Kl-loxP-pNUP57-PYK1-7], met14::[HIS3.Sba-RS-PAND.Tca-PYD4.Lk-YDFG-0.Ec], pyk1::[LEU2.Kl-loxP-PEPCK-1.Ec-AAT2-PEPCK-1.Ec], ura3::[PAND.Tca-YDFG-0.Ec-URA3]x9 |
| YA4968-12C | jlp1::[TRP1.Kl-loxP-pMET25DF-PYK1], met14::[HIS3.Sba-RS-PAND.Tca-PYD4.Lk-YDFG-0.Ec], pyk1::[LEU2.Kl-loxP-PEPCK-1.Ec-AAT2-PEPCK-1.Ec], ura3::[PAND.Tca-YDFG-0.Ec-URA3]x10 |

In fermentative conditions, PYK1 attenuated strains (YA4963-21C and YA4963-25A) produced more 3-HP (7.8 g/L of 3-HP) than their parental strain (0.9 g/L of 3-HP) without PYK1 attenuation (DA2124-12) (Table 22)

TABLE 22

3-HP production (in-vivo) after PYK1-7 attenuation.

| Strain | OD 600 nm | 3-HP (g · L$^{-1}$) | Glucose (g · L$^{-1}$) | Ethanol (g · L$^{-1}$) | Glycerol (g · L$^{-1}$) | PYK1 Activity (nmol · min$^{-1}$ · mg$^{-1}$) |
|---|---|---|---|---|---|---|
| DA2124-12 | 59 | 0.9 | 0 | 39 | 2 | 6200 |
| YA4963-21C | 37 | 5.1 | 42 | 15 | 5 | 130 |
| YA4963-25A | 22 | 7.8 | 44 | 11 | 8 | 150 |

Pyruvate Kinase activity has been determined as described in Aust, A.; Yun, S. L.; Suelter, C. H. (1975) Methods Enzymol. 42C, 176-182

Example 5: 3-HP Production from Glucose Through Oxaloacetate Decarboxylase

Oxaloacetate decarboxylase enzyme candidates have been prospected and successfully engineered to deliver an active enzyme to convert oxaloacetate into malonate semialdehyde and in a second step to leverage a novel fermentative metabolic pathway to produce MSA, 3-HP and derivatives from glucose.

To illustrate the oxaloacetate decarboxylase enzyme engineering R&D efforts and the magnitude of the MDLC enzyme (*Pseudomonas putida*) engineering results, the resulting activity can be compared to the value obtained in a similar approach with the wild type aspartate decarboxylase (PAND.Tca of *Tribolium castaneum*), that catalyzes the aspartate conversion to (3-alanine. As described previously, 5-8 g/L of 3-HP was successfully produced from glucose through the β-alanine route by the use of the enzyme aspartate decarboxylase (PAND.Tca). As described in the table below, the variant MDLC-54 has been shown to be as active as the aspartate decarboxylase PAND.Tca (4× lower activity only), indicating such variant would be able to sustain the in-vivo production of 3-HP from glucose (Table 23).

TABLE 23

Activities of MDLC-54 and PAND.Tca

| Enzyme | Activity (nmol/min/mg) |
|---|---|
| Engineered variant MDLC-54 | 10-15 |
| Wild type Pand.Tca | 2-2.5 |

An Oxaloacetate decarboxylase assay was carried out with yeast cell extracts containing 50, 100, 150 and 200 μg of total protein in 100 mM phosphate buffer pH 6 for 40 min at 30° C. in the presence of oxaloacetate (20 mM), $MgSO_4.7H_2O$ (2 mM), TPP (2 mM), NADPH (2 mM) and a purified YdfG enzyme (4 μg/100 μL) The formation of 3-HP was measured by GC/MS/MS after derivatization with BSTFA.

Aspartate decarboxylase (PAND.Tca) was carried out with yeast cell extracts containing 20, 40, 60 and 80 μg of total protein in 100 mM phosphate buffer pH 7 for 20 min at 30° C. in the presence of aspartate (20 mM). The formation of Beta-alanine was measured by UPLC/UV after derivatization with AQC (6-Aminoquinolyl-n-hydroxysuccimidyl carbamate).

Based on these results, assays are additionally performed to analyse the kinetic properties of enzymes of the invention through the measure of their $K_m$ and $V_{max}$, using extracts of yeasts expressing the different MDLC variants.

The kinetic assays are carried out with 100 μg of yeast extracts for 30 minutes in the presence of increasing concentrations of oxaloacetate (2.5, 5, 10, 20, 40, 80 and 120 mM), of purified YdfG (NADP-dependent 3-hydroxy acid hydrogenase—EC 1.1.1.298) from *E. coli* (4 μg/100 μL) and 2 mM NADPH.

The efficiency of the enzymes of the invention is assayed through the formation of 3-HP that is measured by GC/MS/MS after derivatization with BSTFA (N,O-bis(trimethylsilyl)trifluoroacetamide).

As negative control, this assay is performed on a yeast extract not comprising an enzyme according to the invention. No significant activity is detected.

The results obtained with yeast strains comprising either enzyme N° 1 (SEQ ID NO: 2), enzyme N° 6 (SEQ ID NO: 242), enzyme N° 7 (SEQ ID NO: 243), enzyme N° 8 (SEQ ID NO: 244) or enzyme N° 9 (SEQ ID NO: 245) are in particular represented in FIG. 21, FIG. 22, FIG. 23, FIG. 24, and FIG. 25, respectively.

It can be observed that very low $K_m$ are obtained, demonstrating that the enzymes of the invention are very effective.

Example 6: Acetone Production from MSA

Acetyl-CoA Production from MSA

Genes of table 2 were cloned and expressed on a plasmid under the control of a strong promoter in *Saccharomyces cerevisiae* cells (Table 24).

No MSD activity was detected using NADP as a cofactor. Using NAD as the co-enzyme, both MSD.Cal and MSD.Pa were active with an activity of 40 $nmol.min^{-1}.mg^{-1}$ (Table 25).

Yeast extract from the considered strains was incubated in the presence of 80 mM Beta-alanine, 20 mM Oxoglutarate, 100 M Pyridoxal Phosphate, 1 mM NAD, 0.5 mM Coenzyme A and 1 mM DTT in phosphate buffer 100 mM pH 7.5. Beta-alanine and oxoglutarate were converted in MSD and β-alanine by the PYD-4 transaminase. The MSD activity was then monitored by following NADH appearance by UV absorbance at 340 nM. No increase of absorbance at 340 nM was observed if either oxoglutarate or beta-alanine was omitted, or in a strain in which no MSD activity was expressed. This assay was adapted from Andersen and Piskur FEBS journal, (2007) 274, 1804-1817 and Waters and Venables FEMS Microbiology Letters 34 (1986) 279-282.

TABLE 24

Strains constructed to acetone production.

| Strain | Genotype |
|---|---|
| YA4666-1 | MAT-a, ade2, can1-100, fms1::ADE2.Sba-RS, his3, jlp1::[HIS3.Sba-RS-PYD4.Lk], trp1, ura3 |
| YA4750-2/-4 | MAT-a, ade2, can1-100, fms1::ADE2.Sba-RS, his3, jlp1::[HIS3.Sba-RS-PYD4.Lk], met14::[TRP1.Kl-RS-MSD.Cal], trp1, ura3 |
| YA4751-2 | MAT-a, ade2, can1-100, fms1::ADE2.Sba-RS, his3, jlp1::[HIS3.Sba-RS-PYD4.Lk], met14::[TRP1.Kl-RS-MSD.Pa], trp1, ura3 |

TABLE 25

Activity of malonate semialdehyde dehydrogenase based on cofactor consumption.

| Strain | Relevant genotype | Activity (nmol · $min^{-1}$ · $mg^{-1}$) NADP | Activity (nmol · $min^{-1}$ · $mg^{-1}$) NAD |
|---|---|---|---|
| YA4666-1 | WT | Not detected | |
| YA4750-2 | YA4666-1 + pSTRONG-MSD.Cal | Not detected | 40 |
| YA4751-2 | YA4666-1 + pSTRONG-MSD.Pa | | 40 |
| YA4750-4 | | | 40 |

Acetoacetyl-CoA Production from Acetyl-CoA

For the conversion of acetyl-CoA to acetoacetyl-CoA, the enzyme ERG10 (*S. cerevisiae*) that is able to catalyze this reaction was preferentially used (data not shown), according to Hiser L, et al. (1994) ERG10 from *Saccharomyces cerevisiae* encodes acetoacetyl-CoA thiolase. J Biol Chem 269(50):31383-9.

Acetone Production from Acetyl-CoA In Vivo

To identify the best combination of acetoacetyl-CoA transferase/acetoacetate decarboxylase, a combination of different gene candidates have been integrated as clusters in the YA4565-2 strain (Table 26), in which the carbon flux is directed through the β-Alanine shunt allowing malonate semialdehyde production (FIG. 3).

TABLE 26

Constructed strains to produce acetone.

| Strain | Relevant Genotype |
|---|---|
| YA4565-2 | his3, leu2, met14::[HIS3.Sba-RS-PAND.Tca-PYD4.Lk], trp1, ura3 |
| YA5060 | YA4565-2 + jlp1::[LEU2.Sba-RS-MSD.Pa-MSD.Cal-ERG10-ATOA-0.Ec-ATOD-0.Ec-ADC-0.Ca-PTA.Cg-ACKA.Ec] |
| YA5061 | YA4565-2 + jlp1::[LEU2.Sba-RS-MSD.Pa-MSD.Cal-ERG10-ATOA-0.Ec-ATOD-0.Ec-ADC-0.Cbe-PTA.Cg-ACKA.Ec] |
| YA5062 | YA4565-2 + jlp1::[LEU2.Sba-RS-MSD.Pa-MSD.Cal-ERG10-ATOA-0.Ec-ATOD-0.Ec-ADC-0.Pp-PTA.Cg-ACKA.Ec] |
| YA5063 | YA4565-2 + jlp1::[LEU2.Sba-RS-MSD.Pa-MSD.Cal-ERG10-CTFA-0.Ca-CTFB-0.Ca-ADC-0.Ca-PTA.Cg-ACKA.Ec] |
| YA5064 | YA4565-2 + jlp1::[LEU2.Sba-RS-MSD.Pa-MSD.Cal-ERG10-CTFA-0.Ca-CTFB-0.Ca-ADC-0.Cbe-PTA.Cg-ACKA.Ec] |
| YA5065 | YA4565-2 + jlp1::[LEU2.Sba-RS-MSD.Pa-MSD.Cal-ERG10-CTFA-0.Ca-CTFB-0.Ca-ADC-0.Pp-PTA.Cg-ACKA.Ec] |

TABLE 27

Acetone production (in vivo) using proposed genes.

| Strain | OD 600 nm | Total culture Acetone (g · L$^{-1}$) | Supernatant Acetone (g · L$^{-1}$) |
|---|---|---|---|
| YA4565-2 | 36 | 0 | 0 |
| YA5063-1 | 31 | 0.1 | 0.1 |
| YA5063-2 | 35 | 0.1 | 0.1 |
| YA5064-2 | 31 | 0.1 | 0.1 |
| YA5064-3 | 33 | 0.1 | 0.1 |
| YA5065-1 | 37 | 0.2 | 0.2 |
| YA5065-2 | 36 | 0.2 | 0.2 |
| YA5060-1 | 31 | 0.3 | 0.3 |
| YA5060-2 | 33 | 0.3 | 0.3 |
| YA5061-1 | 39 | 0.1 | 0.1 |
| YA5061-2 | 31 | 0.1 | 0.1 |
| YA5062-1 | 33 | 0.5 | 0.5 |
| YA5062-2 | 33 | 0.5 | 0.5 |

In both series of strains, the most efficient acetoacetate decarboxylase was ADC-0 of *Paenibacillus polymyxa*. The best combination of enzymes corresponded to acetoacetyl-CoA transferase ATOA-0-ATOD-0 of *Escherichia coli* and acetoacetate decarboxylase ADC-0 of *Paenibacillus polymyxa*. To increase acetone production, additional copies of MSD.Pa and PanD.Tca were integrated within the genome of the YA5060 and YA5062 strains (Table 28).

TABLE 28

Strains constructed with additional copies of genes to produce acetone.

| Strain | Relevant Genotype |
|---|---|
| YA4565-2 | his3, leu2, met14::[HIS3.Sba-RS-PAND.Tca-PYD4.Lk], trp1, ura3 |
| YA5060-1 | jlp1::[LEU2.Sba-RS-MSD.Pa-MSD.Cal-ERG10-ATOA-0.Ec-ATOD-0.Ec-ADC-0.Ca-PTA.Cg-ACKA.Ec] leu2, met14::[HIS3.Sba-RS-PAND.Tca-PYD4.Lk] |
| YA5182-4/-11 | YA5060-1 ura3:: [PAND.Tca-MSD.Pa-URA3]x2/x4 |
| YA5062-1 | jlp1::[LEU2.Sba-RS-MSD.Pa-MSD.Cal-ERG10-ATOA-0.Ec-ATOD-0.Ec-ADC-0.Pp-PTA.Cg-ACKA.Ec], leu2, met14::[HIS3.Sba-RS-PAND.Tca-PYD4.Lk |
| YA5183-1/-23 | YA5062-1 ura3::[PAND.Tca-MSD.Pa-URA3]x1/x5 |

Strains were cultured in 25 mL of rich medium in the presence of 200 glucose in Erlenmeyer flask closed with a silicon cap with two 1 mL pipette tip with filter and stirring was maintained at 135 rpm (50 mm shaking diameter). Samples are kept in ice until analysis or frozen at −20° C. The acetone was measured by GC/MS head space after 24 h of growth (Table 27).

The resulting strains YA5182 and YA5183 were grown in 25 mL of rich medium in the presence of 8% glucose in Erlenmeyer flask with a silicon cap+two 1 mL pipette tips with filter. Stirring was maintained at 135 rpm (50 mm shaking diameter) and the production of acetone was measured after 48 h of growth by GC/MS-MS head space analysis (Table 29).

TABLE 29

Acetone production by strains having more genes copies of MSD.Pa and PanD.Tca.

| Strain | OD 600 nm | Acetone (g · L$^{-1}$) | Ethanol (g · L$^{-1}$) |
|---|---|---|---|
| YA4565-2 | 51 | 0 | 39 |
| YA5060-1 | 69 | 0.7 | 36 |
| YA5182-4 | 77 | 1.0+/−0.1 | 34 |
| YA5182-11 | 75 | 1 | 35 |
| YA5062-1 | 68 | 0.8 | 35 |
| YA5183-1 | 70 | 1.1 | 34 |
| YA5183-23 | 79 | 1.2+/−0.1 | 34 |

Example 7. Propanol Production from 3-HP

Propionyl-CoA Production from 3-HP Using Propionyl-CoA Synthase of *Chloroflexus aurantiacus* In Vitro The PCS of *Chloroflexus aurantiacus* activity was measured using two strategies: a) integration of multiple copies of the PCS.Cau gene under the control of a strong promoter and b) usage and evaluation of different synonymous sequences of the gene obtained by several re-encoding algorithms to avoid any deleterious recombination event. The best variant was PCS-A.Cau and the activity was higher according to the number of gene copies. It is noteworthy that at 30° C., the enzyme activity was 8-10-fold lower than at 50° C.

The results were measured by production of Propionyl-CoA by UPLC/UV as described in Alder and Fuchs (2002) Journal of biological chemistry, 277 (14), 12137-12143

TABLE 30

Strains constructed with different PCS genes to produce propanol.

| Strain | Relevant Genotype |
|---|---|
| YA4788-2 | MAT-a, can1-100, his3, jlp1::[LEU2.Sba-RS-PCS.Cau], leu2, met14::[HIS3.Sba-RSPAND.Tca-PYD4.Lk-YDFG-0.Ec], trp1, ura3: :[PAND.Tca-URA3]x14 |
| YA4971 | MAT-a, can1-100, his3, jlp1::[LEU2.Sba-RS-PCS-A.Cau], leu2, met14:: [HIS3. Sba-RS-PAND.Tca-PYD4.Lk-YDFG-0.Ec], trp1, ura3: :[PAND.Tca-URA3]x14 |
| YA5068 | his3, jlp1::[LEU2.Sba-RS-PCS-A.Cau-PCS-A.Cau-PCS-A.Cau-PCS-A.Cau], leu2, met14::[HIS3.Sba-RS-PAND.Tca-PYD4.Lk-YDFG-0.Ec],trp1, ura3:: [PAND.Tca-URA3 ]x14 |
| YA5133 | MAT-a, can1-100, his3, jlp1::[LEU2.Sba-RS-PCS-D.Cau], leu2, met14::[HIS3.Sba-RS-PAND.Tca-PYD4.Lk-YDFG-0.Ec], trp1, ura3:: [PAND.Tca-URA3]x14 |

TABLE 31

Activity of different variants of PCS in different temperatures evaluated by cofactor consumption.

| Strain | Relevant genotype | Activity (nmol · min$^{-1}$ · mg$^{-1}$) 50° C. | Activity (nmol · min$^{-1}$ · mg$^{-1}$) 30° C. |
|---|---|---|---|
| YA4788-2 | PCS.Cau | 15 | ND |
| YA4971-2/-3 | PCS-A.Cau | 42 | 5 |
| YA5133-2/-6 | PCS-D.Cau | 41 | 5 |
| YA5068-18 | 4x PCS-A.Cau | 200 | 21 |

Propionyl-CoA Production from 3-HP Using Single Enzymes (In Vitro)

Screening of 3-HP-CoA Transferase

The 3-hydroxypropionyl-coA transferase activities from *Cupriavidus necator* and *Clostridium propionicum* were assayed. The in vitro activity was measured essentially as described in Volodina E., Schurmann M., Lindenkamp N., Steinbüchel A. (2014) Appl Microbiol Biotechnol 98:3579-3589. Crude extracts of strains YA4951-4, YA4952-2 and YA5067 (Table 32) were diafiltrated (cut-off 3 Kda) and the protein content was evaluated. Extracts containing, 5, 10, 20, 40, 80 or 160 µg of protein were incubated in presence of 20 mM 3 HP, 2 mM acetyl-CoA, 1 mM NADPH and 2 mM MgCl$_2$ for 30 minutes at 30° C. The reaction was then stopped by addition of HClO$_4$ 1% and the quantity of 3 hydroxypropionyl-CoA formed was determined by HPLC. The most active enzyme was PCT from *Clostridium propionicum*.

TABLE 32

Strains constructed with different PCT genes to produce 3-HP-CoA from 3-HP.

| Strain | Relevant Genotype |
|---|---|
| YA4951-4 | jlp1::[LEU2.Sba-RS-PCT-0.Cne-PCT-0.Cne-PCT-0.Cne-PCT-0.Cne] |
| YA4952-2 | jlp1::[LEU2.Sba-RS-PCT-0.Cp-PCT-0.Cp-PCT-0.Cp-PCT-0.Cp] |
| YA5067 | MAT-a, ade2, can1-100, his3, leu2::[HIS3.Sba-RS-PCT-0.Cp-HPCD-0.Sac-HPCD-0.Sac-HPCD-0.Sac-HPCD-0.Sac], trp1, ura3 |

TABLE 33

Activity of PCT measured by acetyl-CoA consumption.

| Strain | Relevant genotype | Activity (nmol · min$^{-1}$ · mg$^{-1}$) |
|---|---|---|
| YA4951-4 | PCT-0.Cne x4 | 140 |
| YA4952-2 | PCT-0.Cp x4 | 240 |
| YA5067-1 | PCT-0.Cp x1 | 77 |
| YA5067-4 | | 64 |

Screening of 3-HP-CoA Dehydratase

3-HP-CoA dehydratases from *Metallosphaera sedula* (HPCD.Mse), *Bacillus* sp. (HPCD.Bsp), *Sporanaerobacter acetigenes* (HPCD-0.Sac) and enoyl-CoA hydratase of *Ruegeria pomeroyi* (ENCD.Rp) were assayed. The strain YA4952-2 was transformed with the following plasmids.

TABLE 34

Plasmids constructed with 3-hydroxypropionyl-CoA dehydratases/Enoyl-CoA hydratase.

| Plasmid | Description |
|---|---|
| pAD3967 | pFL45L-pCCW12.Sba-HPCD.Mse-tRPL15A |
| pAD3968 | pFL45L-pCCW12.Sba-HPCD.Bsp-tRPL15A |
| pAD3969 | pFL45L-pCCW12.Sba-HPCD-0.Sac-tRPL15A |

TABLE 34-continued

Plasmids constructed with 3-hydroxypropionyl-CoA dehydratases/Enoyl-CoA hydratase.

| Plasmid | Description |
|---|---|
| pAD3970 | pFL45L-pCCW12.Sba-ENCD.Rp-tRPL15A |

The in vitro activity was measured essentially as described in Asao, M. & Alber, B. E (2013). Journal of Bacteriology 195, 4716-4725. Crude extracts of the strain YA4952-2 transformed with the plasmids described in table 34 were diafiltrated (cut-off 3 Kda) and the protein content was evaluated. Extracts containing, 5, 10, 20, 40 or 80 µg of protein were incubated in presence of 20 mM 3 HP, 2 mM acetyl-CoA, 1 mM NADPH and 2 mM $MgCl_2$ for 30 minutes at 30° C. The reaction was then stopped by addition of $HClO_4$ 1% and the quantity of acrylyl-CoA formed was determined by HPLC—The 3-HP-CoA dehydratases of *Metallosphaera sedula* and *Sporanaerobacter acetigenes* were slightly more active than the other candidates.

TABLE 35

Activity of 3-hydroxypropionyl-CoA dehydratase measured by acrylyl-CoA peak area.

| Strain | µg of crude extract | Peak area |
|---|---|---|
| YA4952-2 | 80 | <LOQ* |
| YA4952-2 + pAD3970 | 80 | <LOQ |
| YA4952-2 + pAD3968 | 10 | 4000 |
| | 20 | 5000 |
| | 40 | 7000 |
| | 80 | 8000 |
| YA4952-2 + pAD3969 | 10 | 5000 |
| | 20 | 8000 |
| | 40 | 9000 |
| | 80 | 10000 |
| YA4952-2 + pAD3967 | 10 | 5000 |
| | 20 | 8000 |
| | 40 | 11000 |
| | 80 | 13000 |

*limit of quantification

Screening of Acrylyl-CoA Reductase

The acrylyl-CoA reductase of *Ruegeria pomeroyi* was assayed in vitro.essentially as described in Asao, M. & Alber, B. E (2013). Journal of Bacteriology 195, 4716-4725. Crude extracts of the strain YA4952-2 were diafiltrated (cut-off 3 Kda) and the protein content was evaluated. Extracts containing, 5, 10, 20 or 30 µg of protein were incubated in presence of 20 mM 3 HP, 2 mM acetyl-CoA, 1 mM NADPH and 2 mM $MgCl_2$ for 30 minutes at 30° C. The reaction was then stopped by addition of $HClO_4$ 1% and the quantity of propionyl-CoA formed was determined by HPLC. It was possible to observe that ACR from *Ruegeria pomeroyi* was highly active in yeast cells.

TABLE 36

Strains constructed with acrylyl-CoA reductase from *Ruegeria pomeroyi*.

| Strain | Relevant Genotype |
|---|---|
| YA5057 | MAT-a, ade2, can1-100, his3, jlp1::[LEU2.Sba-RS-PCT-0.Cp-PCT-0.Cp-PCT-0.Cp-PCT-0.Cp], leu2::[HIS3.Sba-RS-ACR-0.Rp-HPCD-0.Sac-HPCD-0.Sac-HPCD-0.Sac-HPCD-0.Sac], trp1, ura3 |
| YA5058 | MAT-a, ade2, can1-100, his3, jlp1::[LEU2.Sba-RS-PCT-0.Cp-PCT-0.Cp-PCT-0.Cp-PCT-0.Cp], leu2::[HIS3.Sba-RS-HPCD-0.Sac-ACR-0.Rp-ACR-0.Rp-ACR-0.Rp-ACR-0.Rp], trp1, ura3 |

TABLE 37

Activity of acrylyl-CoA reductase measured by cofactor consumption.

| Strain | Relevant genotype | Activity (nmol · $min^{-1}$ · $mg^{-1}$) |
|---|---|---|
| YA4952-2 | WT | ND |
| YA5057-2 | ACR-O.Rp x1 | 700 |
| YA5057-9 | | 400 |
| YA5058-5 | ACR-O.Rp x4 | 1200 |
| YA5058-15 | | 1700 |

Propanol Production from Propionyl-CoA In Vitro

To this step, two different pathways can be used to convert propionyl-CoA into 1-propanol. The first one relies on the implementation of the multifunctional ADHE enzyme of *Clostridium arbusti*, while the second one proceeds through the intermediary formation of propionaldehyde by a propionyl-CoA reductase from Paraburkholderia xenovorans or *Salmonella enterica* with or without endogenous overexpression of the alcohol dehydrogenase ADH1. The reaction was measured by monitoring NADH consumption at 340 nm using 1 mM propionyl-CoA as substrate. Results demonstrated that the PDUP enzyme from *Salmonella enterica* was the best candidate to catalyze the reaction.

TABLE 38

Strains constructed to test activity of propionyl-CoA reductase and alcohol/aldehyde dehydrogenase.

| Strain | Relevant Genotype |
|---|---|
| YA5051 | jlp1::[LEU2.Sba-RS-PCT-0.Cne-PCT-0.Cne-PCT-0.Cne-PCT-0.Cne] |
| YA5212 | MAT-a, ade2::[TRP1.Sba-loxP-ADHE-0A.Car-ADHE-0A.Car-ADHE-0A.Car], can1-100, his3, jlp1::[LEU2.Sba-RS-PCT-0.Cp-PCT-0.Cp-PCT-0.Cp-PCT-0.Cp], leu2::[HIS3.Sba-RS-ACR-0.Rp-HPCD-0.Sac-HPCD-0.Sac-HPCD-0.Sac-HPCD-0.Sac |
| YA5214 | MAT-a, ade2::[TRP1.Sba-loxP-PDUP.Sen-PDUP.Sen-PDUP.Sen], can1-100, his3, jlp1::[LEU2.Sba-RS-PCT-0.Cp-PCT-0.Cp-PCT-0.Cp-PCT-0.Cp], leu2::[HIS3.Sba-RS-ACR-0.Rp-HPCD-0.Sac-HPCD-0.Sac-HPCD-0.Sac-HPCD-0.Sac] |
| YA5215 | MAT-a, ade2::[TRP1.Sba-loxP-PDUP.Sen-PDUP.Sen-PDUP.Sen-ADH1], can1-100, his3, jlp1::[LEU2.Sba-RS-PCT-0.Cp-PCT-0.Cp-PCT-0.Cp-PCT-0.Cp], leu2::[HIS3.Sba-RS-ACR-0.Rp-HPCD-0.Sac-HPCD-0.Sac-HPCD-0.Sac-HPCD-0.Sac] |

TABLE 39

Activity of propionyl-CoA reductase and alcohol/aldehyde dehydrogenase measured by cofactor consumption.

| Strain | Relevant genotype | Activity (nmol · min$^{-1}$ · mg$^{-1}$) |
|---|---|---|
| YA5057-2 | WT | ND |
| YA5051-1 | +MHPF.Px x3 | ND |
| YA5212-4 | YA5057-2 + ADHE-0.Car x3 | 45 |
| YA5214-1 | YA5057-2 + PDUP. Sen x3 | 1500 |
| YA5214-4 |  | 2200 |
| YA5215-1 | YA5057-2 + PDUP. Sen x3 +ADH1 | 2200 |

Propanol Production from 3-HP In Vitro

The production of propanol from 3-HP was assayed in vitro using cell extracts of the YA5214 and YA5215 strains. The assay was carried out in phosphate buffer 0.1 M pH 6.5 in the presence of 2 mg/mL of cell extract at 30° C. for 60 minutes, using 20 mM of 3-HP+2 mM of acetyl-CoA+2.8 mM of NADPH+4 mM of NADH. 1-propanol production was monitored by GC/MS-MS head space analysis.

TABLE 40

In-vitro production of 1-propanol

| Strain | Propanol (mg · L$^{-1}$) | Activity (nmol · min$^{-1}$ · mg$^{-1}$) | Propionyl-CoA (mg · L$^{-1}$) |
|---|---|---|---|
| YA5214-1 | 28 | 4 | 59 |
| YA5214-4 | 29 | 4 | 60 |
| YA5215-2 | 35 | 5 | 6 |

Propanol Production from 3-HP In Vivo

To evaluate 1-propanol synthesis, YA5212, YA5214 and YA5215 strains were growth in the presence of glucose and fed with 3-HP. The cells were grown in 25 mL of rich medium in the presence of 400 glucose in Erlenmeyer flasks with a silicon cap+two 1 mL pipette tip with filter. After 24 h of culture, another amount of 4% glucose was added. The stirring was maintained at 135 rpm (50 mm shaking diameter). The presence of 1-propanol into the growth medium was measured by GC/MS-MS head space analysis.

TABLE 41

Strains constructed to produce 1-propanol

| Strain | Relevant Genotype |
|---|---|
| YA4613-7 | MAT-a, can1-100, his3, leu2, met14::[HIS3.Sba-RS-PAND.Tca-PYD4.Lk-YDFG-0.Ec], trp1, ura3::[PAND.Tca-URA3]x8 |

TABLE 42

1-Propanol production after 48 h of culture.

| Strain | 3-HP added | OD 600 nm | 1-propanol (mg · L$^{-1}$) |
|---|---|---|---|
| YA4613-7 | — | 74 | <20 |
|  | 5 g · L−1 | 70 | <20 |
| YA5212-1 | — | 37 | <20 |
|  | 5 g · L−1 | 51 | 44 |
| YA5214-1 | — | 40 | 26 |
|  | 1 g · L−1 | 40 | 58 |
|  | 2 g · L−1 | 49 | 90 |
|  | 5 g · L−1 | 46 | 178 |
| YA5214-4 | — | 37 | 31 |
|  | 5 g · L−1 | 41 | 159 |
| YA5215-1 | — | 40 | 26 |
|  | 1 g · L−1 | 50 | 43 |
|  | 2 g · L−1 | 51 | 76 |
|  | 5 g · L−1 | 46 | 159 |
| YA5215-2 | — | 38 | 27 |
|  | 5 g · L−1 | 50 | 162 |

Example 8: Replacement of Yeast Native GAPDH Genes by Gdp1 from *Kluyveromyces lactis* to Favor Reaching a Neutral Redox Balance of a 1-Propanol and Acetone Co-Production Pathway As described herein, there are metabolic engineering ways to generate anaerobic strains for the co-production of 1-propanol and acetone with neutral redox balance. It is described here an example, which is the replacement of Glyceraldehyde-3-phosphate dehydrogenase (GAPDH) of *Saccharomyces cerevisiae*, encoding by 3 genes (TDH1, TDH2 and TDH3), an enzyme with strict requirement for the oxidized NAD+ cofactor by GAPDH (encoded by GDP1.KI) from crabtree negative yeast *Kluyveromyces lactis*, which accepts either NAD+ or NADP+ and also displays a similar affinity for both compounds.

To determine the minimal GAPDH activity required to sustain an adequate carbon flux towards PEP, the contribution of each of the three yeast GAPDH isozymes was assayed in both a wild type and mutant strains. As the TDH1Δ, TDH2Δ, TDH3Δ triple mutant yeast cells were not viable, strains bearing either single or double TDH deletions were engineered and the GAPDH activity was assayed within crude extract of the resulting strains.

TABLE 43

Strains constructed to test TDHs activity.

| Strain | Relevant Genotype |
|---|---|
| YA4693-1A | ade2, his3, leu2, tdh1::URA3.Sba-loxP, tdh3::LEU2.K1-loxP, trp1, ura3 |
| YA4693-1B | ade2, his3, leu2, tdh1::URA3.Sba-loxP, tdh2::HIS5.Sp-loxP, trp1, ura3 |
| YA4693-1D | ade2, his3, leu2, tdh2::HIS5.Sp-loxP, trp1, ura3 |
| YA4693-2D | ade2, his3, leu2, tdh1::URA3.Sba-loxP, trp1, ura3 |
| YA4693-3D | ade2, his3, leu2, tdh2::HIS5.Sp-loxP, tdh3::LEU2.K1-loxP, trp1, ura3 |
| YA4693-4C | ade2, his3, leu2, tdh3::LEU2.K1-loxP, trp1, ura3 |

TDH3 activity assay is as described in Nakajima H, Itakura M, Kubo T, Kaneshige A, Harada N, Izawa T, Azuma Y T, Kuwamura M, Yamaji R, Takeuchi T. (2017) J Biol Chem 292(11):4727-4742

TABLE 44

Activity of GAPDH isozymes to NAD consumption.

| Strain | Active genes | Activity (nmol · min$^{-1}$ · mg$^{-1}$) NAD |
|---|---|---|
| Wild type | TDH1, TDH2, TDH3 | 24000 |
| YA4693-2D | TDH2, TDH3 | 24000 |
| YA4693-1D | TDH1, TDH3 | 24000 |
| YA4693-4C | TDH1, TDH2 | 6000 |
| YA4693-1B | TDH3 | 24000 |
| YA4693-1A | TDH2 | 6000 |
| YA4693-3D | TDH1 | 3500 |

Deletion of TDH3 leads to a 4-fold decrease of GAPDH activity. TDH1, TDH2 or both TDH1 and TDH2 had no effect on GAPDH activity and deletion of both TDH2 and TDH3 led to an 8-fold activity decrease. It is also important to note that TDH3 gene is responsible for most of the GAPDH activity in yeast cells.

To measure the activity of the *Kluyveromyces lactis* GAPDH enzyme, GDP1.Kl was expressed under the control of a strong promoter in a TDH1 deleted strain and compared with wild type cells.

TABLE 45

Strain constructed to measure the GDP1.Kl activity.

| Strain | Relevant Genotype |
|---|---|
| YA4807-1 | MAT-a, ade2, his3, leu2, tdh2::loxP, tdh3::loxP, trp1, ura3 |
| YA4857-3 | ade2, his3, jlp1::[ADE2.Sba-loxP-GDP1.Kl], leu, tdh2::loxP, thd3::loxP, trp1, ura3 |
| YA4915-25C | tdh1::loxP, tdh2::loxP, tdh3::loxP, ura3::[GDP1.Kl-URA3]x8 |
| YA4918-67C | tdh1::loxP, tdh2::loxP, tdh3::loxP, ura3::[GDP1.Kl-URA3]x11 |

TABLE 46

Activity of GDP1.Kl to co-factor consumption

| | | Activity (nmol · min$^{-1}$ · mg$^{-1}$) | |
|---|---|---|---|
| Strain | Active genes | NAD | NADP |
| Wild type | TDH1, TDH2, TDH3 | 24000 | 0 |
| YA4807-1 | TDH1 | 3200 | Not detected |
| YA4857-3 | TDH1 + pStrong-GDP1.Kl | 7500 | 2800 |
| YA4915-25C | [pStrong-GDP1.Kl] x8 | 25000 | 32000 |
| YA4918-67C | [pStrong-GDP1.Kl] x11 | 35000 | 47000 |

Expressed in *Saccharomyces cerevisiae* cells, GDP1.Kl consumed either NAD+ or NADP+. This activity appears to be strong to complement the deletion of the three *S. cerevisiae* TDH genes with the increment of the copy number of GDP1.Kl.

Besides, the replacement of GAPDH in combination with the use of HPD1 enzyme (*Candida albicans*), that catalyzes the conversion of malonate semialdehyde to 3-hydroxypropionic acid (3-HP), can be used to reaching neutral redox balance.

Example 9: Co-Production of 1-Propanol and Acetone

As described on previous examples, the in-vivo production of 3-HP, MSA and acetone have been demonstrated from glucose through the B-alanine route. Besides, the in-vivo conversion of 3HP into 1-propanol has been successfully demonstrated too supplementing culture media with 1-5 g/L 3HP. Considering engineered variants of oxaloacetate decarboxylase have increased activity for the conversion of oxaloacetate into malonate semialdehyde, it is expected that such enhanced oxaloacetate decarboxylase engineered variants are able to sustain the production of malonate semialdehyde and malonate semialdehyde-derivatives such as 1-propanol from glucose fermentation. For example, one of the best engineered oxaloacetate decarboxylase variants showed to be 4-5× lower only compared to PAND enzyme (panD, *Tribolium castaneum*), that catalyzes the aspartate conversion to β-alanine, under in-vitro enzymatic experiment, indicating such engineered variant would sustain in-vivo production of 3-HP from glucose (data not shown).

Based on the information here disclosed, an engineered microbial strain can be generated to co-produce 1-propanol and acetone by introducing for example the target 1-propanol pathway enzymes into an already acetone-producing engineered strain such as the ones previously described. Besides, it's been successfully demonstrated previously the in-vivo production of 3-HP from glucose through the β-alanine pathway under anaerobic fermentation conditions. So, it is expected that such 3HPA-producing strain starts to co-produce 1-propanol and acetone after introducing both target enzymes of the 1-propanol and acetone pathways.

For example, such 1-propanol and acetone co-producing engineered strains could be grown in 25 mL of rich medium in the presence of 4% glucose in Erlenmeyer flasks with or without silicon cap plus two 1 mL pipette tip with filter. After 24 h of culture, another amount of 4% glucose is added. Stirring is maintained at 135 rpm (50 mm shaking diameter). The presence of 1-propanol and acetone into the culture medium is measured by standard GC/MS-MS head space analysis.

Example 10: Co-Production of 1-Propanol and 2-Propanol

As described on Example 9, an engineered microbial strain can be generated to co-produce 1-propanol and acetone by introducing for example the target 1-propanol pathway enzymes into an already acetone-producing engineered strain such as the ones previously described. Besides, it is been successfully demonstrated previously the in-vivo production of 3-HP from glucose through the β-alanine pathway under anaerobic fermentation conditions. So, it is expected that such 3HPA-producing strain starts to co-produce 1-propanol and acetone after introducing both target enzymes of the 1-propanol and acetone pathways. Then, to co-produce 1-propanol and 2-propanol, the 2-propanol dehydrogenase, for example as listed in Table 15, can be introduced on strain described on example 9.

To evaluate 1-propanol and 2-propanol co-production, the strains could be grown in 25 mL of rich medium in the presence of 4% glucose in Erlenmeyer flasks with or without silicon cap plus two 1 mL pipette tip with filter. After 24 h of culture, another amount of 4% glucose is added. Stirring is maintained at 135 rpm (50 mm shaking diameter). The presence of 1-propanol and 2-propanol into the culture medium is measured by standard GC/MS-MS head space analysis.

Numbered Embodiments

Embodiment 1. A recombinant microorganism capable of co-producing 3-hydroxypropionic acid (3-TP) and acetyl-CoA, and/or derivatives thereof, from a feedstock comprising one or more carbon sources, wherein the recombinant microorganism comprises one or more of the following:
  (a) at least one endogenous and/or exogenous nucleic acid molecule encoding a 3-hydroxypropionic acid dehydrogenase that catalyzes the production of 3-HP from malonate semialdehyde;
  (b) at least one endogenous and/or exogenous nucleic acid molecule encoding a
    (i) malonate semialdehyde dehydrogenase that catalyzes the production of acetyl-CoA from malonate semialdehyde, and/or
    (ii) malonyl-CoA reductase and/or 2-keto acid decarboxylase that catalyzes the conversion of malonate semialdehyde into malonyl-CoA, and malonyl-CoA decarboxylase that catalyzes the production of acetyl-CoA from malonyl-CoA;
  (c) at least one endogenous and/or exogenous nucleic acid molecule encoding an enzyme that is able to catalyze the decarboxylation of oxaloacetate into malonate semialdehyde.

Embodiment 2. The recombinant microorganism of embodiment 1, wherein the recombinant microorganism is capable of producing 1-propanol.

Embodiment 3. The recombinant microorganism of embodiment 2, wherein the recombinant microorganism comprises one or more of the following:
  (a) at least one endogenous and/or exogenous nucleic acid molecule encoding a propionyl-CoA synthase that catalyzes the conversion of 3-HP into propionyl-CoA;
  (b) at least one endogenous and/or exogenous nucleic acid molecule encoding a 3-hydroxypropionyl-CoA synthetase/CoA transferase, 3-hydroxypropionyl-CoA dehydratase, and acrylyl-CoA reductase that catalyzes the conversion of 3-HP into propionyl-CoA;
  (c) at least one endogenous and/or exogenous nucleic acid molecule encoding an alcohol/aldehyde dehydrogenase that catalyzes the conversion of propionyl-CoA from (a) or (b) into 1-propanol, or an aldehyde dehydrogenase (acetylating) and alcohol dehydrogenase that catalyzes together the production of 1-propanol from propionyl-CoA.

Embodiment 4. The recombinant microorganism of embodiment 1, wherein the recombinant microorganism is capable of producing acetone.

Embodiment 5. The recombinant microorganism of embodiment 4, wherein the recombinant microorganism comprises one or more of the following:
  (a) at least one endogenous and/or exogenous nucleic acid molecule encoding a thiolase or an acetyl-CoA acetyltransferase that catalyzes the production of acetoacetyl-CoA from acetyl-CoA;
  (b) at least one endogenous and/or exogenous nucleic acid molecule encoding an acetoacetyl-CoA synthase that catalyzes the production of acetoacetyl-CoA from malonyl-CoA;
  (c) at least one endogenous and/or exogenous nucleic acid molecule encoding an acetoacetyl-CoA transferase that catalyzes the production of acetoacetate from acetoacetyl-CoA;
  (d) at least one endogenous and/or exogenous nucleic acid molecule encoding a
    (i) hydroxymethylglutaryl-CoA synthase that catalyzes the production of HMG-CoA from acetoacetyl-CoA, and
    (ii) hydroxymethylglutaryl-CoA lyase that catalyzes the production of acetoacetate from HMG-CoA; and
  (e) at least one endogenous and/or exogenous nucleic acid molecule encoding an acetoacetate decarboxylase that catalyzes the production of acetone from acetoacetate.

Embodiment 6. The recombinant microorganism of embodiment 5, wherein the endogenous and/or exogenous nucleic acid molecule encoding a thiolase or an acetyl-CoA acetyltransferase encodes an amino acid sequence comprising ERG10 (SEQ ID NO: 209), thlA (SEQ ID NO: 210), atoB (SEQ ID NO: 211), H16_B0759 (SEQ ID NO: 212), Msed_0656 (SEQ ID NO: 213), or AAT1 (SEQ ID NO: 214).

Embodiment 7. The recombinant microorganism of embodiment 6, wherein the endogenous and/or exogenous nucleic acid molecule encoding a thiolase or an acetyl-CoA acetyltransferase encode an amino acid sequence comprising ERG10 (SEQ ID NO: 209).

Embodiment 8. The recombinant microorganism of embodiment 5, wherein the endogenous and/or exogenous nucleic acid molecule encoding an acetoacetyl-CoA synthase encodes an amino acid sequence comprising nphT7 (SEQ ID NO: 285).

Embodiment 9. The recombinant microorganism of embodiment 5, wherein the endogenous and/or exogenous nucleic acid molecule encoding a acetoacetyl-CoA transferase encodes an amino acid sequence comprising atoA/atoD (SEQ ID NO: 215 and 216), ctfA/ctfB (SEQ ID NO: 219 and 220), ctfA/ctfB (SEQ ID NO:221 and 222) or ctfA/ctfB (SEQ ID NO:223 and 224).

Embodiment 10. The recombinant microorganism of embodiment 9, wherein the endogenous and/or exogenous nucleic acid molecule encoding an acetoacetyl-CoA transferase encodes an amino acid sequence comprising atoA/atoD (SEQ ID NO: 215 and 216)

Embodiment 11. The recombinant microorganism of embodiment 5, wherein the endogenous and/or exogenous nucleic acid molecule encoding a hydroxymethylglutaryl-CoA synthase and a hydroxymethylglutaryl-CoA lyase encode an amino acid sequence comprising ERG13 (SEQ ID NO: 283) and yngG (SEQ ID NO: 284).

Embodiment 12. The recombinant microorganism of embodiment 5, wherein the endogenous and/or exogenous nucleic acid molecule encoding a acetoacetate decarboxylase encodes an amino acid sequence comprising Adc.Ca (SEQ ID NO: 225), Adc.Cbe (SEQ ID NO: 226), Adc (SEQ ID NO: 227), Adc (SEQ ID NO: 228), Adc (SEQ ID NO: 229) or Adc.Pp (SEQ ID NO: 230).

Embodiment 13. The recombinant microorganism of embodiment 12, wherein the endogenous and/or exogenous nucleic acid molecule encoding a acetoacetate decarboxylase encodes an amino acid sequence comprising Adc.Pp (SEQ ID NO: 230).

Embodiment 14. The recombinant microorganism of embodiment 1, wherein the recombinant microorganism catalyzes malonate semialdehyde for the production of both 3-HP and acetyl-CoA, and/or derivatives thereof.

Embodiment 15. The recombinant microorganism of embodiment 1, wherein the derivatives of 3-HP are selected from the group consisting of: acrylic acid, 1-propanol, propene, and polypropylene.

Embodiment 16. The recombinant microorganism of embodiment 1, wherein the derivatives of acetyl-CoA are selected from the group consisting of: acetone, 2-propanol, propene, and polypropylene.

Embodiment 17. The recombinant microorganism of embodiment 1, wherein the microorganism is selected from a bacterium, a fungus, or a yeast.

Embodiment 18. The recombinant microorganism of embodiment 1, wherein the recombinant microorganism is derived from a parental microorganism selected from the group consisting of: *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella* thermoautotrophica, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema* azotonutricium, *Escherichia coli*, *Saccharomyces cerevisiae*, *Pseudomonas putida*, *Bacillus* sp, *Corynebacterium* sp., *Yarrowia lipolytica*, *Scheffersomyces stipitis*, and Terri *sporobacter glycolicus*.

Embodiment 19. The recombinant microorganism of embodiment 17, wherein the recombinant microorganism is a yeast.

Embodiment 20. The recombinant microorganism of embodiment 19, wherein the yeast is *Saccharomyces cerevisiae*.

Embodiment 21. The recombinant microorganism of embodiment 19, wherein the yeast is capable of aerobic and anaerobic production.

Embodiment 22. The recombinant microorganism of embodiment 14, wherein the recombinant microorganism comprises a decarboxylase capable of acting on oxaloacetate to produce malonate semialdehyde.

Embodiment 23. A method of producing 3-hydroxypropionic acid (3-HP) and acetyl-CoA, and/or derivatives thereof, the method comprising culturing the recombinant microorganism in a culture medium containing a feedstock comprising a carbon source until the 3-hydroxypropionic acid (3-HP) and acetyl-CoA, and/or derivatives thereof, are produced.

Embodiment 24. A method of producing a recombinant microorganism capable of co-producing 3-hydroxypropionic acid (3-HP) and acetyl-CoA, and/or derivatives thereof, from a feedstock comprising one or more carbon sources, the method comprising introducing into and/or overexpressing in the recombinant microorganism one or more of the following:
  (a) at least one endogenous and/or exogenous nucleic acid molecule encoding a 3-hydroxypropionic acid dehydrogenase that catalyzes the production of 3-HP from malonate semialdehyde;
  (b) at least one endogenous and/or exogenous nucleic acid molecule encoding a
    (i) malonate semialdehyde dehydrogenase that catalyzes the production of acetyl-CoA from malonate semialdehyde, and/or
    (ii) malonyl-CoA reductase and/or 2-keto acid decarboxylase that catalyzes the conversion of malonate semialdehyde into malonyl-CoA, and malonyl-CoA decarboxylase that catalyzes the production of acetyl-CoA from malonyl-CoA;
  (c) at least one endogenous and/or exogenous nucleic acid molecule encoding an enzyme that is able to catalyze the decarboxylation of oxaloacetate into malonate semialdehyde.

Embodiment 25. The method of embodiment 24, wherein the recombinant microorganism is capable of producing 1-propanol.

Embodiment 26. The method of embodiment 24, wherein the method further comprises introducing into and/or overexpressing in the recombinant microorganism one or more of the following:
  (a) at least one endogenous and/or exogenous nucleic acid molecule encoding a propionyl-CoA synthase that catalyzes the conversion of 3-HP into propionyl-CoA;
  (b) at least one endogenous and/or exogenous nucleic acid molecule encoding a 3-hydroxypropionyl-CoA synthetase/CoA transferase, 3-hydroxypropionyl-CoA dehydratase, and acrylyl-CoA reductase that catalyzes the conversion of 3-HP into propionyl-CoA;
  (c) at least one endogenous and/or exogenous nucleic acid molecule encoding an alcohol/aldehyde dehydrogenase that catalyzes the conversion of propionyl-CoA from (a) or (b) into 1-propanol, or an aldehyde dehydrogenase (acetylating) and alcohol dehydrogenase that catalyzes together the production of 1-propanol from propionyl-CoA.

Embodiment 27. The method of embodiment 24, wherein the recombinant microorganism is capable of producing acetone.

Embodiment 28. The method of embodiment 27, wherein the method further comprises introducing into and/or overexpressing in the recombinant microorganism one or more of the following:
  (a) at least one endogenous and/or exogenous nucleic acid molecule encoding a thiolase or an acetyl-CoA acetyltransferase that catalyzes the production of acetoacetyl-CoA from acetyl-CoA;
  (b) at least one endogenous and/or exogenous nucleic acid molecule encoding an acetoacetyl-CoA synthase that catalyzes the production of acetoacetyl-CoA from malonyl-CoA;
  (c) at least one endogenous and/or exogenous nucleic acid molecule encoding an acetoacetyl-CoA transferase that catalyzes the production of acetoacetate from acetoacetyl-CoA;
  (d) at least one endogenous and/or exogenous nucleic acid molecule encoding a
    (i) hydroxymethylglutaryl-CoA synthase that catalyzes the production of HMG-CoA from acetoacetyl-CoA, and
    (ii) hydroxymethylglutaryl-CoA lyase that catalyzes the production of acetoacetate from HMG-CoA; and
  (e) at least one endogenous and/or exogenous nucleic acid molecule encoding an acetoacetate decarboxylase that catalyzes the production of acetone from acetoacetate.

Embodiment 29. The method of embodiment 24, wherein the recombinant microorganism catalyzes malonate semialdehyde for the production of both 3-HP and acetyl-CoA, and/or derivatives thereof.

Embodiment 30. The method of embodiment 24, wherein the derivatives of 3-HP are selected from the group consisting of: acrylic acid, 1-propanol, propene, and polypropylene.

Embodiment 31. The method of embodiment 24, wherein the derivatives of acetyl-CoA are selected from the group consisting of: acetone, 2-propanol, propene, and polypropylene.

Embodiment 32. The method of embodiment 24, wherein the microorganism is selected from a bacterium, a fungus, or a yeast.

Embodiment 33. The method of embodiment 24, wherein the recombinant microorganism is derived from a parental microorganism selected from the group consisting of: *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema azotonutricium*, *Escherichia coli*, *Saccharomyces cerevisiae*, *Pseudomonas putida*, *Bacillus* sp, *Corynebacterium* sp., *Yarrowia lipolytica*, *Scheffersomyces stipitis*, and *Terrisporobacter glycolicus*.

Embodiment 34. The method of embodiment 32, wherein the recombinant microorganism is a yeast.

Embodiment 35. The method of embodiment 34, wherein the yeast is *Saccharomyces cerevisiae*.

Embodiment 36. The method of embodiment 34, wherein the recombinant microorganism co-produces 3-HP, and/or derivatives and Acetyl-CoA and/or derivatives, in an aerobic, microanaerobic or anaerobic production process, preferably an anaerobic process.

Embodiment 37. The method of embodiment 29, wherein the recombinant microorganism comprises a decarboxylase capable of acting on oxaloacetate to produce malonate semialdehyde.

Embodiment 38. The method of embodiment 24, wherein at least a portion of excess NAD(P)H produced in the production of acetyl-CoA is utilized as a source of reducing equivalents in the production of 3-HP and/or derivatives thereof.

Embodiment 39. The recombinant microorganism of embodiment 1, wherein at least a portion of excess NAD(P)H produced in the production of acetyl-CoA is utilized as a source of reducing equivalents in the production of 3-HP and/or derivatives thereof.

Embodiment 40. A recombinant microorganism capable of co-producing 3-hydroxypropionic acid (3-HP) and acetyl-CoA, and/or derivatives thereof, from a feedstock comprising one or more carbon sources, wherein the recombinant microorganism comprises one or more of the following:
  (a) at least one endogenous and/or exogenous nucleic acid molecule encoding an 3-hydroxypropionic acid dehydrogenase that catalyzes the production of 3-HP from malonate semialdehyde;
  (b) at least one endogenous and/or exogenous nucleic acid molecule encoding a
    (i) malonate semialdehyde dehydrogenase that catalyzes the production of acetyl-CoA from malonate semialdehyde, and/or
    (ii) malonyl-CoA reductase and/or 2-keto acid decarboxylase that catalyzes the conversion of malonate semialdehyde into malonyl-CoA, and malonyl-CoA decarboxylase that catalyzes the production of acetyl-CoA from malonyl-CoA; and
  (c) at least one endogenous and/or exogenous nucleic acid molecule encoding an aspartate amino transferase, aspartate decarboxylase, β-alanine pyruvate amino transferase and/or β-alanine transaminase that catalyze the production of malonate semialdehyde from oxaloacetate, having beta-alanine as an intermediate.

Embodiment 41. The recombinant microorganism of embodiment 40, wherein the recombinant microorganism is capable of producing 1-propanol wherein the recombinant microorganism comprises one or more of the following:
  (a) at least one endogenous and/or exogenous nucleic acid molecule encoding a propionyl-CoA synthase that catalyzes the production of propionyl-CoA from 3-HP;
  (b) at least one endogenous and/or exogenous nucleic acid molecule encoding a 3-hydroxypropionyl-CoA synthetase, 3-hydroxypropionyl-CoA dehydratase, and acrylyl-CoA reductase that catalyzes the production of propionyl-CoA from 3-HP; and
  (c) at least one endogenous and/or exogenous nucleic acid molecule encoding an alcohol/aldehyde dehydrogenase that catalyzes the production of 1-propanol from propionyl-CoA.

Embodiment 42. The recombinant microorganism of embodiment 40, wherein the recombinant microorganism is capable of producing acetone wherein the recombinant microorganism comprises one or more of the following:
  (a) at least one endogenous and/or exogenous nucleic acid molecule encoding a thiolase or an acetyl-CoA acetyltransferase that catalyzes the production of acetoacetyl-CoA from acetyl-CoA;
  (b) at least one endogenous and/or exogenous nucleic acid molecule encoding an acetoacetyl-CoA synthase that catalyzes the production of acetoacetyl-CoA from malonyl-CoA;
  (c) at least one endogenous and/or exogenous nucleic acid molecule encoding an acetoacetyl-CoA transferase that catalyzes the production of acetoacetate from acetoacetyl-CoA;
  (d) at least one endogenous and/or exogenous nucleic acid molecule encoding a
    (i) hydroxymethylglutaryl-CoA synthase that catalyzes the production of HMG-CoA from acetoacetyl-CoA, and
    (ii) hydroxymethylglutaryl-CoA lyase that catalyzes the production of acetoacetate from HMG-CoA; and
  (e) at least one endogenous and/or exogenous nucleic acid molecule encoding an acetoacetate decarboxylase that catalyzes the production of acetone from acetoacetate.

Embodiment 43. The recombinant microorganism of embodiments 40 through 42, wherein the derivatives of 3-HP are selected from the group consisting of: acrylic acid, 1-propanol, propene, and polypropylene.

Embodiment 44. The recombinant microorganism of embodiments 40 through 42, wherein the derivatives of acetyl-CoA are selected from the group consisting of: acetone, 2-propanol, propene, and polypropylene.

Embodiment 45. A recombinant microorganism capable of producing acetone and/or derivatives thereof, from a feedstock comprising one or more carbon sources, wherein the recombinant microorganism comprises one or more of the following:
(a) at least one endogenous and/or exogenous nucleic acid molecule encoding:
  (i) at least one endogenous and/or exogenous nucleic acid molecule encoding an enzyme that is able to catalyze the decarboxylation of oxaloacetate into malonate semialdehyde or
  (ii) at least one endogenous and/or exogenous nucleic acid molecule encoding an aspartate amino transferase, aspartate decarboxylase, β-alanine pyruvate amino transferase and/or β-alanine transaminase that catalyze the production of malonate semialdehyde from oxaloacetate, having beta-alanine as an intermediate,
  (iii) malonate semialdehyde dehydrogenase that catalyzes the production of acetyl-CoA from malonate semialdehyde from (i) or (ii), or
  (iv) malonyl-CoA reductase and/or 2-keto decarboxylase that catalyzes the conversion of malonate semialdehyde from (i) or (ii) into malonyl-CoA, and malonyl-CoA decarboxylase that catalyzes the production of acetyl-CoA from malonyl-CoA
(b) at least one or more endogenous and/or exogenous nucleic acid molecules capable of catalyze the conversion of acetyl-CoA to acetone.

Embodiment 46. The recombinant microorganism of embodiment 45, wherein the recombinant microorganism further comprises one or more of the following:
(a) at least one endogenous and/or exogenous nucleic acid molecule encoding a thiolase or an acetyl-CoA acetyltransferase that catalyzes the production of acetoacetyl-CoA from acetyl-CoA;
(b) at least one endogenous and/or exogenous nucleic acid molecule encoding an acetoacetyl-CoA synthase that catalyzes the production of acetoacetyl-CoA from malonyl-CoA;
(c) at least one endogenous and/or exogenous nucleic acid molecule encoding an acetoacetyl-CoA transferase that catalyzes the production of acetoacetate from acetoacetyl-CoA;
(d) at least one endogenous and/or exogenous nucleic acid molecule encoding a
  (i) hydroxymethylglutaryl-CoA synthase that catalyzes the production of HMG-CoA from acetoacetyl-CoA, and
  (ii) hydroxymethylglutaryl-CoA lyase that catalyzes the production of acetoacetate from HMG-CoA; and
(e) at least one endogenous and/or exogenous nucleic acid molecule encoding an acetoacetate decarboxylase that catalyzes the production of acetone from acetoacetate.

Embodiment 47. The recombinant microorganism of embodiment 46, wherein the derivatives of acetone are selected from the group consisting of: 2-propanol, propene, and polypropylene.

Embodiment 48. The recombinant microorganism of embodiment 46, wherein at least a portion of excess NAD(P)H produced in the production of acetone is utilized as a source of reducing equivalents on a coproducing pathway.

Embodiment 49. The recombinant microorganism of embodiment 48, wherein a co-producing pathway is a 3-HP pathway.

Embodiment 50. The recombinant microorganism of embodiments 40-48, wherein the recombinant microorganism produces acetone in an aerobic, microaerobic or anaerobic production process.

Embodiment 51. A method of co-producing 3-HP, and/or derivatives thereof and Acetyl-CoA and/or derivatives thereof by contacting the recombinant microorganism of any of the embodiments 1 with a fermentable carbon source under conditions and for a sufficient period of time to produce 3-HP, or derivatives and Acetyl-CoA or derivatives.

Embodiment 52. A method of producing Acetone or derivatives by contacting the recombinant microorganism of embodiment with a fermentable carbon source under conditions and for a sufficient period of time to produce acetone or derivatives.

Embodiment 53. The methods of embodiments 51 or 52, wherein the carbon source is selected from sugars, glycerol, alcohols, organic acids, alkanes, fatty acids, lignocellulose, proteins, carbon dioxide, and carbon monoxide.

Embodiment 54. The recombinant microorganism of embodiments 51 or 52, wherein the recombinant microorganism produces acetone in an aerobic, microaerobic or anaerobic production process.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Further, the following references are hereby incorporated by reference:

What is claimed is:

1. A recombinant microorganism capable of producing acetone and/or isopropanol from a feedstock comprising one or more carbon sources, wherein the recombinant microorganism comprises:
   (a) at least one endogenous and/or exogenous nucleic acid molecule encoding an aspartate amino transferase that catalyzes the production of aspartate from oxaloacetate;
   (b) at least one exogenous nucleic acid molecule encoding an aspartate decarboxylase that catalyzes the production of β-alanine from aspartate from (a);
   (c) at least one endogenous and/or exogenous nucleic acid molecule encoding a β-alanine pyruvate amino transferase and/or a β-alanine transaminase that catalyzes the conversion of β-alanine from (b) to malonate semialdehyde; and
   (d) a pathway for the conversion of malonate semialdehyde to acetone.

2. The recombinant microorganism of claim 1, wherein the endogenous and/or exogenous nucleic acid molecule encoding an aspartate amino transferase encodes an amino acid sequence comprising SEQ ID NO: 233.

3. The recombinant microorganism of claim 1, wherein the exogenous nucleic acid molecule encoding an aspartate decarboxylase encodes an amino acid sequence comprising SEQ ID NO: 234 or SEQ ID NO: 275.

4. The recombinant microorganism of claim 1, wherein the endogenous and/or exogenous nucleic acid molecule encoding a β-alanine pyruvate amino transferase encodes an amino acid sequence comprising SEQ ID NO: 235.

5. The recombinant microorganism of claim 1, wherein the endogenous and/or exogenous nucleic acid molecule encoding a β-alanine transaminase encodes an amino acid sequence comprising SEQ ID NO: 236.

6. The recombinant microorganism of claim 1, wherein the pathway for the conversion of malonate semialdehyde to acetone comprises:
   (a) at least one endogenous and/or exogenous nucleic acid molecule encoding
      (i) a malonate semialdehyde dehydrogenase that catalyzes the production of acetyl-CoA from malonate semialdehyde, and/or
      (ii) a malonyl-CoA reductase and/or 2-keto acid decarboxylase that catalyzes the conversion of malonate semialdehyde into malonyl-CoA, and a malonyl-CoA decarboxylase that catalyzes the production of acetyl-CoA from malonyl-CoA; and
   (b) at least one or more endogenous and/or exogenous nucleic acid molecules encoding enzymes capable of catalyzing the conversion of acetyl-CoA to acetone.

7. The recombinant microorganism of claim 6, wherein the endogenous and/or exogenous nucleic acid molecule encoding a malonate semialdehyde dehydrogenase encodes an amino acid sequence comprising MSD.Pa (SEQ ID NO: 111), MSD.Cal (SEQ ID NO: 112), iolA (SEQ ID NO: 113), iolA (SEQ ID NO: 114), iolA (SEQ ID NO: 115), mmsA (SEQ ID NO: 116), dddC (SEQ ID NO: 117), or iolA (SEQ ID NO: 118).

8. The recombinant microorganism of claim 6, wherein the endogenous and/or exogenous nucleic acid molecule encoding a malonyl-CoA reductase and/or 2-keto acid decarboxylase encodes an amino acid sequence comprising mcr (SEQ ID NO: 278), matA, MLYCD (SEQ ID NO: 279), kivD (SEQ ID NO: 280), kdcA (SEQ ID NO: 281), or ARO10 (SEQ ID NO: 282).

9. The recombinant microorganism of claim 6, wherein the at least one or more endogenous and/or exogenous nucleic acid molecules encoding enzymes capable of catalyzing the conversion of acetyl-CoA to acetone comprise:
   (a) at least one endogenous and/or exogenous nucleic acid molecule encoding a thiolase or an acetyl-CoA acetyltransferase that catalyzes the production of acetoacetyl-CoA from acetyl-CoA;
   (b) at least one endogenous and/or exogenous nucleic acid molecule encoding
      (i) an acetoacetyl-CoA transferase that catalyzes the production of acetoacetate from acetoacetyl-CoA; and/or
      (ii) at least one endogenous and/or exogenous nucleic acid molecule encoding
         (1) a hydroxymethylglutaryl-CoA synthase that catalyzes the production of HMG-CoA from acetoacetyl-CoA, and
         (2) a hydroxymethylglutaryl-CoA lyase that catalyzes the production of acetoacetate from HMG-COA; and
   (c) at least one endogenous and/or exogenous nucleic acid molecule encoding an acetoacetate decarboxylase that catalyzes the production of acetone from acetoacetate.

10. The recombinant microorganism of claim 9, wherein the endogenous and/or exogenous nucleic acid molecule encoding a thiolase or an acetyl-CoA acetyltransferase encodes an amino acid sequence comprising ERG10 (SEQ ID NO: 209), thlA (SEQ ID NO: 210), atoB (SEQ ID NO: 211), H16_B0759 (SEQ ID NO: 212), Msed_0656 (SEQ ID NO: 213), or AAT1 (SEQ ID NO: 214).

11. The recombinant microorganism of claim 9, wherein the endogenous and/or exogenous nucleic acid molecule encoding an acetoacetyl-CoA transferase encodes an amino acid sequence comprising atoA/atoD (SEQ ID NO: 215 and 216), ctfA/ctfB (SEQ ID NO: 219 and 220), ctfA/ctfB (SEQ ID NO: 221 and 222), or ctfA/ctfB (SEQ ID NO: 223 and 224).

12. The recombinant microorganism of claim 9, wherein the endogenous and/or exogenous nucleic acid molecule encoding a hydroxymethylglutaryl-CoA synthase and a hydroxymethylglutaryl-CoA lyase encode an amino acid sequence comprising ERG13 (SEQ ID NO: 283) and yngG (SEQ ID NO: 284).

13. The recombinant microorganism of claim 9, wherein the endogenous and/or exogenous nucleic acid molecule encoding an acetoacetate decarboxylase encodes an amino acid sequence comprising Adc.Ca (SEQ ID NO: 225), Adc.Cbe (SEQ ID NO: 226), Adc (SEQ ID NO: 227), Adc (SEQ ID NO: 228), Adc (SEQ ID NO: 229) or Adc.Pp (SEQ ID NO: 230).

14. The recombinant microorganism of claim 1, wherein the recombinant microorganism produces isopropanol.

15. The recombinant microorganism of claim 14, further comprising a 2-propanol dehydrogenase.

16. The recombinant microorganism of claim 1, wherein the recombinant microorganism co-produces 3-hydroxypropionic acid (3-HP), and/or derivatives of 3-HP, and acetone, and/or isopropanol, wherein the recombinant microorganism comprises at least one endogenous and/or exogenous nucleic acid molecule encoding a 3-hydroxypropionic acid dehydrogenase that catalyzes the production of 3-HP from malonate semialdehyde;
   wherein the derivatives of 3-HP are selected from acrylic acid, 1-propanol, propene, polypropylene.

17. The recombinant microorganism of claim 16, wherein at least a portion of excess NAD (P) H generated in the production of acetone and/or isopropanol is utilized as a source of reducing equivalents in the production of 3-HP and/or derivatives of 3-HP.

18. The recombinant microorganism of claim 16, wherein the endogenous and/or exogenous nucleic acid molecule encoding a 3-hydroxypropionic acid dehydrogenase encodes an amino acid sequence comprising MCR-Nterm.Cau (SEQ ID NO: 105), ADH.Ae (SEQ ID NO: 106), MMSB.Bce (SEQ ID NO: 107), YDFG-0.Ec (SEQ ID NO: 108), YMR226C (YDF1) (SEQ ID NO: 109), or HPD1 (SEQ ID NO: 110).

19. The recombinant microorganism of claim 1, wherein the microorganism is selected from a bacterium, a fungus, or a yeast.

20. A method of producing acetone and/or isopropanol by contacting the recombinant microorganism of claim 1 with a fermentable carbon source under conditions and for a sufficient period of time to produce acetone and/or isopropanol.

21. The method of claim 20, wherein the carbon source is selected from sugars, glycerol, alcohols, organic acids, alkanes, fatty acids, lignocellulose, proteins, carbon dioxide, and carbon monoxide.

22. The method of claim 20, wherein the recombinant microorganism produces acetone and/or isopropanol in an aerobic, microanaerobic or anaerobic production process.

* * * * *